US011980738B1

(12) United States Patent
Lipman et al.

(10) Patent No.: US 11,980,738 B1
(45) Date of Patent: May 14, 2024

(54) INJECTION AND INFUSION SITE TREATMENT DEVICES AND METHODS

(71) Applicant: Neodyne Biosciences, Inc., Fremont, CA (US)

(72) Inventors: Kelley J. Lipman, Livermore, CA (US); Jasper Jackson, Newark, CA (US); John A. Zepeda, Los Altos, CA (US); Philip J. Wadlow, Campbell, CA (US); Reuben E. Lasrado, Mangalore (IN)

(73) Assignee: Neodyne Biosciences, Inc., Fremont, CA (US)

( * ) Notice: Subject to any disclaimer, the term of this patent is extended or adjusted under 35 U.S.C. 154(b) by 0 days.

(21) Appl. No.: 18/537,391

(22) Filed: Dec. 12, 2023

Related U.S. Application Data

(63) Continuation of application No. 17/838,027, filed on Jun. 10, 2022, which is a continuation-in-part of application No. PCT/US2020/064378, filed on Dec. 10, 2020.

(60) Provisional application No. 63/211,359, filed on Jun. 16, 2021, provisional application No. 62/946,345, filed on Dec. 10, 2019.

(51) Int. Cl.
*A61M 5/142* (2006.01)
*A61F 13/02* (2024.01)

(52) U.S. Cl.
CPC ......... *A61M 5/14248* (2013.01); *A61F 13/02* (2013.01); *A61M 2005/14252* (2013.01)

(58) Field of Classification Search
CPC ............ A61F 2013/00174; A61F 13/02; A61F 13/05; A61M 1/90; A61M 1/91; A61M 1/912; A61M 1/915; A61M 1/916; A61M 1/92; A61M 1/962
See application file for complete search history.

(56) References Cited

U.S. PATENT DOCUMENTS

| 114,750 | A | 5/1871 | Battersby |
| 363,538 | A | 5/1887 | Penny |
| 633,050 | A | 9/1899 | Spenard |
| 1,074,413 | A | 9/1913 | Baun et al. |
| 1,774,489 | A | 8/1930 | David |

(Continued)

FOREIGN PATENT DOCUMENTS

| CA | 2321491 A1 | 9/1999 |
| CA | 2621387 A1 | 3/2007 |

(Continued)

OTHER PUBLICATIONS

Davison, et al., (Jan. 2006). "Ineffective Treatment of Keloids with Interferon Alpha-2b," Plastic and Reconstructive Surgery 117(1):247-252.

(Continued)

*Primary Examiner* — James D Ponton
(74) *Attorney, Agent, or Firm* — Dorsey & Whitney LLP

(57) ABSTRACT

Devices, kits and methods described herein are be used at chronic injection site or in conjunction with an indwelling catheter or cannula. A book-like packaging, applicator and/or tensioning device with an opening and optional indicia to align the catheter or cannula to the opening may be used to apply a dressing to a subject. The packaging, applicator and/or tensioning device may apply and/or maintain a strain in an elastic dressing.

20 Claims, 121 Drawing Sheets

(56) References Cited

U.S. PATENT DOCUMENTS

| | | |
|---|---|---|
| 1,969,188 A | 8/1934 | Spicer |
| 2,018,517 A | 10/1935 | Edward |
| 2,303,131 A | 11/1942 | Morgan |
| 2,371,978 A | 3/1945 | Perham |
| 2,421,193 A | 5/1947 | James |
| 2,472,009 A | 5/1949 | James |
| 2,714,382 A | 8/1955 | Solis |
| 2,722,220 A | 11/1955 | Mestrand |
| 2,762,371 A | 9/1956 | Guio |
| 3,103,218 A | 9/1963 | Ajemian |
| 3,402,716 A | 9/1968 | Baxter |
| 3,487,836 A | 1/1970 | Niebel et al. |
| 3,528,426 A | 9/1970 | Vukojevic |
| 3,575,782 A | 4/1971 | Hansen |
| 3,613,679 A | 10/1971 | Bijou |
| 3,645,835 A | 2/1972 | Hodgson |
| 3,698,395 A | 10/1972 | Hasson |
| 3,863,640 A | 2/1975 | Haverstock |
| 3,926,193 A | 12/1975 | Hasson |
| 3,933,158 A | 1/1976 | Haverstock |
| 3,983,878 A | 10/1976 | Kawchitch |
| 4,038,989 A | 8/1977 | Romero-Sierra et al. |
| 4,073,298 A | 2/1978 | Le |
| 4,114,624 A | 9/1978 | Haverstock |
| 4,141,363 A | 2/1979 | James et al. |
| 4,173,131 A | 11/1979 | Melton et al. |
| 4,222,383 A | 9/1980 | Schossow |
| 4,282,005 A | 8/1981 | Sato et al. |
| 4,346,700 A | 8/1982 | Dunshee et al. |
| 4,370,981 A | 2/1983 | Sanderson |
| 4,413,621 A | 11/1983 | Mccracken et al. |
| 4,423,731 A | 1/1984 | Roomi |
| 4,425,176 A | 1/1984 | Shibano et al. |
| 4,447,482 A | 5/1984 | Heinzelman et al. |
| 4,496,535 A | 1/1985 | Gould et al. |
| 4,531,521 A | 7/1985 | Haverstock |
| 4,535,772 A | 8/1985 | Sheehan |
| 4,539,990 A | 9/1985 | Stivala |
| 4,549,653 A | 10/1985 | Lauritzen |
| 4,598,004 A | 7/1986 | Heinecke |
| 4,605,005 A | 8/1986 | Sheehan |
| 4,646,731 A | 3/1987 | Brower |
| 4,653,492 A | 3/1987 | Parsons |
| 4,696,301 A | 9/1987 | Barabe |
| 4,699,133 A | 10/1987 | Schaefer et al. |
| 4,702,251 A | 10/1987 | Sheehan |
| 4,706,661 A | 11/1987 | Barrett |
| 4,732,146 A | 3/1988 | Fasline et al. |
| 4,742,826 A | 5/1988 | Mclorg |
| 4,753,232 A | 6/1988 | Ward |
| 4,780,168 A | 10/1988 | Beisang et al. |
| 4,787,381 A | 11/1988 | Hubbard et al. |
| 4,807,613 A | 2/1989 | Koehnke et al. |
| 4,815,457 A | 3/1989 | Mazars et al. |
| 4,815,468 A | 3/1989 | Annand |
| 4,825,866 A | 5/1989 | Pierce |
| 4,881,546 A | 11/1989 | Kaessmann |
| 4,915,102 A | 4/1990 | Kwiatek et al. |
| 4,917,929 A | 4/1990 | Heinecke |
| 4,924,866 A | 5/1990 | Yoon |
| 4,950,282 A | 8/1990 | Beisang et al. |
| RE33,353 E | 9/1990 | Heinecke |
| 4,984,584 A | 1/1991 | Hansen et al. |
| 5,011,492 A | 4/1991 | Heimerl et al. |
| 5,026,389 A | 6/1991 | Thieler |
| 5,047,047 A | 9/1991 | Yoon |
| 5,058,579 A | 10/1991 | Terry et al. |
| 5,066,299 A | 11/1991 | Bellingham |
| 5,106,629 A | 4/1992 | Cartmell et al. |
| 5,127,412 A | 7/1992 | Cosmetto et al. |
| 5,176,703 A | 1/1993 | Peterson |
| 5,234,462 A | 8/1993 | Pavletic |
| 5,259,835 A | 11/1993 | Clark et al. |
| 5,263,970 A | 11/1993 | Preller |
| 5,333,753 A | 8/1994 | Etheredge |
| 5,383,900 A | 1/1995 | Krantz |
| 5,507,775 A | 4/1996 | Ger et al. |
| 5,520,762 A | 5/1996 | Rasmussen et al. |
| 5,522,879 A | 6/1996 | Scopelianos |
| 5,545,713 A | 8/1996 | Krejci et al. |
| 5,549,713 A | 8/1996 | Kim |
| 5,552,162 A | 9/1996 | Lee |
| 5,562,705 A | 10/1996 | Whiteford |
| 5,628,724 A | 5/1997 | Debusk et al. |
| 5,649,960 A | 7/1997 | Pavletic |
| 5,662,624 A | 9/1997 | Sundstroem et al. |
| 5,662,714 A | 9/1997 | Charvin et al. |
| 5,662,717 A | 9/1997 | Burns |
| 5,713,842 A | 2/1998 | Kay |
| 5,723,009 A | 3/1998 | Frechet et al. |
| 5,758,662 A | 6/1998 | Hall |
| 5,759,560 A | 6/1998 | Dillon |
| 5,779,659 A | 7/1998 | Allen |
| 5,885,254 A | 3/1999 | Matyas |
| 5,891,076 A | 4/1999 | Fabo |
| 5,919,476 A | 7/1999 | Fischer et al. |
| 5,931,800 A | 8/1999 | Rasmussen et al. |
| 5,947,998 A | 9/1999 | Cartmell et al. |
| 5,998,694 A | 12/1999 | Jensen et al. |
| 6,007,564 A | 12/1999 | Haverstock |
| 6,043,406 A | 3/2000 | Sessions et al. |
| 6,093,465 A | 7/2000 | Gilchrist et al. |
| 6,120,525 A | 9/2000 | Westcott |
| 6,255,552 B1 | 7/2001 | Cummings et al. |
| 6,264,976 B1 | 7/2001 | Heinecke et al. |
| 6,284,941 B1 | 9/2001 | Cox et al. |
| 6,297,420 B1 | 10/2001 | Heincke |
| 6,297,423 B1 | 10/2001 | Schoenfeldt et al. |
| 6,343,224 B1 | 1/2002 | Parker |
| 6,346,653 B1 | 2/2002 | Sessions et al. |
| 6,410,818 B1 | 6/2002 | Oyaski |
| 6,469,066 B1 | 10/2002 | Dosch et al. |
| 6,472,581 B1 | 10/2002 | Muramatsu et al. |
| 6,485,503 B2 | 11/2002 | Jacobs et al. |
| 6,495,230 B1 | 12/2002 | Do |
| 6,570,051 B1 | 5/2003 | Beaudry |
| 6,572,878 B1 | 6/2003 | Blaine |
| 6,573,419 B2 | 6/2003 | Naimer |
| 6,634,653 B2 | 10/2003 | Chatterjea |
| 6,726,696 B1 | 4/2004 | Houser et al. |
| 6,759,481 B2 | 7/2004 | Tong |
| 6,822,133 B2 | 11/2004 | Lebner |
| 6,831,205 B2 | 12/2004 | Lebner |
| 6,870,074 B2 | 3/2005 | Gilman |
| 6,986,855 B1 | 1/2006 | Hood et al. |
| 7,066,182 B1 | 6/2006 | Dunshee |
| 7,066,934 B2 | 6/2006 | Kirsch |
| 7,122,712 B2 | 10/2006 | Lutri et al. |
| 7,135,606 B1 | 11/2006 | Dozier et al. |
| 7,227,050 B2 | 6/2007 | Sigurjonsson et al. |
| 7,332,641 B2 | 2/2008 | Lebner et al. |
| 7,354,446 B2 | 4/2008 | Lebner |
| 7,414,168 B2 | 8/2008 | Lebner |
| 7,456,332 B2 | 11/2008 | Beaudry |
| 7,511,185 B2 | 3/2009 | Lebner |
| 7,563,941 B2 | 7/2009 | Lebner et al. |
| 7,683,234 B2 | 3/2010 | Gurtner et al. |
| 7,744,568 B2 | 6/2010 | Douglas et al. |
| 7,834,232 B2 | 11/2010 | Rastegar et al. |
| RE42,126 E | 2/2011 | Ye et al. |
| 8,063,263 B2 | 11/2011 | Gurtner et al. |
| 8,168,850 B2 | 5/2012 | Gurtner et al. |
| 8,183,428 B2 | 5/2012 | Gurtner et al. |
| 8,389,791 B2 | 3/2013 | Gurtner et al. |
| 8,395,011 B2 | 3/2013 | Zepeda et al. |
| 8,592,640 B2 | 11/2013 | Zepeda et al. |
| 8,674,164 B2 | 3/2014 | Zepeda et al. |
| 9,248,048 B2 | 2/2016 | Jackson et al. |
| 9,248,049 B2 | 2/2016 | Gurtner et al. |
| 9,248,051 B2 | 2/2016 | Gurtner et al. |
| 9,358,009 B2 | 6/2016 | Yock et al. |
| 9,492,329 B2 | 11/2016 | Zepeda et al. |
| 9,844,470 B2 | 12/2017 | Jackson et al. |
| 10,420,557 B2 | 9/2019 | Yock et al. |

(56) References Cited

U.S. PATENT DOCUMENTS

| | | |
|---|---|---|
| 10,517,768 B2 | 12/2019 | Zepeda et al. |
| 11,013,638 B2 | 5/2021 | Jackson et al. |
| 2002/0013300 A1 | 1/2002 | Capelli-Schellpfeffer |
| 2002/0193723 A1 | 12/2002 | Girardin et al. |
| 2003/0014053 A1 | 1/2003 | Nguyen et al. |
| 2003/0040687 A1 | 2/2003 | Boynton et al. |
| 2003/0092969 A1 | 5/2003 | Omalley et al. |
| 2003/0220700 A1 | 11/2003 | Hammer et al. |
| 2004/0059280 A1 | 3/2004 | Makower et al. |
| 2004/0236360 A1 | 11/2004 | Cohn et al. |
| 2005/0033215 A1 | 2/2005 | Lebner |
| 2005/0034731 A1 | 2/2005 | Rousseau et al. |
| 2005/0070956 A1 | 3/2005 | Rousseau |
| 2005/0080453 A1 | 4/2005 | Lebner et al. |
| 2005/0095275 A1 | 5/2005 | Zhu et al. |
| 2005/0095276 A1 | 5/2005 | Kartheus et al. |
| 2005/0125051 A1 | 6/2005 | Eidenschink et al. |
| 2005/0245966 A1 | 11/2005 | Hammerslag et al. |
| 2005/0274453 A1 | 12/2005 | Anvar |
| 2006/0009099 A1 | 1/2006 | Jonn et al. |
| 2006/0020235 A1 | 1/2006 | Siniaguine |
| 2006/0037091 A1 | 2/2006 | Gurtner et al. |
| 2006/0246802 A1 | 11/2006 | Hughes et al. |
| 2006/0282135 A1 | 12/2006 | Tankovich |
| 2007/0093161 A1 | 4/2007 | Eede et al. |
| 2007/0129776 A1 | 6/2007 | Robins et al. |
| 2007/0142761 A1 | 6/2007 | Aali |
| 2007/0191752 A1 | 8/2007 | Lebner |
| 2007/0282235 A1 | 12/2007 | Beaudry |
| 2007/0282374 A1 | 12/2007 | Sogard et al. |
| 2008/0033334 A1 | 2/2008 | Gurtner et al. |
| 2008/0051687 A1 | 2/2008 | Rogers |
| 2008/0208098 A1 | 8/2008 | Rennix |
| 2008/0228220 A1 | 9/2008 | Weiser |
| 2009/0131845 A1 | 5/2009 | Gurtner et al. |
| 2009/0163844 A1 | 6/2009 | Gurtner et al. |
| 2009/0177136 A1 | 7/2009 | Liedtke et al. |
| 2009/0326487 A1* | 12/2009 | Vitaris .............. A61M 35/00 604/305 |
| 2010/0056873 A1 | 3/2010 | Allen et al. |
| 2010/0191253 A1 | 7/2010 | Oostman et al. |
| 2010/0280428 A1 | 11/2010 | Widgerow et al. |
| 2011/0152738 A1 | 6/2011 | Zepeda et al. |
| 2011/0319798 A1 | 12/2011 | Digrazia |
| 2012/0035521 A1 | 2/2012 | Zepeda et al. |
| 2012/0046586 A1 | 2/2012 | Gurtner et al. |
| 2012/0046590 A1 | 2/2012 | Yock et al. |
| 2012/0046591 A1 | 2/2012 | Gurtner et al. |
| 2012/0203273 A1 | 8/2012 | Riskin et al. |
| 2012/0209377 A1 | 8/2012 | Machold et al. |
| 2012/0221044 A1 | 8/2012 | Archibald et al. |
| 2012/0226214 A1 | 9/2012 | Gurtner et al. |
| 2012/0226306 A1 | 9/2012 | Jackson et al. |
| 2013/0012858 A1 | 1/2013 | Jackson et al. |
| 2013/0184629 A1 | 7/2013 | Gurtner et al. |
| 2013/0190673 A1 | 7/2013 | Gurtner et al. |
| 2013/0281904 A1 | 10/2013 | Jackson et al. |
| 2014/0074033 A1 | 3/2014 | Sonderegger et al. |
| 2014/0088481 A1 | 3/2014 | Jackson et al. |
| 2014/0135677 A1 | 5/2014 | Zepeda et al. |
| 2014/0135678 A1 | 5/2014 | Zepeda et al. |
| 2014/0276323 A1 | 9/2014 | Zepeda et al. |
| 2014/0276324 A1* | 9/2014 | Zepeda .............. A61F 13/0243 602/53 |
| 2015/0141836 A1 | 5/2015 | Naumann et al. |
| 2016/0213522 A1 | 7/2016 | Gurtner et al. |
| 2017/0020522 A1 | 1/2017 | Yock et al. |
| 2017/0112673 A1 | 4/2017 | Jackson et al. |
| 2021/0113384 A1 | 4/2021 | Zepeda et al. |
| 2022/0379018 A1 | 12/2022 | Lipman et al. |
| 2023/0040187 A1 | 2/2023 | Lipman et al. |

FOREIGN PATENT DOCUMENTS

| | | |
|---|---|---|
| CN | 1414842 A | 4/2003 |
| CN | 1608604 A | 4/2005 |
| CN | 102665623 A | 9/2012 |
| CN | 115103639 A | 9/2022 |
| EP | 2161011 A1 | 3/2010 |
| EP | 2464322 A2 | 6/2012 |
| JP | 2004515256 A | 5/2004 |
| JP | 2004223087 A | 8/2004 |
| JP | 2004536898 A | 12/2004 |
| JP | 2006513748 A | 4/2006 |
| JP | 2007537781 A | 12/2007 |
| JP | 2009545382 A | 12/2009 |
| JP | 2013501591 A | 1/2013 |
| KR | 20170116803 A | 10/2017 |
| RU | 2019138 C1 | 9/1994 |
| WO | 9717919 A1 | 5/1997 |
| WO | 9730700 A2 | 8/1997 |
| WO | 9730700 A3 | 10/1997 |
| WO | 0053139 A1 | 9/2000 |
| WO | 0139693 A2 | 6/2001 |
| WO | 0139693 A3 | 12/2001 |
| WO | 0215816 A2 | 2/2002 |
| WO | 0245698 A2 | 6/2002 |
| WO | 0245698 A3 | 7/2002 |
| WO | 02092783 A2 | 11/2002 |
| WO | 2002087645 A1 | 11/2002 |
| WO | 0215816 A3 | 10/2003 |
| WO | 2004060413 A1 | 7/2004 |
| WO | 02092783 A3 | 7/2005 |
| WO | 2005079674 A1 | 9/2005 |
| WO | 2005096981 A2 | 10/2005 |
| WO | 2005096981 A3 | 3/2006 |
| WO | 2006124671 A2 | 11/2006 |
| WO | 2006124671 A3 | 4/2007 |
| WO | 2008019051 A2 | 2/2008 |
| WO | 2008019051 A3 | 4/2008 |
| WO | 2011019859 A2 | 2/2011 |
| WO | 2011019859 A3 | 4/2011 |
| WO | 2012094648 A1 | 7/2012 |
| WO | 2012119131 A1 | 9/2012 |
| WO | 2014021934 A2 | 2/2014 |
| WO | 2021119360 A1 | 6/2021 |

OTHER PUBLICATIONS

Escoffier, et al., (Sep. 1989). "Age-Related Mechanical Properties of Human Skin: An In Vivo Study," J. Invest. Dermatol. 9(3)3:353-357.

Evans, et al., (2009). "Measuring the Mechanical Properties of Human Skin in vivo Using Digital Correlation and Finite Element Modeling," J. Strain Analysis 44:337-345.

Fairclough, et al., (1987). "The Use of Sterile Adhesive Tape in the Closure of Arthroscopic Puncture Wounds: A Comparison with a Single Layer Nylon Closure," Annals of the Royal College of Surgeons of England 69:140-141.

Gorney, (Mar. 2006). "Scar: The Trigger to the Claim," Plastic and Reconstructive Surgery 117(3):1036-1037.

Hof, et al., (Jul. 2006). "Comparing Silicone Pressure-Sensitive Adhesives to Silicone Gels for Transdermal Drug Delivery," presented at 33 Annual Meeting and Exposition of the Controlled Release Society, Vienna, Austria, Jul. 22-26, 2006, seven pages.

Koval, K.J. et al. (Oct. 2003). "Tape Blisters Following Hip Surgery. A Prospective Randomized Study of Two Types of Tape," The Journal of Bone and Joint Surgery, 85-5(10):1884-1887.

Kuo, F. et al. (May 2006). "Prospective Randomized, Blinded Study of a New Wound Closure Film Versus Cutaneous Suture for Surgical Wound Closure," Dermatological Surgery 32(5):676-681.

O'Brien, L. et al. (2009). "Silicon Gel Sheeting for Preventing and Treating Hypertrophic and Keloid Scars," The Cochrane Collaboration, pp. 1-47.

Pitcher, D. (Feb. 1983). "Sutureless Skin Closure for Pacemaker Implantation: Comparison with Subcuticular Suture," Postgraduate Medical Journal 59:83-85.

(56) References Cited

OTHER PUBLICATIONS

Shirado, et al., "Realization of Human Skin-Like Texture by Emulating Surface Shape Pattern and Elastic Structure," presented at Symposium on Haptic Interfaces for Virtual Environment and Teleoperator Systems 2006, Mar. 25-26, 2006, Alexandria, VA, pp. 295-296.
Sullivan, S.R. et al. (2007). "Acute Wound Care," Chapter 7 in ACS Surgery: Principles and Practice, 24 pages.
Téot, L. (2005). "Scar Control" European Tissue Repair Society, located at <http://www.etrs.org/bulletin12_1/section11.php>, last visited on Nov. 30, 2007, 13 pages.
Vaughan, P. et al. (2006). "Optimal Closure of Surgical Wounds in Forefoot Surgery: Are Adhesive Strips Beneficial?" Acta Orthop. Belg. 72(6):731-733.
Vowden, K. (Mar. 2003). "Wound Management. Policy and Resource Pack," Bradford Teaching Hospitals NHS Foundation Trust, pp. 1-70.
Watson, G.M. (1983). "Op-Site Skin Closure: A Comparison with Subcuticular and Interrupted Sutures," Annals of the Royal College of Surgeons of England 65:83-84.
Webster, et al. (Sep. 1975). "Closure of Abdominal Wounds by Adhesive Strips: A Clinical Trial," British Medical Journal 20:696-698.
Westaby, (1980). "Evaluation of a New Product for Sutureless Skin Closure," Annals of the Royal College of Surgeons of England 62:129-132.
International Search Report and Written Opinion issued in International Application No. PCT/US2022/033369, issued no Nov. 2, 2022, 12 pages.
3M HealthCare (May 2004). "Tips for Trouble-Free Taping," 3M HealthCare: St. Paul, MN, four pages.
3M HealthCare. (2001). "Reducing the Risk of Superficial Skin Damage Related to Adhesive Use," 3M HealthCare: St Paul, MN, two pages.
3M HealthCare. (2003). "Steri-Strip: Skin Closures," Product Insert, 3M HealthCare: St. Paul, MN, one page.
3M HealthCare. (2006). "3M™ Steri-Strip™ S Surgical Skin Closure. The Simple, Non-Invasive Alternative to Staples and Sutures from the Steri-Strip Family," HealthCare: St. Paul, MN, two pages.
3M HealthCare. (Date Unknown). "3M™ Steri-Strip™ S Surgical Skin Closure," 3M HealthCare: St. Paul, MN, one page.
3M HealthCare. (Date unknown). 3M™ Steri-Strip™ S Surgical Skin Closure. Poster of Available Sizes, 3M HealthCare: St Paul, MN, three pages.
3M HealthCare. (Jun. 27, 2002). "3M™ Steri-Strip™ Adhesive Skin Closures (reinforced): Commonly Asked Questions," 3M HealthCare: St Paul, MN, pp. 1-4.
3M Healthcare. (Oct. 19, 2006). "3M™ Steri-Strip™ S Surgical Skin Closure: Commonly Asked Questions," 3M Healthcare: St. Paul, MN, pp. 1-8.
3M Medical. (2006). "3M™ Steri-Strip™ S Surgical Skin Closure. Patient Care Information," 3M HealthCare: St. Paul, MN, two pages.
3M Medical. (2007). "3M™ Steri-Strip™ S Surgical Skin Closure. Application Examples, Comparisons and Results," 3M HealthCare: St. Paul, MN, four pages.
Anonymous (2003). "3M™ Steri-Strip™ Adhesive Skin Closures," 3M HealthCare Brochure, twelve pages.
Anonymous. (2005). "3M™ Tegaderm™ Family of Transparent Dressings," 3M HealthCare Brochure, six pages.
Anonymous. (2006). "Avocet Polymer Technologies," located at <http://www.avocetcorp.com/index.html>, last visited on Nov. 5, 2007, one page.
Anonymous. (2006). "Avogel Scar Hydrogel," located at <http://www.avocetcorp.com/avogel_scar_hydrogel.html>, last visited on Nov. 5, 2007, two pages.
Anonymous. (2006). "Avosil Ointment," located at <http://www.avocetcorp.com/avosil.html>, last visited on Nov. 5, 2007, three pages.
Anonymous. (Date Unknown). "Mepiform Instructions of Use," Tendra Corporation Brochure, two pages.
Anonymous. (Date Unknown). "Silicone Scar Bandage: Standard Wound Healing Application," located at <http://www.thejamushop.com/silicon_sheet_for_keloids.htm>, last visited on Mar. 18, 2009, four pages.
Brace, "Definition of Brace", Merriam Webster, Available Online at <www.merriam-webster.com>, 2015, 4 pages.
Canica Design Inc. (Date Unknown). "ABRA® Abdominal Wall Closure Set," located at < http://www.canica.com/instructions/1D1544RA%20-%20ABRA%20CWK08%20IFU.pdf>, last visited on Sep. 10, 2009, pp. 1-11.
Canica Design Inc. (Date Unknown). "ABRA® Surgical Skin Closure Set," located at <http://www.canica.com/instructions/1D0830RH.pdf>, last visited on Sep. 10, 2009, pp. 1-4.
Corrected Notice of Allowability mailed on Jan. 23, 2013, for U.S. Appl. No. 13/315,214, filed Dec. 8, 2011, 2 pages.
Decision for Grant received for Korean Patent Application No. 10-2009-7003220, mailed on May 14, 2014, 3 pages.
Decision for Grant received for Korean Patent Application No. 10-2014-7005383, mailed on Dec. 10, 2014, 3 pages.
English translation of IN OA for Application No. 6583/DELNP/2013, dated May 12, 2019.
English translation of Office Action for BR Application No. 1120120032437, dated Sep. 2, 2020.
English translation of Office Action for BR Application No. 122020025483-1, mailed May 4, 2021.
English translation of Written Opinion for BR Application No. 1120120032437, dated Feb. 22, 2021.
Extended European Search Report (includes Supplementary European Search Report and Search Opinion) received for European Patent Application No. 12752239.9, mailed on Oct. 1, 2014, 7 pages.
Extended European Search Report mailed on Aug. 19, 2013 for European Patent Application No. 10808724.8, filed on Aug. 11, 2010, 8 pages.
Extended European Search Report mailed on Feb. 23, 2016, for European Patent Application No. 13825488.3, filed on Feb. 8, 2013, 6 pages.
Extended European Search Report mailed on Jun. 19, 2017 for European Patent Application No. 16205575.0, filed Aug. 11, 2010, 8 pages.
Extended European Search Report received for European Patent Application No. 12732236.0, mailed on Jun. 29, 2015, 6 pages.
International Preliminary Report on Patentability received for PCT Patent Application No. PCT/US2007/017320, issued on Feb. 3, 2009, 8 pages.
International Preliminary Report on Patentability received for PCT Patent Application No. PCT/US2010/045239, mailed on Feb. 23, 2012, 10 pages.
International Preliminary Report on Patentability received for PCT Patent Application No. PCT/US2012/025510, mailed on Aug. 29, 2013, 10 pages.
International Preliminary Report on Patentability received for PCT Patent Application No. PCT/US2012/027618, mailed on Sep. 12, 2013, 12 pages.
International Preliminary Report on Patentability received for PCT Patent Application No. PCT/US2013/025449, mailed on Feb. 5, 2015, 7 pages.
International Search Report and Written Opinion mailed May 1, 2012, for PCT Patent Application No. PCT/US2012/020561, filed Jan. 6, 2012, three pages.
International Search Report and Written Opinion mailed on Feb. 7, 2008, for PCT Application No. PCT/US2007/017320, filed on Aug. 3, 2007, 11 pages.
International Search Report and Written Opinion mailed on Feb. 8, 2011, for PCT Patent Application No. PCT/US2010/045239, filed on Aug. 11, 2010, one page.
International Search Report and Written Opinion received for PCT Patent Application No. PCT/US2013/025449, mailed on Feb. 5, 2015, 8 pages.
International Search Report and Written Opinion received in PCT/US2020/064378 dated May 13, 2021.

(56) References Cited

OTHER PUBLICATIONS

International Search Report mailed Jun. 28, 2012, for PCT Patent Application No. PCT/US2012/027618, filed Mar. 2, 2012, two pages.
International Search Report mailed May 29, 2012, for PCT Patent Application No. PCT/US2012/025510, filed Feb. 16, 2012, three pages.
Invitation to Pay Additional Fees and, Where Applicable, Protest Fee, for PCT Application No. PCT/US2020/064378, mailed Feb. 23, 2021.
Mask, "Definition of Mask", Merriam Webster, Available Online at <www.merriam-webster.com>, 2015, 4 pages.
Nahabedian, M.Y. (Dec. 2005). "Scar Wars: Optimizing Outcomes with Reduction Mammaplasty," Plastic and Reconstructive Surgery, 116(7):2026-2029.
NHSSB Wound Management Manual, Northern Health and Social Services Board, 2005, pp. 1-97.
Notice of Allowance received for Japanese Patent Application No. 2009-522879, mailed on Mar. 17, 2014, 6 pages.
Notice of Allowance received for Japanese Patent Application No. 2012-524855, mailed on Apr. 30, 2015, 3 pages.
Notice of Allowance received for Japanese Patent Application No. 2013-037053 mailed on Jan. 6, 2015, 3 pages.
Office Action (no EN translation) for CR Application No. 2013-0356, dated Jun. 24, 2019.
Office Action (no Eng. translation) for BR Application No. 1120130175060, dated Aug. 11, 2020.
Office Action for BR Application No. 1120130175060, dated Sep. 19, 2019.
Office Action Received for Australian Patent Application No. 2010282523, mailed on May 6, 2014, 4 pages.
Office Action received for Canadian Patent Application No. 2,659,772, mailed on Oct. 30, 2013, 3 pages.
Office Action received for Canadian Patent Application No. 2,659,772, mailed on Sep. 11, 2014, 2 pages.
Office Action received for Chinese Patent Application No. 201080045471.4, mailed on May 21, 2014, 6 pages.
Office Action received for Chinese Patent Application No. 201080045471.4, mailed on Sep. 29, 2013, 4 pages.
Office Action received for Chinese Patent Application No. 201280012003.6, mailed on Jun. 30, 2014, 9 pages.
Office Action received for Chinese Patent Application No. 201280021431.5, mailed on Sep. 22, 2014, 3 pages.
Office Action received for Chinese Patent Application No. 201310474149.9, mailed on Jan. 27, 2015, 10 pages.
Office Action received for European Patent Application No. 07836471.8, mailed on Jul. 13, 2010, 7 pages.
Office Action received for European Patent Application No. 10808724.8, mailed on Jan. 15, 2015, 4 pages.
Office Action received for Indian Patent Application No. 654/DELNP/2009, mailed on Jul. 31, 2014, 4 pages.
Office Action received for Israeli Patent Application No. 218020, issued on Dec. 1, 2013, 12 pages.
Office Action received for Japanese Patent Application No. 2012-524855, mailed on Apr. 14, 2014, 7 pages.
Office Action received for Japanese Patent Application No. 2012-524855, mailed on Oct. 24, 2014, 5 pages.
Office Action received for Japanese Patent Application No. 2013-037053, mailed on Mar. 17, 2014, 5 pages.
Office Action received for Korean Patent Application No. 10-2009-7003220, mailed on Oct. 28, 2013, 6 pages.
Office Action received for Korean Patent Application No. 10-2014-7005383, mailed on May 14, 2014, 6 pages.
Office Action received in EP Application No. 16205575.0, mailed Jan. 30, 2020.
Shanghai Dongyue Medical Health Product Co., Ltd. (2005). Silicon-gel Membrane—Scar Bandage, located at <http://www.shdongyue.com/cp/shaos/shaos02b.asp>, last visited on Nov. 6, 2008, two pages.

Smith & Nephew. (Date Unknown). "CICA-CARE. Silicone Gel Sheeting," located at <http://wound.smith-nepehew.com/za/Product/asp?NodeId=569&Tab=5&hide=True>, last visited on Jun. 9, 2009, one page.
Wound Care Technologies. (2008). "DERMACloseTM RC: Continuous External Tissue Expander, Brochure No. PL-0020-F," located at < http://www.woundcaretech.com/sell-sheet.pdf>, last visited on Sep. 10, 2009, two pages.
Wound Care Technologies. (2008). "Instructions for Use. DERMACloseTM RC, Brochure No. DR-0079-A," located at < http://www.dermaclose.com/instructions.pdf>, last visited on Sep. 10, 2009, two pages.
Written Opinion of the International Searching Authority mailed Jun. 28, 2012, for PCT Application No. PCT/US2012/027618, filed Mar. 2, 2012, 10 pages.
Written Opinion of the International Searching Authority mailed May 29, 2012, for PCT Application No. PCT/US2012/25510, filed on Feb. 16, 2012, 8 pages.
Decision to Grant received for Chinese Patent Application No. 201280012003.6, mailed on Feb. 3, 2015, 2 pages., pp. all.
Intention to Grant received for European Patent Application No. 12752239.9 mailed on Sep. 24, 2015, 5 pages., pp. all.
Notice of Allowance received for Australian Patent Application No. 2010282523, mailed on Jul. 2, 2015, 2 pages., pp. all.
Notice of Allowance received for Israel Patent Application No. 218020, mailed on Dec. 11, 2014, 4 pages., pp. all.
Office Action for European Patent Application No. 07836471.8, mailed on Nov. 6, 2015, 7 pages., pp. all.
Office Action received for Australian Patent Application No. 2012204174, mailed on Aug. 4, 2015, 2 pages., pp. all.
Office Action received for Chinese Patent Application No. 201280021431.5 mailed on Jul. 17, 2015, 4 pages., pp. all.
Office Action received for Chinese Patent application No. 201310474149.9, mailed on Jul. 27, 2015, 10 pages., pp. all.
Office Action received for Japanese Patent Application No. 2013-548594, mailed on Jul. 7, 2015, 6 pages., pp. all.
Office Action received for Japanese Patent Application No. 2014-123100, mailed on May 18, 2015, 1 page., pp. all.
Office Action received for Japanese Patent Application No. 2014-143959 mailed on May 18, 2015, 1 page., pp. all.
Office Action received in EP Application No. 16205575.0 mailed Dec. 10, 2018, pp. all.
3M Medical, (2006). "They Say Every Scar Tells a Story," 3M HealthCare: St. Paul, MN, one page.
Aarabi, et al., (Oct. 2007). "Mechanical Load Initiates Hypertrophic Scar Formation Through Decreased Cellular Apoptosis," The FASEB Journal 21(12):3250-3261.
Al-Attar, et al., (Jan. 2006). "Keloid Pathogenesis and Treatment," Plastic and Reconstructive Surgery 117(1):286-300.
Angelini, et al., (1984). "Comparative Study of Leg Wound Skin Closure in Coronary Artery Bypass Graft Operations," Thorax 39:942-945.
Atkinson, et al., (Nov. 2005). "A Randomized, Controlled Trial to Determine the Efficacy of Paper Tape in Preventing Hypertrophic Scar Formation in Surgical Incisions that Traverse Langer's Skin Tension Lines," Plastic and Reconstructive Surgery 116(6)., 1648-1656.
Bachert, et al., (2003). "Probing Elastic Modulus and Depth of a Two Layer Human Skin Model with Piezoelectric Cantilevers," Biomedical Engineering Senior Design Team, Drexel University, 27 pages.
Berman, et al., (Mar. 3, 2005). "Keloid and Hypertrophic Scar," located at <http://www.emedicine.com/DERM/topic205.htm>, last visited on Nov. 19, 2007, 23 pages.
Bunker, (1983). "Problems with the Use of Op-Site Sutureless Skin Closures in Orthopaedic Procedures," Annals of the Royal College of Surgeons of England 65:260-262.
Burd, et al., (Dec. 2005). "Hypertrophic Response and Keloid Diathesis: Two Very Different Forms of Scar," Plastic and Reconstructive Surgery 116(7):150-157.

(56) References Cited

OTHER PUBLICATIONS

Chen, et al., (Jul. 2001). "Prospective Study Comparing Wounds Closed With Tape With Sutured Wounds in Colorectal Surgery," Arch. Surg. 136:801-803.

* cited by examiner

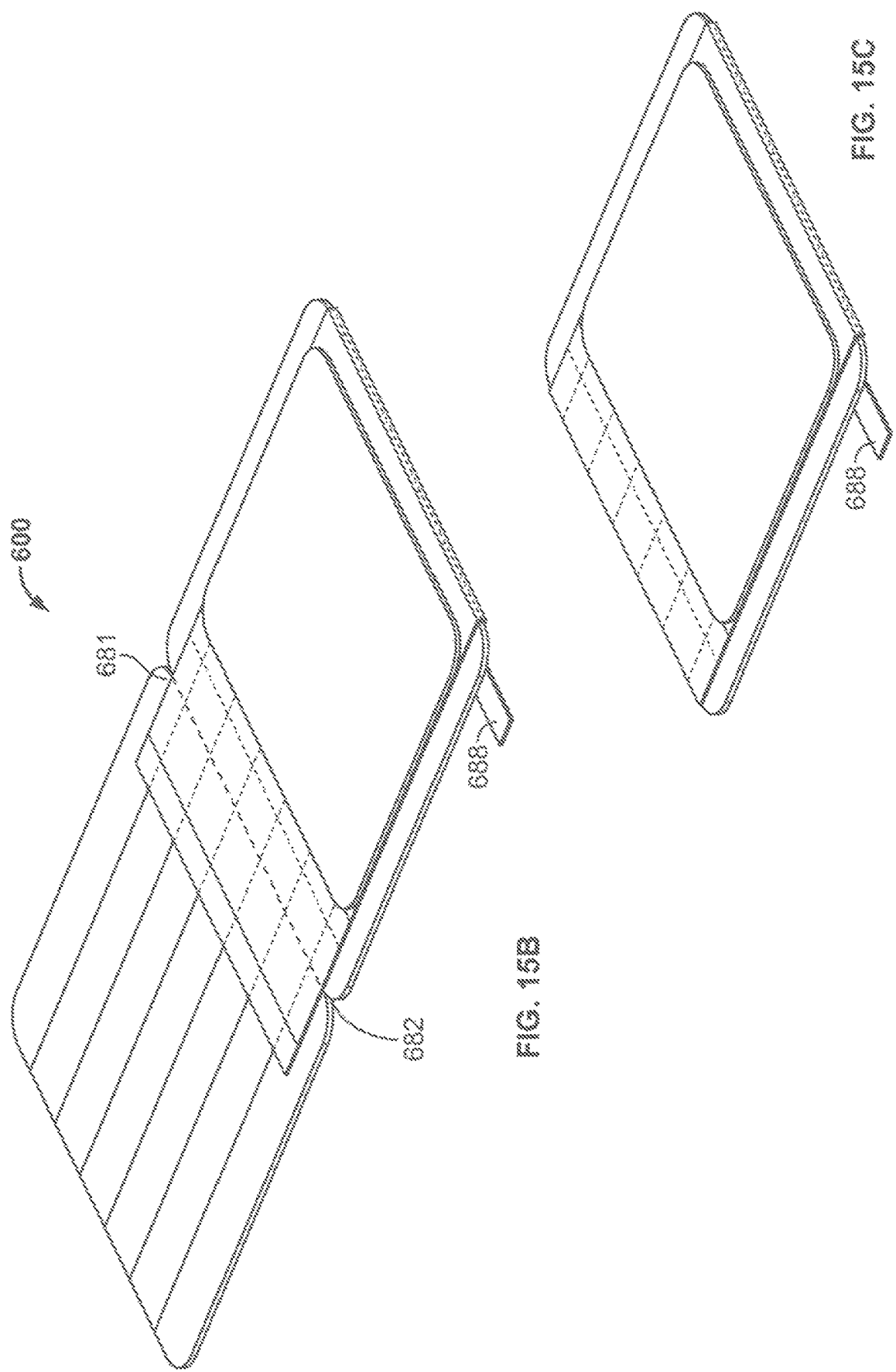

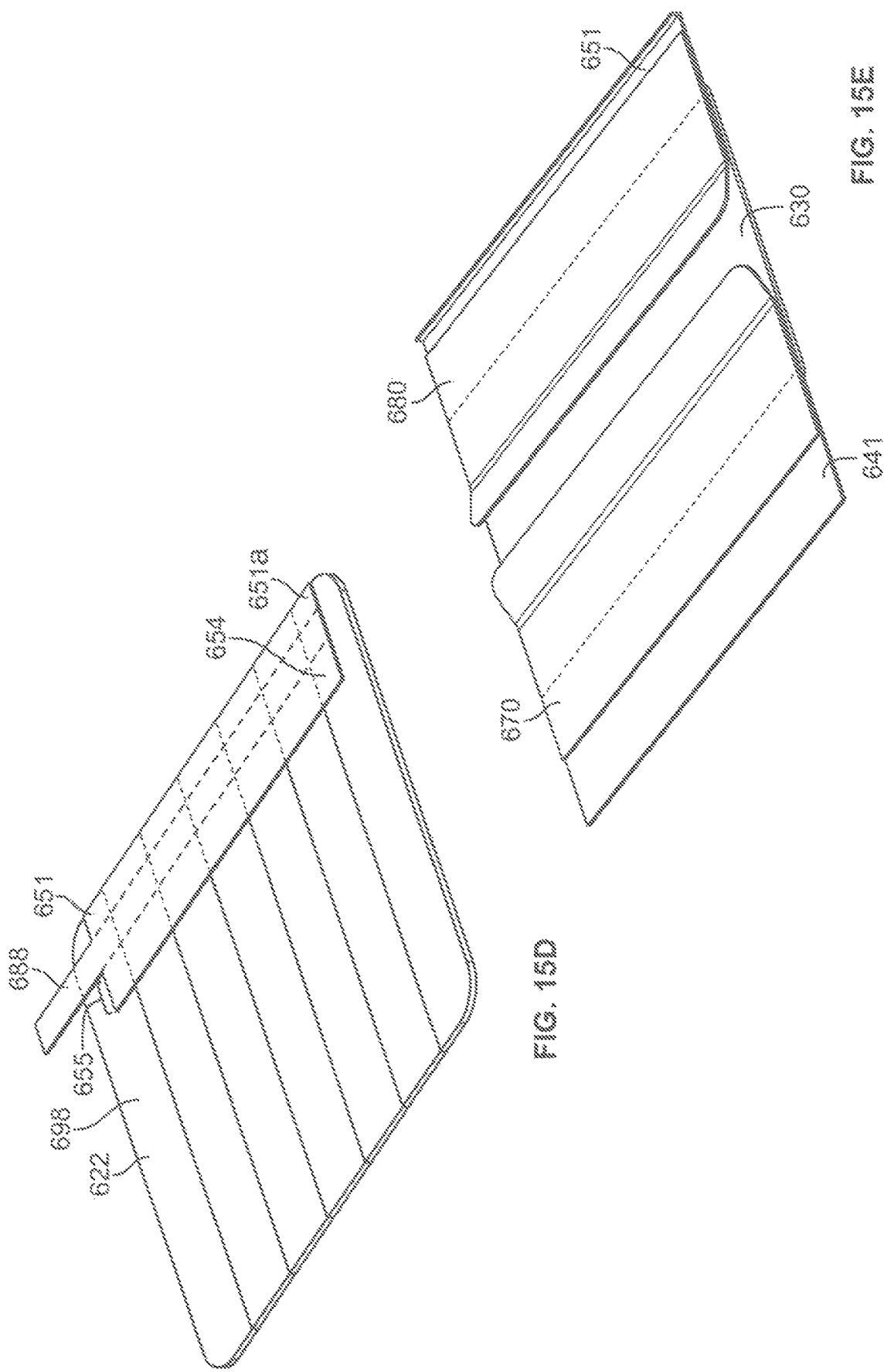

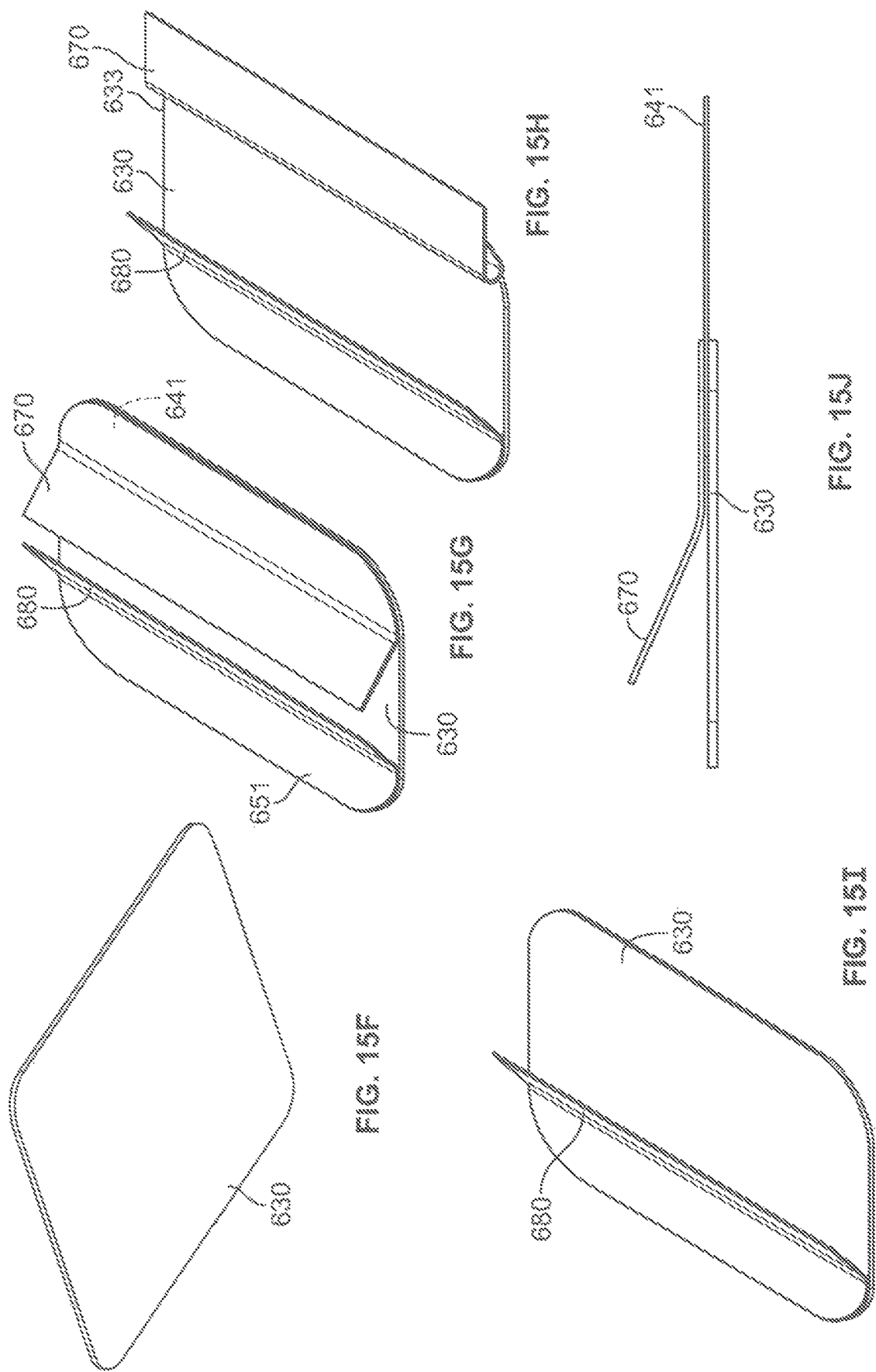

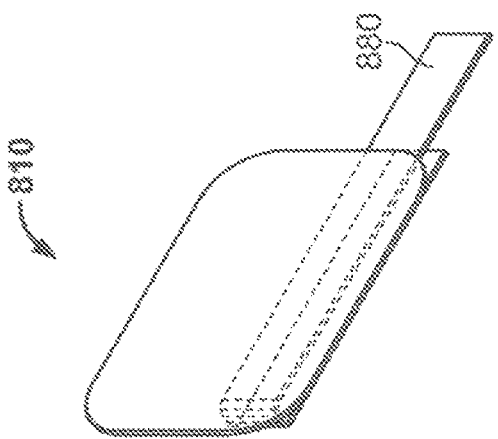
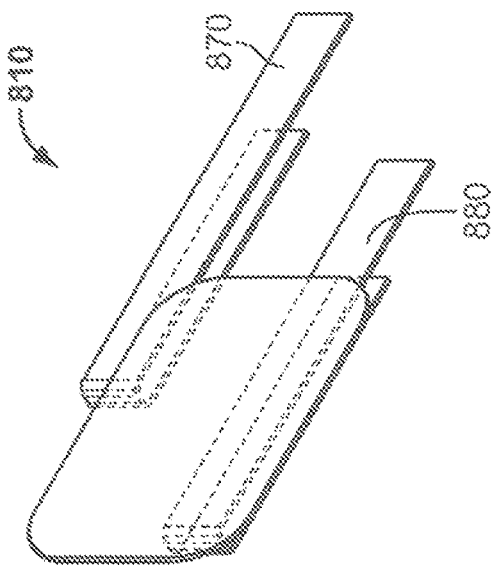
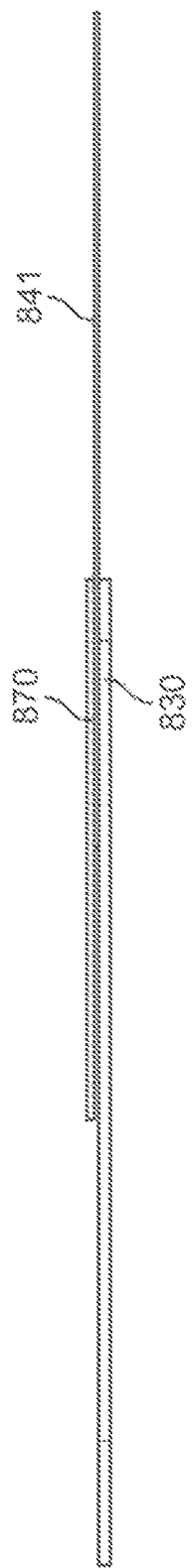
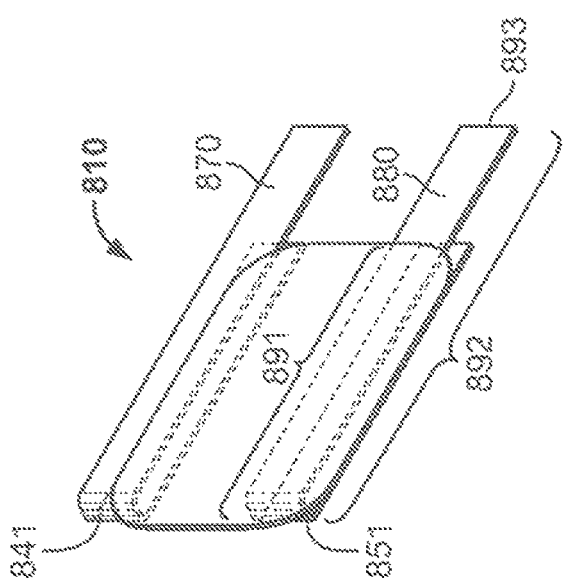

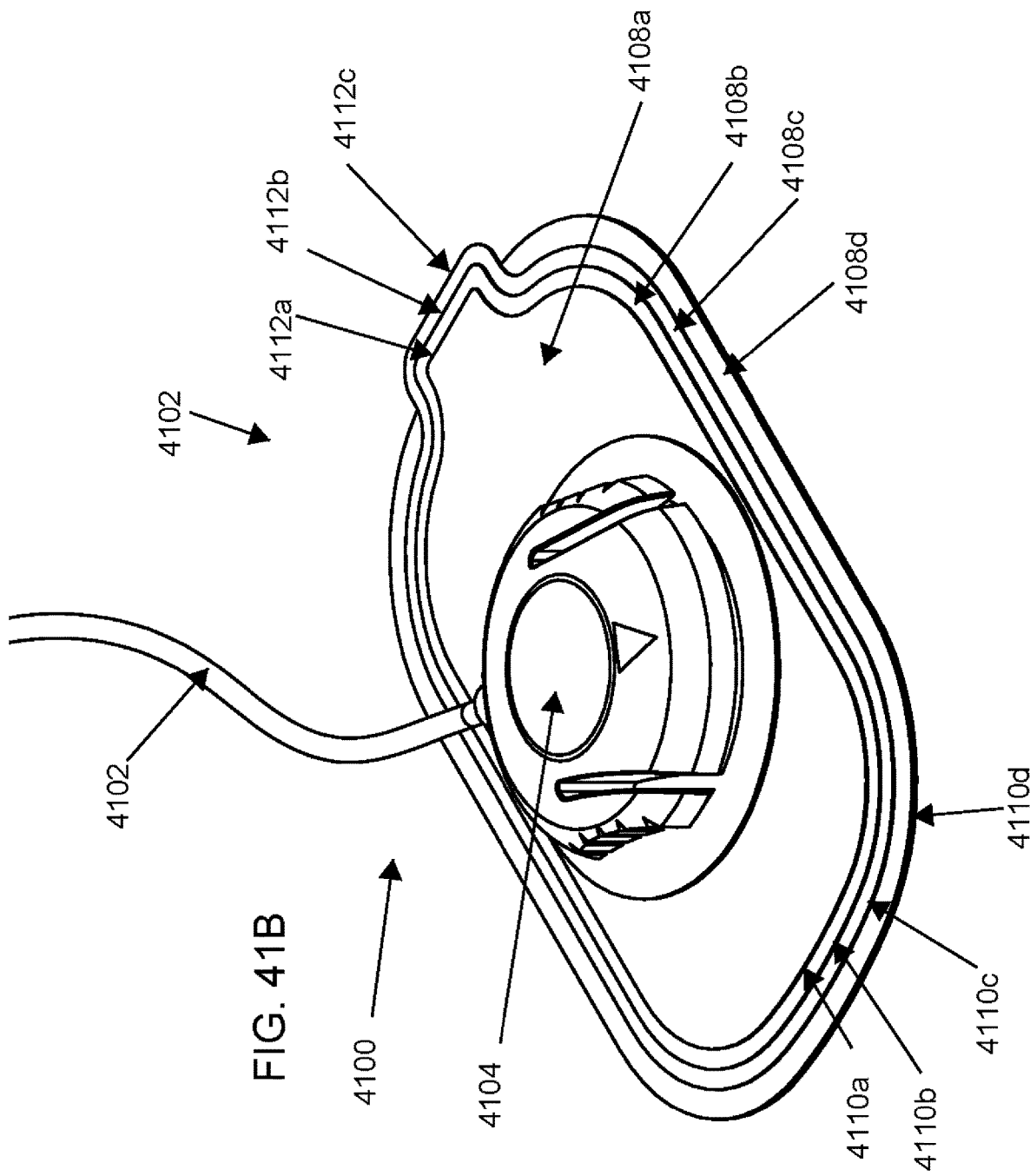

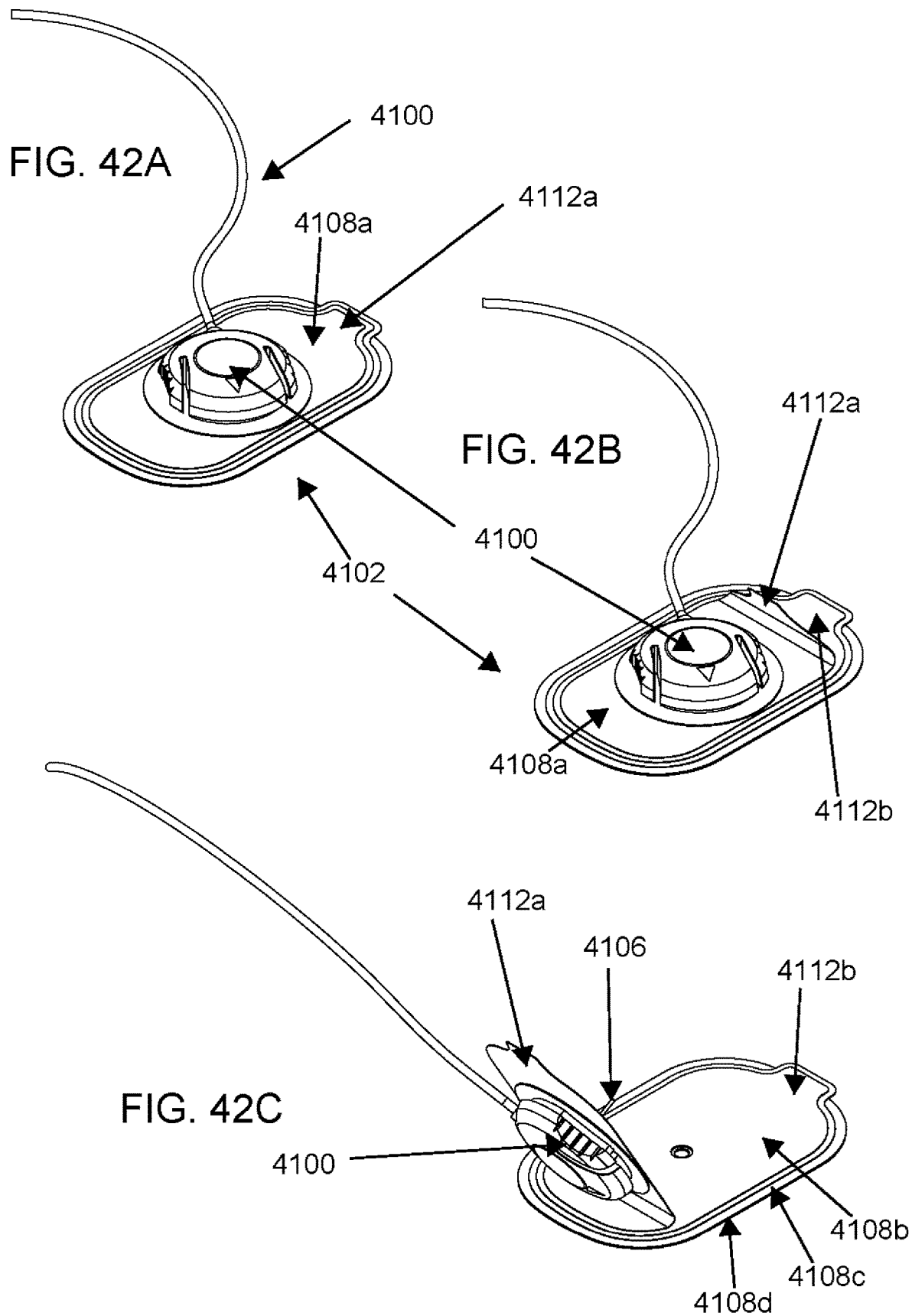

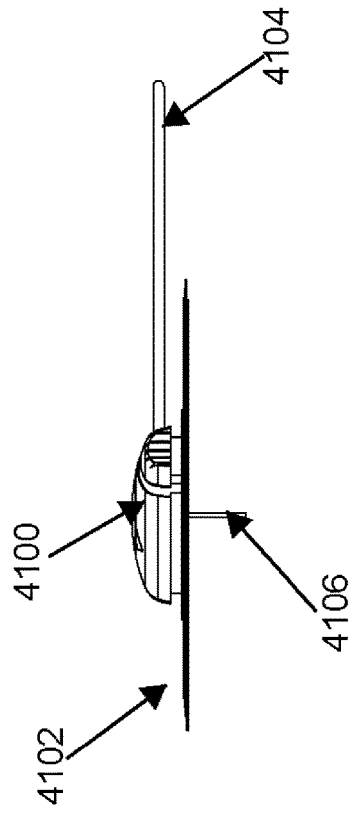
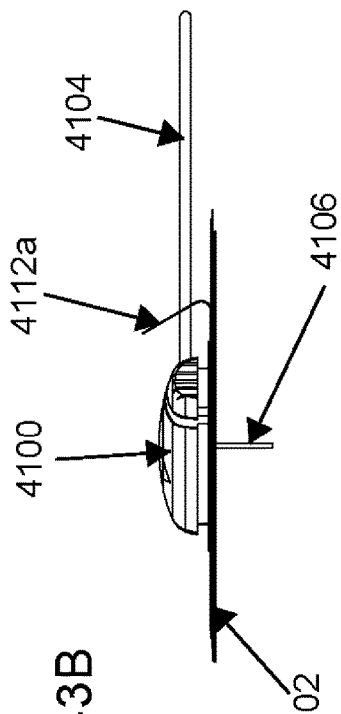
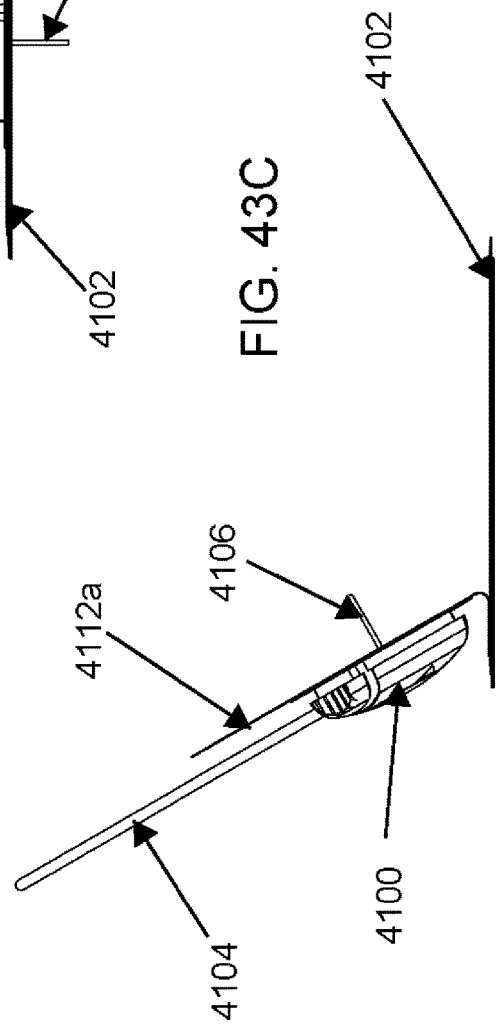

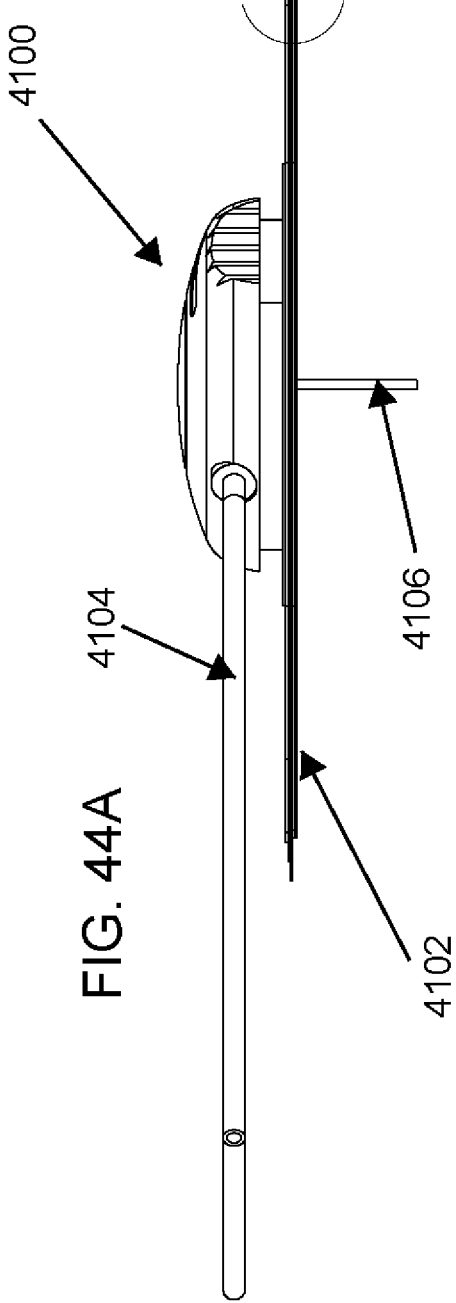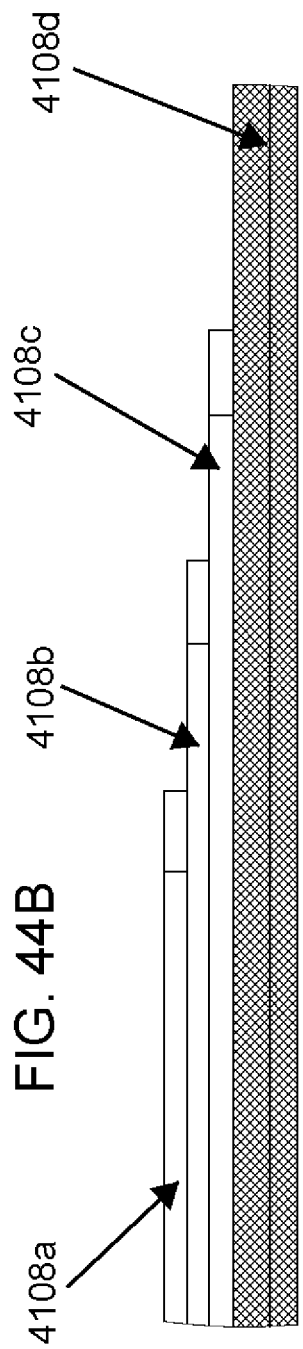
FIG. 44A
FIG. 44B

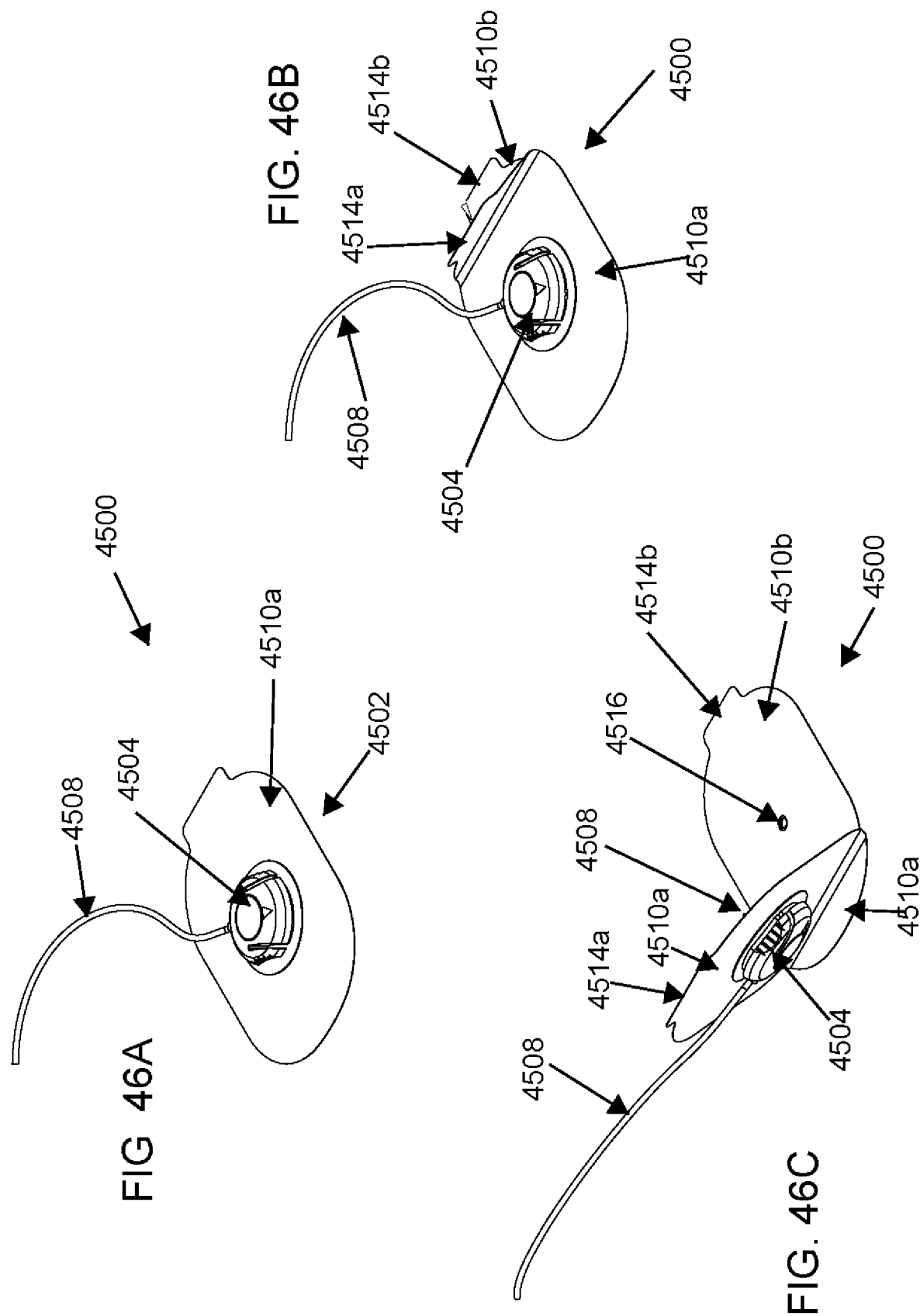

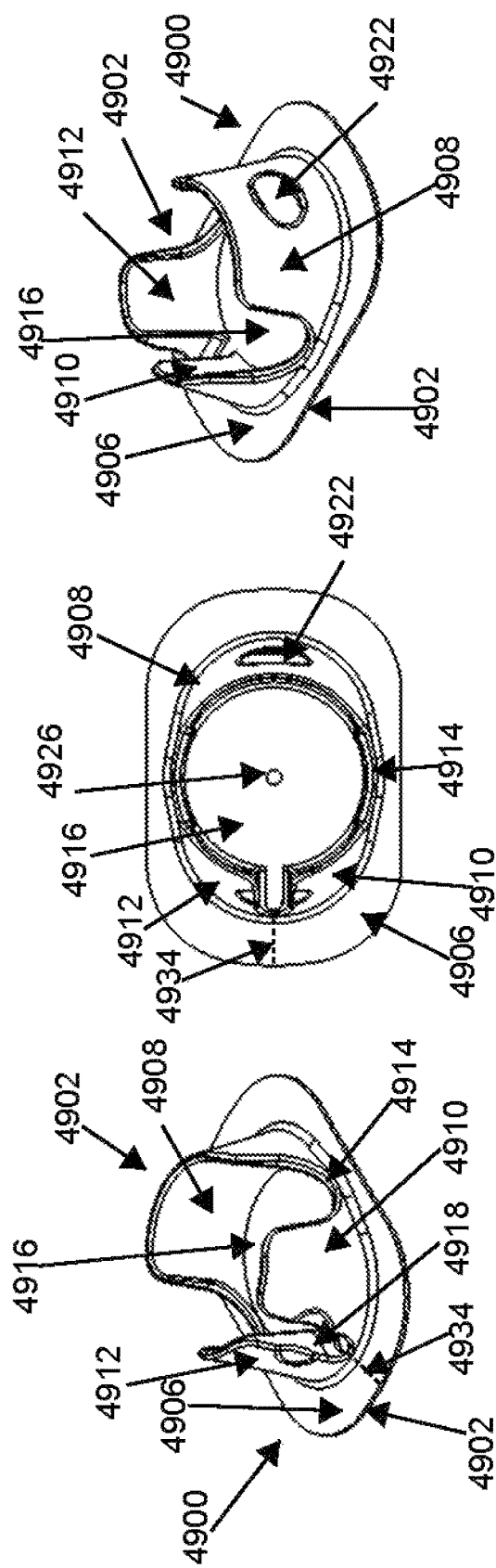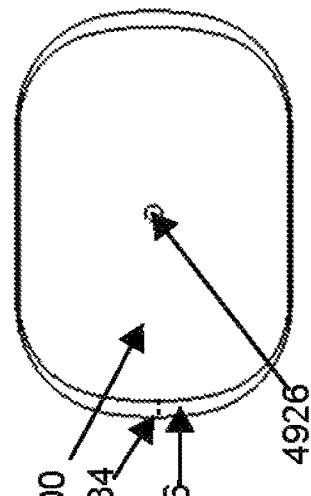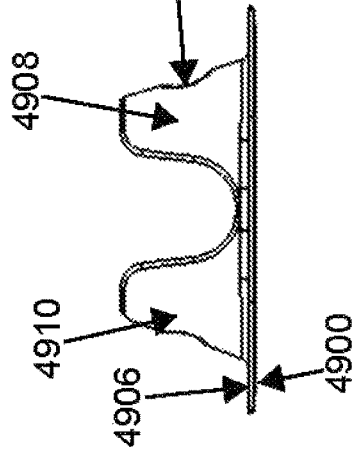

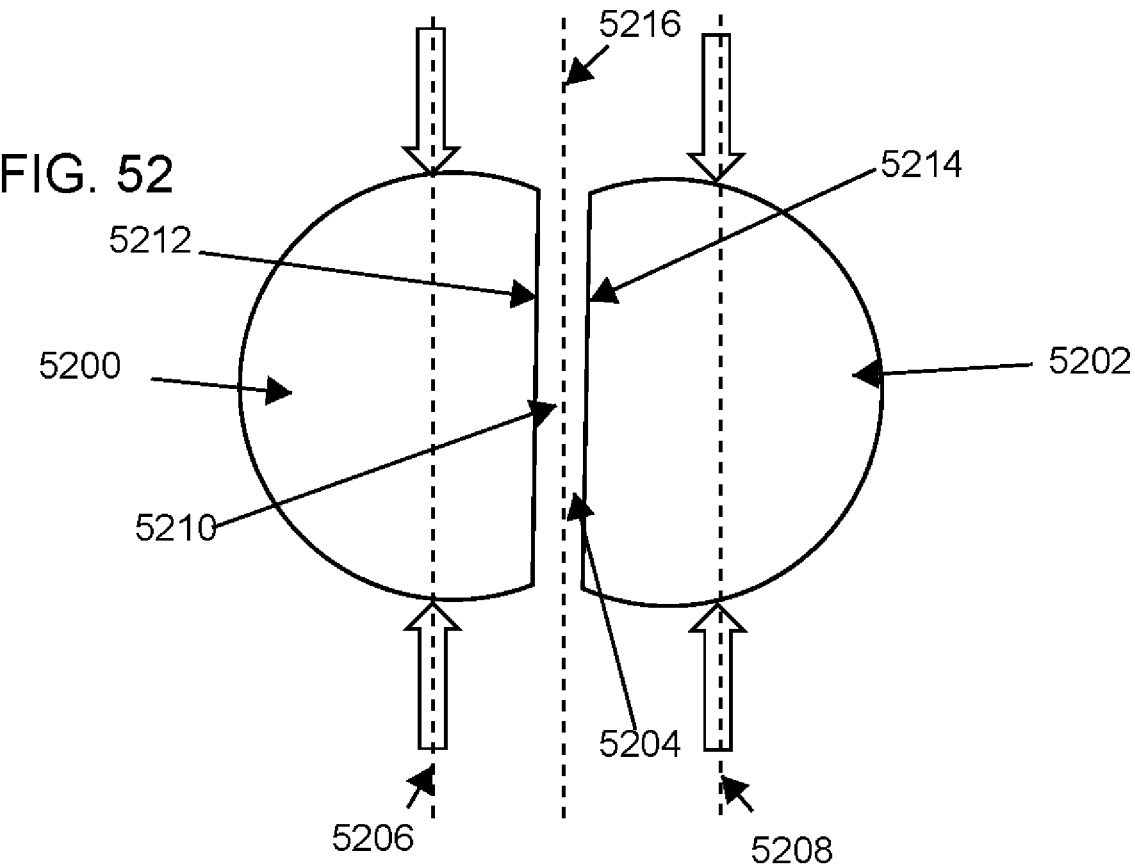
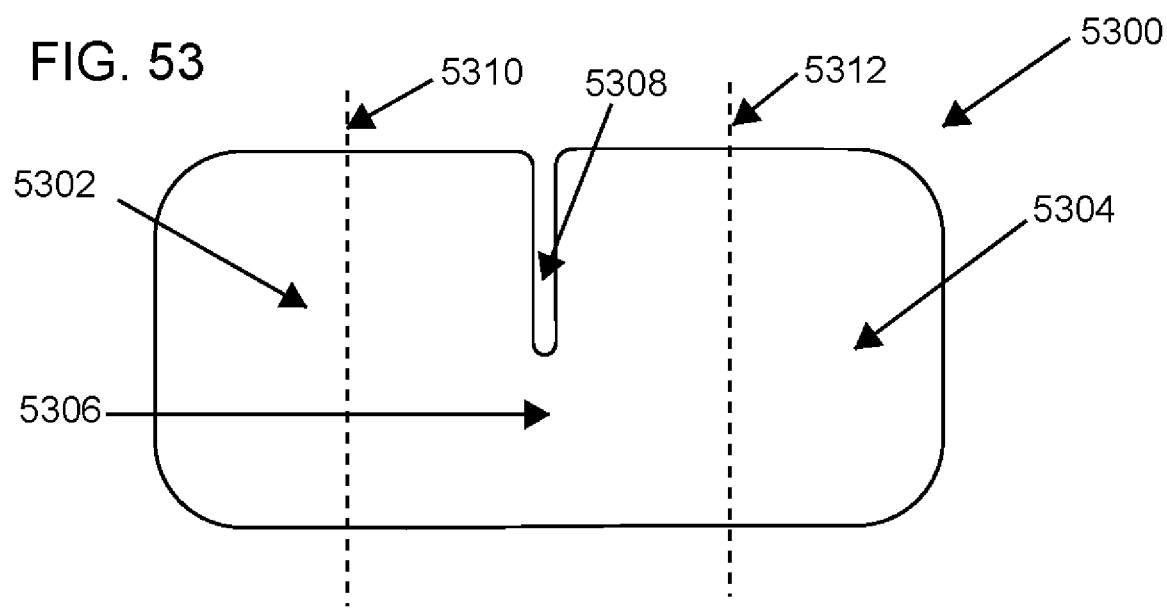

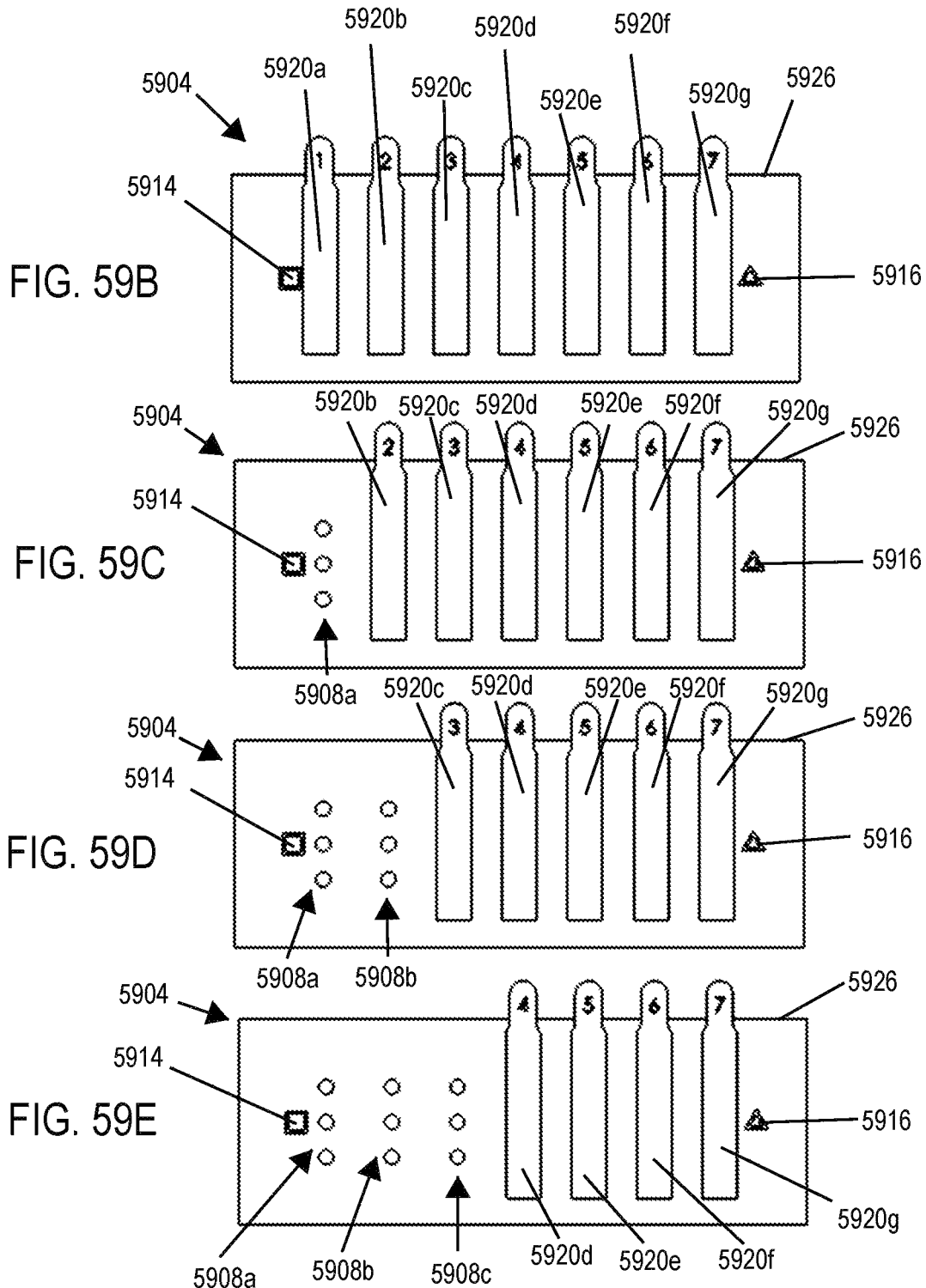

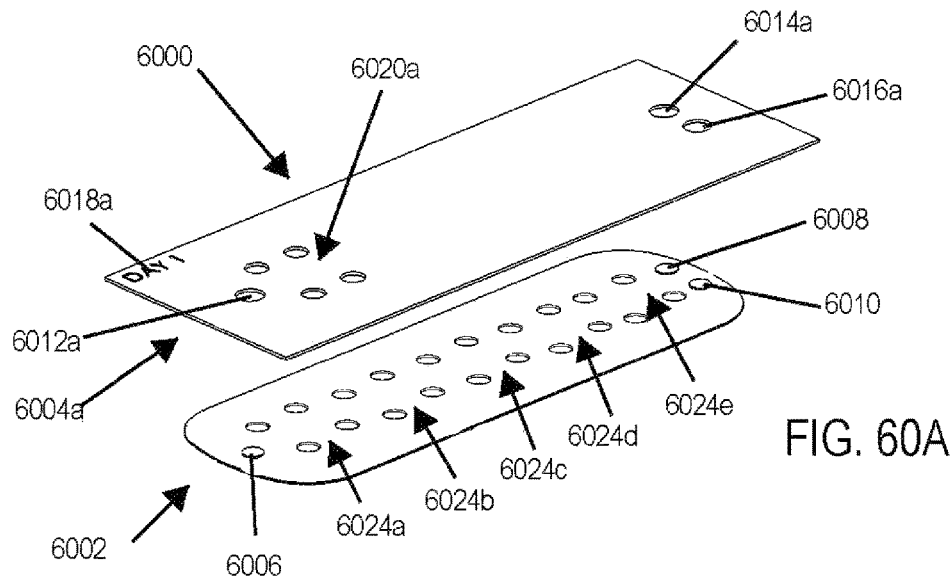
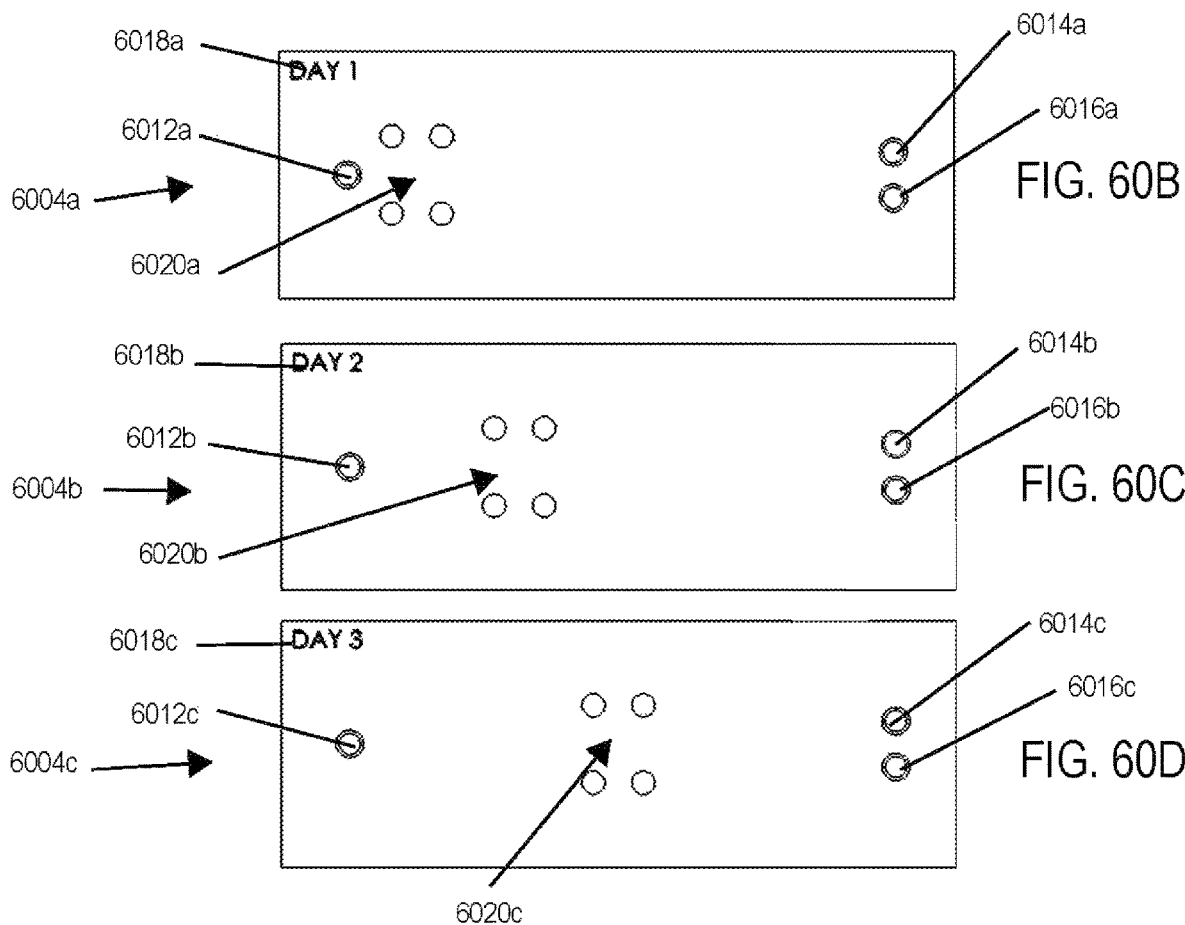

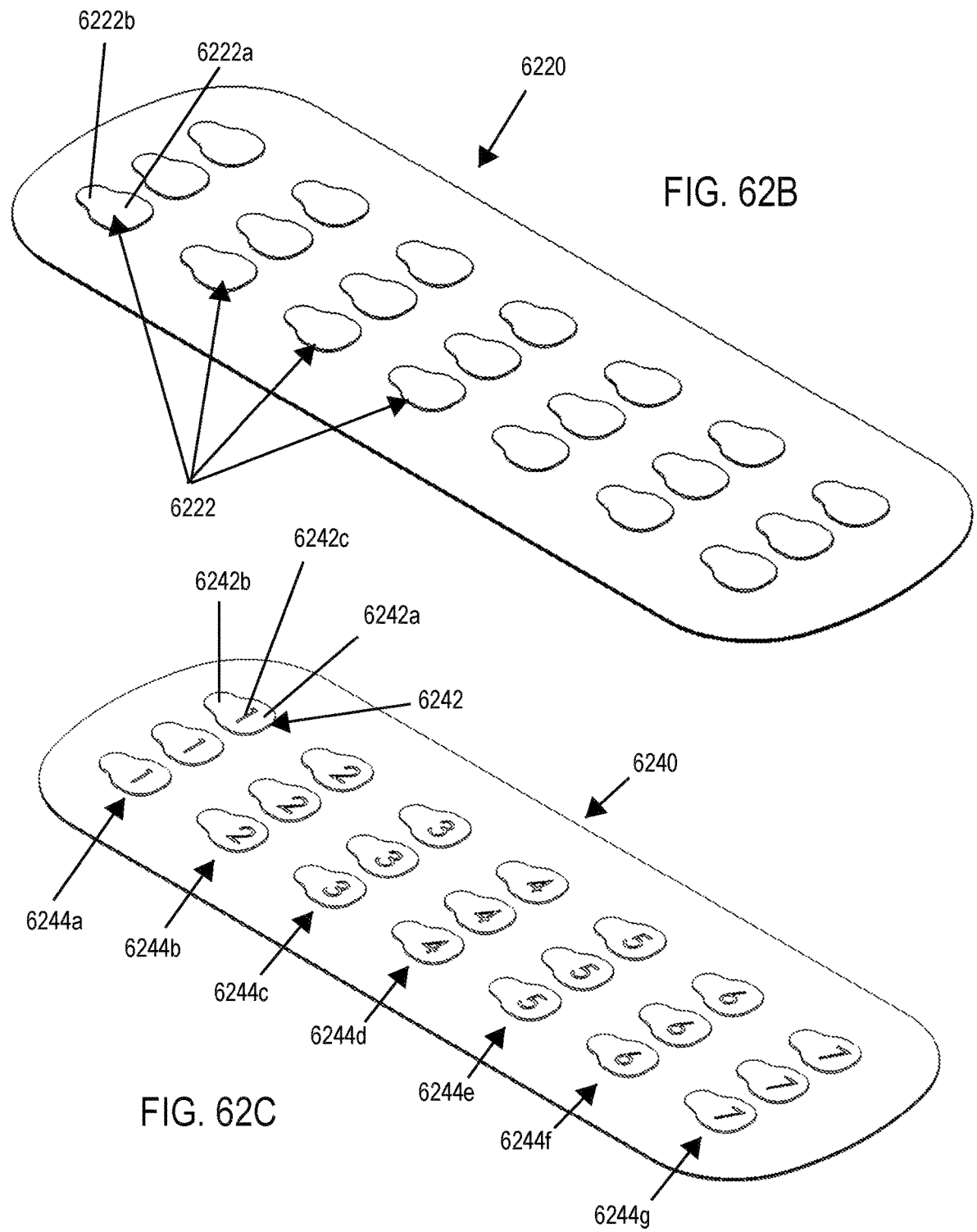

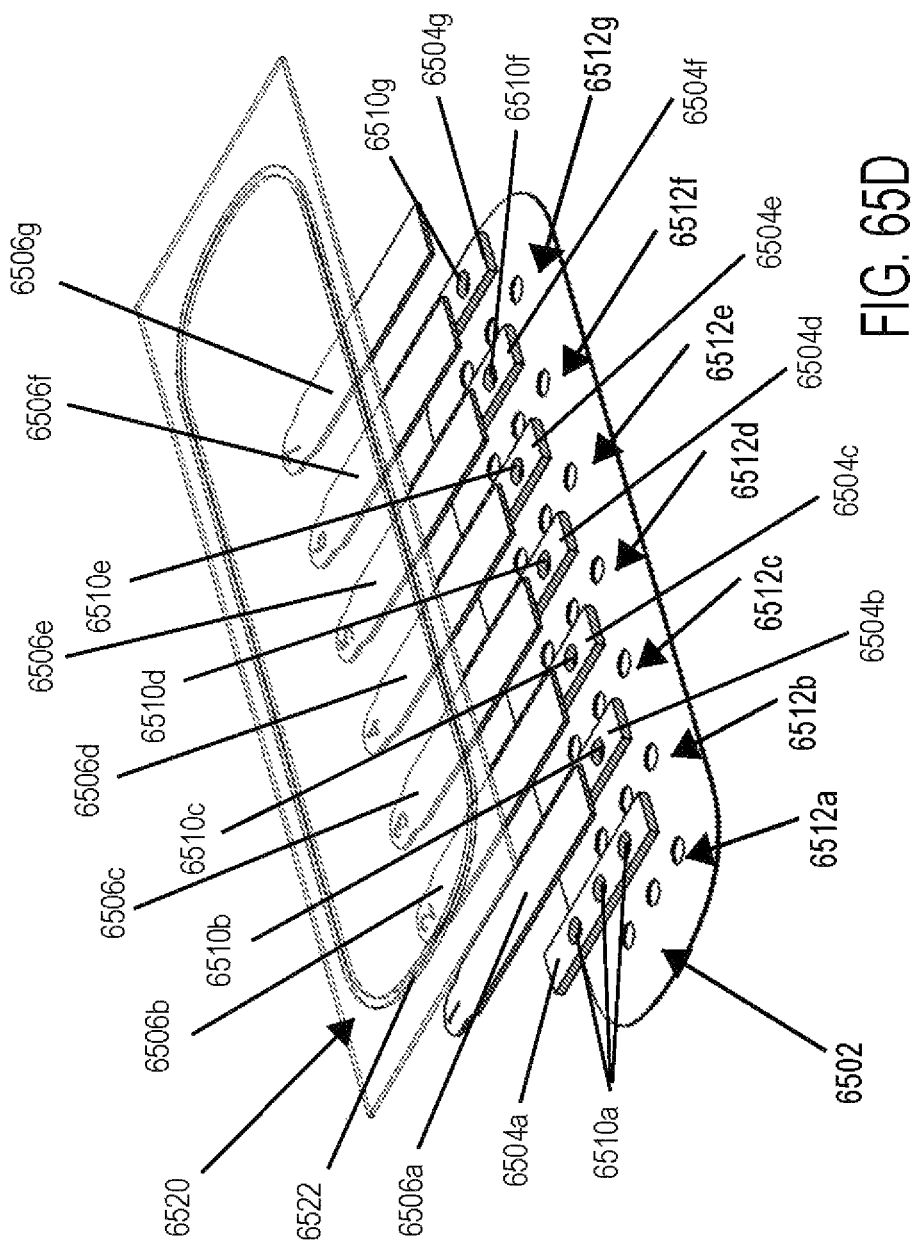

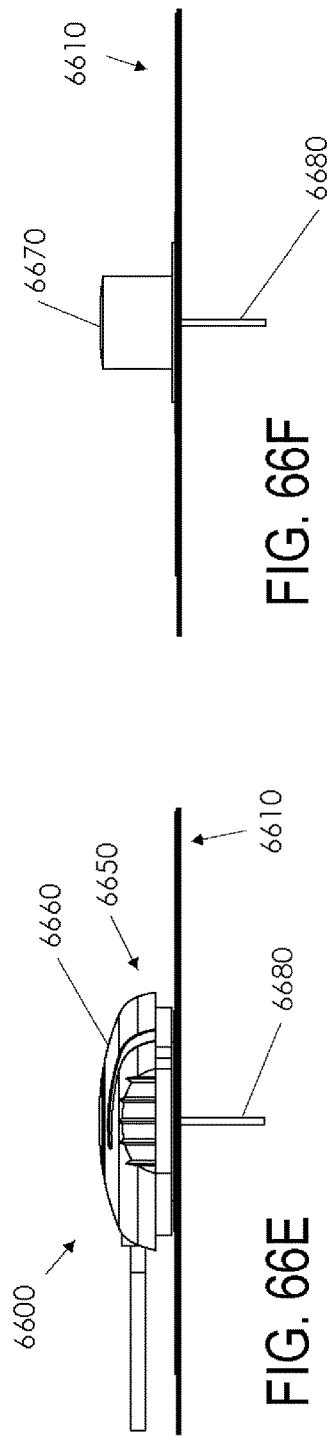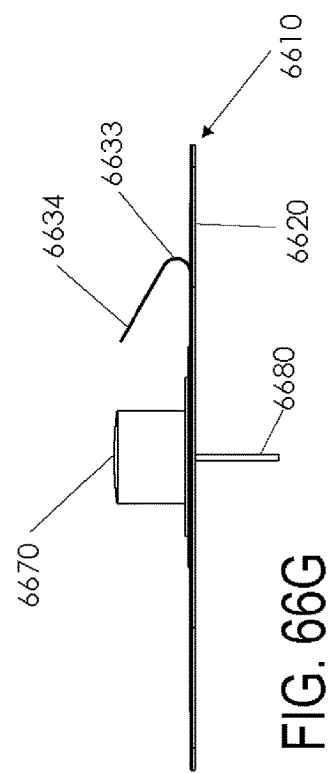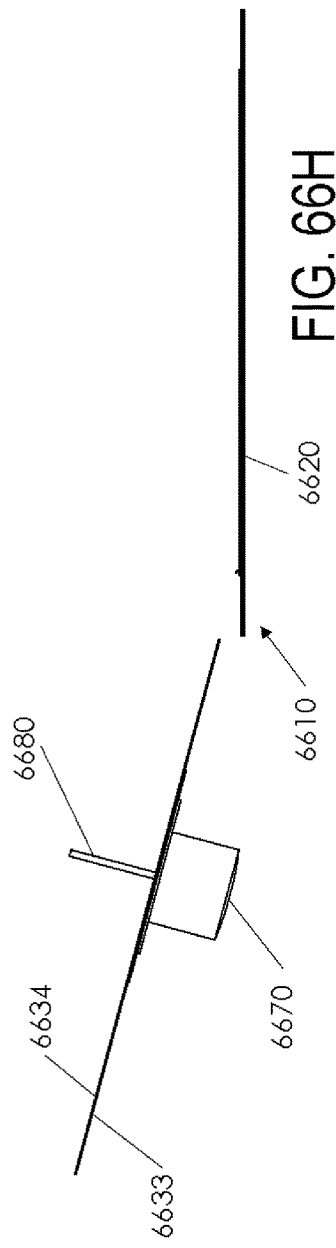

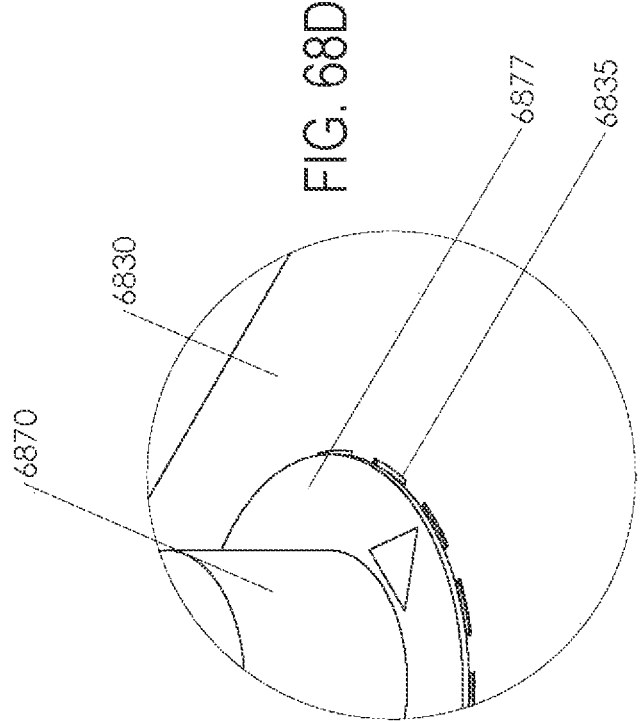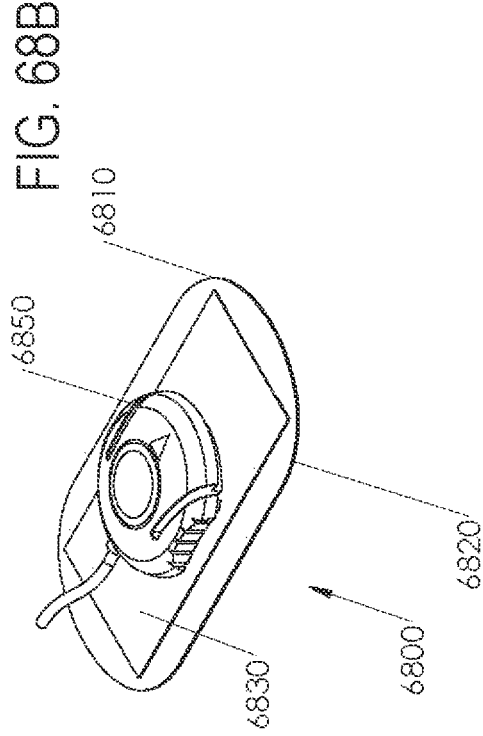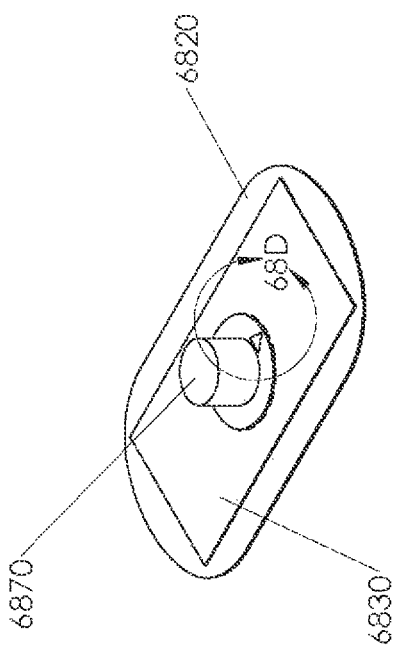

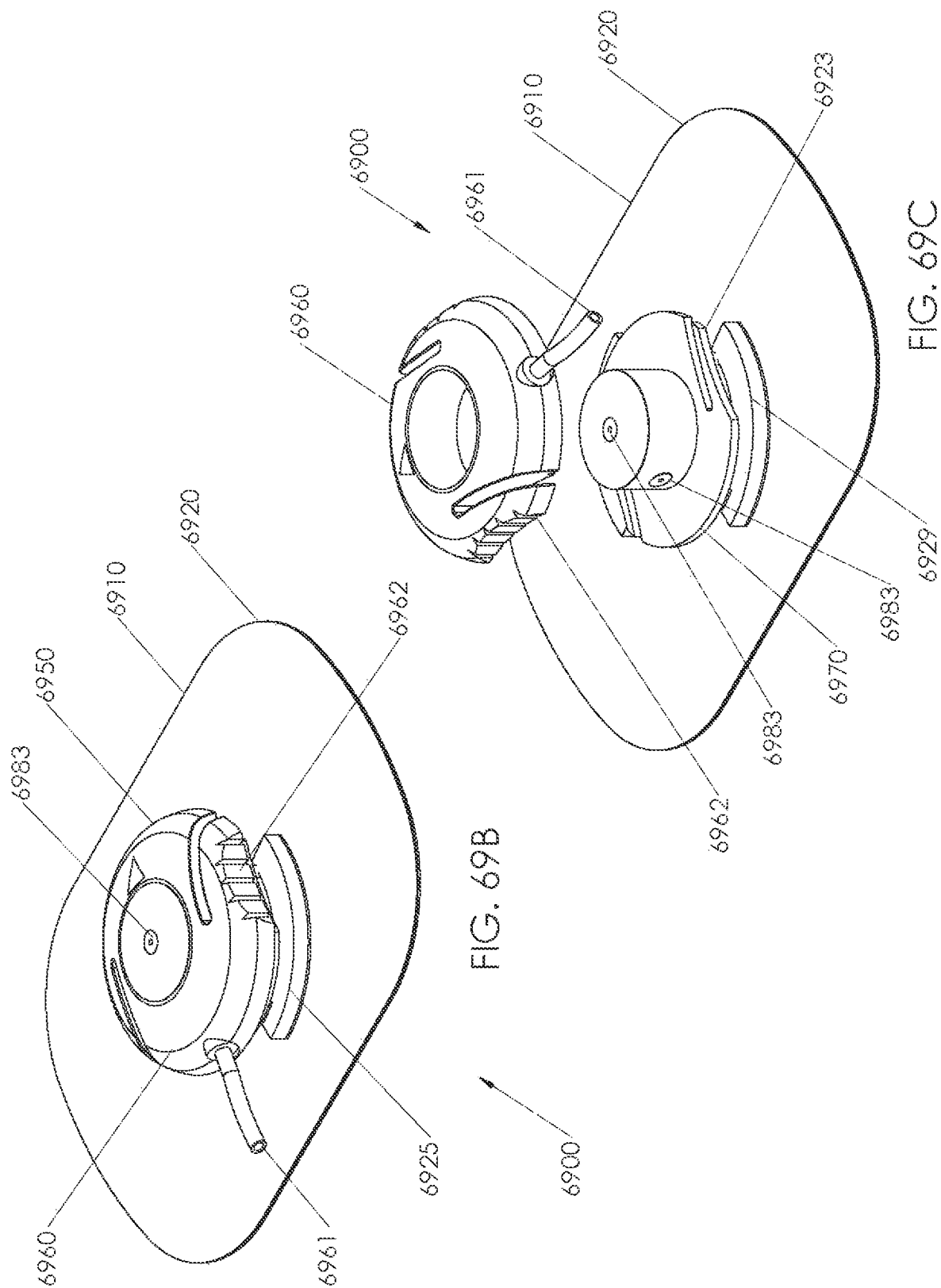

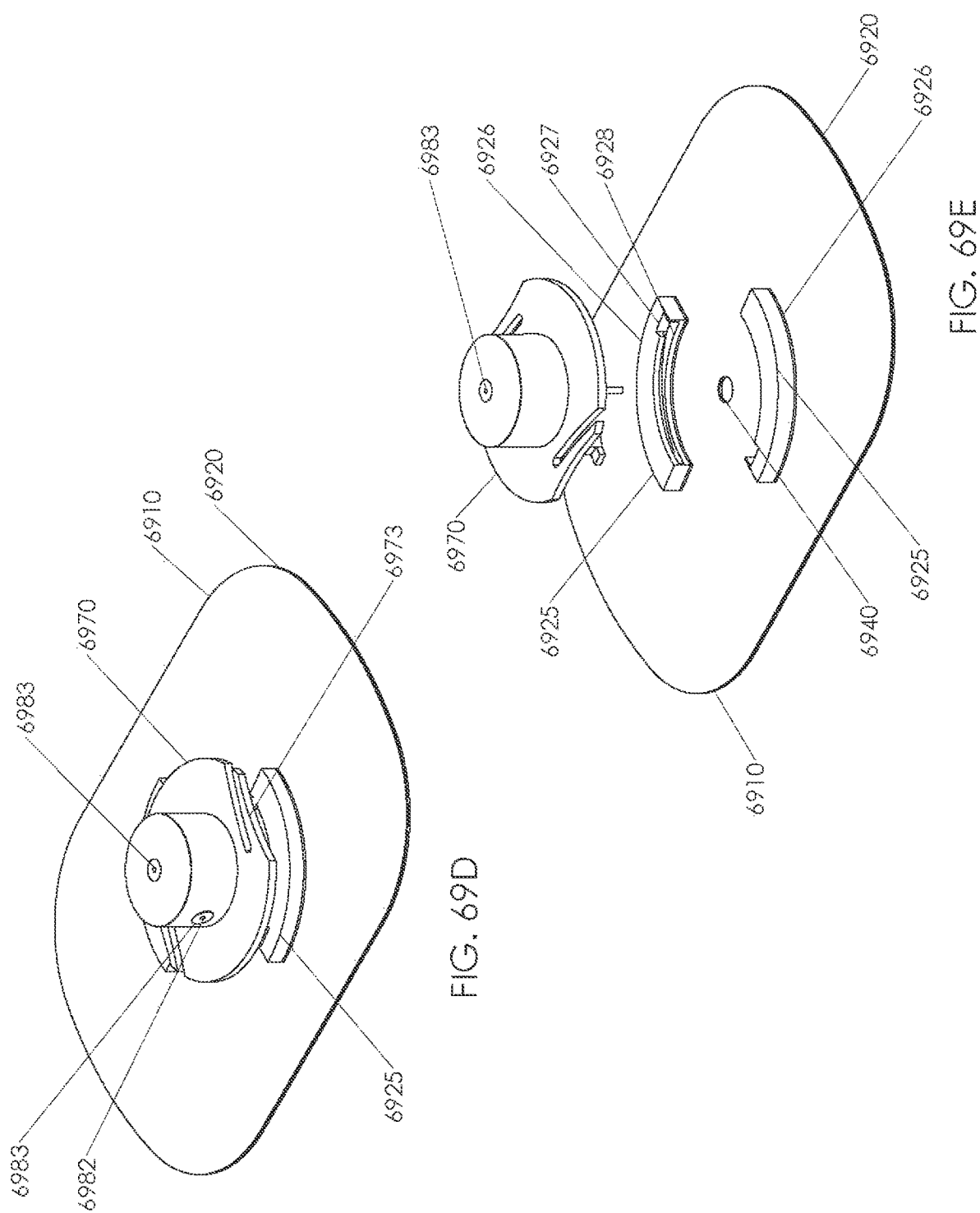

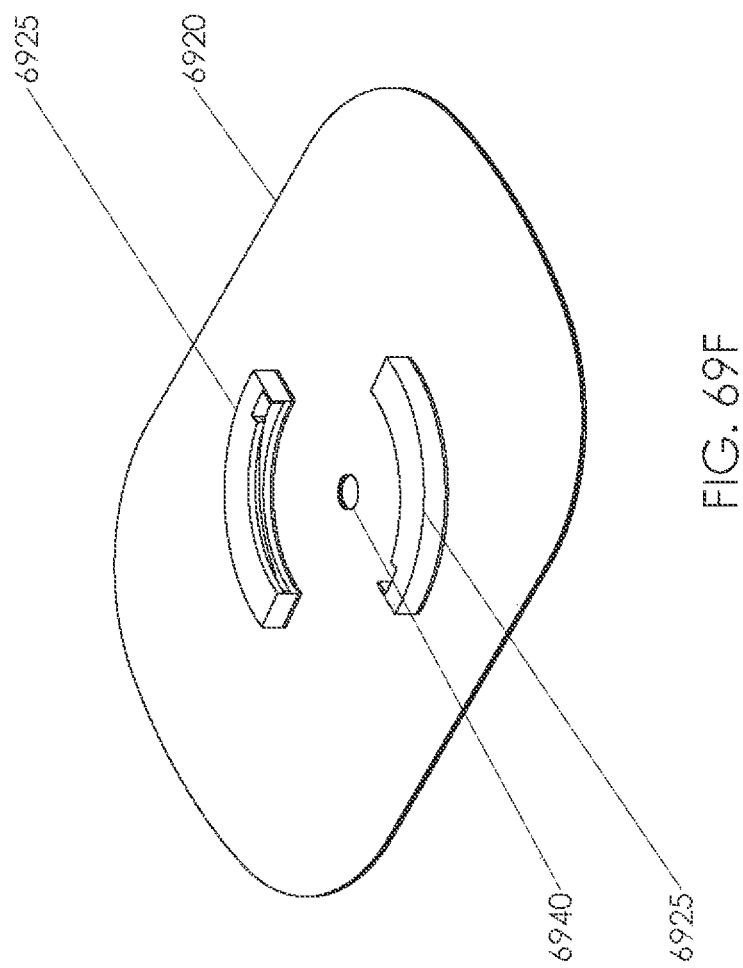

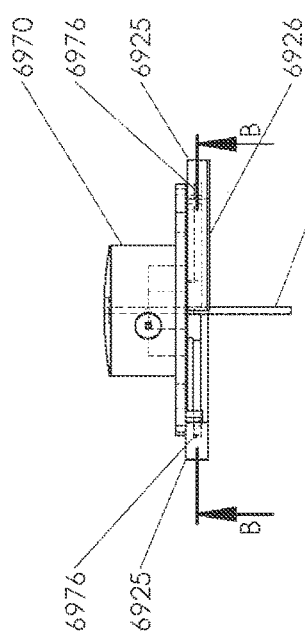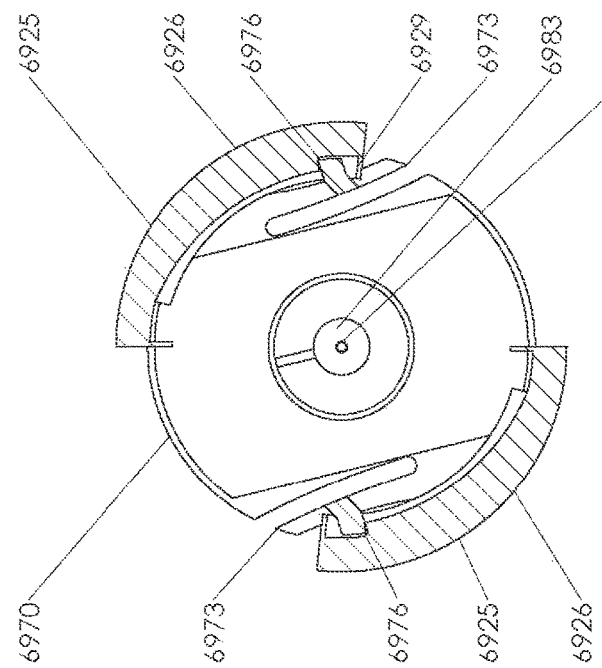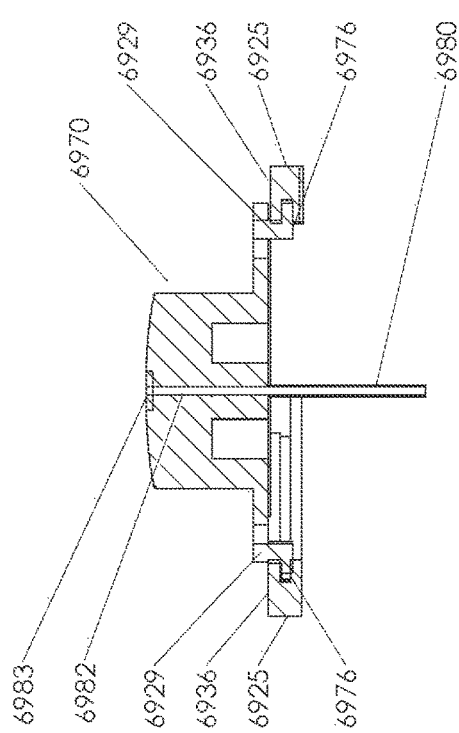

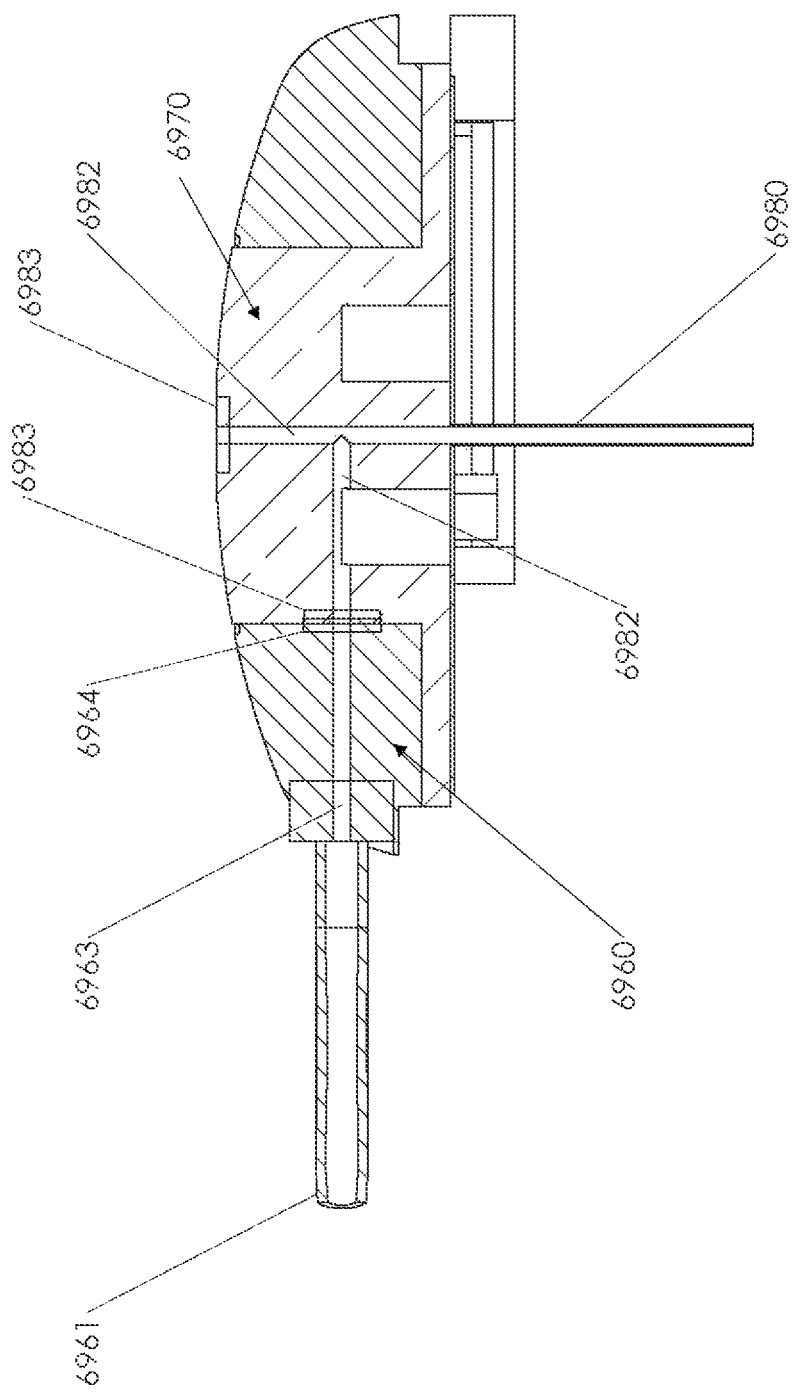

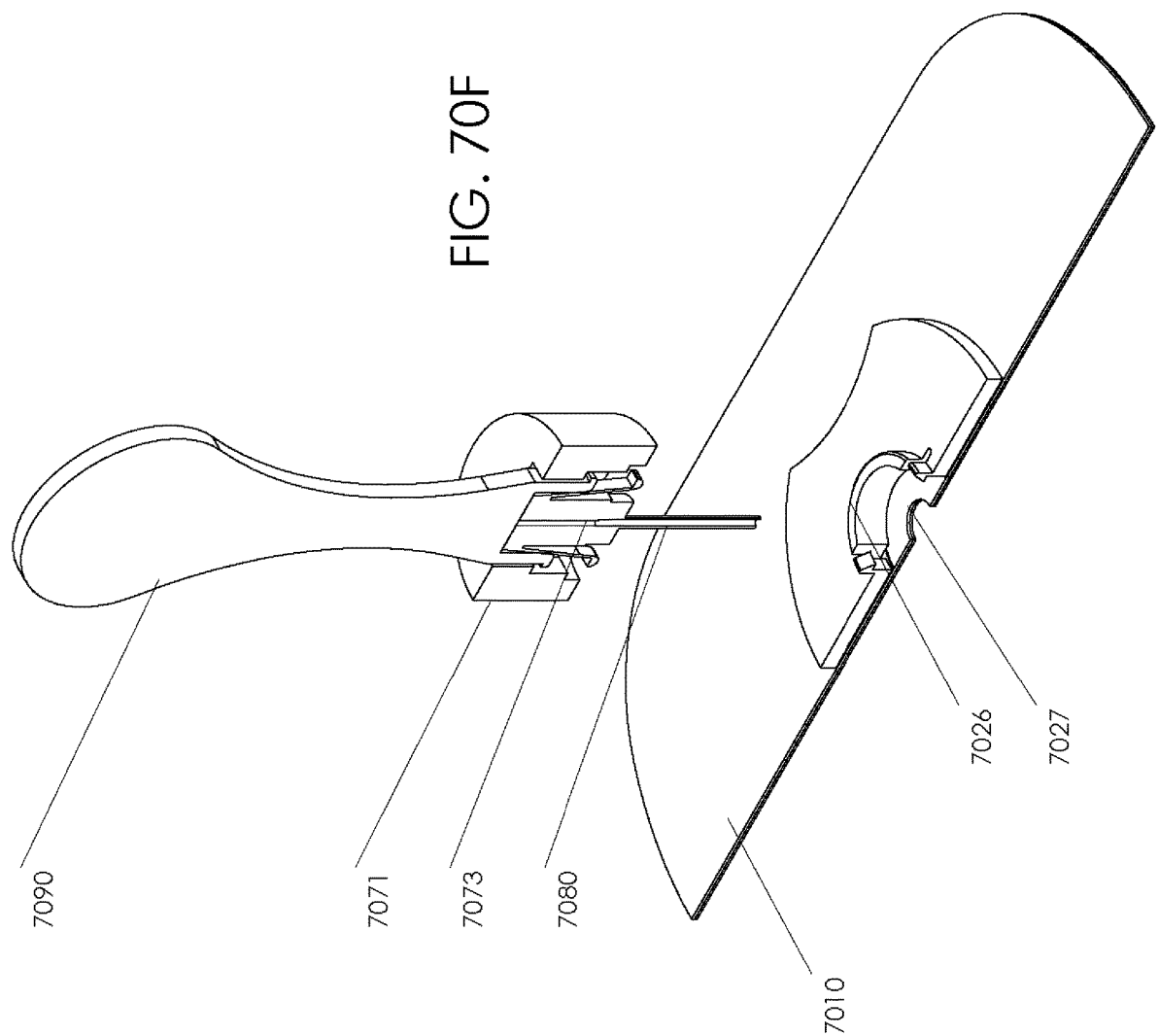

INJECTION AND INFUSION SITE TREATMENT DEVICES AND METHODS

CROSS-REFERENCE TO RELATED APPLICATIONS

This application is a) a continuation of U.S. application Ser. No. 17/838,027, filed Jun. 10, 2022 which is a continuation-in-part of PCT Application No. PCT/US2020/064378, filed Dec. 10, 2020, which claims priority to U.S. Provisional Application No. 62/946,345, filed on Dec. 10, 2019, and b) claims priority to U.S. Provisional Application No. 63/211,359, filed Jun. 16, 2021, which are hereby incorporated by reference in their entirety. This application is also related to U.S. Pat. Nos. 8,592,640, 9,248,048, 9,844,470, and 11,013,638, which are hereby incorporated by reference in their entirety.

BACKGROUND

Scar formation in response to cutaneous injury is part of the natural wound healing process. Wound healing is a lengthy and continuous process, although it is typically recognized as occurring in stages. The process begins immediately after injury, with an inflammatory stage. During this stage, which typically lasts from two days to one week (depending on the wound), damaged tissues and foreign matter are removed from the wound. The proliferative stage occurs at a time after the inflammatory stage and is characterized by fibroblast proliferation and collagen and proteoglycan production. It is during the proliferative stage that the extracellular matrix is synthesized in order to provide structural integrity to the wound. The proliferative stage usually lasts about four days to several weeks, depending on the nature of the wound, and it is during this stage when hypertrophic scars usually form. The last stage is called the remodeling stage. During the remodeling stage, the previously constructed and randomly organized matrix is remodeled into an organized structure that is highly cross-linked and aligned to increase mechanical strength.

While the histological features characterizing hypertrophic scars have been well documented, the underlying pathophysiology is not well known. Hypertrophic scars are a side effect of excessive wound healing, and generally result in the overproduction of cells, collagen, and proteoglycans. Typically, these scars are raised and are characterized by the random distribution of tissue bundles. The appearance (i.e., size, shape, and color) of these scars varies depending on the part of the body in which they form, and the underlying ethnicity of the person affected. Hypertrophic scars are very common, and may occur following any full thickness injury to the skin. Recently, it has been shown in U.S. Patent Application Publication 2006/0037091 (U.S. patent application Ser. No. 11/135,992 entitled "Method for Producing Hypertrophic Scarring Animal Model for Identification of Agents for Prevention and Treatment of Human Hypertrophic Scarring," filed May 24, 2005) which is hereby incorporated by reference in its entirety, that mechanical stress may increase hypertrophic scarring in a murine model.

Keloids are typically characterized as tumors consisting of highly hyperplastic masses that occur in the dermis and adjacent subcutaneous tissue in susceptible individuals, most commonly following trauma. Keloids are often more severe than hypertrophic scars, since they tend to invade normal adjacent tissue, while hypertrophic scars tend to remain confined within the original scar border.

Scar tissue may also be formed from repetitive tissue injuries, such as patients who require repeated needle insertions for blood draws or injections or infusions of therapeutic agents for treatment of chronic health issues, including but not limited growth hormone injection, autoimmune diseases such rheumatoid arthritis, and diabetes, and also from other therapeutic or diagnostic procedures or devices that may utilize an indwelling catheter or needle.

BRIEF SUMMARY

Devices, kits and methods described herein may be for treatment of a subject at a skin site including without limitation for wound treatment or the treatment, amelioration, or prevention of scars and/or keloids, by manipulating mechanical or physical properties of skin or by shielding skin from stresses, and/or by controllably stressing or straining the epidermis and layers of dermal tissue at or near a skin site, i.e., at or adjacent a wound or a treatment site of a subject's skin.

Some tissue responses and diseases, however, are associated with tissues below the dermal layer of the skin. The subcutaneous region, or hypodermis, is the deepest layer in the skin and varies in depth from the epidermis. Skin thickness averages between 1.5 mm and 2.7 mm at various body sites, and has a different density and elasticity compared to the subcutaneous tissue below it. While dermal tissues are developmentally derived from endoderm and comprises collagen and other connective tissue having higher tensile strength, the hypodermis is developmentally derived from mesoderm and comprises loose areolar connective tissue. For these reasons, it is unclear whether planar load forces acting on the epidermis will transmit through the dermis and to the hypodermis or other anatomical structures below the epidermis. Nevertheless, it is hypothesized herein that the mechanical interplay between the epidermis/dermis and the subcutaneous tissue may have some mechanobiologic effect on subcutaneous tissues and structures.

Also, the impact of scar tissue formation are not limited to cosmetic effects. For example, diabetes patients may develop scar tissue and/or lipohypertrophy at chronic injections sites. Lipohypertrophy is an increased formation of fat tissue that is thought to be a hypertrophic effect from chronic localized insulin injections on adipose cells. The lipohypertrophy can adversely affect insulin injection or infusion rates due to structural changes in the tissue that can decrease the diffusion of insulin. Typical infusion using insulin pumps involves the placement of a cannula or needle into the delivery site (e.g., abdomen, arms, buttocks, thighs) every few days. Over time, this can induce lipodystrophic changes in the skin and subcutaneous structure, which can result in unpredictable or erratic insulin absorption. Eventually the patient may be limited in the available infusion sites on their body due to lipohypertrophy. Although, the effects of lipohypertrophy and lipodystrophy are thought to be induced by the insulin itself, it is hypothesized that tension offloading of the infusion location may also reduce this insulin effect, and may improve the variability and/or overall absorption rates at the infusion site. This may occur by reducing the formation of fibrosis, improving the vascularization, and/or reducing vascular resistance to perfusing the tissue under or about the insertion site. In some variations, it is hypothesized that the change in skin tension and/or the increased adhesive properties of the tensioned dressing or dressing component may extend the usable duration of the infusion set or sensor, e.g. from 2-3 days to 4 to 7 days. This may also result in a reduction of the size, surface area, depth and/or severity of inflammation at the injection/infusion site(s).

It is also believed that treatment of the injection and/or infusion sites of diabetes therapy may also have other effects separate from affecting the development of scar tissue or lipohypertrophy. For example, treatment of an injection site and/or injection at a site that has already been treated with a skin tensioning device may improve the dispersion of insulin at the injection site by altering the mechanical environment. For example, insulin leakage at the injection or infusion site may be reduced because of increased mechanical pressure at the skin surface, which may drive injected therapy deeper into the tissue because of the pressure gradient generated in the tissue by the tensioning device. This and other mechanical effects of skin tension treatment may result in an increased insulin bolus volume and/or surface area per unit injection. The mechanomodulation effects may results in improved insulin absorption, with a reduced average total daily, weekly and/or monthly insulin dosage, and/or improved daily, weekly and/or monthly time-in-range of blood glucose, with a reduced frequency or degree of hyperglycemia. The tensioning device may also reduce pain at the injection site, as a result of mechanomodulation of the nociceptors, and/or may reduce the risk of infection and/or pump alarms from occlusion, as a result of mechanically stabilizing the tissue.

The therapies described herein are not limited to treatment of the sequelae of diabetes or diabetes treatment, but may also be applied to other disease states involving injectable therapies or subcutaneous lesions or disease states, or even intramuscular injections. It is hypothesized that general changes in drug absorption or diffusion in the subcutaneous layer subcutaneous layer, or relative changes in vascular flow between the dermis and subcutaneous tissue, reduced tissue inflammation in the dermis and/or hypodermis, and/or the prevention or reduction in the development of subcutaneous tissue lesions, may be achieved. This may include treatment or prevention of other lipodystrophies, both acquired and genetic. The therapies described herein may be used for continuous, one-time or intermittent treatment of chronic injection, infusion, or implantation sites, or temporary or intermittent treatment. This may include, for example, treatment of sites for indwelling insulin pumps, indwelling or implanted continuous glucose monitoring sensors, chronic injection of autoimmune or oncology therapies, hemodialysis, joint or sleep apnea implants, neurostimulator electrodes, contraceptive implants, and the like.

In one embodiment, an integrated infusion set is provided, comprising an infusion assembly attached to an upper surface of the tension dressing layer, wherein the infusion assembly comprises an infusion conduit configured for insertion into a treatment location, and a releasable attachment structure attaching the infusion hub to an upper surface of the tensioned dressing layer; a pre-strained dressing, the pre-strained dressing comprising a tensioned dressing layer, a skin adhesive on a lower surface of the tension dressing layer, one or more adhesive protective liners removably covering the skin adhesive, and a tension support structure configured to maintain the tension dressing layer in a stressed configuration, the tension support structure comprising one or more pull tabs. The infusion assembly may further comprise an infusion housing attachable to the infusion hub, the infusion housing comprising tubing in fluid communication with a cavity of the infusion housing, wherein the cavity is configured to receive the infusion hub and to provide fluid communication between the tubing and the infusion conduit. The infusion conduit may be an infusion needle or infusion catheter. The infusion set may further comprise an infusion set applicator releasably attachable to the infusion hub and further comprising a needle configured to removably extend through the infusion hub and out of a distal end of the infusion conduit. The releasable attachment structure may comprise a removable section to which the infusion hub is attached. The releasable attachment structure may comprise two or more non-removable sections coupled to the removable section. The two or more non-removable sections coupled to the removable section may be coupled via a tear or frangible structure. The tear structure may comprise a plurality of perforations. The frangible structure may comprise a frangible strut. The removable section may comprise a pull tab or handle. The non-removable section may comprise a split ring or plurality of arcuate bodies attached to the tensioned dressing layer. The non-removable sections may comprise slots configured to movably receive tabs located on the removable section. The removable section may be integrally formed with the infusion hub. The slots may be arcuate slots. The infusion hub may further comprise a hub body and a hub base, and wherein the hub body is releasably attachable to the hub base, and the hub base is attached to the tensioned dressing layer. The hub body may comprise a releasable latch. The infusion set may further comprise a removal tool, the removal tool configured to actuate the releasable latch of the hub body and to facilitate separation of the hub body from the hub base. The hub base may comprise a softer material than the hub body. The removal tool may comprise prongs with tabs, wherein the prongs are configured to actuate the releasable latch of the hub body, and the tabs of the prongs are configured to lock to the hub body. The hub body may comprise access channels to the release latch which configured to receive the prongs with tabs. The infusion housing may comprise a release latch configured to unlock the infusion housing from the infusion hub.

In another embodiment, a method treating a treatment site is provided, comprising removing a first infusion housing from an infusion hub attached to a treatment site via a tensioned dressing, and separating at least some the infusion hub from the tensioned dressing while leaving the tensioned dressing attached to the treatment site. The method may further comprise inserting a cannula of the infusion hub into the treatment site, and adhering the tensioned dressing around the treatment site. Inserting the cannula may be performed with an applicator coupled to the infusion hub. The cannula of the infusion hub may comprise inserting the cannula of the infusion hub concurrently with a needle of the applicator into the treatment site. The method may further comprise decoupling the applicator from the infusion hub after inserting the cannula of the infusion hub. Decoupling the applicator form the infusion hub may also cause withdrawal of the needle from the cannula of the infusion hub. The method may further comprise attaching an infusion housing to the infusion hub, and infusing therapy through a tubing of the infusion housing and through the cannula of the infusion hub. The method may further comprise leaving the tensioned dressing on the treatment site for at least 12, 24 or 48 hours after separating the infusion hub. The method may further comprise separating an infusion housing from the infusion hub prior to separating the infusion hub from the tensioned dressing. Separating the infusion hub from the tensioned dressing may comprise inserting a removal tool into an infusion body of the infusion hub, and pulling away the infusion body from an infusion base of the infusion hub. Separating at least some the infusion hub from the tensioned dressing may comprise separating all of the infusion hub from the tensioned dressing. Separating at least some the infusion hub from the tensioned dressing may comprise pulling a tab of an attachment structure attaching the infusion hub to the tensioned dressing, and tearing the attachment structure along perforations to separate the infusion hub from the tensioned dressing and a non-removable portion of the attachment structure. Separating at least some the infusion hub from the tensioned dressing may comprise breaking off the infusion hub from the tensioned dressing. Breaking of the infusion hub from the tensioned dressing may comprise breaking off frangible struts of an attachment structure attached to the tensioned dressing and to the infusion hub. Separating at least some the infusion hub from the tensioned dressing may comprise rotating the infusion hub from attachment slots of an attachment structure. Separating at least some the infusion hub from the tensioned dressing may comprise rotating the infusion hub from a helical interface of an attachment structure.

According to variations, manipulating mechanical or physical properties may thereby modulate tensile or compressive stress at the skin site. The stress at the skin site may be reduced to levels below that experienced by normal skin and tissue. The stress at the skin site may be increased to levels above that experienced by normal skin and tissue. The stress or strain may be applied to surrounding tissue in one, two, or more directions to manipulate endogenous or exogenous stress at the skin site in one, two or more directions. According to variations, devices and methods described herein may reduce or otherwise manipulate the stress experienced by skin and/or a wound and surrounding tissues in order to treat a subject. The devices may also assist in preventing or reducing the incidence of wound dehiscence.

According to the devices, kits and methods described herein, a skin treatment device, skin device, wound treatment device, scar or keloid treatment device, scar or keloid amelioration or prevention device, bandage, or dressing may be provided that may be applied, attached to or coupled to one or more layers of the skin or tissue of a subject (hereinafter referred to as "dressing", "skin device" or "skin treatment device").

In addition to amelioration of scar formation, other uses for such skin treatment device may or may not include without limitation, for example, treating skin related conditions such as acne, blemishes, rosacea, warts, rashes (including but not limited to erythematous, macular, papular and/or bullous conditions), psoriasis, skin irritation/sensitivity, allodynia, telangiectasia, port wine stains and other arteriovenous malformations, and ectopic dermatitis; treating or improving existing scars, wrinkles, stretch marks, loose or sagging skin or other skin irregularities; lifting, pinning, holding, moving skin for various purposes such as during pre-operative preparation, during surgical procedures for example as a low-profile tissue retractor, to stabilize blood vessels during needle or catheter insertion, postoperatively, pre or post operatively for pre-treating or preconditioning skin for example, prior to scar revision, wound incision, body contouring, in mastectomy skin expansion, aesthetic skin treatment or resurfacing whether topical or subdermal, whether or not using an energy modality such as, for example, microwave, radio-frequency ablation, high-intensity focused ultrasound, laser, Infrared, incoherent light, during weight loss, or for aesthetic purposes; hair removal or hair loss; treating and/or closing skin injuries for example, incisions, wounds, chronic wounds, bed sores, ulcers (including venous stasis ulcers), preventing or reducing the incidence of wound dehiscence, diabetic skin or wound conditions, burn healing and/or relief; acting as an occlusive or negative-pressure wound dressing; protecting incisions or wounds, e.g. prevention of splitting or opening, protecting newborn belly buttons after cutting umbilical cord. Such treatments may include use of a drug or other therapeutic agent that may be applied to the skin with such device. The agents may include but are not limited to antibiotics, antifungals, immune modulators including corticosteroids and non-steroidal immune modulators. The agents may be provided in any of a variety of formulations, including but not limited powders, gels, lotions, creams, pastes, suspensions, etc. The devices may also be used for purposes of delivering a drug to the skin or through the skin, for example by stretching the skin and applying a drug thereto. Different configurations of the device may be amenable to the size or geometry of different body regions. The treatments may be applied to regions of any shape (e.g. linear, curved, stellate), size or depth, and to one or more regions of the body, including but not limited to the scalp, forehead, face (e.g. nose, eyelid, cheeks, lips, chin), ears, neck, shoulder, upper arm, lower arm, palm, dorsum of the hand, fingers, nailbed, axilla, chest, nipple, areola, back, abdomen, inguinal region, buttocks, perineal region, labia, penis, scrotum, thigh, lower leg, plantar surface of the foot, dorsal surface of the foot, and/or toes. Such devices may also be referred to herein as a "dressing", "skin device" or "skin treatment device".

In some situations, an immediate, quick or simple application of a dressing may be desired. Devices, kits and methods described herein may be for the preparation and/or application of a dressing to the skin and the separation of the applicator, tensioning device or dressing carrier, support or base from the skin device.

The devices, kits or methods described herein may include a packaging, carrier, support, base, applicator or tensioning device, each of which may: contain, hold, carry or support a dressing at least temporarily; may be used to prepare a dressing for application; may be used to deliver, orient or apply a dressing; may be used to maintain a dressing in a stressed or strained configuration; may be used to stress or strain a dressing; may be used to separate the dressing from the packaging, carrier, support, base, applicator or tensioning device and/or may be used during or after application of a dressing to provide additional treatment to a wound, incision or other treatment location; and/or may be used to apply pressure to a wound, incision or other treatment location. According to some variations, a packaging and/or applicator may provide structural support for a dressing while or after an adhesive liner is released. According to some variations, the assembly may be constructed to avoid folding or bending of the dressing to the extent that the adhesive on the dressing sticks to itself. For example, when some variations of the dressing are held or supported at one point or along one edge of the dressing in a cantilever configuration, the dressings will not bow, laterally deform, or otherwise deform out of plane, under their own mass or configuration.

In some other variations of the devices and methods herein, a device with a substantially rigid support structure or that provides structural support to a dressing and that provides a particular resistance to bending or column strength when two opposing edges of the device and support structure are placed under a compressive load that causes axial compression or lateral deformation, e.g. a force similar to a hand grasping force is applied to an edge of the device, before the device buckles or folds. For example, a resistance to bending may be characterized as the peak force that is achieve as the device and support structure are compressed without compressed by 25% of its original dimension. This column strength or rigidity may vary, depending upon the direction along the device and support structure being measured. In some further variations, the peak force may be at least about 0.02 Newtons per millimeter (N/mm), about 0.03 N/mm, about 0.05 N/mm, about 0.1 N/mm, about 0.15 N/mm, about 0.2 N/mm, about 0.3 N/mm, about 0.4 N/mm or about 0.5 N/mm. In some variations of devices comprising generally flat or planar devices and support structures having a thickness, the peak force may be measured by applying a compressive force along the shortest dimension of the device/support structure that is transverse to the thickness of the device/support structure. According to such variations, the device may have an aspect ratio of length to width that is greater than 1:1, 2:1 or 3:1, for example.

A resistance to bending in the direction of dressing strain may also be measured by three-point bending, applying a transverse force to the midpoint of the applicator simply supported on two outer points at a given distance apart or support span. For example, the distance between the two points of a sample may be approximately 0.75 inches and a force that ranges from about 1 to 1.25 pounds may be applied to a sample approximately 0.35 inches in width resulting in a deflection of approximately 0.05 inches. A resistance to bending may also be measured by characterizing the force at which buckling occurs on a simply supported beam. For example, a force of approximately 0.45 pounds may be applied to a simply supported sample approximately 0.35 inches in width and may result in a deflection of approximately 0.004 inches. The resistance to bending may also be characterized by the strain of the outer surface before fracture or permanent deformation. By taking measurements of the support structure and the deflections during the test procedure, a load deflection curve may be generated and the flexural modulus of the support structure may also be calculated. In some variations, the support structure may comprise a flexural modulus of at least about 0.9 GPa, while in other embodiments, the flexural modulus is at least about 1 GPa, at least about 1.1 GPa, at least about 1.2 GPa, at least about 1.3 GPa, or at least about 1.4 GPa.

In another example, a device of 7 cm wide by 19 cm long may be configured with a support structure comprising a paperboard, support sheet or support structure. The support structure may have an average thickness in the range of about 0.008" to about 0.028" or greater. In some specific variations, the support structure may have a thickness of about 0.012", about 0.016", about 0.018", about 0.024", about 0.28" or about 0.032", about 0.036", about 0.04", about 0.05" or greater. Upon the application of force along the lengthwise edge of the 19 centimeter length, i.e. across the 7 cm width of the device, the support structure may provide sufficient rigidity or column strength to achieve peak forces of about 3 pound or more, 4 pounds or more, or of about 10 pounds or more, while being compressed, collapsed, bowed, buckled or otherwise deformed by 25% along its 7 cm width (i.e. about 1.75 cm). In some variations, the support structure may comprise scoring or regions of reduced thickness to permit some bending it at least one direction or in both directions.

According to some variations, a device that provides structural support may have a plurality or supporting cross elements or segments extending from one edge of the length to an opposing edge or the length (or from one edge of a width to an opposing edge of a width); According to some variations there may be three or more cross elements, e.g., a cross element extending along two opposing edges and transversely across a width (or a length) and one or more cross elements extending across the width (or length) and between the cross elements along the two opposing edges. Such cross elements may or may not be coupled or connected to each other, for example, with a relatively flexible material. Such cross elements may have a total aggregate width with respect to the length of an opposing edge of about 20% or more, about 25% or more, about 30% or more, or about 35% or more. According to some variations, one or more cross elements may be provided that have a total aggregate width, relative to the length of the opposing side, between about 20% to 100%. Such cross elements may be segmented and may provide flexibility when bending in a direction and rigidity relative to the flexibility, in another direction.

The packaging and/or applicator may also provide structural support or stability of the dressing as it is oriented and/or applied to the skin of a subject. According to some variations, the dressing and packaging is configured to be pre-oriented in a position facing a wound before or after the wound device is prepared for application, e.g., the adhesive liner is removed. According to some variations, the packaging or applicator is configured to be used with one hand to orient and/or apply the device to the skin of a subject. For example, in some situations, particularly where a longer or larger dressing is used, a packaging or applicator provides structural support for a dressing such that a user can effectively hold onto, manipulate and/or apply a prepared dressing with one-hand. According to some variations, the assembly comprises a support structure. A dressing support structure is defined herein to mean a structure that is coupled whether directly or indirectly, to a back surface of a dressing that is to be applied to a subject. The support structure may further comprise at least in part, a material or structure that is more rigid than the dressing to be applied to a subject. The support structure may comprise one or more elements or segments. It may be constructed of a single substrate, a laminate or a plurality of elements coupled together and/or to the dressing. According to some variations at least 20%, 25%, 30%, 35%, or 40% of a length or width of the dressing is supported by one or more support structures extending from a first opposing side to an opposite side along a length or width of the dressing. In some further variations, the percentage of a length or width that is supported by the support structure(s) is a minimum average of support across the entire length or entire width of the device, e.g. at least a 20%, 25%, 30%, 35% or 40% average support across an entire dimension of the device, e.g. length or width. According to some variations, an entire area of a dressing is supported by a support structure. According to some variations, a base, carrier or support of a dressing may comprise at least three support structures extending transversely between opposing sides of the dressing. According to some variations, a support structure comprises interconnected members or elements. According to some variations, a base, carrier or support remains coupled to the dressing as it is applied. According to some variations, greater structural support is provided to a dressing carrier, support or base in a first direction while greater flexibility is provided in a second direction, while lesser flexibility is in the first direction and lesser structural support is provided in the second direction. According to some variations, one or more support structures may extend beyond an edge of the first opposing side. According to some variations, one or more support structures, at least in part, may extend beyond at least a portion of an edge of a first opposing side and at least in part beyond at least a portion of an edge of an opposite side. According to some variations, a support structure may extend at least 3 mm from at least a portion of an edge of the dressing. According to some variations, the packaging or applicator is configured to improve a sterile transfer of a dressing to a wound of a subject. According to variations, the packaging or applicator may be sufficiently wider or longer, or have a sufficiently larger area than a dressing providing the ability to maneuver or manipulate the support or applicator so that it provides sterile application and/or one-handed application without the need to touch the dressing. According to some variations, a margin of distance is provided from the outer edges of the dressing carrier, support or base to the dressing supported on the base or adhesive on the dressing. Such margins may be selected to prevent or resist a user from touching the dressing or dressing adhesive when grasping the edges to manipulate the dressing carrier, support, applicator or base.

Devices, kits and methods described herein may be for the treatment, amelioration, or prevention of scars and/or keloids by creating and/or maintaining a pre-determined strain in an elastic skin treatment device that is then affixed to the skin surface using skin adhesives to transfer a generally planar (e.g. compressive) force from the bandage to the skin surface.

In some variations, a dressing is provided, comprising an elastic sheet structure (e.g., a comprising a silicone polyurethane, TPE (thermoplastic elastomers), synthetic rubber or co-polyester material) comprising an upper surface, a lower surface, a first edge and a second edge opposite the first edge, and one or more adhesive regions. The dressing may further comprise a first release liner releasably attached to the adhesive region or regions. The adhesive region(s) may comprise a pressure sensitive adhesive. The dressing may be tapered or otherwise shaped to reduce skin tension at the edges. The dressing may have modified, reduced or no adhesive near its edges to reduce skin tension at the edges. Portions of the dressing may be unstrained and may thereby reduce strain in certain areas of the skin where the dressing is applied. In some specific examples, the unstrained area or areas are found between the edges of the dressing and the strained area(s). In some further examples, the unstrained areas are limited to this area and are not found, during application or use, between the strained areas of a single dressing, in use. In still further examples, the unstrained areas are limited to areas along the edges of a dressing that intersect the strain axis of the strained area(s), but not to areas along the edges of the dressing that are generally parallel to the strain axis.

A packaging device, dressing carrier, dressing support, dressing base, applicator and/or tensioning device may be provided. The packaging device, dressing carrier, dressing support, dressing base, applicator and/or tensioning device may be configured to stress and/or strain a dressing prior to application to a subject. A device may be used to strain and/or maintain a strain on a dressing. In one variation, a dressing is provided, comprising a first device attachment structure, zone or region, a second device attachment structure, zone or region, and a structure or mechanism configured to exert a separation force between the first and second device attachment structures, zones or regions. The device may further comprise a releasable locking mechanism, attachment mechanism or adhesive, configured to maintain the member or mechanism in a strained configuration.

In some situations, application of a compressive force to a wound is desirable to reduce bleeding. According to some variations, the packaging, carrier, base, applicator or tensioning device described herein may be further used to help reduce bleeding, e.g., by allowing application of a compressive force using the device while or after the dressing is applied. A coagulative additive may also be provided on a dressing.

According to one aspect, the packaging, carrier, support, base, applicator and/or tensioning device may be sufficiently rigid or supportive in at least one direction, to hold a dressing's form so that it is easy to manipulate.

According to some variations, the packaging is also sufficiently flexible in at least one direction to permit curving or shaping of the dressing to conform to the curvature or shape of the location on the body or skin where the dressing is applied. Generally, the flexibility of the packaging used to conform the dressing to the treatment site may be configured so that the treatment site is not substantially deformed during the application of the dressing; so that the application of the dressing is relatively smooth or uniform on the skin; and/or provides a uniform, predetermined, or relatively predictable strain or force to an area of skin The packaging or applicator may have flexibility in a first direction and greater rigidity in another direction. The packaging or applicator may include elements or segments that permit flexibility with respect to adjacent elements or segments.

According to some variations, the packaging is also sufficiently flexible in at least one direction to permit curving or shaping of the dressing to conform to the curvature or shape of the location on the body or skin where the dressing is applied. Generally, the flexibility of the packaging used to conform the dressing to the treatment site may be configured so that the treatment site is not substantially deformed during the application of the dressing; and/or so that the application of the dressing is relatively smooth or uniform on the skin; and/or provides a uniform, predetermined, or relatively predictable strain and/or force to an area of skin. The packaging or applicator may have flexibility in a first direction and greater rigidity in a second direction. The first direction may be transverse to the direction of straining or have a component that is transverse to the direction of straining. The second direction may by the direction of straining or have a component that is in the direction of straining. The first direction may or may not be transverse with respect to the second direction. The packaging or applicator may include elements or segments that permit flexibility with respect to adjacent elements or segments.

According to some variations a desired flexibility, for example having at least one component transverse to the direction of straining, may be characterized by a modified cantilevered beam bending model, i.e. applying a force to the free end of a beam, simply supported from the other end, while wrapping it around a cylindrical object with a known radius of curvature or curvature, defined as the reciprocal of the radius of the curvature. According to one variation, the force to bend the packaging or applicator around an object with a predetermined curvature may be no greater than about 3 pounds. According to one variation, the force may be no greater than about 0.3 pounds. According to one variation, the force to bend around a predetermined curvature of about a 2.5 inch radius may be no greater than about 3 pounds. In another variation, the force to bend around a predetermined curvature of about a 2.5 inch radius may be no greater than about 0.3 pounds.

According to some variations, a packaging, applicator or tensioning device is provided comprising a base having an inner surface to which a dressing is removably attached, and a cover or lid having an inner surface interfacing the inner surface of the base when in an initial closed configuration. According to some variations, the base and cover are coupled at corresponding edges along their corresponding lengths to form a book-like structure whereby the cover may be rotated with respect to the base to open the device. Alternatively the cover may be lifted off of the base. According to variations, a liner is attached to the cover and will expose an adhesive side of a dressing when the cover is lifted or opened.

In some variations, the book-like structure, in the closed configuration, comprises a layered structure comprising a cover/lid, a treatment device and a base, in that relative order, while in the open configuration, the relative order of the layered structure changes to a cover/lid, a base, and a treatment device. The treatment device may also comprise one or more release layers. In one variation, in the closed configuration, a first face of the cover/lid is in contact with a first face of the treatment device, and a first face of the base is in contact with the second surface of the treatment device opposite the first surface, while in the open configuration, a second face of the cover/lid (opposite the first face of the cover/lid) is in contact with a second face of the base (opposite the first face of the base) but not with the first face of the treatment device. In some variations, the cover/lid may be separated from the base during or after tensioning of the treatment device. In some variations, the treatment device may be attached asymmetrically to the book-like structure, relative to the bending region of the book-like structure. In some instances, the asymmetric attachment may provide the user with a mechanical advantage when tensioning the dressing, and/or may reduce manufacturing costs by optimizing the amount of elastic material used in the dressing. In other variations, the dressing or skin treatment device may be attached symmetrically to the book-like structure, relative to the bending region of the book-like structure.

In another embodiment, a method of applying a dressing to a surface is provided. According to some variations the method may comprise providing a dressing packaging comprising: an applicator comprising a base structure having an inner surface and a manipulation portion; a dressing comprising a first surface configured to be applied to a skin or wound of a subject; and a back surface, wherein the back surface of the dressing is removably coupled or anchored to the inner surface of the base structure, and wherein the first surface faces away from the inner surface of the base structure; and a cover configured to removably cover the first surface of the dressing. A method may further comprise removing the cover to expose a first surface of a dressing; and using the manipulation portion of the base structure to apply the first surface of the dressing to a wound or skin of a subject. In another variation, a method for treating a wound is provided, comprising straining an inner region of an elastic bandage between a first unstrained region and a second unstrained region, and attaching at least the strained inner region of the dressing to a skin site or both strained and unstrained regions.

According to some variations, a dressing packaging assembly comprises: a base structure having an inner surface; a cover structure having an opposing surface, wherein the base structure is movably coupled to the cover structure; and a dressing comprising a first surface configured to be applied to a wound or skin of a subject, and a back surface, wherein at least a portion of the back surface is removably coupled to the inner surface of the base structure; and wherein the cover structure is configured to move from a first position where the opposing surface interfaces with and is substantially parallel to the first surface to the dressing to a second position where the opposing surface is separated from the first surface of the dressing. According to variations, the first surface of the dressing comprises an adhesive region. According to variations the first surface of the dressing comprises an adhesive backing interfacing an adhesive region on the dressing. According to variations, the opposing surface of the cover structure comprises an adhesive backing covering the adhesive region when the cover structure is in the first position and separated from the adhesive region when the cover structure is in the second position. According to variations, the dressing comprises an elastic material. According to variations, the dressing comprises a first attachment region coupled to the inner surface of the base structure and a second attachment region coupled to the opposing surface of the cover structure, wherein the cover and base are configured to exert a straining force to strain the dressing when the cover is moved from the first position to the second position. According to variations, a tensioning structure is configured to exert the straining force on the dressing. According to variations, the tensioning structure comprises: a first structure configured to couple the dressing at the first attachment region to the inner surface of the base structure; and a second structure configured to couple the dressing at the second attachment region to the opposing surface of the cover; wherein the tensioning structure is configured to exert the straining force to the dressing between the first attachment region and the second attachment region when the cover structure is moved with respect to the base structure from the first position to the second position. According to some variations, the dressing has a first width when the cover is in the first position and a second width when the cover is in the second position, wherein the second width is greater than the first width. According to variations, the second width is at least 20% greater than the first width. According to variations, the second width is at least 40% great than the first width. According to variations, the base structure comprise at least one relatively rigid element and at least one relatively flexible element, wherein the relatively rigid element is sufficiently rigid to support the dressing when the straining force is applied in a first direction; and wherein the relatively flexible element permits the base structure to flex in a second direction. According to variations, the at least one relatively rigid element comprises a plurality of flexible coupled, relatively rigid elements. According to variations, the cover structure comprises at least one relatively rigid element and at least one relatively flexible element. According to variations, a release device is configured to release the dressing from the base structure after the dressing is applied to a wound or skin of a subject. According to some variations, base structure is pivotably coupled to the cover structure.

According to variations, a dressing packaging assembly comprises: a base structure having an inner surface and comprising at least one support element and at least one flexible element; and a dressing comprising a first surface configured to be applied to a wound or skin of a subject, and a back surface, wherein at least a portion of the back surface is removably coupled to the inner surface of the base structure. According to variations, the at least one rigid element comprises a plurality of rigid elements coupled to each other with the at least one flexible element. According to variations, a cover structure comprises an opposing surface configured to interface with the first surface of the dressing, wherein the cover structure is moveably coupled to the base structure to move from a first position where the opposing surface interfaces with the first surface of the dressing, to a second position where the cover is separated from the first surface of the dressing. According to variations, the cover structure is pivotably coupled to the base structure. According to variations, the cover structure comprises at least one support element and at least one flexible element sufficiently flexible to permit shaping of the cover structure. According to variations, the first surface of the dressing comprises an adhesive region. According to variations, the first surface of the dressing comprises an adhesive backing interfacing an adhesive region on the dressing. According to variations, the opposing surface of the cover structure comprises an adhesive backing covering the adhesive region in the first position and separated from the adhesive region in the second position. According to variations, the dressing comprises and elastic material. According to variations, the dressing comprises a first attachment region coupled to the inner surface of the base structure and a second attachment region coupled to the opposing surface of the cover structure, wherein the cover and base are configured to exert a straining force to strain the dressing when the cover is moved from the first position to the second position. According to variations, the assembly further comprises a tensioning structure configured to exert the straining force on the dressing. According to variations, the tensioning structure comprises: a first structure configured to couple the dressing at the first attachment region to the inner surface of the base structure; and a second structure configured to couple the dressing at the second attachment region to the opposing surface of the cover wherein the tensioning structure is configured to exert the straining force to the dressing between the first attachment region and the second attachment region when the cover structure is moved with respect to the base structure from the first position to the second position. According to variations, the dressing between the first and second attachment regions has a first width when the cover is in the first position and a second width when the cover is in the second position, wherein the second width is greater than the first width. According to variations, the second width is at least 4% greater than the first width. According to variations, the second width is at least 20% greater than the first width. According to variations, the second width is at least 40% great than the first width.

According to variation, a method of applying a dressing to a wound or skin of a subject comprises: providing a dressing packaging assembly comprising: a base structure having an inner surface; a cover structure having an opposing surface, wherein the base structure is movably coupled to the cover structure; and a dressing comprising a first surface including an adhesive region, and a back surface, wherein at least a portion of the back surface is removably coupled to the inner surface of the base structure, and wherein the opposing surface of the cover structure comprises an adhesive backing covering the adhesive region when the cover structure is in the first position; pivoting the cover structure with respect to the base structure to a second position to separate the opposing surface from the first surface of the dressing and to separate the adhesive backing from the adhesive region; applying the first surface of the dressing to a wound or skin of a subject, then subsequently releasing the dressing from the base structure. According to variations of the method, at least a portion of the back surface of the dressing is coupled to the cover structure and further comprising pivoting the cover structure with respect to the base structure to strain the dressing.

According to variations, a dressing applicator comprises a first dressing attachment region and a second dressing attachment region comprising a variable separation distance between the first dressing attachment region and the second dressing attachment region, and a bending region between the first dressing attachment region and the second dressing attachment region that alters the variable separation distance, and wherein a first distance from a center of the bending region to the first dressing attachment area is different from a second distance from the center of the bending region to the second dressing attachment area.

According to variations, a dressing tensioning device comprises: a dressing carrier comprising a first carrier edge and a second opposing carrier edge defining a carrier width therebetween; a tensioning element configured to move with respect to the dressing carrier from a first position to a second dressing tensioning position; and a dressing assembly comprising a dressing including a first dressing edge coupled to the carrier adjacent the first carrier edge; a second dressing edge coupled to an attachment element wherein the attachment element coupled to the tensioning element; wherein in the first position of the tensioning element, the second dressing edge is a first distance from the second carrier edge within the width of the carrier, and in the second position of the tensioning element, the second dressing edge is a second distance from the second carrier edge within the width of the carrier, wherein the first distance is greater than the second distance. According to variations, the first dressing edge is relatively fixed with respect to the second dressing edge when the tensioning element is moved between the first and second positions.

According to variations, a dressing packaging assembly comprises: a base structure having an inner surface; a cover structure having an opposing surface, wherein the base structure is movably coupled to the cover structure; and a dressing comprising a first surface configured to be applied to a wound or skin of a subject, and a back surface, wherein at least a portion of the back surface is removably coupled to the inner surface of the base structure; wherein the cover structure is configured to move from a first position where the opposing surface interfaces with the first surface to the dressing to a second position where the opposing surface is separated from the first surface of the dressing where the second position is at least about 180 degrees rotated with respect to the first position. According to variations, the first surface of the dressing comprises an adhesive region. According to variations, the first surface of the dressing comprises an adhesive backing interfacing an adhesive region on the dressing. According to variations, the opposing surface of the cover structure comprises an adhesive backing covering the adhesive region when the cover structure is in the first position and separated from the adhesive region when the cover structure is in the second position. According to variations, the dressing comprises an elastic material. According to variations, the dressing comprises a first attachment region coupled to the inner surface of the base structure and a second attachment region coupled to the opposing surface of the cover structure, wherein the cover and base are configured to exert a straining force to strain the dressing when the cover is moved from the first position to the second position. According to variations, the assembly further comprises a tensioning structure configured to exert the straining force on the dressing. According to variations, the tensioning structure comprises: a first structure configured to couple the dressing at the first attachment region to the inner surface of the base structure; and a second structure configured to couple the dressing at the second attachment region to the opposing surface of the cover; wherein the tensioning structure is configured to exert the straining force to the dressing between the first attachment region and the second attachment region when the cover structure is moved with respect to the base structure from the first position to the second position. According to variations, the dressing has a first width when the cover is in the first position and a second width when the cover is in the second position, wherein the second width is greater than the first width. According to variations, the second width is at least 20% greater than the first width. According to variations, the second width is at least 40% great than the first width. According to variations, the base structure comprises at least one relatively rigid element and at least one relatively flexible element, wherein the relatively rigid element is sufficiently rigid to support the dressing when the straining force is applied in a first direction; and wherein the relatively flexible element permits the base structure to flex in a second direction.

According to variations, a dressing packaging comprises: a dressing carrier comprising a first carrier edge, a second carrier edge opposing the first carrier edge, and a support structure extending between the first edge and the second edge, configured to support a dressing during application of the dressing to a subject; and a dressing comprising a first dressing edge, a second dressing edge opposing the first dressing edge, a back surface and an opposing skin interfacing surface, wherein at least a portion of the back surface is removably coupled to the dressing carrier wherein the first dressing edge and the second dressing edge are positioned between the first carrier edge and the second carrier edge, and wherein the first dressing edge defines a first margin between the first dressing edge and the first carrier edge and the second dressing edge defines a second margin between the second dressing edge and the second carrier edge, wherein each of the first and second margins have a width of at least three millimeters.

In one variation, a dressing system is provided, comprising a first support, a second support, and a primary bending region therebetween, the primary bending region comprising a primary bending axis, and a treatment device comprising a first attachment region attached to the first support and a second attachment region attached to the second support, a first separation region configured to separate from first attachment region and a second separation region configured to separate from the second attachment region. The first and second separation regions may comprise perforations. The dressing system may further comprise a pull element located along the perforations. The treatment device may be asymmetrically attached to the first and second supports, relative the primary bending region. A first distance between the first support and the primary bending axis may be different from a second distance between the second support and the primary bending axis. The dressing system may further comprise a closed configuration wherein the treatment device is located between the first support and the second support, and a closed configuration wherein the second support is located between the first support and the treatment device. The second support may comprise at least one secondary bend region comprising a secondary bending axis that is not parallel to the primary bending axis. The secondary bending axis may be orthogonal to the primary bending axis. The first support may comprise at least one secondary bend region comprising a secondary bending axis that is not parallel to the primary bending axis. The at least one secondary bend region of the first support may be aligned with the at least one secondary bend region of the second support. The treatment device may further comprise a release liner coupled to an adhesive surface of the treatment device. The treatment device may comprise a perforation region. The dressing system may further comprise an elongate element attached adjacent to the perforation region. The elongate element may protrude beyond the perforation region of the treatment device. In some variations, at least a portion of the elongate element may be folded, and the fold may be along a substantial length of the treatment device. At least one of the first and second supports may comprise indicia identifying a center region of the treatment device. The indicia may comprise a recessed edge, ink mark, embossing, or window. The primary bending region may also perforated. The first support may be configured to detach from the second support and the treatment device, and may or may not do so while maintaining the treatment device in a strained configuration. The second support may comprise an adhesive element configured to adhere to the treatment device when the dressing system is in the open configuration but not in the closed configuration. The first support may comprise an attached release liner. The release liner may be attached to the first support between an outer edge of the first support and the attached treatment device. An inner surface of the first and/or second support facing the treatment device may include an adhesive, such as an adhesive coating or adhesive tape, which is configured to maintain the treatment device either in a tensioned state as it is stretched and contacts the adhesive, and/or to maintain the treatment device against the first and/or second supports.

In another variation, a dressing system is provided, comprising a first tensioning member, a second tensioning member, and a primary bending region therebetween, the primary bending region comprising a primary bending axis, and a treatment device asymmetrically attached to the first and second tensioning members, relative the primary bending region. The treatment device may comprises a first end attached to the first tensioning member and a second end attached to a second tensioning member, wherein a first distance between the first tensioning member and the primary bending axis is different from a second distance between the second tensioning member and the primary bending axis. The dressing system may further comprise a closed configuration wherein the treatment device is located between the first tensioning member and the second tensioning member, and an open configuration wherein the second tensioning member is located between the first tensioning member and the treatment device. The second tensioning member may comprise at least one secondary bend region comprising a secondary bending axis that is not parallel to the primary bending axis. The secondary bending axis may be orthogonal to the primary bending axis. The first tensioning member may comprise at least one secondary bend region comprising a secondary bending axis that is not parallel to the primary bending axis. The at least one secondary bend region of the first tensioning member may be aligned with the at least one secondary bend region of the second tensioning member. The treatment device may further comprise a release liner coupled to an adhesive surface of the treatment device. The treatment device may comprise a perforation region. The dressing system may further comprise an elongate element attached adjacent to the perforation region. The elongate element may protrude beyond the perforation region of the treatment device. In some variations, at least a portion of the elongate element may be folded, and the fold may be along a substantial length of the treatment device. At least one of the first and second tensioning members may comprise indicia identifying a center region of the treatment device. The indicia may comprise a recessed edge, ink mark, embossing, or window. The primary bending region may be perforated. The first tensioning member may be configured to detach from the second tensioning member and the treatment device. The first tensioning member may be configured to detach from the second tensioning member and the treatment device while maintaining the treatment device in a strained configuration. The second tensioning member may comprise an adhesive element configured to adhere to the treatment device when the dressing system is in the open configuration but not in the closed configuration. The first tensioning member may comprise an attached release liner. The release liner may be attached to the first tensioning member between an outer edge of the first tensioning member and the attached treatment device.

In another variation, a dressing system is provided, comprising a first applicator member, a second applicator member, and a primary bending region therebetween, the primary bending region comprising a primary bending axis, and a treatment device attached to the first and second applicator members, wherein the dressing system comprises a closed configuration wherein the treatment device is located between the first applicator member and the second applicator member, and a closed configuration wherein the second applicator member is located between the first applicator member and the treatment device. The second applicator member may comprise at least one secondary bend region comprising a secondary bending axis that is not parallel to the primary bending axis. The secondary bending axis may be orthogonal to the primary bending axis. The first applicator member may comprise at least one secondary bend region comprising a secondary bending axis that is not parallel to the primary bending axis. The at least one secondary bend region of the first applicator member may be aligned with the at least one secondary bend region of the second applicator member. The treatment device may further comprise a release liner coupled to an adhesive surface of the treatment device. The treatment device may comprise a perforation region. The dressing system may further comprise an elongate element attached adjacent to the perforation region. The elongate element may protrude beyond the perforation region of the treatment device. At least a portion of the elongate element may be folded, and the fold may be along a substantial length of the treatment device. At least one of the first and second applicator members may comprise indicia identifying a center region of the treatment device. The indicia may comprise a recessed edge, ink mark, embossing, or window. The primary bending region may be perforated. The first applicator member is configured to detach from the second applicator member and the treatment device. The first applicator member may be configured to detach from the second applicator member and the treatment device while maintaining the treatment device in a strained configuration. The second applicator member may comprise an adhesive element configured to adhere to the treatment device when the dressing system is in the open configuration but not in the closed configuration. The first applicator member may comprise an attached release liner. The release liner may be attached to the first applicator member between an outer edge of the first applicator member and the attached treatment device.

Devices kits and methods herein may include a support, packaging and/or applicator configured to maintain a pre-strained dressing in a strained configuration for a period of time after straining and prior to application to skin of a subject. Devices and methods herein may include a method of manufacturing such a pre-strained dressing.

According to one variation, a pre-strained and strain shielded dressing assembly may be stored for a period of time after straining and prior to use. In some variations, the dressing may be configured to maintain a predictable and/or desired amount of tensile force during a pre-determined period of time after initial straining. In some variations, the dressing may be configured to lose a predetermined maximum and/or minimum amount of tensile force (measured in a direction of tensile straining of the dressing) during one or more periods of time.

A desired time for application of the dressing to a subject may be when the dressing, in its pre-strained and strain shielded configuration, has a tensile force characteristic or range thereof that is desired. Such desired range may be selected to provide sufficient modulation of the forces on the skin to treat the skin while avoiding or minimizing disruption irritation to the skin. As noted herein, for a given dressing, different levels of stress or strain may be imparted to the skin at different locations and/or on different subjects. Also different levels of force offloading may be desirable for different individuals or different locations on a subject's skin. Thus different ranges of dressing force properties may be appropriate for different skin treatment applications.

Such desired force range may be selected based on a determination desired force properties to be applied to a particular subject, portion of skin and/or for a particular skin treatment purpose. Such desired force may be high enough to provide a therapeutic mechanomodulation of the skin while be low enough to prevent significant skin irritation.

Force properties of a pre-strained dressings may vary over time. An initial strain may be applied to the dressing where the elastic material or other structure, of the dressing has an initial tensile force characteristic. The dressing may be maintained in a strained configuration at a particular strain level after it is pre-strained for an initial period of time. During the initial period of time, the force properties of the elastic material may diminish, decay or exhibit a loss of force. After an initial predetermined period of time, the force properties of the elastic material may reach, diminish to or decay to a desired force level and/or range of force levels. The dressing elastic material force characteristics may be within the desired range for at least a subsequent period of time. In some variations, the dressing material may have an elastic modulus in the range of about 1 MPa to about 15 MPa, sometimes about 1.5 MPa to about 6 MPa, and other times about 2 MPa to about 5 MPa, about 3 MPa to about 4 MPa, or about 3.5 MPa to 5 MPa, while having a peak load per width up to a 0.6 strain of less than 3 N/mm, sometimes less than about 2.5 N/mm, sometimes less than 2 N./mm, sometimes less than 1 N/mm, sometimes less than about 0.75 N/mm and other times less than about 0.6 N/mm or less than about 0.5 N/mm. The peak load per width up to a 0.6 strain, may be at least about 0.35 N/mm, sometimes at least about 0.5 N/mm, and other times at least about 0.6 N/mm, 0.7 N/mm, 0.8 N/mm, 0.9 N/mm or 1 N/mm. The material may be selected such that the material, at a constant engineering strain of 20%, is able to maintain an engineering stress of at least about 200 kPa, 250 kPa, 300 kPa, 400 kPa, or 500 kPa, 1000 kPa, 1500 kPa, 2000 kPa, 2500 kPa, 3000 kPa or more for at least 8 hours with less than a 10% or 5% variation or decrease in engineering stress.

According to a variation, for example, the initial force or strain properties of a dressing may be selected so that the desired range of force values occur during a period of time where the percentage loss of force is reduced and occurs over a longer period of time.

The initial strain and/or force level of the dressing may be selected so that the time of use falls within a desired time frame or period based on the percentage loss of force of the dressing over time.

According to variations, the dressing may be initially strained or over-stressed to provide a greater initial force per unit width than that of a desired range at the time of application to skin. According to variations, the initial strain and resulting initial force per width of a dressing may be selected based on desired final and resulting force properties and/or a desired time frame for use of the dressing. Such initial strain level may be, for example, 20% or more, 30% or more, 40% or more, 50% or more, 60% or more, 70% or more, 80% or more, 90% or more, 100% or more. According to variations, the initial force is greater than a desired force range. Such initial force level may be for example about or up to 25%, about or up to 35%, about or up to 50%, about or up to 75% or more than the desired force at time of application of the dressing. Such initial force level may be but is not limited to, for example, between 2 and 5 Lbf/inch, 1.54 and 3.85 Lbf/inch, 1.33 and 3.33 Lbf/inch. or 0.85 to 2.20 Lbf/inch According to variations, a dressing may be configured to be initially strained or tensile stressed to a desired strain or force level and maintained in the strained configuration for an initial time frame. According to variations, the initial time frame may be, for example, 1 hour or more, 1 day or more, 1 week or more, or up to 1 month or more prior to application. According to variations, the initial time frame may be 1 hour or more, 1 day or more, 1 week or more, or up to 1 month or more in a material pre-conditioning state prior to final assembly or manufacture. Such preconditioning state may be straining the material at a constant strain or straining the material at varied levels of strain.

Then according to some variations, for the duration of a subsequent pre-determined time frame after the initial time frame, the dressing may be configured to maintain a desired minimum final force or force range. During the subsequent time frame, the device may be applied to a subject's skin for treatment. Such desired force range may be from about 0.5 to 1.0 Lbf/inch, 1.0 to 2.5 Lbf/inch or from about 1.6 to 2.1 Lbf/inch. The force loss during the subsequent time period may be up to 3%, up to 5%, up to 8%, up to 10%, up to 15%, up to 20%, up to 25% or more. The duration of the subsequent time period may be, for example 2 months, or more 3 months or more, 6 months or more, 12 months or more, 36 months or more, or 48 months or more.

The pre-strained dressing may then be coupled to a strain maintaining element during an initial period of time. The strain maintaining element may remain on the dressing during a portion of the subsequent period of time until it is used.

According to a variation for example, the average initial force or strain properties (average may include or may comprise an average, for example, per manufacturing lot, or a specified average within a given tolerance level) of a dressings pre-strained at manufacturing may be provided so that the desired range of average force values occur during a period of time where the average percentage loss of force is reduced and occurs over a longer period of time. In other variations, the pre-straining is initiated at the point-of-use. In still other variations, a portion of the pre-straining is performed at the point-of-manufacture, and additional straining or strain relief is performed at the point-of-use. After pre-straining, the dressing may then be packaged, sealed and sterilized for future use.

The initial average strain and/or force level of the dressings may be selected so that the time of use falls within a desired time frame or period based on the average percentage loss of force of the dressings over time.

According to variations, the dressings may be initially strained or over-stressed to provide a greater average initial force per unit width than that of a desired range at the time of application to skin. According to variations, the average initial strain and resulting initial force per width of a dressing may be selected based on desired final and resulting force properties and/or a desired time frame for use of the dressing. Such average initial strain level may be, for example, less than 20%, 20% or more, 30% or more, 40% or more, 50% or more, 60% or more, 70% or more, 80% or more, 90% or more, 100% or more. According to variations, the average initial force is greater than a desired force range. Such average initial force level may be for example about or up to 25%, about or up 35%, about or up to 50%, about or up to 75%, or more than the desired force at the time of application of the dressing. Such average initial force level may be but is not limited to, for example, between 2 and 5 Lbf/inch, 1.54 and 3.85 Lbf/inch, 1.33 and 3.33 Lbf/inch. or 0.85 to 2.20 Lbf/inch According to variations, a dressing may be configured to be initially strained or tensile stressed to a desired average strain or force level and maintained in the strained configuration for an initial time frame. According to variations, the initial time frame may be 1 hour or more, 1 day or more, 1 week or more, or up to 1 month or more prior to application. According to variations, the initial time frame may be 1 hour or more, 1 day or more, 1 week or more or up to 1 month or more in a material pre-conditioning state prior to final assembly or manufacture. Such preconditioning state may be straining the material at an average constant strain or straining the material at varied levels of average strain.

Then according to some variations, for the duration of a subsequent pre-determined time frame after the initial time frame, the dressings may be configured to maintain a desired minimum average final force or average force range. During the subsequent time frame, the devices may be applied to a subject's skin for treatment. Such desired average force range may be from about 0.5 to 1.0 Lbf/inch, 1.31 Lbf/inch to 1.41 Lbf/inch. The average force loss during the subsequent time period may be up to 3%, up to 5%, up to 8%, up to 10%, up to 15%, up to 20%, up to 25% or more. The duration of the subsequent time period may be, for example 2 months or more, 3 months or more, 6 months or more, 12 months or more, 36 months or more, or 48 months or more.

A pre-strained dressing may be coupled to a strain maintaining element during an initial period of time during one or more manufacturing steps. The strain maintaining element may remain on the dressing during a portion of the subsequent period of time during manufacturing or in transport or storage until it is used.

In another example, a method for modulating tissue response at a target site is provided, comprising providing a strained elastic structure with an access opening and a support structure, placing the strained elastic structure against a target site, releasing the strained elastic structure from the support structure, and inserting an access structure into the target site, wherein the access structure is located in the access opening. The strained elastic structure may be an elastic sheet with an adhesive layer. Attaching the strained elastic structure to the target site may comprise adhering the strained elastic structure to a skin location. The support structure may comprise at least one pull tab, and releasing the strained elastic structure from the support structure may comprise actuating the pull tab to release the strained elastic structure from the support structure. The method may further comprise inserting the access structure through the access opening. The access structure may be a delivery tube, and wherein the method may further comprise passing a sensor or infusion cannula using the delivery tube. The access structure may be attached to a housing. The housing may comprises a skin configured to attach the housing to a skin surface. The housing may further comprise a support layer, and the adhesive may be located on the inferior surface of the support layer. The method may further comprise adhering the housing to the elastic structure. The method may further comprise releasing the access structure from a delivery device after inserting the access structure into the target site. The method may further comprise aligning the delivery device with indicia or alignment structures located on the strained elastic structure.

In another embodiment, a tissue treatment device is provided, comprising a strained elastic layer comprising a top surface, a bottom surface and a treatment opening, a skin adhesive layer adhered to the bottom surface of the strained elastic layer, a protective layer releasably contacting the adhesive layer, a strain support removably attached to the top surface of the elastic layer, the strain support comprising a layer structure with a center opening surrounding the treatment opening of the strained elastic layer, the strain support having sufficient rigidity to maintain the strained elastic layer in a strained configuration, and at least one alignment structure located on the strain support and surrounding the center opening of the strain support. The strain support may further comprise a perforation region from the center opening to an edge of the strain support. The alignment structure may comprise a separation region aligned with the perforation region of the strain support. The strain support may comprise a first end, a second end, and an arcuate body therebetween defining the center opening of the strain support. The device may further comprise a strain support adhesive layer between the strained elastic layer and the strain support, wherein the strain support adhesive layer has a lower T-peel force than the skin adhesive layer. The strained elastic layer may be heat staked to the strain support. The strain support may further comprise perforations to facilitate separation of the strain support from the strained elastic layer.

In another embodiment, a multi-layer tissue treatment device is provided, comprising a strained elastic base layer comprising a top surface, a bottom surface, a perimeter edge and a treatment opening, a skin adhesive layer adhered to the bottom surface of the strained elastic layer, a protective layer releasably contacting the skin adhesive layer, at least one strained elastic intermediate layer, wherein each elastic intermediate layer comprises a top surface, a bottom surface, a perimeter edge and a treatment opening aligned with the treatment opening of the strained elastic base layer, and wherein the bottom layer of one of the at least one intermediate elastic layer is attached to a top surface of the strained elastic base layer, a strained elastic top layer, comprising a top surface, a bottom surface, a perimeter edge and a treatment opening, wherein the treatment opening of the strained elastic top layer is aligned with the treatment opening of the strained elastic base layer, and the bottom surface of the strained elastic top layer is attached to the top surface of one of the at least one intermediate elastic layer, and a strain support releasably attached to at least one of the strained elastic top layer, strained elastic bottom layer, and the at least one elastic intermediate layer, wherein the strain support is configured to maintain the strain of the elastic base layer, the at least one intermediate layer, and the elastic top layer. The perimeter edge of the elastic top layer may be offset from the perimeter edge of the intermediate elastic layer that is attached to the elastic top layer, and wherein the perimeter edge of the elastic intermediate layer that is attached to the elastic base layer may be offset from the perimeter edge of the elastic base layer. The perimeter edge of the elastic top layer may be offset inward from the perimeter edge of the intermediate elastic layer that is attached to the elastic top layer, and wherein the perimeter edge of the elastic intermediate layer that is attached to the elastic base layer may be offset inward from the perimeter edge of the elastic base layer. The device of claim 8, wherein the bottom surface of the elastic top layer is smaller than the top surface of the intermediate elastic layer that is attached to the elastic top layer, and wherein the bottom surface of the elastic intermediate layer that is attached to the elastic base layer is smaller than the top surface of the elastic base layer. The bottom surface of the elastic top layer may be larger than the top surface of the intermediate elastic layer that is attached to the elastic top layer, and wherein the bottom surface of the elastic intermediate layer that may be attached to the elastic base layer is larger than the top surface of the elastic base layer. The strained elastic top layer, the strained elastic base layer, and each of the at least one elastic intermediate layers, may each have a different size. The elastic top layer may be smaller than all of the at least one elastic intermediate layers, and wherein all of the at least one elastic intermediate layers may be smaller than the elastic base layer. The elastic top layer may be larger than all of the at least one elastic intermediate layers, and wherein all of the at least one elastic intermediate layers may be larger than the elastic base layer. The at least one elastic intermediate layer may comprise two elastic intermediate layers. The at least one elastic intermediate layer may comprise two elastic intermediate layers. The strained elastic top layer and the at least one elastic intermediate layer may each comprise a pull tab. The pull tab of the strained elastic top layer and the pull tab of the at least one elastic intermediate layer may each be a different size. The pull tab of the elastic top layer may be smaller than all of the pull tabs of the at least one elastic intermediate layers. The pull tab of the elastic top layer may be larger than all of the pull tabs of the at least one elastic intermediate layers. The strain support may be releasably attached to the top surface of the strained elastic top layer. The attachments of the top layer and the at least one intermediate layer may utilize anisotropic adhesive patterns. The anisotropic adhesive pattern may have a reduced amount of adhesive along a peel direction as compared to a strain direction of the strained layers.

In another embodiment, a multi-layer tissue treatment device is provided, comprising at least two strained elastic layers, comprising at least a top elastic layer and at least a base elastic layer, wherein each of the at least two strained elastic layers comprises a top surface, a bottom surface, a size, a perimeter edge and a treatment opening, and wherein the at least two strained elastic layers are releasably attached together in a stacked configuration, a skin adhesive layer adhered to the bottom surface of the base elastic layer, a strain support releasably attached to the base elastic layer, wherein the strain support is configured to maintain the strains of the at least two strained elastic layers. A force per width level in the base elastic layer may be higher than a force per width level of any other of the at least two strained elastic layers. The base elastic layer may comprise at least 70% of a total force per width in the at least two strained elastic layers. The base elastic layer may comprise at least 90% of the total force per width in the at least two strained elastic layers. The base elastic layer may comprise a higher durometer material or a greater thickness than the other at least two strained elastic layers. The at least two strained elastic layers may further comprise at least one intermediate elastic layer, located in the stacked configuration between the top elastic layer and the base elastic layer. The perimeter edge of each of the at least two strained elastic layers may be offset from the perimeter edge of an adjacent strained elastic layer in the stacked configuration. The perimeter edge of each of the at least two strained elastic layers may be offset inward from the perimeter edge of an adjacent higher strained elastic layer in the stacked configuration. The perimeter edge of each of the at least two strained elastic layers may be offset outward from the perimeter edge of an adjacent higher strained elastic layer in the stacked configuration. The perimeter edge of each of the at least two strained elastic layers may be offset inward from the perimeter edge of an adjacent lower strained elastic layer in the stacked configuration. The size of each of the at least two strained elastic layers may be different. The size of each of the at least two strained elastic layers may be smaller than any adjacent lower strained elastic layer in the stacked configuration. The size of each of the at least two strained elastic layers may be larger than an adjacent higher strained elastic layer in the stacked configuration. The size of each of the at least two strained elastic layers may be smaller than any adjacent higher strained elastic layer in the stacked configuration. The size of each of the at least two strained elastic layers may be larger than an adjacent lower strained elastic layer in the stacked configuration. The device of claim 35, wherein at least one of the at least two strained elastic layers comprises a pull tab. Each pull tab of the at least one of at least two strained elastic layers may comprise a different pull tab size. The attachment of at least two strained elastic layers may utilize an anisotropic adhesive pattern. The attachments of the at least two strained elastic layers may comprises adhesive layers therebetween with a reduced amount of adhesive along an orthogonal direction to a strain direction of the strained layers. The orthogonal direction is a peel direction of the at least two strained elastic layers. The attachments of the at least two strained elastic layers may comprises a thinner adhesive layer than the skin adhesive layer of the strained base layer.

In still another embodiment, a treatment device is provided, comprising a strained elastic layer comprising an upper surface, a lower surface and an opening therebetween, a skin adhesive on the lower surface of the strained elastic layer, an infusion hub located on the upper surface of the strained elastic layer, with a catheter or needle extending through the opening of the strained elastic layer, fluid tubing attached to the infusion hub and in fluid communication with the catheter or needle, a strain support configured to maintain the strain in the strained elastic layer, and at least one pull tab configured to releasably attach the strained elastic layer and strain support together. The treatment device may further comprise an infusion set applicator that is releasably attached to the infusion hub. The device may further comprise two pull tabs located on opposite sides of the strained elastic layer. Each of the two pull tabs may comprise perforations configured to tear and so that the strained elastic layer and infusion hub can separate from the strain support.

In another example, a treatment device is provided, comprising a strained elastic layer comprising an upper surface, a lower surface and an opening therebetween, a skin adhesive on the lower surface of the strained elastic layer, an infusion hub located on the upper surface of the strained elastic layer, with a catheter or needle extending through the opening of the strained elastic layer, fluid tubing attached to the infusion hub and in fluid communication with the catheter or needle, a strain support configured to maintain the strain in the strained elastic layer, and at least one pull tab configured to releasably attach the strained elastic layer and strain support together. The treatment device may further comprise an infusion set applicator that is releasably attached to the infusion hub. The device may comprises two pull tabs located on opposite sides of the strained elastic layer. Each of the two pull tabs may comprise perforations configured to tear and so that the strained elastic layer and infusion hub can separate from the strain support.

In another example, a method for modulating tissue response at a target site is provided, comprising providing a strained elastic structure with an access opening and a support structure, placing the strained elastic structure against a target site, releasing the strained elastic structure from the support structure, and inserting an access structure into the target site, wherein the access structure is located in the access opening. The strained elastic structure may be an elastic sheet with an adhesive layer. Attaching the strained elastic structure to the target site may comprise adhering the strained elastic structure to a skin location. The support structure may comprise at least one pull tab, and releasing the strained elastic structure from the support structure may comprise actuating the pull tab to release the strained elastic structure from the support structure. The method may further comprise inserting the access structure through the access opening. The access structure may be a delivery tube, and wherein the method further comprises passing a sensor or infusion cannula using the delivery tube. The access structure is attached to a housing. The housing may comprise an adhesive. The housing may further comprise a support layer, and the adhesive is located on the inferior surface of the support layer. The method may further comprise adhering the housing to the elastic structure. The method may further comprise releasing the access structure from a delivery device after inserting the access structure into the target site. The method may further comprise aligning the delivery device with indicia or an alignment structure located on the strained elastic structure.

In another embodiment, a method of treating a therapeutic site is provided, comprising placing a first tensioning member at a first location next to a target site, wherein the first tensioning member is pre-tensioned along a first tensioning axis, placing a second tensioning member at a second location next to the target site, wherein the second tensioning member is pre-tensioned along a second tensioning axis and wherein the second location is spaced apart from the first location by a gap no greater than 20 mm and wherein the target site is located in the gap, and injecting or infusing a therapeutic agent at the target site. The first tensioning axis and the second tensioning axis may be parallel. The first tensioning member and the second tensioning member may be completely separate. The first and second tensioning members may be integrally formed with a predetermined longitudinal gap therebetween, the longitudinal gap comprising a longitudinal gap axis. The longitudinal gap axis may be located between the first and second tensioning axes. The longitudinal gap, the first tensioning axis and the second tensioning axis may each be parallel to each other. The predetermined longitudinal gap has an average of width of less than 20 mm, less than 10 mm, or less than 5 mm. The method may further comprise adhering an infusion set to the first and second tensioning members before using the infusion set to infuse the therapeutic agent.

In another embodiment, a method of treating lipodystrophy is provided, comprising applying an adhesive skin tensioning device to an injection or infusion site of a patient to reduce the risk of lipodystrophy. The injection or infusion site may be an insulin or insulin analogue injection or infusion site. The patient may be diabetic and the lipodystrophy may be lipohypertrophy. The patient may have no prior history of lipohypertrophy, or may have a prior history of lipohypertrophy. The method may further comprise reducing the risk of insulin resistance, and/or reducing the rate of insulin or insulin analogue dosage increase over a time period. The time period may be one year.

In another embodiment, a method of treating diabetes is provided, comprising applying an adhesive skin tensioning device to an injection or infusion site of diabetes patient to reduce the rate of insulin or insulin analog dosage increase over time.

In still another embodiment, a method of treating diabetes may be provided, comprising applying an adhesive skin tensioning device to an injection or infusion site of diabetes patient to improve glucose time-in-range. The glucose time-in-range may be a daily, weekly, or monthly glucose time-in-range.

In another example, a method of reducing diabetes treatment costs in a diabetic population may be provided, comprising applying an adhesive skin tensioning device to an insulin or insulin analogue injection or infusion site of diabetes patient to reduce the costs of blood glucose variability or serious adverse events.

In still another example, a method of treating a therapy site is provided, comprising adhering a multi-layer strained dressing to a treatment site, releasing the strain of the multi-layer strained dressing to transfer strain from the dressing to the treatment site to reduce tissue tension at the treatment site, attaching a first hub and a first catheter to the multi-layer dressing, delivering a therapeutic agent through the first hub and first catheter to the treatment site, removing the first hub and first catheter from the multi-layer dressing by removing a first layer from the multi-layer dressing, attaching a second hub and a second catheter to the multi-layer dressing, delivering the therapeutic agent through the second hub and second catheter to the treatment site, removing the second hub and second catheter from the multi-layer dressing by removing a second layer from the multi-layer dressing.

In another embodiment, a method of positioning an infusion set is provided, comprising adhering a strained skin tension off-loading device to a treatment location, wherein the skin tension off-loading device comprises a strained elastic layer with a treatment opening, a strain support and a protruding alignment structure surrounding the treatment opening, positioning an infusion set applicator over the treatment opening by using the alignment structure, actuating the infusion set applicator to decouple an infusion set hub from the infusion set applicator and to insert a catheter of the infusion set hub through the treatment opening, removing the infusion set applicator, and removing the strain support and protruding alignment structure from the strained skin tension off-loading device to release the strain in the strained elastic layer. The method may further comprise selecting the protruding alignment structure from a plurality of different protruding alignment structures and attaching the selected protruding alignment structure to the strain support. The protruding alignment structure may be integrally formed with the strain support.

According to some variations, the elastic device may be strained at different strain values during pre-conditioning.

In one embodiment, a method of treating subcutaneous tissue may be provided, comprising applying an adhesive skin tensioning device to a treatment site of a patient to reduce the development or progression of a subcutaneous lesion comprising calcifications, cellular proliferation or hypertrophy. The treatment site may be a device implantation, injection or infusion site. The subcutaneous lesion may be a lipodystrophy lesion. The lipodystrophy lesion may be a lipohypertrophy lesion. The injection or infusion site may be an insulin or insulin analogue injection or infusion site. The patient may be diabetic and the subcutaneous lesion may be lipohypertrophy. The patient may have no prior history of lipohypertrophy or a prior history of lipohypertrophy. The method may further comprise reducing the risk of insulin resistance, and/or reducing the rate of insulin or insulin analogue dosage increase over a time period. The time period may be one year. The infusion site may be a hemodialysis fistula or graft site. The injection site may be an oncologic therapy injection site. The oncology therapy injection site may be a pertuzumab and/or trastuzumab injection site. The treatment site may be an implantation site of an implantable pulse generator, implantable pacemaker or defibrillator. The treatment site may be an implantation site of a subcutaneous infusion port.

In another embodiment, a method of modifying drug pharmacokinetics is provided, comprising applying an adhesive skin tensioning device with a predetermined tension to an injection or infusion site of a therapeutic agent. The injection or infusion may be performed while the skin tensioning device activated at the injection or infusion site.

In still another embodiment, a method of treating diabetes is provided, comprising applying an adhesive skin tensioning device to an injection or infusion site of diabetes patient to improve or slow the progression of tissue stiffness in an injection or infusion site.

In another embodiment, a method of treating diabetes is provided, comprising applying an adhesive skin tensioning device to an injection or infusion site to increase the percentage of time-in-range of glycemic control. Time-in-range may be the percentage of time with blood glucose levels between 70 mg/dl and 180 mg/dl.

In another variation, a method of treating diabetes is provided, comprising applying an adhesive skin tensioning device to an injection or infusion site to decrease the percentage of time in hypoglycemia. Hypoglycemia may be a blood glucose levels less than 70 mg/dl.

In another variations, a method of treating diabetes is provided, comprising applying an adhesive skin tensioning device to an injection or infusion site to decrease the percentage of time in hyperglycemia. Hyperglycemia may be a blood glucose levels greater than 180 mg/dl.

In still another variation, a method of treating diabetes is provided, comprising applying an adhesive skin tensioning device to an injection or infusion site of diabetes patient to decrease variability in insulin absorption compared to untreated controls. The decrease in variability of insulin absorption may be a decreased coefficient of variation of insulin $C_{max}$ or $AUC_{INS}$ as measured by a hyperinsulinemic euglycemic clamp testing or mixed-meal tolerance testing.

In another variation, a method of treating diabetes is provided, comprising applying a tissue tensioning device to an injection or infusion site of diabetes patient to increase insulin absorption compared to untreated controls. The increased insulin absorption may be an increased insulin $c_{max}$ or $AUC_{INS}$ as measured by a hyperinsulinemic euglycemic clamp testing or mixed-meal tolerance testing.

In another example, a system for treating chronic injection sites is provided, comprising an adhesive tensionable elastic dressing, the dressing comprising a first attachment structure and a second attachment structure, and at least one injection template, comprising a plurality of injection openings, a first attachment opening and a second attachment opening, wherein the first attachment structure may be configured to form a releasable interlock with the first attachment opening, and wherein the second attachment structure may be configured to form a releasable interlock with the second attachment opening. The adhesive tensionable dressing may comprise a plurality of dressing openings, wherein at least one dressing opening may be aligned with each of the injection openings of the plurality of openings of the at least one injection template. The at least one injection template may comprise one injection template, and wherein each of the dressing openings of the plurality of dressing openings may be aligned with an injection opening of the plurality of openings of the one injection template. The at least one injection template comprises a plurality of injection templates. The plurality of injection templates consists of seven injection templates. The plurality of injection openings of each injection template of the plurality of injection templates may comprise a different location from the other injection templates of the plurality of injection templates. The at least one injection template may comprise one injection template. The plurality of injection openings of the one injection template may be arranged in a rectangular grid pattern. The plurality of injection openings of the one injection template may be arranged in a staggered grid pattern. A plurality of adhesive strips may be removably coupled to the plurality of injection openings. The number of the plurality of adhesive strips may be lower than a number of the plurality of injection openings. The number of the plurality of injection openings may be a three or four times multiple of the number of plurality of adhesive strips. The plurality of adhesive strips may be longitudinally aligned to a longitudinal axis of the injection template or transversely aligned to a transverse axis orthogonal to the longitudinal axis of the injection template. The plurality of adhesive strips may be parallel to each other, and not parallel to a longitudinal axis or transverse axis of the injection template. Each of the plurality of adhesive strips may extend beyond an edge of the injection template. The first attachment structure and the second attachment structures may have different shapes. The first attachment opening and the second attachment opening may have different shapes. The system may further comprising an applicator configured to maintain a predetermined tension in the tensionable tissue treatment device. The applicator may comprise a carrier sheet and optionally a release liner.

In another example, a system for treating chronic injection sites is provided, comprising an adhesive tensionable tissue treatment device comprising a plurality of injection openings surrounded by a plurality of removable adhesive rings, wherein the adhesive rings have a lower t-peel force than the adhesive tensionable tissue treatment device. The plurality of injection openings are arranged in a rectangular grid pattern. The system may further comprise an applicator configured to maintain a predetermined tension in the tensionable tissue treatment device.

In another variation, a method of treating injection sites is provided, comprising adhering a tensioned tissue treatment device to a skin surface, releasing some tension in the tensioned tissue treatment device to transfer tension force to the adhered skin surface, attaching a first injection template to the tensioned tissue treatment device, the first injection template comprising a plurality of needle insertion openings, inserting a first needle through a first needle insertion opening of the plurality of needle insertion openings, and detaching the first injection template from the tensioned tissue treatment device. The method may further comprise removing a first cover strip of the first injection template, wherein the first cover strip surrounds or covers the first needle opening. The method may also comprise reattaching the first injection template to the tensioned tissue device, inserting a second needle through a second needle insertion opening of the plurality of needle insertion openings, and detaching the first injection template, wherein the first cover strip also surrounds or covers the second needle insertion opening. Removing the first cover strip may be performed before inserting the first needle through the first needle insertion opening.

In another embodiment, an injection guide system is provided, comprising a plurality of injection guides, each injection guide comprising at least one opening and an adhesive lower surface, and the plurality of injection guides in a separated configuration with each injection guide being spaced apart from the other injection guides, an adhesive carrier sheet, the adhesive carrier sheet maintaining the plurality of injection guides in a separated configuration, and a release liner, the release liner removably adhered to the adhesive lower surfaces of the plurality of injection guides. The system may further comprise a plurality of adhesive injection guide covers, the plurality of adhesive injection guide covers releasably adhered to the plurality of injection guides and located between the plurality of injection guides and the adhesive carrier sheet. The system may further comprise a dressing comprising a plurality of dressing openings, wherein the plurality of dressing openings are configured to be in alignment with the at least opening of each injection guide of the plurality of injection guides. The plurality of injection guides may comprise adhesive foam strips. The adhesive lower surface of each injection guide may have an adhesive property stronger than the adhesive carrier sheet. The adhesive injection guide covers may have a stronger adhesive property than the adhesive carrier sheet. The adhesive property of the adhesive lower surface of each injection guide may be stronger than the adhesive injection guide covers.

In another embodiment, a method of preparing a dressing may be provided, comprising aligning a plurality of separate injection guides to a plurality of dressing openings on a dressing, wherein each injection guide comprises multiple openings, and adhering the plurality of separate injection guides to the dressing. Adhering the plurality of separate injection guides to the plurality of dressing openings may be performed so that the multiple openings of each injection guide are aligned to the dressing openings. The method may further comprise removing a release liner from the plurality of separate injection guides. The method may further comprise removing a carrier sheet from the plurality of separate injection guides after adhering the plurality of separate injection guides to the dressing. Adhering the plurality of separate injection guides to the dressing may be performed so the adhering of the plurality of separate injection guides is performed simultaneously. Each injection guide of the plurality of separate injection guides further comprises a removable guide cover.

BRIEF DESCRIPTION OF THE DRAWINGS

FIG. 15B is a bottom 15F perspective view of the dressing and packaging assembly of FIG. 15A in a strained configuration.

FIG. 15C is a bottom perspective view of the dressing and packaging assembly of FIG. 15A after removing the cover of the carrier, support or base.

FIG. 15D is a top perspective view of the device of FIG. 15A after removing the cover of the carrier, support or base.

FIG. 15E is a top perspective view of the device of FIG. 15A after removing the carrier, support or base.

FIG. 15F is a perspective view of a strained dressing after it is separated from the attachment sheets.

FIG. 15G is a perspective view of a dressing assembly with attachment sheets.

FIG. 15H is a perspective view of the dressing assembly of FIG. 15G with an attachment sheet peeled back.

FIG. 15I is a perspective view of the dressing assembly of FIG. 15G with an attachment sheet removed.

FIG. 15J is a cross section of the dressing assembly with attachment sheets of FIG. 15G.

FIG. 17A is a perspective view of a variation of a dressing assembly with removable attachment sheets.

FIG. 17B is a perspective view of the dressing assembly of FIG. 17A with a peeled removable attachment sheet.

FIG. 17C is a perspective view of the dressing assembly of FIG. 17A with a removed attachment sheet.

FIG. 17D is a cross section of the dressing assembly with attachment sheets of FIG. 17A.

FIG. 41B is a superior perspective view of the embodiment in FIG. 41A.

FIGS. 42A to 42C are superior perspective view of a method of using the combined infusion set and multiple tensioning layers depicted in FIGS. 41A and 41B.

FIGS. 43A to 43C are side elevational views of the method depicted in FIGS. 42A to 42C.

FIG. 44A is a detailed side elevational view of the method in FIG. 42A; FIG. 44B is a detailed view of the edges of the multiple tensioning layers in FIG. 44A.

FIGS. 46A to 46C are superior perspective view of a method of using the combined infusion set and multiple tensioning layers depicted in FIGS. 41A and 41B.

FIGS. 49A to 49E are front perspective, superior plan, rear perspective, side elevational and inferior plan views, respectively, of a skin tensioning device with pre-attached alignment structure to facilitate placement of an infusion set delivery system.

FIG. 52 is a schematic illustration of another exemplary embodiment of a skin tensioning system comprising two separate skin straining device placed on opposing sides of an injection or infusion site.

FIG. 53 is a schematic illustration of another exemplary embodiment of a skin tensioning system comprising interconnected lobes separated by a longitudinal gap or slot.

FIGS. 59B to 59E depicts the serial removal of the indicator strips.

FIG. 60A is a perspective view of another exemplary tensioned skin treatment system comprising removable injection templates. FIGS. 60B to 60D depict different injection templates that are usable with the system in FIG. 60A.

FIGS. 62B and 62C are perspective views of an additional skin treatment system comprising individual removable covers for each dressing opening.

FIG. 65D is an exploded view of the system in FIG. 65B, with a dressing.

FIG. 66E to 66H are side views depicting the use of the system to remove an infusion set from a dressing while leaving the dressing adhered to a subject. FIG. 66E to FIG. 66H correspond respectively to FIG. 66A to FIG. 66D.

FIGS. 68B to 68F are superior perspective views illustrating steps of removing the infusion set of FIG. 68A from the dressing.

FIG. 69B is a superior perspective view of the treatment system, of FIG. 69A. FIG. 69C is a superior perspective view of the system in FIGS. 69A and 69B, with the infusion set connector and tubing being removed. FIG. 69D is a superior perspective view of the system in FIGS. 69A-69C, with the infusion set connector and tubing removed and the infusion hub in a secured position on dressing connectors. FIG. 69E is a superior perspective view of the system in FIGS. 69A-69D, with the infusion hub rotated to an unsecured position and being removed from dressing connectors FIG. 69F is a superior perspective view of the dressing and dressing connector with the infusion hub removed. FIG. 69G is a superior view of an infusion hub engaged with a dressing connector. FIG. 69H is a cross section of FIG. 69G along the lines A-A. FIG. 69I is a side view of an infusion hub engaged with a dressing connector. FIG. 69J is a partial cross section inferior view of the infusion hub and dressing connector of FIG. 69I. FIG. 69K is a side cross sectional view of the infusion housing and hub.

FIG. 70F is a superior perspective cross section of the system of FIG. 70G.

DETAILED DESCRIPTION

Figure 1:
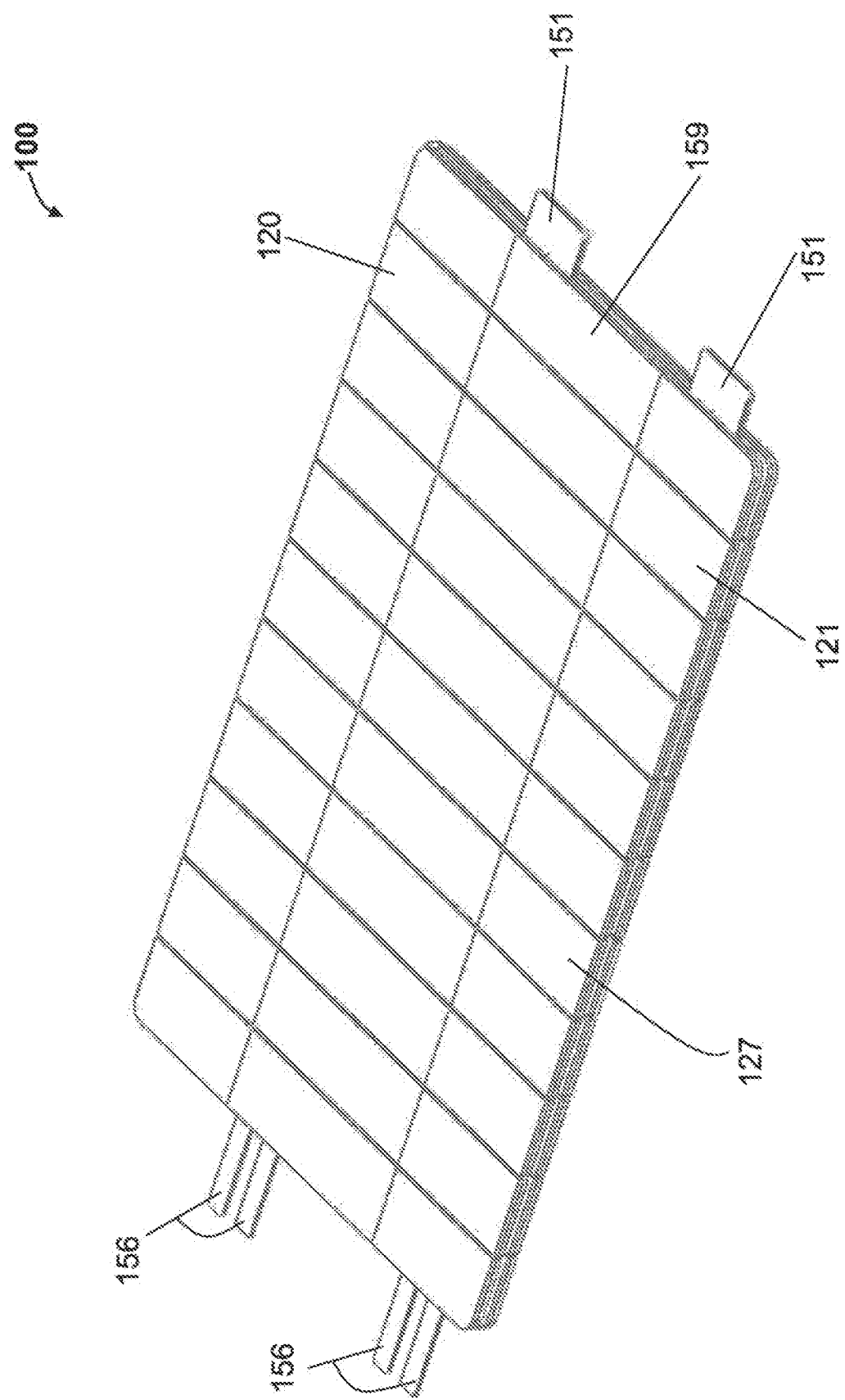
FIG. 1 is a perspective view of a variation of a dressing and packaging assembly in a closed configuration.

Previous attempts to treat scars and keloids have included surgery, silicone dressings, steroids, x-ray irradiation, and cryotherapy. Each of these techniques has disadvantages. Perhaps the biggest disadvantage is that none of them effectively prevent or ameliorate the formation of scars or keloids in the first instance. That is, these techniques have primarily been used to treat scars after they are already well established.

Unloading of exogenous and/or endogenous stress in the vicinity of the wound may ameliorate the formation of scars, hypertrophic scars, or keloids. The mechanical environment of an injury may be an important factor in tissue response to that injury. The mechanical environment includes exogenous stress (i.e., physiological stress which includes stress transferred to the wound via muscle action or physical body movement) and endogenous stress (i.e., dermal stress originating from the physical properties of the skin itself, including stress induced at the wound site due to swelling or contraction of the skin). The devices, dressings, kits and methods described herein may control or regulate the mechanical environment of a skin including but not limited to the mechanical environment of a wound. The devices, dressings, kits and methods described herein may also control or regulate the mechanical environment to ameliorate scar and/or keloid formation. The mechanical environment of skin may include stress, strain, or any combination of stress and strain. The control of a wound's mechanical environment may be active or passive, dynamic (e.g., by applying an oscillating stress) or static. The stresses and strains acting on the wound may involve the layers of the skin, such as the outer stratum corneum, the epidermis and dermis, as well as the underlying connective tissue layers, such as the subcutaneous fat. Devices and methods described here may shield a wound from its mechanical environment. The term "shield" is meant to encompass the unloading of stress experienced by the wound as well as providing a physical barrier against contact, contaminants, and the like. The devices and methods described here may shield a wound by unloading the wound and surrounding tissues from endogenous stress and/or exogenous stress. Thus, devices and methods described here may reduce the stress experienced by a wound and surrounding tissues to a lower level than that experienced by normal skin and tissue. Unloading of exogenous and/or endogenous stress in the vicinity of the wound may ameliorate the formation of scars, hypertrophic scars, or keloids.

A cell's external mechanical environment may trigger biological responses inside the cells and change cell behavior. Cells can sense and respond to changes in their mechanical environment using integrin, an integral membrane protein in the plasma membrane of cells, and intracellular pathways. The intracellular pathways are initiated by receptors attached to cell membranes and the cell membrane that can sense mechanical forces. For example, mechanical forces can induce secretion of cytokines, chemokines, growth factors, and other biologically active compounds that can increase or trigger the inflammatory response. Such secretions can act in the cells that secrete them (intracrine), on the cells that secrete them (autocrine), on cells surrounding the cells that secrete them (paracrine), or act at a distance from the point of secretion (endocrine). Intracrine interference can alter cell signaling, which can in turn alter cell behavior and biology including the recruitment of cells to the wound, proliferation of cells at the wound, and cell death in the wound. In addition, the extracellular matrix may be affected.

As noted above, the wound healing process may be characterized in three stages: early inflammatory phase, the proliferative phase, and remodeling. The inflammatory phase occurs immediately after injury and typically lasts about two days to one week. Blood clotting takes place to halt blood loss and factors are released to attract cells that can remove debris, bacteria and damaged tissue from the wound. In addition, factors are released to initiate the proliferative phase of wound healing. In the proliferative phase, which lasts about four days to several weeks, fibroblasts grow and build a new extracellular matrix by secreting collagen and proteoglycans. At the end of the proliferative phase, fibroblasts can act to contract the wound further. In the remodeling phase, randomly oriented collagen is organized and crosslinked along skin tension lines. Cells that are no longer needed can undergo apoptosis. The remodeling phase may continue for many weeks or months, or indefinitely after injury. Scars typically reach about 75-80% of normal skin breaking strength about 6-8 weeks after injury. In general, scars typically have a triangular cross-section. That is, a scar is usually smallest in volume near the skin surface (i.e., stratum corneum and epidermis) and increases in volume as it progresses into the deeper layers of the dermis.

There are three common possible outcomes to a wound healing process. First, a normal scar can result. Second, a pathologic increase in scar formation can result, such as formation of a hypertrophic scar or a keloid. Third, the wound may not heal completely and become a chronic wound or ulcer. The devices, kits and methods described herein can ameliorate the formation of any type of scar. In addition, the devices, kits and methods described here can be adapted for a variety of wound sizes, and for different thicknesses of skin, e.g., the devices may be configured for use in different areas of the body. In addition, the devices, kits and methods described here can be adapted to ameliorate scar formation in any type of skin, e.g., body location, age, race, or condition.

Without wishing to be bound by any particular theory, we believe that mechanical strain acting on a wound or incision early in the proliferative phase of the wound healing process may inhibit cellular apoptosis, leading to a significant accumulation of cells and matrix, and hence increased scarring or the production of hypertrophic scars. Given the underlying similarities between hypertrophic scars and keloids with respect to excessive matrix formation, we believe that the devices and methods described herein may also be useful in preventing and treating keloids by offloading or neutralizing at least some of the strain that may be acting on the wound or incision. This tensile strain may be exogenous and/or endogenous strain, and may include but is not limited to the strain from the intrinsic tensile forces found in normal intact skin tissue.

A number of wound dressings have backings, adhesive liners and/or packaging that are removed prior to application of a wound dressing. Many existing dressings can be clumsy to orient and apply and can have a tendency to fold and adhere to themselves.

Devices, kits and methods described herein may treat skin at a skin site ("skin treatment device"), including without limitation, to ameliorate the formation of scars at wound sites by controllably stressing or straining the epidermis and deeper layers of dermal tissue at or near a skin site, i.e., at or adjacent a wound or treatment site of a subject's skin, thereby reducing tensile or compressive stress at the skin site. The stress at the skin site may be reduced to levels below that experienced by normal skin and tissue. The stress or strain may be applied to surrounding tissue in one, two, or more directions to reduce endogenous or exogenous stress at the skin site in one, two or more directions. Thus, devices and methods described herein may reduce the stress experienced by skin and/or a wound and surrounding tissues in order to treat a subject. The device may also assist in preventing or reducing the incidence of wound dehiscence.

Devices, kits and methods described herein may provide a packaging and/or applicator for a dressing. According to one variation, the packaging and/or applicator is configured to provide quick or easy preparation and/or application of a dressing. While some examples herein specifically refer to a packaging that also acts as a tensioning device to pre-strain a dressing, other dressings that are not pre-strained and/or strained prior to application may be provided in accordance with one or more variations or embodiments. The packaging may also operate as an applicator where one or more elements of the packaging may be used to position and/or apply the dressing to the skin of a subject.

Devices kits and methods described herein may be for the preparation and/or application of a dressing. Such preparation may include but is not limited to, for example, removal of an adhesive liner, straining or tensioning a dressing, orienting a dressing for application and/or applying a medicament or other material to a portion of the dressing prior to application.

Backings, adhesive liners or release layers, and/or other packaging may provide some structural stability to a flexible wound dressing. However, when removed, the flexible wound dressing can be somewhat clumsy to use because it may fold and adhere to itself or the user, or otherwise provide for difficult positioning over the wound. Also the act of pulling or removing the liner and reorienting the dressing to the patient may increase the tendency to fold or flop. Furthermore, because of the folding or floppiness of the dressing, during adhesive removal and subsequent reorientation, the user has a significant possibility of compromising the sterility of a portion of the device to be applied to a wound site.

According to another variation, a packaging or applicator is configured to provide support for the dressing after the dressing is prepared and while the dressing is applied to a subject. According to some variations, a backing provides structural support or stability of the dressing as and/or after an adhesive liner is released. According to some variations, a dressing and packaging is configured to be pre-oriented in a position facing a wound. i.e., for immediate application when and after the wound device is prepared for application. According to some variations, the packaging applicator is configured to be used with one hand to orient and/or apply the device to the skin of a subject.

According to some variations, the packaging dressing carrier, support, base tensioning device or applicator tensioning device and/or applicator provide a release mechanism to separate the applied dressing from the packaging and/or applicator after the dressing is applied to the skin. According to a variation, a dressing may be prestrained and coupled to a dressing carrier, support, base tensioning device or applicator, for example as set forth in U.S. Provisional Application Ser. No. 61/512,340 filed on Jul. 17, 2011 and incorporated in its entirety herein by reference. One or more dressing releases described herein may be used with a dressing carrier, support, base tensioning device or applicator.

In some further variations, the dressing or one or more adhesive regions of the dressing may be released, i.e., separated, from the liner by opening a packaging or applicator. According to some variations, a book-like packaging is provided with a cover, and a base to which a dressing is removably attached. When or as the cover is opened, the liner may be manually or automatically released from the adhesive of the dressing. According to variations, a liner is attached to the cover and will expose an adhesive side of a dressing when the cover is lifted or opened. The base may be configured to provide structural support to the dressing while the liner is removed and/or while the dressing is applied to the skin of a subject.

According to some variations, the packaging, tensioning device, dressing carrier, support, base or applicator may further comprise an opening, a window, or a clear or semi-opaque portion through which a wound, incision or other location may be visualized as the dressing is applied to the skin. According to some variations, the window guides the application of a dressing so that there is an optimal or desired distance between the wound and the edges of the dressing and/or so that the dressing is in an optimal location for unloading skin stresses.

According to some variations the applicator, tensioning device, packaging or carrier, support, or base may provide varied or variable flexibility to allow the dressing to be shaped when applied to various body locations or contours.

According to some variations, a packaging or applicator is more rigid or provides sufficient column strength in at least a first direction to be supportive of a dressing, while being relatively more flexible and less rigid in at least second direction to provide for a more conforming application to a curved or shaped skin surface of a subject or to permit curvature or shaping of the dressing where it is applied. The first and second directions may or may not be orthogonal to each other. According to some variations, a packaging applicator, tensioning device or dressing carrier, support or base is sufficiently rigid or supportive of a dressing while permitting shaping of the dressing, According to some variations, the carrier or support which may include a base and/or a cover may comprise segments of relatively more rigid material flexibly coupled to adjacent segments to provide flexibility to permit shaping of packaging/applicator and/or dressing while providing sufficient support of the dressing during application. According to some variations, segments are coupled to adjacent segments by way of a flexible material, such as a low-density polyethylene (LDPE) material, or a composite of adhesive and a thinner more flexible substrate. Alternatively, segments may be formed as a structure by manufacturing a substrate with cut-outs, slots, grooves, scoring or other openings or variations in thickness of the substrate at different locations.

The packaging, applicator, tensioning device, or dressing carrier may have elements or features the provide flexibility in one direction orthogonal to the plane of the support while limiting flexibility in another direction orthogonal to the plane of the support. According to some variations, the flexible elements may limit flexibility when the device is being strained and permit flexibility when the device is being applied to the skin. Each of the elements may permit flexing in a different direction than one or more of the other elements. Flexible elements may be straight, or shaped according to a desired application or location of placement.

According to variations, flexible elements are provided in combination with support elements that provide sufficient support to allow a user to maintain the dressing in a strained configuration. According to variations, one or more elements may be provided to maintain a strained dressing in a strained configuration, for example a securing element that secures the dressing in a strained configuration until it is applied to a subject and is released from the carrier, support, base tensioning device or applicator. For example, after straining the dressing, the dressing may be adhered or attached to one or more elements of a dressing, support, base tensioning device or applicator or dressing assembly until it is released from the carrier, support, base tensioning device or applicator or assembly.

According to some variations, the applicator may be further used to help reduce bleeding, e.g., by allowing application of a compressive force using a support structure while or after the device is applied. One or more hemostatic or coagulative agents may be applied to, or otherwise integrated with dressing to help reduce bleeding. Potential agents include chitosan, calcium-loaded zeolite, microfibrillar collagen, cellulose, anhydrous aluminum sulfate, silver nitrate, potassium alum, titanium oxide, fibrinogen, epinephrine, calcium alginate, poly-N-acetyl glucosamine, thrombin, coagulation factor(s) (e.g. II, VII, VII, X, XIII, Von Willebrand factor), procoagulants (e.g. propyl gallate), anti-fibrinolytics (e.g. epsilon aminocaproic acid), and the like. In some variations, the agents may be freeze-dried and integrated into the dressing and activated upon contact with blood or other fluid. In some further variations, an activating agent may be applied to the dressing or the treatment site before the dressing is used on the subject. In still other examples, the hemostatic agent may be applied separately and directly to the wound before application of the dressing, or after application to the dressing via a catheter or tube. The devices may also comprise one or more other active agents that may be useful in aiding in some aspect of the wound healing process. For example, the active agent may be a pharmaceutical compound, a protein (e.g., a growth factor), a vitamin (e.g., vitamin E), or combinations thereof. A further example of such medicament may include, but is not limited to various antibiotics (including but not limited to cephalosporins, bacitracin, polyxyxin B sulfate, neomycin, polysporin), antiseptics (such as iodine solutions, silver sulfadiazine, chlorhexidine), antifungals (such as nystatin), antiproliferative agents (sirolimus, tacrolimus, zotarolimus, biolimus, paclitaxel), grow factors (such as VEGF) and other treatments (e.g. botulism toxin. Of course, the devices may comprise more than one medicament or agent, and the devices may deliver one or more medicaments or agents.

According to one variation, the applicator and or packaging may be sufficiently supportive or rigid to hold a dressing's form so that it is easy to manipulate. According to a variation, the applicator may be sufficiently wider and/or longer or have a sufficiently larger area than a dressing so that it may provide sterile application and/or one-handed application. According to variations, a support structure is provided for a dressing. According to a variation, a margin is provided as a support structure between the dressing or dressing adhesive and one or more edge portions of the support structure. Such margins provide a supported edge or area to grasp or manipulate the dressing or its carrier, base or support, without necessitating or creating a greater likelihood of inadvertent user contact with the adhesive.

According to some variations, the packaging or applicator may also be used to strain a dressing prior to application to provide a dressing configured to ameliorate scar or keloid formation.

Devices are described here that may be used for ameliorating the formation of scars and/or keloids at a skin or wound site. The scars may be any type of scar, e.g., a normal scar, a hypertrophic scar, etc. In general, the devices may be configured to be removably secured to a skin surface near a wound. The devices may shield the skin or wound from endogenous stress and/or exogenous stress. In some variations, the devices may shield the skin or wound from endogenous stress without affecting exogenous stress on the skin or wound, e.g., devices that modify the elastic properties of the skin, etc. In other variations, the devices may shield the skin or wound from exogenous stress without affecting endogenous stress on the wound. Such variations may include situations where the musculature and surrounding skin or wound tissue has been paralyzed, e.g., through the use of botulinum toxin or the like. In still other variations, the devices shield the skin or wound from both endogenous and exogenous stress.

The devices or dressings described herein may treat skin at a skin site including without limitation to ameliorate the formation of scars at wound sites by controllably stressing or straining the epidermis and deeper layers of dermal tissue at or near a skin site, thereby reducing tensile or compressive stress at the skin site itself. The stress at the skin site may be reduced to levels below that experienced by normal skin and tissue. The stress or strain may be applied to surrounding tissue in one, two, or three directions to reduce endogenous or exogenous stress at the skin site in one, two or three directions. The physical characteristics of the dressing and/ or the method of applying the dressing may also be further configured to resist or reduce the rate of skin stripping or tension blistering from the application of strain to the incision site. For example, the stretching of the adhesive regions when applied to the skin surface may result in an increased tissue density under the adhesive region. This may be the result of generally planar, tangential or parallel compression of skin tissue that is directly attached to that adhesive region, resulting from the relaxation of the adhesive region. In some examples, this tissue compression may reduce the risk of tissue stripping and/or blistering of skin in direct contact with the adhesive, in contrast to bandage "strapping" where one end of a bandage is adhered to the skin and then tensioned or pulled across a wound before the other end is attached to the skin on the opposite side of the wound. Bandage "strapping", while generating tension in the bandage during the application, may simultaneously generate a relatively high tissue strain at the first adhesion site. This high tissue strain then decreases when the bandage is attached to the skin at a second adhesion site as the high peak stresses are redistributed along the skin under the bandage. In contrast, when a pre-strained bandage is applied to the skin, little if any strain may be transferred or generated in the skin as the adhesive regions are applied to the desired locations. When the pre-strained bandage is permitted to relax, however, the strain (or peak strain) in the skin may be increased. Thus, with a pre-strained bandage, temporary high tissue strain may be avoided or otherwise reduced during the application procedure. In other variations, however, the dressing may also be applied to the skin by strapping, or by a combination of pre-straining and strapping.

The dressing may comprise an elastic member, such as a sheet of elastic material. The elastic material of the dressing may comprise a single layer of material or multiple layers of the same or different materials. The material may have any of a variety of configurations, including a solid, foam, lattice, or woven configuration. The elastic material may be a biocompatible polymer, e.g., silicone, polyurethane, TPE (thermoplastic elastomers), synthetic rubber or co-polyester material. The thickness of polymer sheets may be selected to provide the dressings with sufficient load carrying capacity to achieve desired recoverable strains, and to prevent undesired amounts of creep deformation of the dressings over time. In some variations, the thickness across dressings is not uniform, e.g., the thickness across the dressing may be varied to change the stiffness, the load carrying capacity, or recovery strains in selected orientations and/or locations. The elastic material of the exemplary dressing may have a thickness in the range of about 50 microns to 1 mm or more, about 100 microns to about 500 microns, about 120 microns to about 300 microns, or in some variations about 200 microns to about 260 microns. The exemplary dressings have an edge thickness of about 500 microns or less, 400 microns or less, or about 300 microns or less may exhibit less risk of skin separation from inadvertent lifting when inadvertently brushed against clothing or objects. In some variations, the dressings are tapered near the edges to reduce thickness. A tapered edge may also ameliorate peak tensile forces acting on skin tissue adjacent to the adhesive edges of the dressing. This may or may not reduce the risk of skin blistering or other tension-related skin trauma. In other variations, the edges of the dressing may be thicker than the middle of the dressing. It is hypothesized that in some configurations, a thicker dressing edge may provide a relative inward shift of the location of the peak tensile forces acting near the dressing edge, compared to dressings of uniform thickness. The elastic material may have a load per width of at least 0.35 Newtons per mm at an engineering strain of 60% or a load per width of at least 0.25 Newtons per mm at an engineering strain of 45%. The elastic material may have a load per width of no greater than about 2 Newtons per mm at the engineering strain of about 45% to 60%, about 1 Newtons per mm at the engineering strain of about 45% to 60%, about 0.7 Newtons per mm at the engineering strain of about 45% to 60%, or no greater than about 0.5 Newtons per mm at the engineering strain of about 45% to 60%. The system elastic material may have a load per width that does not decrease from an engineering strain of 0% to 60%, a load per width plot that increases linearly from an engineering strain of 0% to 60%, or a load per width plot that is not convex from an engineering strain of 0% to 60%. The elastic material may comprise an adhesive configured to maintain a substantially constant stress in the range of 200 kPa to about 500 kPa for at least 8 hours when strained to an engineering strain of about 20% to 30% and attached to a surface. The elastic material may comprise an adhesive configured to maintain a substantially constant stress in the range of 200 kPa to about 400 kPa for at least 8 hours when strained to an engineering strain of about 20% to 30% and attached to a surface. The substantially constant stress may vary by less than 10% over at least 8 hours, or by less than 5% over at least 8 hours.

Although the depicted dressings may have a generally rectangular configuration with a length and/or width of about 160 mm to about 60 mm, in other variations the dressing may have any of a variety of lengths and widths, and may comprise any of a variety of other shapes. Also, the corners of the dressing may be squared or rounded, for example. The lengths and/or widths of an exemplary dressing may be in the range of about 5 mm to about 1 meter or more, in some variations about 20 mm to about 500 mm, and in other variations about 30 mm to about 50 mm, and in still other variations about 50 mm to about 100 mm. In some variations, the ratio of the maximum dimension of the dressing (e.g. its length) to an orthogonal dimension to the maximum dimension (e.g. width), excluding the minimum dimension of the dressing (e.g. the thickness), may be in the range of about 1:3, about 1:2, about 1:1, about 2:1, about 3:1, about 4:1 about 5:1, about 6:1, about 7:1, about 8:1, about 9:1 or about 10:1 or greater. In some variations, the strain axis of the dressing in use may be oriented with respect to the maximum dimension or to the orthogonal dimension to the maximum dimension. In some variations, the final compressive stress and strain imposed onto the skin by the elastic material may be the result of the dynamic equilibrium between the tensile stress in the skin and the elastic material of the dressing. The skin at the skin site typically comprises an inherent tension that stretches incision site, whether or not any tissue was excised from the skin site. The elastic material and the adhesive region may be configured to be applied to a skin location so that when the dressing is stretched to a particular tension and then adhered to the incision site, tensile stress in the dressing is transferred to the incision site to compress the tissue directly under the dressing along a tangential axis to the skin surface, the stress and strain imposed onto the skin location has a net or resultant orientation or axis is also generally tangential or planar to the elastic material and/or the outer surface of the skin location, with a similar axis to the orientation or axis of the tensile stress in the dressing. The tension in the dressing will relax to a tension level that maintains equilibrium with increased tension in the skin adjacent to the dressing. The application of the dressing to the skin location may involve the placement of the dressing without overlapping or being wrapped onto itself, e.g. wherein only adjacent regions of the dressing are interconnected and wherein non-adjacent regions of the dressing are not interconnected. The actual amount of stress and strain imposed on the skin may vary, depending upon the particular person, skin location, the thickness or various mechanical characteristics of the skin layers (e.g. epidermis, dermis, or underlying connective tissues), and/or the degree of pre-existing scarring, for example. In some further variations, the wound treatment dressing may be selected or configured for use at a specific body location, such as the scalp, forehead, cheek, neck, upper back, lower back, abdominal region, upper torso (including but not limited to the breast folds), shoulder, upper arm, lower arm, palm regions, the dorsum of the hand, finger, thigh, lower leg, the dorsum or plantar surface of the foot, and/or toe. Where applicable, some body regions may be further delineated into anterior, posterior, medial, lateral, proximal and/or distal regions, e.g. the arms and legs.

The dressing may be configured to impose a skin strain in the range of about 10% to about 60% or more, in other configurations about 15% to about 50%, and in still other configurations, about 20% to about 30% or about 40%. To achieve the desired degree of skin strain, the dressing may be configured to undergo elastic tensile strain in the range of about 20% to about 80% or more, sometimes about 30% to about 60%, and other times about 40% to about 50% or about 60%. The dressing may comprise any of a variety of elastic materials, including but not limited to silicones, styrenic block copolymers, natural rubbers, fluoroelastomers, perfluoroelastomers, polyether block amides, thermoplastic elastomers, thermoplastic polyurethane, polyisoprene, polybutadiene, and the like. The material of the exemplary dressing may have a Shore A durometer in the range of about 20 to about 90, about 30 to about 80, about 50 to about 80. The exemplary dressing was constructed of MED 82-5010-05 by NUSIL TECHNOLOGY LLC (Carpinteria, CA). Other examples of suitable materials are described in U.S. application Ser. No. 11/888,978, which was previously incorporated by reference in its entirety.

When the dressing is applied to a skin location and allowed to at least partially recover to its base configuration, the recovery level or equilibrium level of strain in the dressing may be in the range of about 4% to about 60% or more, in other configurations about 15% to about 50%, and in still other configurations, about 20% to about 30% or about 40%. The ratio between the initial engineering tensile strain placed onto the dressing before recovery and the resulting engineering compressive strain in the skin may vary depending upon the skin type and location, but in some examples, may be about 2:1. In other examples, the ratio may be in the range of about 4:1 to about 5:4, about 3:1 to about 5:3, or about 5:2 to about 2:1. These skin strain characteristics may be determined with respect to a reference position of the body or body part, e.g. anatomical position, to facilitate reproducible measurements. The particular degree of strain may be characterized as either an engineering strain or a true strain, but may or may not be calculated based upon or converted from the other type of strain (e.g. the strain may be based upon a 45% engineering strain that is converted to a true strain).

In some further variations, one or more characteristics of the elastic material may correspond to various features on the stress/strain curve of the material. For example, the engineering and true stress/strain curves for one specific example of the dressing comprises a material that exhibits an engineering stress of about 1.2 MPa at about 60% engineering strain, but in other examples, the engineering stress may be in the range of about 900 KPa to about 3.5 MPa, about 1 MPa to about 2.2 MPa, about 1 MPa to about 2 MPa, about 1.1 MPa to about 1.8 MPa, about 1.1 MPa to about 1.5 MPa, about 1.2 MPa to about 1.4 MPa. When unloading or relieving stress from the dressing, the material may be configured with an engineering stress of about 380 KPa at about 40% engineering strain, but in other examples, the engineering stress during unloading of the material to about a 40% strain may be in the range of about 300 KPa to about 700 KPa, about 325 KPa to about 600 KPa, about 350 KPa to about 500 KPa, or about 375 KPA to about 425 KPa. When unloading the material to an engineering strain of about 30%, the material exhibits an engineering stress of about 300 KPa, but in other examples, the engineering stress when unloading the material to about 30% strain may be in the range of about 250 KPa to about 500 KPa, about 275 KPa to about 450 KPa, about 300 KPa to about 400 KPa, or about 325 KPA to about 375 KPa. When unloading to an engineering strain of about 20%, the material may have an engineering stress of about 100 KPa, but in other examples, the unloading engineering stress at about 20% may be in the range of about 50 KPa to about 200 KPa, about 75 KPa to about 150 KPa, or about 100 KPa to about 125 KPa. In some examples, the material may be configured to at least achieve a specific range or level of engineering stress at each of the specified engineering strain levels described above, but in other examples, the material may be configured for lower levels of maximum engineering strain, e.g. up to about 30% or about 40%.

In some examples, certain portions of the stress/strain curve may have a particular morphology. For example, for a particular level of maximum strain the loading curve may be generally linear on the corresponding true stress/strain curve. In an example using a dressing described herein, up to a true strain of about 45%, the loading curve had a generally linear configuration. In other examples, the configuration may only be linear along a portion of the loading curve or may be curved along the entire loading curve. Where the loading curve is non-linear, the loading curve may be convex, concave or both. Also, in some examples, the tangent line of the loading curve (i.e. the line between the two triangles) may also be generally co-linear.

In some variations, the elastic material comprises a material having an elastic modulus E of at least about 1 MPa, about 1.5 MPa, about 2 MPa, about 2.5 MPa, about 3 MPa, about 3.5 MPa, about 4 MPa, about 5 MPa, about 6 MPa, about 7 MPa, about 8 MPa, about 9 MPa or at least about 10 MPa or greater. The material elastic modulus E may be no greater than about 10 MPa, about 9 MPa, about 8 MPA, about 7 MPa, about 6 MPa, or about 5 MPa, or about 4 MPa.

In addition to the absolute stress levels at certain strain levels described above, the material may also be characterized with respect to the ratio between a) the stress to achieve a particular strain during loading, and b) the stress at the same strain during unloading. For example, the material may have a ratio of at least 4:1 to about 3:2 at each of the 20%, 30% and 40% strain levels, but in other examples, the material may exhibit these ratios only at 20%, at 30%, or at 40% strain levels, or at both 20% and 30% but not 40%, or at both 30% and 40% but not 20%. In other examples, the ratio at one, some or all of the strain levels may be in the range of about 3:1 to about 2:1, or about 5:2 to about 2:1.

In some examples, the elastic material of the dressing may be configured under testing conditions to achieve a stable level of stress at a constant strain, e.g. the material exhibits a limited amount of stress relaxation over a particular period of time and at a particular level of strain. The period of time may be at least about 8 hours, about 12 hours, about 18 hours, about 24 hours, about 36 hours, about 48 hours, about 72 hours, about 4 days, about 5 days, about 6 days, or about a week or more. The level of strain may be about 10%, about 20%, about 30%, about 40%, about 50%, about 60%, about 70%, or about 80% or more. The stress of the exemplary dressing over various time curves may be configured to maintain an engineering stress of about 300 KPa at an engineering strain of about 30% without noticeable deviation over a period of about 1 hour, about 2 hours, about 3 hours, about 4 hours, about 5 hours, about 6 hours, about 7 hours, or about 8 hours or more. The stresses at 10% strain, 20% strain, and at 40% may be lower or higher.

In some variations, the elastic material or the dressing may be configured under testing conditions to maintain a particular minimum level of stress when held at a constant strain over a particular time period. In an example to assess the ability of a backing material to maintain a stress and strain on skin over time, engineering strains were measured while each backing material was tensile strained to 60% at a rate of 100 microns per second and held for 10 minutes, and then dropped to a strain of 30% at a rate of 100 microns per second and held for 9 hours. For example, the exemplary dressing is able to maintain an engineering stress level of about 350 KPa at an engineering strain of 30%. In some other examples, the minimum level of stress may be about 100 KPa, about 120 KPa, about 140 KPa, about 160 KPa, about 180 KPa, about 200 KPa, about 220 KPa, about 240 KPa, about 260 KPa, about 280 KPa, about 300 KPa, about 320 KPa, about 340 KPa, about 360 KPa, about 380 KPa, about 400 KPa, about 420 KPa, about 440 KPa, about 460 KPa, about 480 KPa, about 500 KPa, about 600 KPa, about 700 KPa, about 800 KPa, about 900 KPa or about 1000 KPa or greater. The level of constant strain may be different in other configuration, with a level of about 15%, about 20%, about 25%, about 30%, about 35%, about 40%, about 45%, about 50%, about 55%, about 60%, about 65%, about 70%, about 75%, or about 80%. The time period over which the dressing is able to maintain a stress level may be at least about 2000 seconds, about 3000 seconds, about 4000 seconds, about 5000 seconds, about 6000 seconds, about 7000 seconds, about 8000 seconds, about 9000 seconds, about 10000 seconds, about 20000 seconds, about 30000 seconds, about 40000 seconds, about 50000 seconds, about 60000 seconds, about 70000 seconds, about 24 hours, about 36 hours, about 48 hours, about 72 hours, about 4 days, about 5 days, about 6 days, about 7 days, about 10 days, about 2 weeks, about 1 month or more. In some variations, the dressing, the elastic material and/or the adhesive material is configured to exhibit less than about a 15% change in stress or strain level over the particular period when applied to a skin surface or test surface. In other examples, the degree of change may be about 12%, about 10%, about 8%, about 6%, about 5%, about 4%, about 3%, or about 2% or less. The stress or strain may be an engineering stress or strain, and/or a true stress or strain.

The adhesive used may be, for example, a pressure activated adhesive (PSA), as a silicone, acrylic, styrene block copolymer, vinyl ether, nitrile or other PSA. In other variations, a non-pressure sensitive adhesive may be used, including but not limited a heat or light-cured adhesive. The pressure sensitive adhesive may be made from, e.g., polyacrylate-based, polyisobutylene-based, silicone-based pressure sensitive adhesives, synthetic rubber, acrylic, and polyisobutylene (PIB), hydrocolloid, and the like. The T-peel release force and blunt probe tack force of the adhesive may be measured by a standardized test method, such as ASTM D1876 and ASTMD2979 or other appropriate method. In some variations, the T-peel release force or blunt probe tack test value of the adhesive is configured to maintain loads of at least about 50 mPa/mm for at least about 24 hours, about 48 hours, about 72 hours, about 1 week, about 2 weeks, about 3 weeks, about 4 weeks or more. In other variations, the loads may be at least about 75 mPa/mm, about 100 mPa/mm, about 125 mPa/mm, or at least about 150 mPa/mm over the particular time period. The degree of adhesion (e.g.

as measured by the T-peel release force or blunt probe tack test value) may vary depending upon the degree of strain placed onto the skin or incision site, and in some variations, these time periods may be based upon an average skin strain of about 10%, about 20%, about 30%, about 40%, or about 50% or more. In some variations, the adhesive may have a T-peel release force of at least about 150 kg/m, about 160 kg/m, about 170 kg/m, about 180 kg/m, about 190 kg/m, about 200 kg/m, about 210 kg/m, about 220 kg/m, about 230 kg/m, about 240 kg/m, about 250 kg/m, about 260 kg/m, about 270 kg/m, about 280 kg/m, about 290 kg/m, about 300 kg/m, about 310 kg/m, about 320 kg/m, about 330 kg/m, about 340 kg/m, about 350 kg/m, about 400 kg/m, about 450 kg/m, or at least about 500 kg/m or higher. In some further variations, the T-peel release force may be no greater than about 1000 kg/m, about 900 kg/m, about 800 kg/m, about 700 kg/m, about 600 kg/m, about 500 kg/m, about 400 kg/m or about 300 kg/m. The blunt probe tack test value of the adhesive may be at least about 0.50 kg, about 0.55 kg, about 0.60 kg, about 0.65 kg, about 0.70 kg or about 0.75 kg or higher, and may be no greater than about 1 kg, about 0.9 kg, about 0.8 kg, about 0.7 kg, or about 0.6 kg. The T-peel release force and blunt probe tack force may be measured by a standardized test method, such as ASTM D1876 and ASTMD2979 or other appropriate method. Other features or variations of the device are described in U.S. application Ser. No. 11/888,978, filed on Aug. 3, 2007, incorporated in its entirety herein by reference.

The release liners may comprise any of a variety of materials, including both opaque and transparent materials. The release liners may comprise Mylar or paper, or any other material with reduced adhesion to the adhesive material(s) of the device. For example, for a silicone adhesive, a fluoropolymer-treated polyester film may be used, and for an acrylic pressure sensitive adhesive, a silicone treated polyester or Mylar film or silicone treated craft paper may be used. In variations where the device has multiple separate adhesive regions, separate release liners may be provided for each region, or some regions may be covered by the same release liner.

Examples of dressings, applicators or tensioning devices that may be used in the devices kits or methods herein may include those provided in U.S. application Ser. No. 12/854,859 filed Aug. 11, 2010, the disclosure of which is already incorporated in its entirety herein by reference without limitation.

The packaging assembly, applicator and/or tensioning device may comprise a tensioning structure, and a first attachment portion configured to releasably attach to a dressing and a second attachment portion configured to releasably attach to the dressing, wherein the tensioning structure may be configured to exert a separation force between the first attachment portion and the second attachment portion to cause a strain in a dressing attached to the first and second attachment portions. An elastic dressing may be configured to releasably attach to the first and second attachment portions of a dressing and packaging assembly and may include an attachment structure or may be integral with attachment structures of a packaging device, applicator or tensioning member. The tensioning structure may also act as an applicator device or may be configured to permit a user to apply a dressing to skin of a subject.

Attachment structures of a packaging device, dressing assembly, dressing carrier, support, base, applicator, tensioning or straining device may include any structures that are used to attach or couple an applicator, tension or straining device to a dressing. A dressing may or may not have attachment features or structures. Any such attachment features may be integral with or include any of the attachment structures or corresponding structures to the attachment structures of the packaging, applicator dressing and/or tensioning device.

In some variations the assembly may comprise one or more mechanisms or elements configured to facilitate separation, release, removal or detachment of the dressing from the packaging, applicator or tensioning device, other attachment elements or other portions of the dressing assembly, including but not limited to the separation devices and methods described herein. Release elements or releasable attachment structures may include but are not limited to pockets and tabs, hook and loop mechanism, hooks, angled bars, pivoting, rolling, rocking or sliding features associated with or coupled to attachment structures, adhesives, removable adhesives, adhesive tapes or other adhesive devices, pegs, rip cords, towel bar configurations, sliding pins, friction locks, cam locks, vacuum or suction devices, snap connectors, carpet tack, press fit connections or other connections, levers, latches, locking members, spring members, for example, or other mechanisms such as cutters or rip cords or other structures or features to facilitate tearing, cutting or separation of attachment structures or elements perforated or otherwise severable structures, that permit removal of dressing from the applicator, packaging, other portions of the dressing assembly and/or attachment structures, features, elements or portions They may be self-releasing latches or spring members. They may be actuated when a pressure member is applied to a skin treatment device prior to removing the applicator. They may be manually actuated.

As noted, a packaging or applicator, tensioning device and/or straining device may be provided in some embodiments to impart a strain to a skin treatment device with an external force and/or to maintain a strain imparted to the skin treatment device. The packaging, applicator or tensioning device may be configured to pivot or rotate to tension the dressing. In some examples, the straining device may be configured to impart and/or maintain a single predetermined or pre-set strain or a plurality of predetermined or pre-set strains, or predetermined maximum or minimum amounts of strain. Features described herein with respect to a packaging assembly, applicator or tensioning device may also be used in any device that is used to strain a dressing. A packaging or applicator, tensioning or straining device that is described as being in an unstrained configuration is in a configuration in which a dressing may be unstrained or relatively less strained when attached to the packaging, applicator, tensioning or straining device. A packaging, applicator, tensioning, or straining device that is described herein as being in a strained configuration, is in a configuration in which a dressing may be strained or relatively more strained when attached to the packaging, applicator, tensioning or straining device, or with respect to an unstrained configuration, when applied to a subject's skin.

Packaging devices, applicators, tensioning devices, and corresponding attachment features may be configured to provide multi-direction strain or additional strain in an orthogonal direction to a dressing.

The packaging device, applicator, tensioning device and/or attachment structure profile may be straight, curved or otherwise varied. For example, the shape of the elements of a device may be configured to follow the shape of the area of the subject's body to which the skin treatment device is to be attached. A packaging device, tensioning device, applicator or elements thereof may be selected or configured to have a profile that has a desirable profile for a particular body location or profile where the skin treatment device is to be placed on a subject's skin. A packaging device, applicator, tensioning device or elements thereof may be selected or configured to closely match a portion of a subject's body profile. The packaging device, applicator or tensioning device and/or an element or segment thereof, may be curved, curvable, flexible, bendable, malleable, deformable, shapeable or movable to provide alternative shapes or profiles of an attached dressing. They may be relatively curved, curvable, flexible, malleable, bendable, deformable, shapeable or movable in at least one direction while being more rigid in another direction.

A variety of locking, latching, securing, attaching or detent mechanisms may be used to maintain the packaging, applicator or tensioning device in a various configurations including but not limited to unstrained, partially strained, strained configurations. A variety of locking, latching or detent mechanisms may be used to maintain a dressing in a variety of configurations including unstrained, partially strained, strained. By locking the packaging, applicator, tensioning device, or dressing in a strained position, a predetermined strain of a given dressing may be achieved. The predetermined amount of strain may be a predetermined absolute percentage of strain or level of force that is independent of the shape and/or size of the treatment site. As a further example, this absolute percentage of strain or level of force may be independent of the minimum strain or force to achieve sutureless wound closure (e.g. a relative strain or force to achieve opposition of the incision edges of a treatment site). Furthermore, the force needed to achieve wound closure is not a predetermined strain or force, since the final level of strain or force is not known until opposition of the incision edges is achieved.

Referring to FIGS. 1 to 5C, a variation of a dressing and packaging assembly 100 is illustrated. The packaging assembly 100 comprises a book-like applicator and/or tensioning device 120, a dressing assembly 110 including a dressing 130, and a release 150 configured to release the dressing 130 from the applicator and/or tensioning device 120.

The dressing 130 comprises an elastic sheet 131 with one or more adhesive regions comprising a layer of skin adhesive 135 on a first surface 135a. The adhesive used may be, for example, a suitable pressure activated adhesive (PSA), or a non-pressure sensitive adhesive.

The packaging assembly 100, applicator or tensioning device 120 and/or dressing assembly 110 may be configured to pre-strain the dressing 130 and/or permit transfer of the pre-strained dressing 130 to the skin of a subject. The applicator and/or tensioning device 120 may also provide for a convenient, expeditious or sterile transfer of an adhesive portion of the dressing 130 to a skin and/or wound site of a subject.

The device 120 comprises a cover 121 and a base 122. The dressing assembly 110 is removably coupled or anchored to the device 120 which may act as a dressing carrier or a support. The cover 121 may be generally planar and include sides 123, 124 with corresponding edges 123a, 124a along its length, and edges 121a at opposing ends. The dressing carrier or base 122 may be generally planar and include sides 125, 126 with corresponding edges 125a, 126a along its length and edges 122a at opposing ends.

According to some variations, the cover and/or base 121,122 or elements or segments thereof may be constructed to be sufficiently firm or rigid or less flexible relative to an attached dressing to support an attached dressing until it is applied to a subject as described with respect to the variations herein. Such material may comprise, for example, a plastic, e.g., polypropylene, polycarbonate, polytetrafluoroethylene (PTFE or TEFLON®), LDPE, high-density polyethylene (HDPE), ultra high-molecular weight polyethylene (UHMWPE), polyvinyl chloride (PVC) or acrylic, nylon or a paperboard. The elements or segments may be a laminate of a material, such as a solid bleach sulfate paperboard with a layer of flexible material between layers of paperboard, for example, silicone, polyurethane, LDPE or a rubber material. The material may also be a metal as for example, ductile aluminum or stainless steel. The metal may comprise a foil, ribbon, wire or other form.

Cover 121 and base 122 are movably, hingedly or pivotably coupled at sides 123, 125. For example, a layer of material such as silicone, polyurethane, low-density polyethylene or a rubber material may be glued to each of the cover and base, flexibly attaching them together at sides 123, 125. Alternative devices and methods may be used to couple the cover 121 and base 122. For example, various composite structures or laminates may be used. Also devices may be constructed out of a single substrate that provides flexibility in some selected regions and rigidity in others, or a relative or absolute flexibility in a first direction with a relative or absolute rigidity in a second direction that may be transverse to the first direction. Although the cover 121 and base 122 depicted in FIGS. 1 to 5C have generally the same size and shape, in other examples, the cover 121 and base 122 may be different sizes and/or shapes. Cover 121 and/or base 122 may be bendable, foldable, curvable, flexible, malleable or shapeable permitting relatively more even placement on a location with a varying shape or curvature. For example, cover and base 121, 122 as illustrated are each divided into segments 127 along lengths that are bendable or movable with respect to adjacent segments, permitting flexibility of the device 120 along its length. The segments 127 may be constructed of a more rigid material that reduces flexion in a widthwise or other direction. Other configurations that vary the directions of rigidity and/or flexibility may be use. Configurations may include providing rigidity in a direction in which a dressing is strained that is sufficient to create and/or maintain a desired level of strain. The segments 127 may be coupled by a material, such as an elastomer, e.g., silicone that flexibly holds the segments together in relationship to each other. Other construction may also be used to flexibly couple segments or other elements. The material coupling or binding the cover and base 121, 122, may or may not be continuous with the material that couples the segments 127 to adjacent segments 127, and may or may not be attached to all or a portion of a side of cover and base 121, 122. The various attached structures, e.g. the segments and/or the cover and base and coupling elements may provide a structural support for the dressing carrier to be manipulated by a user. Margins between at least a portion of the structural support elements, dressing carrier or backing, and the dressing may be provided at or near edges 121a, 123a, 124a, 122a, 125a, and/or 126a, for example as described further herein. In some further embodiments, the material attaching the cover 121 and base 122 may comprise a semi-rigid structure that may be biased to an open or a closed configuration, or a configuration therebetween. In still other variations, the cover 121 and base 122 may be attached by any of a variety of articulations, including but not limited to one or more a pin-based hinge joints, rings attached to holes in the cover 121 and base 122, or ball-and-socket joints.

Figure 5A:
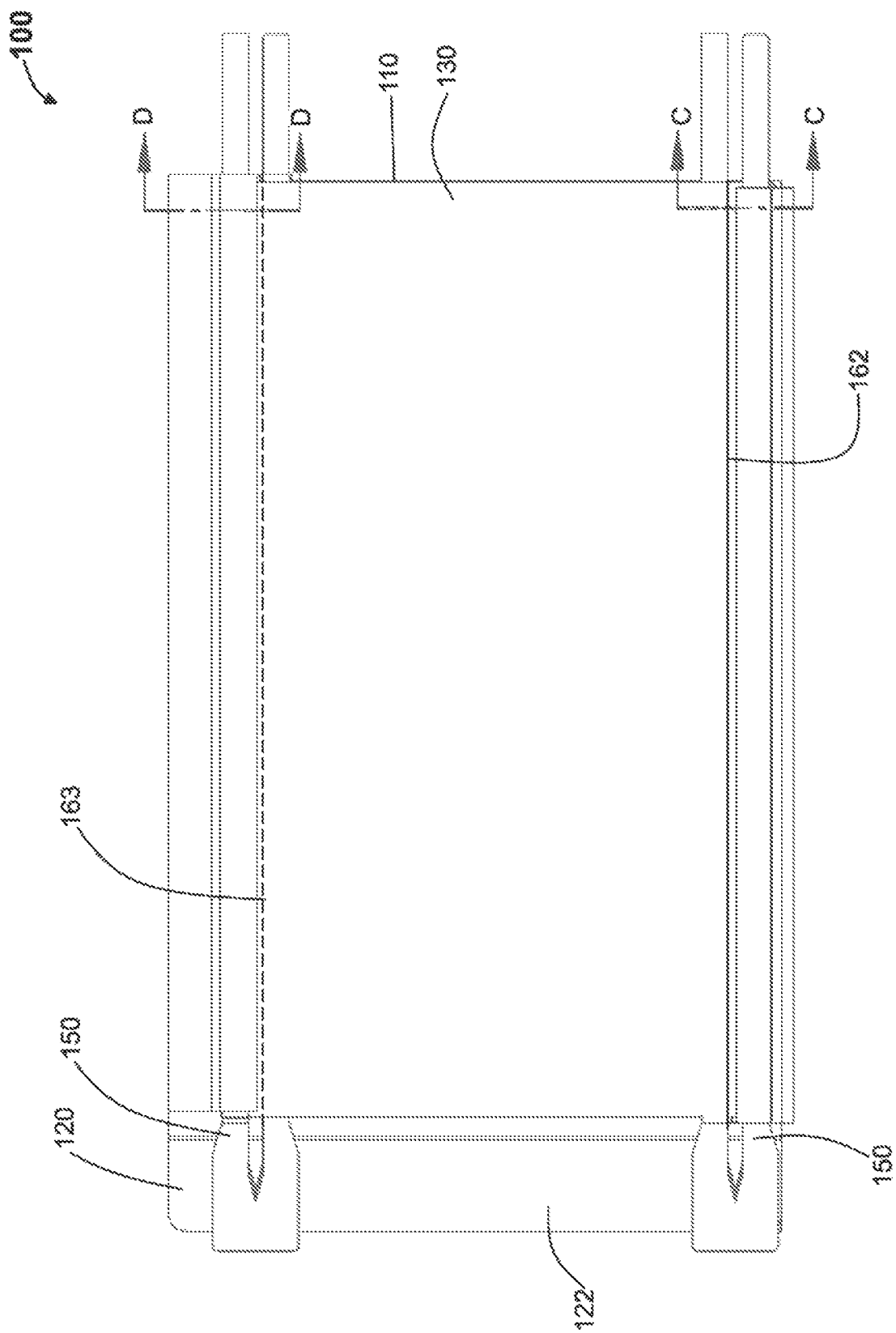
FIG. 5A is a schematic bottom view of the dressing and packaging assembly in the position illustrated in FIG. 3.
Figure 5B:
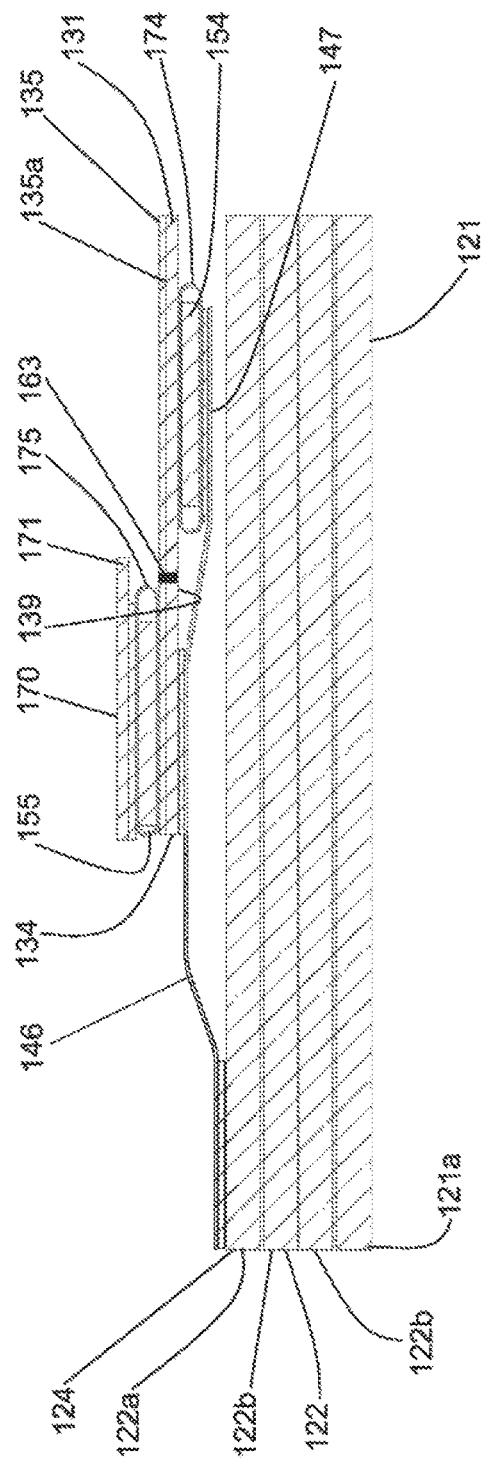
FIG. 5B is a cross section of FIG. 5A along the lines C-C.
Figure 5C:
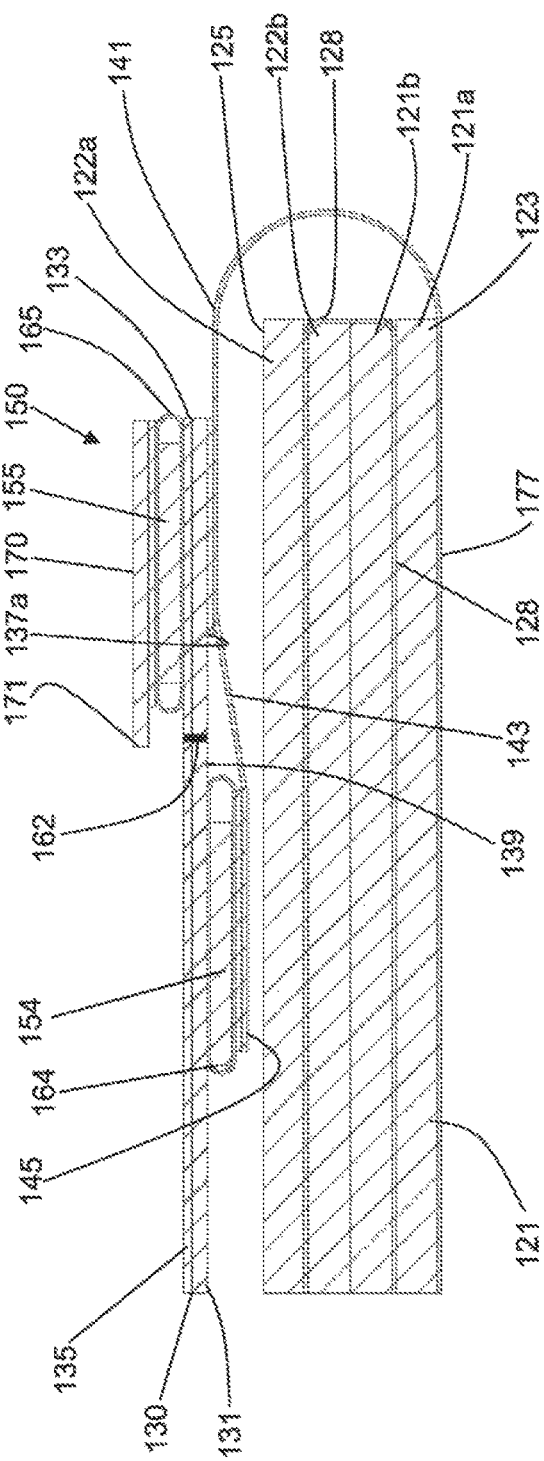
FIG. 5C is a cross section of FIG. 5A along the lines D-D.

As exemplified in FIGS. 5A-5C, a variation of construction of a package is shown. Cover 121 and base 122 comprise relatively firm or rigid elements, for example battens 121a, 121b and battens 122a, 122b respectively that are attached by way of a sheet 128 of material, such as, e.g., silicone, polyurethane, low-density polyethylene or a rubber material that also flexibly couples cover and base 121, 122 at sides 123, 125. Segments 127 may have alternative shapes and construction coupling the segments 127 together. Thus, the device 120 may be constructed to bend or curve to varied extents or in multiple directions. Accordingly, a device may be constructed to be used on a specific anatomical location or with varying sizes, or may be constructed to have a shape for a particular situation or individual.

According to some variations each of the cover 121 and base 122 is constructed at least in part of a clear plastic, semi-opaque or other material that provides a window portion 159 through which a wound, incision, or other location may be visualized for accurate placement of the dressing 130. The cover 121 and base 122 may or may not comprise the same material. The elastic sheet 131 and adhesive layer 135 may also be sufficiently clear to permit visualization through them. A more opaque material may be provided on portions of the material to create boundaries of a window 159. The segments 127 may be clear or semi-opaque to provide the window for viewing, positioning, and/or centering the location of a wound or position on skin with respect to the dressing 130 or for positioning the wound within an optimal or most effective strain zone of the dressing. The boundaries or other markings may assist a user in placing the dressing 130 in an appropriate position over the wound or incision.

The dressing 130 of the dressing assembly 110 has a first side or edge 133 having a length, and a second side or edge 134 having a length. The dressing 130 is coupled to the packaging assembly 100 along the lengths of the dressing's sides 133, 134. When the device 120 is closed, the adhesive layer 135 faces away from the base 122 and is covered by a release liner 149 that is attached to the inside surface 177 of the cover 121. The dressing assembly 110 also includes an attachment sheet 141 having a first side 143 and a second side 144. The attachment sheet 141 couples the dressing 130 to the cover of the device 120 which when opened, exerts a straining force on the dressing 130 through the attachment sheet 141. According to some variations, the attachment sheet 141 is flexible while being relatively inelastic with respect to the dressing 130 and may be constructed, e.g., out of a low density polyethylene. When assembled, the attachment sheet 141 is bonded to the elastic sheet 131 of the dressing at (for example, using a combination of a silicone PSA/acrylic PSA) or near the sides 134 and 143 of the dressing 130 and attachment sheet 141 respectively. The attachment sheet 141 is coupled at its side 144 to the cover 121 at attachment points 137 defining a line or area of attachment 137a along the length of the cover 121. The dressing 130 is coupled to the second side 124 of the base 122 at a location near the first side 133 of the dressing 130. As such, the elastic sheet 131 is attached at attachment points 138 defining a line or area of attachment 138a along a length of the base 122. A number of bonding methods or adhesives may be used to attach the attachment sheet 141 to the cover 121, for example, a low surface energy PSA such as an acrylic adhesive.

Figure 2:
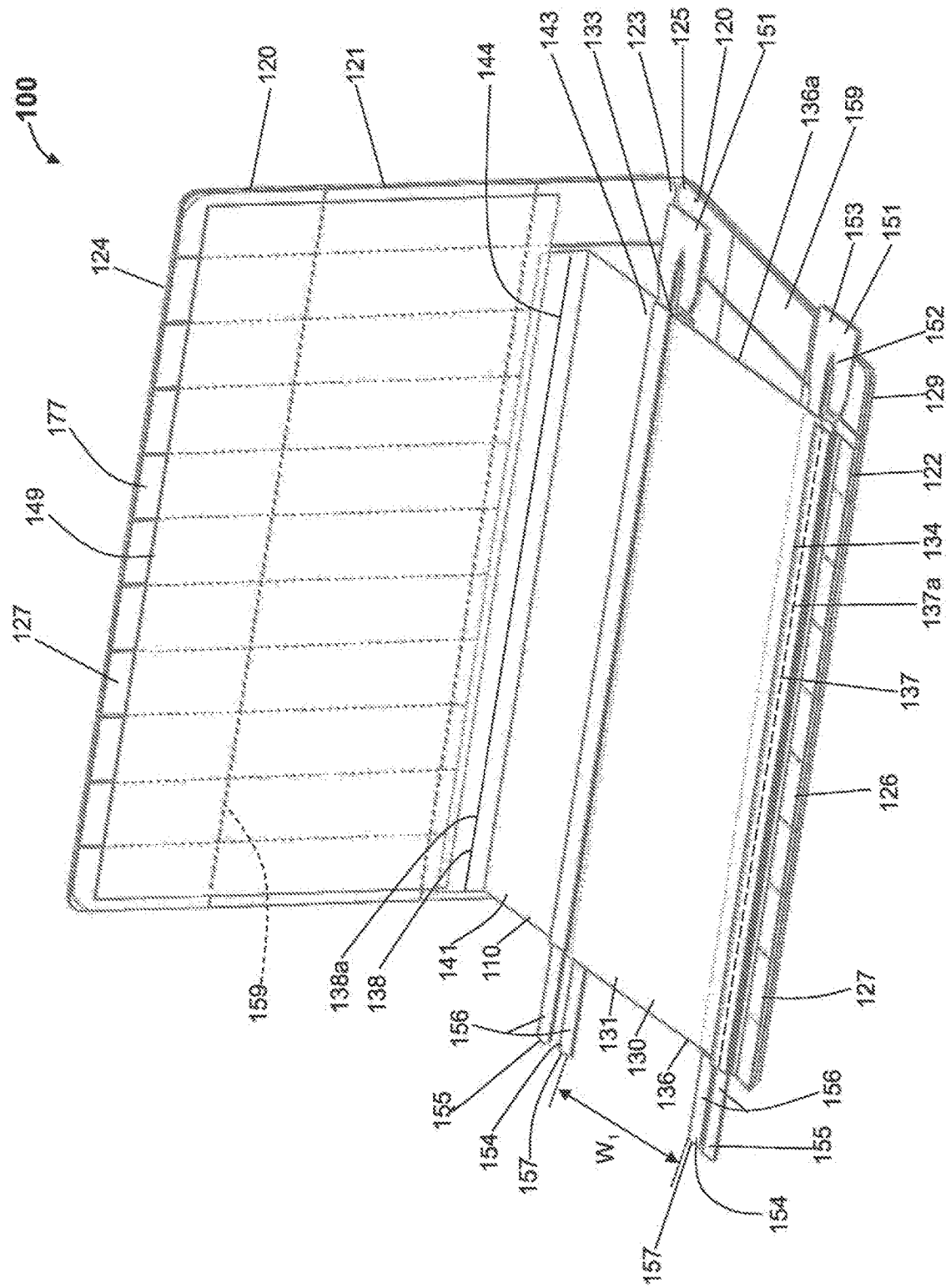
FIG. 2 is a perspective view of the dressing and packaging assembly of FIG. 1 with a cover open at about a ninety degree position from the closed position.

When the assembly 100 is in a closed configuration as illustrated in FIG. 1 and at an open 90 degree configuration as shown in FIG. 2, the elastic sheet 131 is relaxed or unstrained, with the elastic sheet 131 having an unstrained width w1. As the assembly 100 is opened to 180 degrees or up to about 360 degrees (e.g. by rotating or pivoting the cover 121 with respect to the base 122), the orthogonal distance increases between lines or areas of attachment 137a, 138a. According to some variations the assembly is opened to no less than about 180 degrees (minimum angular change) to provide for application of a dressing without interference of the assembly 100. When the device 120 is opened, it exerts a separation force between attachment regions defined by attachment lines or areas 137a, 138a or corresponding attachment areas. The force tensions the elastic sheet, creating a strain. Tensioning and imparting a strain on the dressing 130 increases the width between attachment lines or areas 137a, 138a to w2. The increase in the width, i.e., w2 minus w1, may be a percentage of w1 or a percent strain as described herein. While straining is illustrated as starting when the cover 121 is opened about 90 degrees from the base 122, the dressing 130 may be attached to the cover 121 at a number of locations or in a number of configurations that may vary the cover position or configuration at which straining begins. The edge 124a or side 124 of the cover 121 may act as a lever arm to provide a mechanical advantage, which may depend, among other things, on the distance of the point of attachment 138 of the dressing assembly 110 on the cover to the edge 124a of the cover 121 as well as the angle of the cover 121 with respect to the base 122 at which the tensioning of the dressing occurs. Additionally, the point of attachment 138 of the inelastic attachment sheet 141 to the cover 121 may determine amount of strain applied to the dressing, assuming among other things, the length of the attachment sheet 141 remains the same and the point of attachment 137 of the dressing assembly 110 to the base 122 remains the same According to one variation, the dressing 130 may be substantially fixed at one edge, (e.g. at edge 134 at the side 126 of the base 122) while not being fixed at an opposite edge (e.g., edge 133 moves when strained with respect to edge 125a of base 122). When the cover 121 is opened and the dressing 130 is strained, the width of the strained dressing may be less than the width of the base 122 and/or the cover 121 so that the area of the dressing is located over the area of the base 122 and or the cover 121, i.e. the base 122 and/or cover 121 margins outside of the area of the dressing. According to other variations the dressing may be fixed at both edges.

According to some variations, the dressing is sufficiently large with respect to the device 120 so that when applied to the skin, there is relatively less interference by the device 120. According to one example, the width of the strained portion of the dressing may be about 10 mm, about 20 mm, about 30 mm, about 40 mm, or about 50 mm Other strained dimensions may be used. According other variations, the distance between each of edges 133, 134 of the dressing 130 and the edges 125a, 126a of the base 122 respectively (and/or the edges 123a, 124a of the cover 121) is no greater than about 10 mm, 15 mm or 20 mm According to some variations, the distance between the edges 136a, 136b of the dressing and the edges 122a of the base is no greater than about 10 mm, about 15 mm or about 20 mm.

Figure 3:
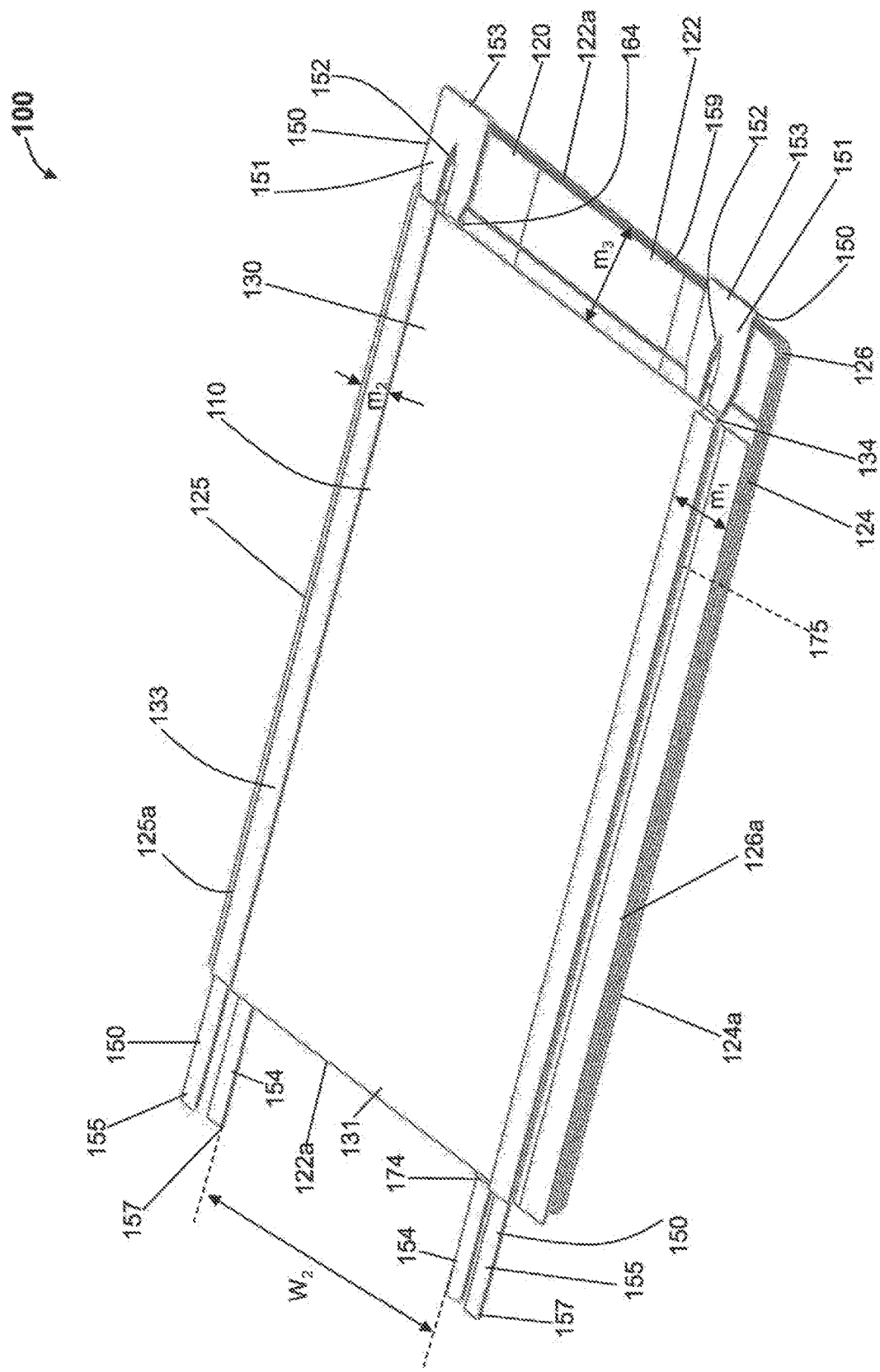
FIG. 3 is a bottom perspective view of the dressing and packaging assembly of FIG. 1 with a cover open at about a 360 degree configuration from the closed position.
Figure 4:
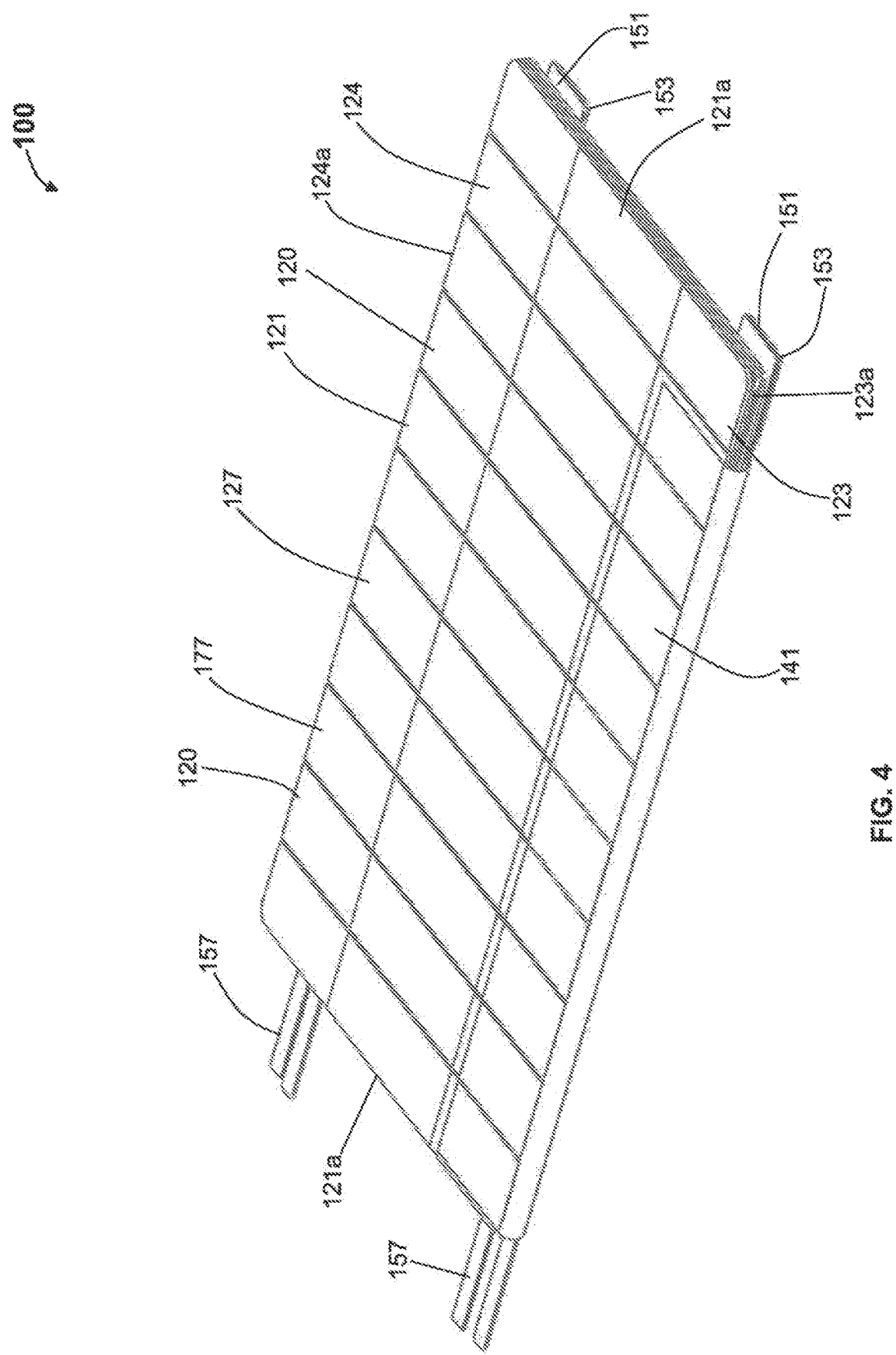
FIG. 4 is a top perspective view of the dressing and packaging assembly of FIG. 1 with a cover open at about a 360 degree configuration from the closed position.

According to some variations, edges 133, 134, 136a, 136b of the dressing 130 are at least about 1.0 mm inward of at least a portion of the edges 125a, 126a, and/or 122a of the base 122 so that the edges 125a, 126a, and/or 122a of the base 122 may be gripped by a user with a reduced likelihood of touching the dressing 130 or the adhesive layer 135. According to some variations, the ends 136a, 136b of the dressing 130 have a margin of at least about 1.0 mm inward of the ends 122a of the base 122. According to some variations the sides 133, 134 and ends 136a, 136b of the dressing 130 have a margin of about 10 mm from the sides 125, 126 and ends 122a of the base respectively. According to some variations the sides 133, 134 and ends 136a, 136b of the dressing 130 have a margin of about 15 mm from the sides 125, 126 and ends 122a of the base respectively. Each of the margins between sides 133,134 or ends 136a, 136b of the dressing 130 and sides 125, 125, and ends 122a of the base 122 may be different. As illustrated in FIG. 3, for example, margins m1 and m2 are about no less than 3 mm and margin m3 is about 15 mm Similar margins may be provided between the dressing 130 and the edges 121a, 123a, and/or 124a of the cover 121, for example if the edges of the cover 121 are used alternatively or additionally to grasp the device 120 or manipulate the dressing 130. Then, once the cover 121 is opened and the adhesive layer 135 is exposed, the adhesive side of the dressing 130 may be placed on a skin or wound site using the device 120. As shown in FIGS. 3 and 4 the cover 121 and base 122 may be rotated an additional amount, with respect to each other, e.g., up to approximately 360 degrees from the closed configuration prior to applying the dressing 130. A locking mechanism may optionally be provided to lock or secure the device in an open, partially opened or closed position. In some examples, the locking mechanism may comprise magnets, hook-and-look attachment structures, snaps, latches, clips and the like.

Figure 6:
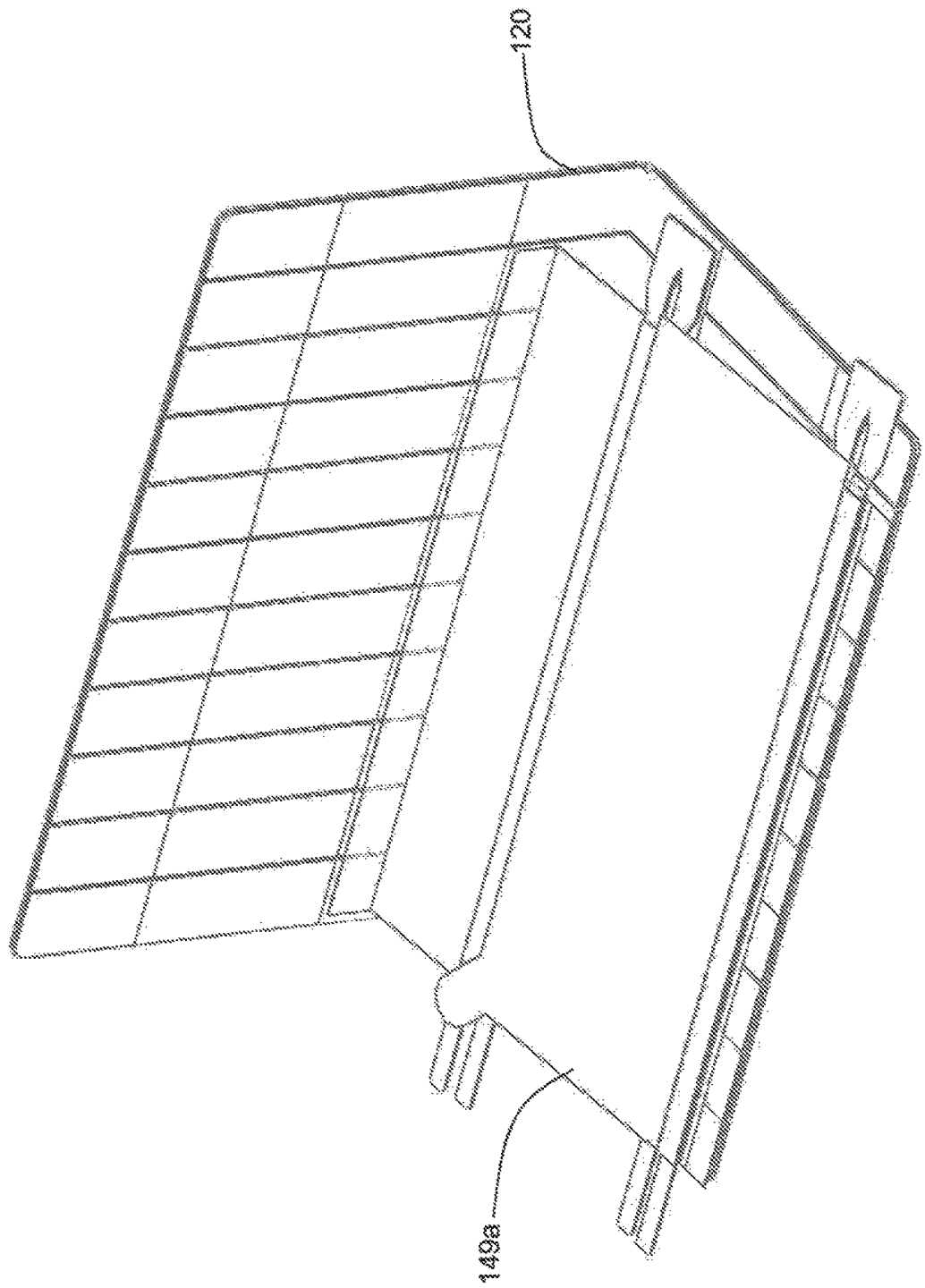
FIG. 6 illustrates a variation of a dressing and packaging assembly.

The adhesive layer 135 of the elastic sheet 131 is protected by a release liner 149 before the applicator or tensioning device 120 is opened. The release liner 149 is attached or glued to the inside surface 177 of the cover 121 so that when the cover 121 is opened as shown in FIG. 2, and is separated from the base 122 (prior to straining the elastic sheet 131), the release liner 149 is pulled away from the elastic sheet 131 exposing the adhesive layer 135. Alternatively, as shown in FIG. 6, a release liner 149a may be provided on the adhesive layer 135 that is not attached to the cover 121. When the device 120 is opened, and prior to straining the dressing 130, the release liner 149a may be manually removed from the elastic sheet 131 to expose the adhesive layer 135.

After the dressing 130 is strained, and the liner 149 or 149a is released, the dressing 130 may be applied to a desired location on a subject's skin. The window 159 may be used to visualize proper placement. The user may apply pressure to the back side 129 of the device 120 to activate the adhesive on the elastic sheet 131 and/or to apply compression to a wound. Alternatively, if the cover 121 is rotated to 360 degrees, pressure may be applied to the inside 177 of the cover 121. Once applied to a subject, the elastic sheet 131 may be released from the packaging, applicator or tensioning device 120 using a release structure or mechanism 150.

The release mechanism 150 may comprise cutters 151 each positioned on opposite sides 133, 134 of the elastic sheet 131. Each cutter 151 comprises a blade 152 on one end 153 with legs 154, 155 extending to opposing pull tab or tabs 156 on an opposite end 157. The blade 152 comprises a sharp surface that may be generally v-shaped or otherwise shaped. The blade may be constructed, e.g., of stainless steel, ceramic or hard plastic. The blade 152 and the pull tabs 156 each extend proud of the ends 136a, 136b of elastic sheet 131, respectively and ends 122a of the base 122. Cutters 151 are attached to the dressing assembly 110 in a manner that defines general cutting paths 162, 163 (depicted best in FIG. 5A) along which the blades 152 are pulled by tabs 156 to cut the dressing assembly 110 to release the dressing 130. In some variations, the dressing may be scored, perforated or otherwise configured to facilitate separation by the release mechanism.

As best shown in FIGS. 5B and 5C, tubes 164, 165 for receiving and guiding legs 154, 155 respectively of a cutter 151, are positioned along the side 133 of the elastic sheet 131. The tubes 164, 165 may be positioned so that the cutting path 162 is between the tube 164 and the tube 165. The tube 165 is coupled, e.g., glued to the adhesive surface 135 of the elastic sheet 131 at a location closer to the side 133 than the cutting path 162. The tube 164 is coupled to the back surface 139 of the elastic sheet 131 by way of the attachment sheet 141, which is also coupled to the elastic sheet 131 at a location closer to the side 133 than the cutting path 162. The tube 164 is coupled to a free end 145 of the attachment sheet 141 that extends inward of the cutting path 162 with respect to the side 133. Thus, the tube 164 may be positioned inside of the cutting path 162 without being attached to the elastic sheet 131 inside of the cutting path 162. This allows the dressing 130 to be released from the remainder of the packaging assembly 100 including the cutter 151 with tube 164 and attachment sheet 141. A protective member 170 is attached, e.g. glued to the top of tube 165. The protective member 170 includes a ledge 171 that extends over the cutting path 162 so that when the adhesive layer 135 is positioned on the skin of a subject and the cutter 151 is actuated, the skin is protected from the blade 152.

Tubes 174, 175 for receiving and guiding legs 154, 155 respectively are positioned along the side 134 of the elastic sheet 131. The tubes 174, 175 are positioned so that the cutting path 163 is between the tube 174 and the tube 175. The tube 175 is coupled, e.g., glued to the adhesive surface 135 of the elastic sheet 131 at a location closer to the side 134 of elastic sheet 131 than the cutting path 163. The tube 174 is coupled to the back surface 139 of the elastic sheet 131 by way of the extender sheet 146. The tube 174 is coupled to a free end 147 of the extender sheet 146 that extends inward of the cutting path 163 with respect to the side. Tube 174 is also coupled to the elastic sheet 131 at a location closer to the side 134 than the cutting path 163. Thus the tube 174 may be positioned inside of the cutting path 163 without being attached to the elastic sheet 131 inside of the cutting path 163. This allows the dressing 130 to be released from the remainder of the packaging assembly 100 including the cutter 151 with tube 175 and extender sheet 146. A protective member 170 is attached, e.g., glued to the top of tube 175. The protective member 170 includes a ledge 171 that extends over the cutting path 163 so that when the adhesive layer 135 is positioned on the skin of a subject and the cutter 151 is actuated, the skin is protected from the blade 152.

The inside of the tubes 164, 165, 174, 175 may be coated with a lubricious material, e.g. with Kapton tape. The guiding legs 154, 155 may be constructed of a low friction material such as, e.g., HDPE or UHMWPE, so the legs 154, 155 may readily slide in the tubes 164, 165, 174, 175 to permit smooth cutting of the dressing 130 from the remainder of the packaging assembly 100.

When the dressing 130 is strained and the adhesive 135 is exposed, the dressing 130 may be applied with the adhesive side 135 towards the skin of a subject. The side 133 of the elastic sheet may then be released from the applicator by pulling the tabs 146 to draw the blade 152 across cutting path 162. Also, the side 134 of the elastic sheet may then be released from the applicator by pulling the tabs 146 to draw the blade 152 across cutting path 163. Thus the elastic sheet 131 is released from the packaging 100 (including the release 150).

Figure 7:
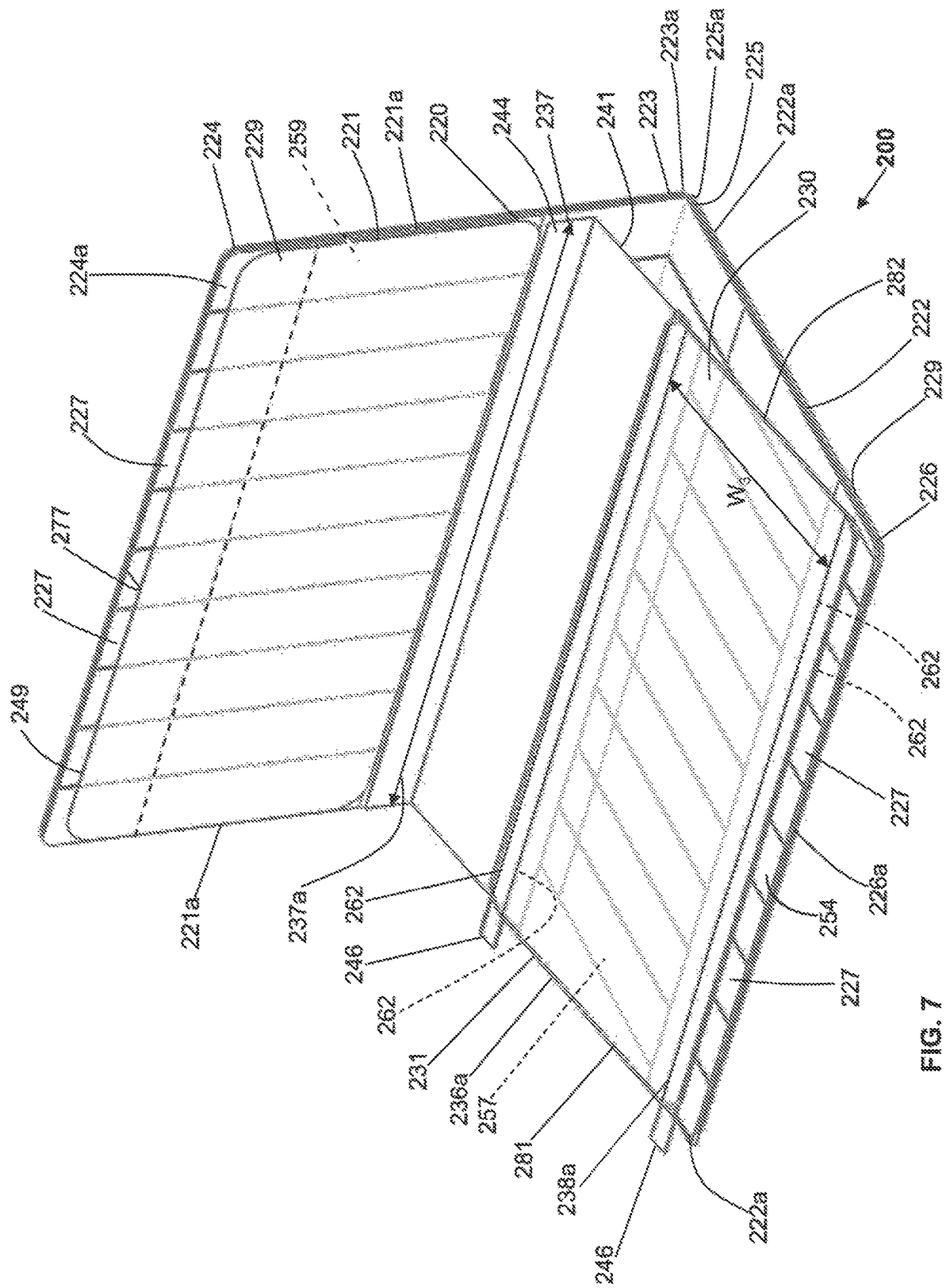
FIG. 7 is a perspective view of a dressing and packaging assembly with a cover in an open position 90 degrees from a closed position.
Figure 8A:
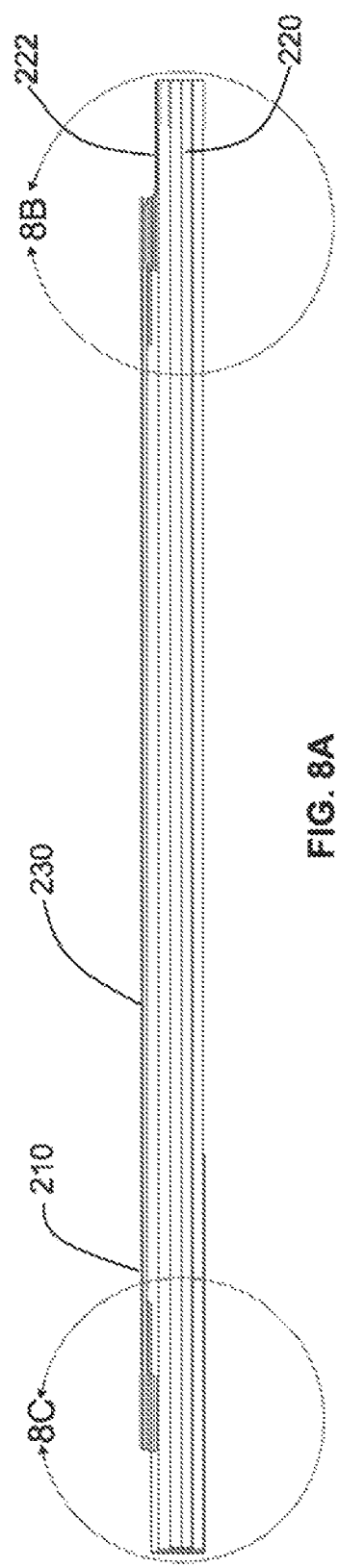
FIG. 8A is a schematic end view of the dressing and packaging assembly of FIG. 7 in a strained configuration with the cover open at about 360 degrees from a closed configuration.
Figure 8B:
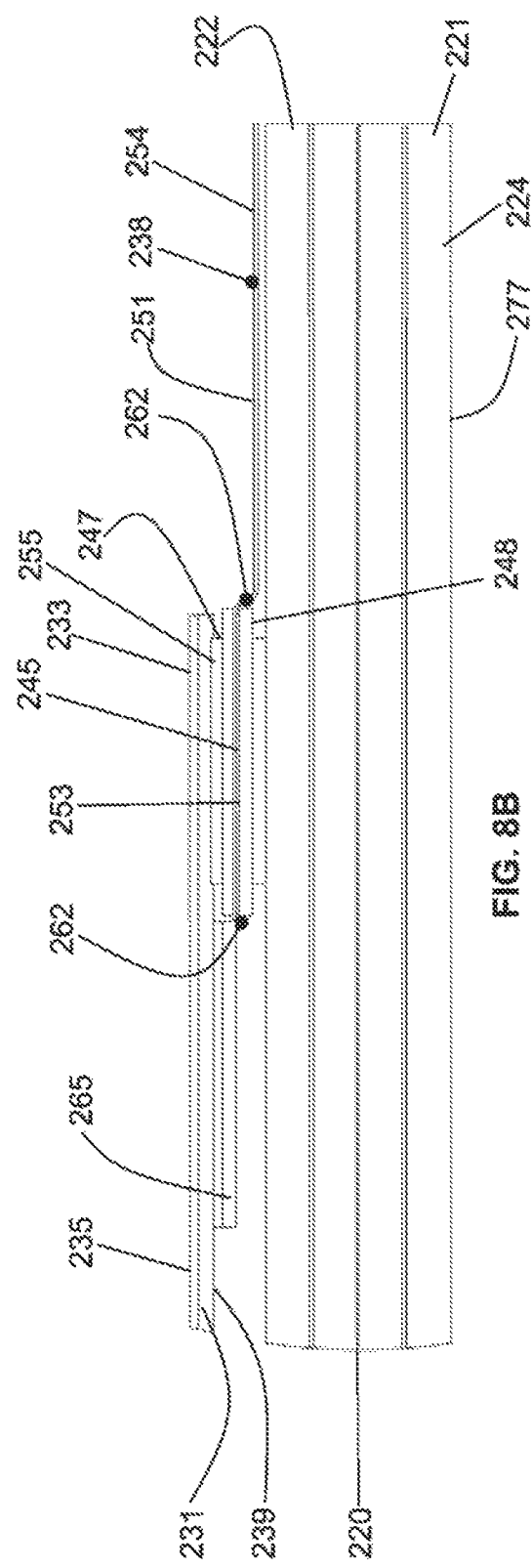
FIG. 8B is an expanded view of section B of FIG. 8A.
Figure 8C:
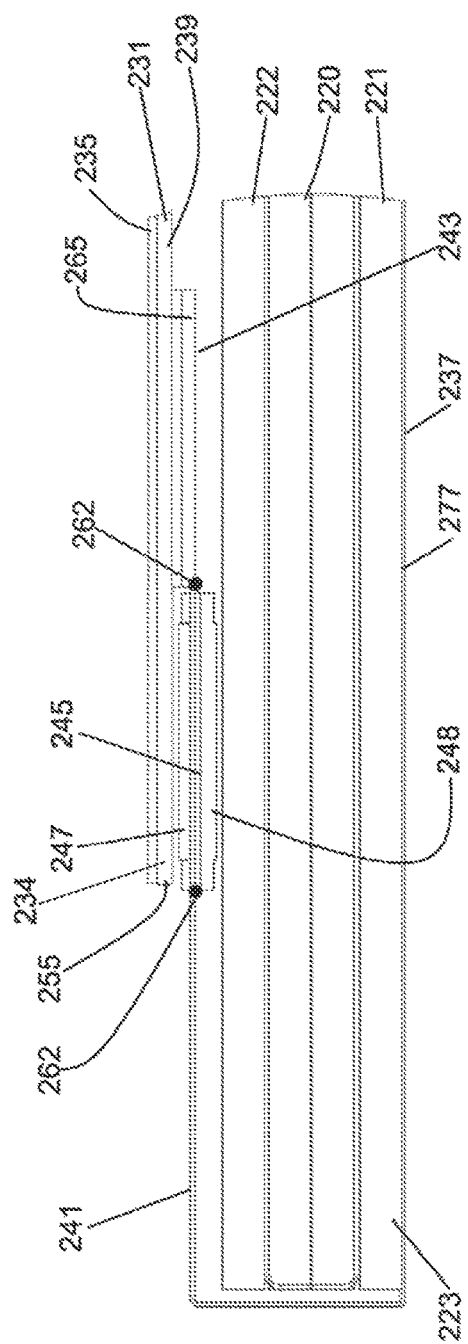
FIG. 8C is an expanded view of section C of FIG. 8A.
Figure 9:
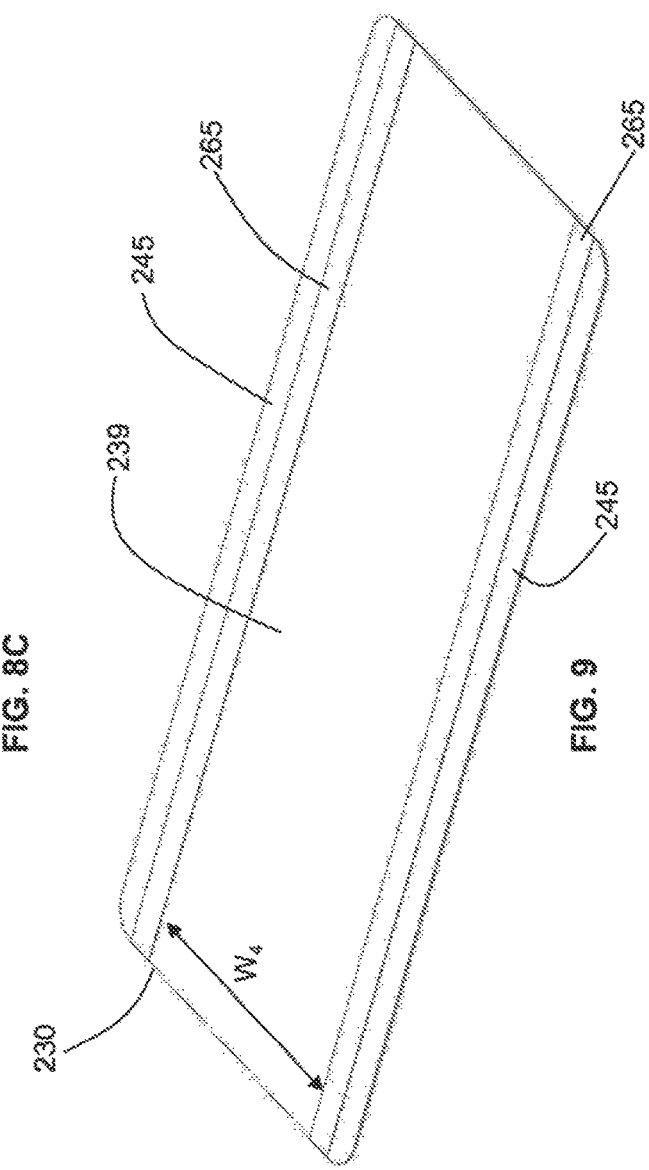
FIG. 9 is a top perspective view of the dressing and packaging assembly of FIG. 7 after release.
Figure 10:
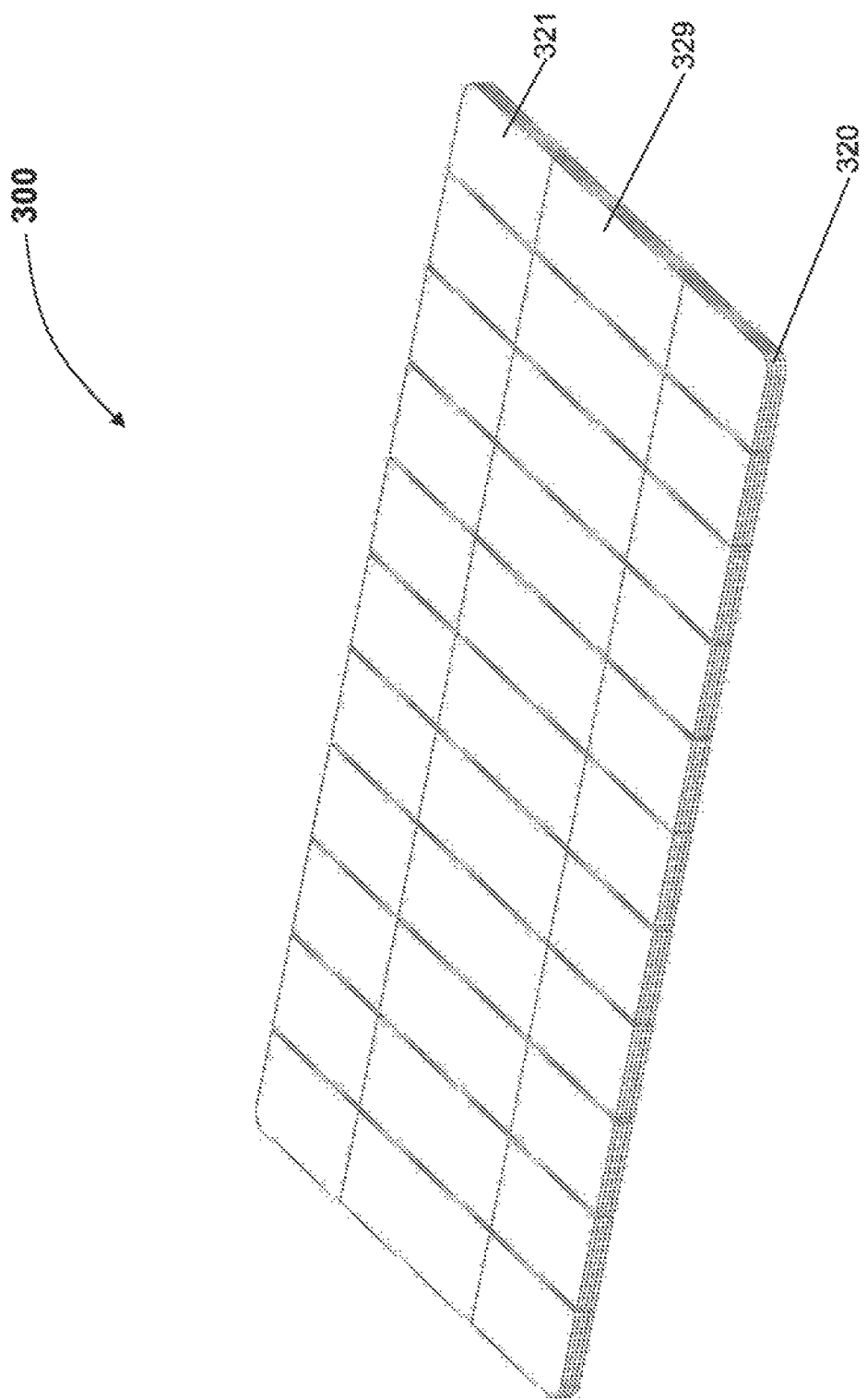
FIG. 10 is a perspective view of another example of a dressing and packaging assembly in a closed configuration
Figure 11:
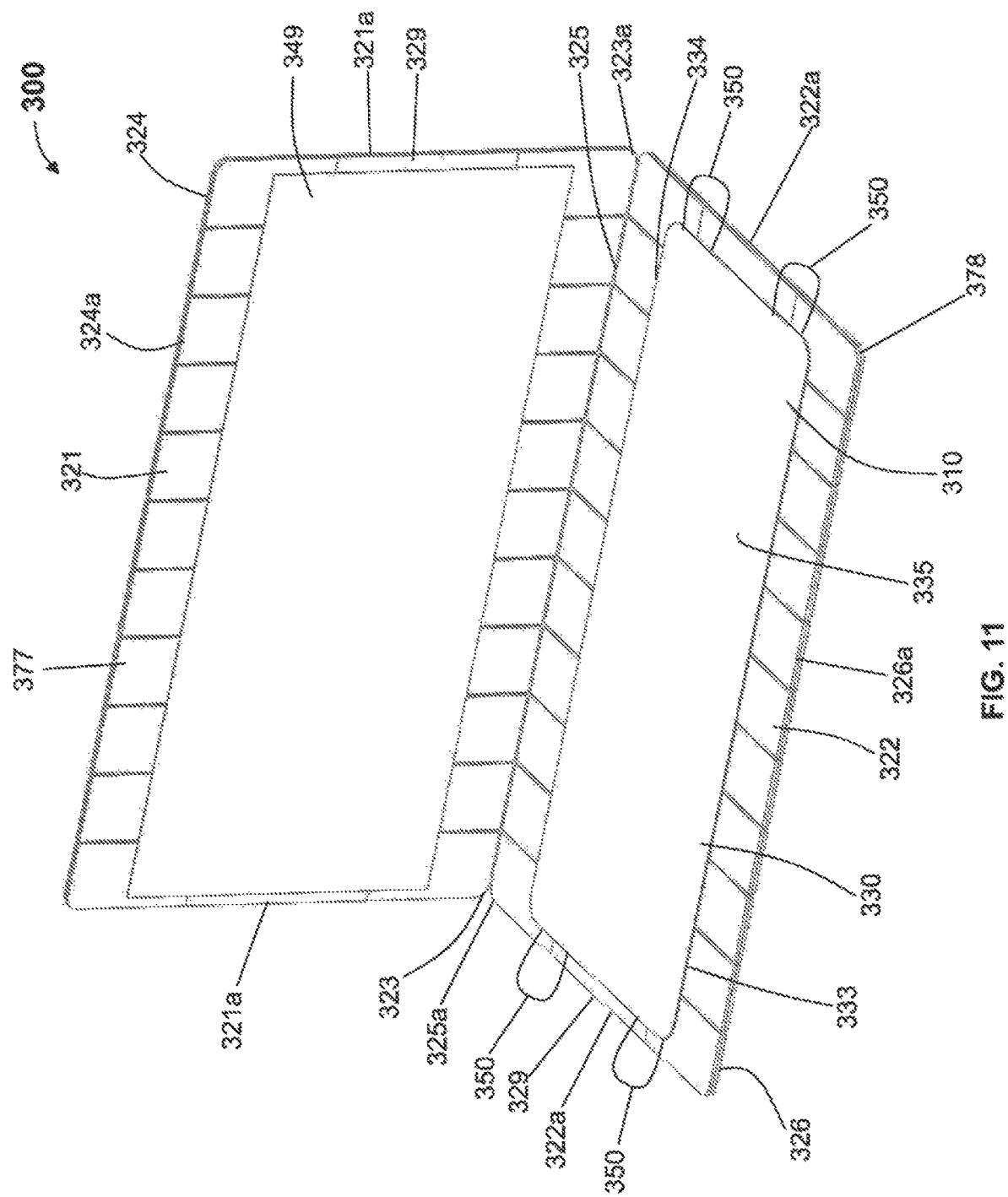
FIG. 11 is a perspective view of the dressing and packaging assembly of FIG. 10 with a cover in approximately 90 degree configuration from the closed configuration.
Figure 12A:
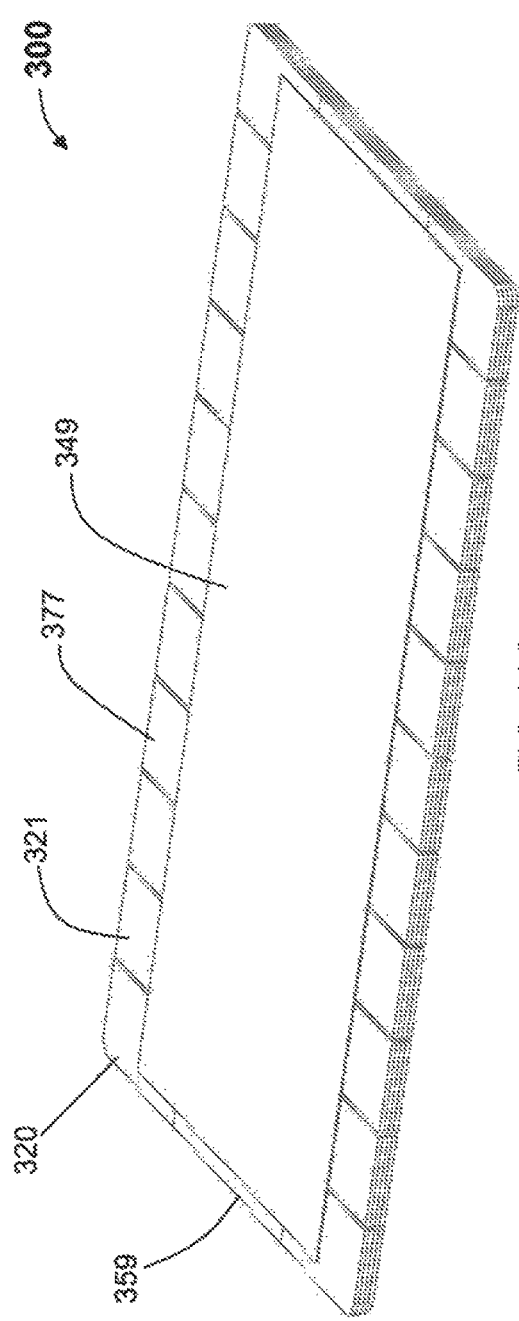
FIG. 12A is a top perspective view of the dressing and packaging assembly of FIG. 10 with a cover in approximately a 360 degree configuration from the closed configuration.
Figure 12B:
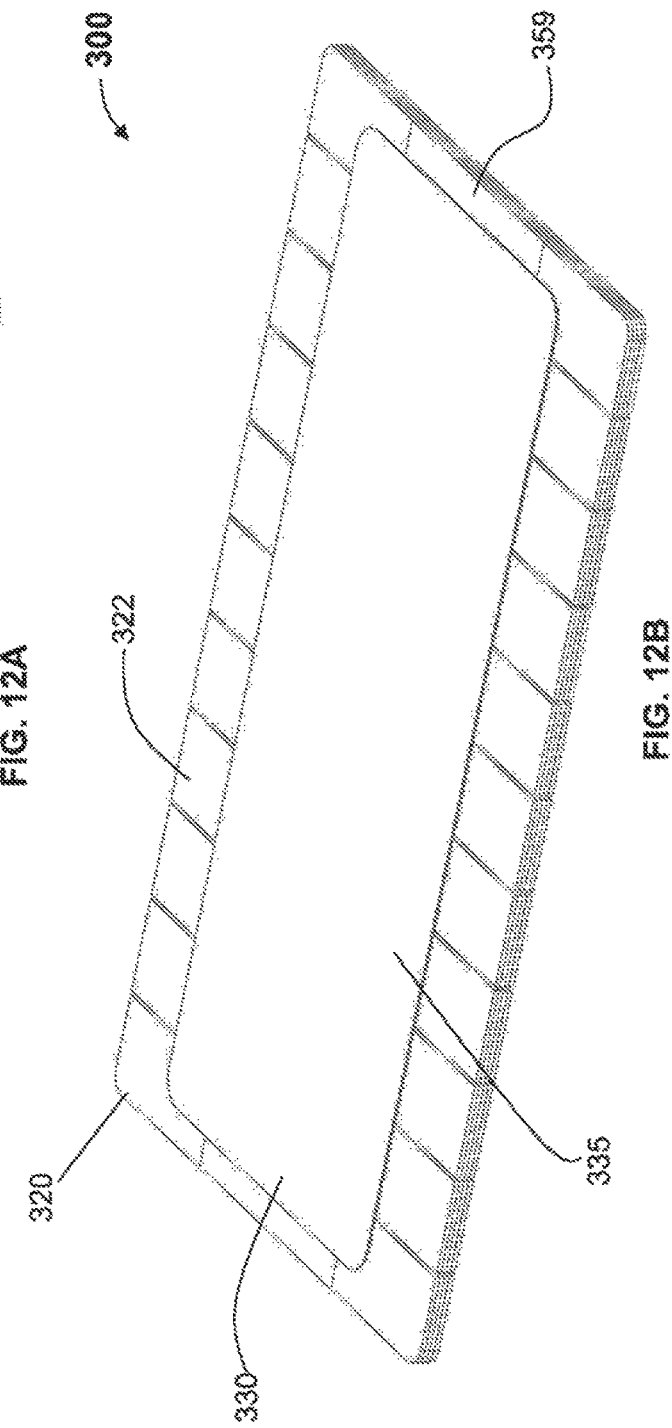
FIG. 12B is a bottom perspective view of the dressing and packaging assembly of FIG. 10 with a cover in approximately a 360 degree configuration from the closed configuration.

Referring to FIGS. 7 to 9, another variation of a dressing and packaging assembly 200 is illustrated. The packaging assembly 200 comprises an applicator and/or tensioning device 220 and a dressing assembly 210 including a dressing 230. The dressing 230 comprises an elastic sheet 231 with one or more adhesive regions comprising a layer of skin adhesive 235. The adhesive used may be, for example, a suitable pressure activated adhesive (PSA), or a non-pressure sensitive adhesive.

The packaging assembly 200, applicator or tensioning device 220, and/or dressing assembly 210 may be configured to pre-strain the dressing 230 and/or permit transfer of the pre-strained dressing 230 to the skin of a subject. The applicator or tensioning device 220 may also provide for a convenient sterile transfer of an adhesive portion of the dressing to a skin and/or wound site of a subject.

The device 220 may comprise a cover 221 and a base 222. The dressing assembly 210 is removably coupled or anchored to the device 220, and may serve as a dressing carrier. The cover 221 may be generally planar and include sides 223, 224 with corresponding edges 223a and 224a defining its length and edges 221a at opposing ends. The base 222 may be generally planar and include sides 225, 226 with corresponding edges 225a and 226a defining its length and edges 222a at opposing ends.

According to some variations, the cover and/or base 221,222 or elements or segments thereof may be constructed to be sufficiently firm or rigid or less flexible relative to an attached dressing to support an attached dressing until it is applied to a subject as described with respect to the variations herein. Such material may comprise, for example, a plastic, e.g., polypropylene, polycarbonate, PTFE, LDPE, HDPE, UHMWPE, PVC or acrylic, nylon or a paperboard. The elements or segments may be a laminate of a material, such as a solid bleach sulfate paperboard with a layer of flexible material between layers of paperboard, for example, silicone, polyurethane, low-density polyethylene or a rubber material, The material may also be a metal as for example, ductile aluminum or stainless steel. The metal may comprise a foil, ribbon, wire or other form. The other variations as described for application or tensioning device 100 may be applied to device 200 also.

The cover and base 221 and 222 may be movably, pivotably, bendably or hingedly coupled at sides 223, 225 in a manner similar to that described with respect to cover and base 121, 122 herein and may be constructed in a manner similar to cover and base 121, 122 herein, among other things, with segments 227 similar to segments 127 and dressing 230 attached to device 220 and strained by device in a similar manner as dressing 130 is attached to device 120.

The various attached structures, e.g. the segments and/or the cover and base and coupling elements may provide a structural support for the dressing carrier to be manipulated by a user. Margins between at least a portion of the structural support elements, dressing carrier or backing and the strained or unstrained dressing may be provided at or near edges 221a, 223a, 224a, 222a, 225a, and/or 226a, such as, for example, margins m1, m2, m3 shown in FIG. 3 herein.

According to some variations, each of the cover 221 and base 222 is constructed at least in part of a clear plastic, semi-opaque or other material that provides a window portion 259 through which a wound, incision or other location may be visualized for accurate placement of the dressing 230. The cover 221 and base 222 may or may not comprise the same material. The elastic sheet 231 and adhesive layer 235 may also be sufficiently clear to permit visualization through them. A more opaque material may be provided on portions of the material to create boundaries of a window. Segments 227 may be clear or semi-opaque to provide a window for viewing, positioning, and/or centering the location of a wound or position on skin with respect to the dressing 230 or for positioning the wound within an optimal or most effective strain zone of the dressing. The boundaries or other markings may assist a user in placing the dressing in an appropriate position over the wound or incision.

The dressing assembly 210 also includes an attachment sheet 241, attachment sheet 251, and a dressing release structure or mechanism 250 comprising pull tabs 246 as described in more detail herein. The dressing 230 of the dressing assembly 210 has a first side 233 having a length, and a second side 234 having a length. When the device 220 is closed, the adhesive layer 235 faces away from the base 222 and is covered by a release liner 249 that is attached to the inside surface 277 of the cover 221.

The attachment sheet 241 has a first side 243 and a second side 244. The attachment sheet 241 couples the dressing 230 to the cover 221 of the device 220 near the second side 234 of the dressing 230. The cover 221, when opened, exerts a straining force on the dressing 230 through the attachment sheet 241. The attachment sheet 241 is coupled at its side 244 to the cover 221 at attachment points 237, which may be provided as an attachment line or area 237a, for example, by bonding with a low surface energy PSA such as an acrylic adhesive. When assembled, the attachment sheet 241 is bonded to the elastic sheet 231 of the dressing 230 at section 265 of attachment sheet 241 at or near the side 243 of the attachment sheet 241, for example, using a combination of a silicone PSA/acrylic PSA. The attachment sheet 251 has a first side 253 and a second side 254. The attachment sheet 251 couples the dressing 230 to the base 222 of the device 220 near the first side 233 of the dressing 230. The attachment sheet 251 is coupled at its side 254 to the base 222 at attachment points 238 defining the attachment line or area 238a, for example, by bonding with a low surface energy PSA, such as an acrylic adhesive. When assembled, the attachment sheet 251 is bonded to the elastic sheet 231 of the dressing at section 265 of attachment sheet 251 at or near the side 253 of the attachment sheet 251, for example, using a combination of a silicone PSA/acrylic PSA.

Dressing 230 has unattached portions or edges 255 at its sides 233, 234 where the elastic sheet 231 is free from the attachment sheets 241, 251 respectively. Accordingly, the dressing 230 is not strained at unattached portions 255. The pull tabs 246 are each coupled to ends 281, 282 of the device 220. Each pull tab 246 comprises a top section 247 and bottom section 248. The bottom sections 248 are attached to the base 222 or cover 221 as illustrated while top sections 247 are adjacent but unattached to the dressing 230.

According to some variations, the attachment sheets 241, 245 are flexible while being relatively inelastic with respect to the dressing 230 and may be constructed, e.g., out of a low density polyethylene. The attachment sheets 241, 245 may be manufactured to be tearable along the material length while providing tensile strength in other directions, in particular in the tensioning direction of the material of the attachment sheet 241 (direction in which dressing is tensioned, stressed or strained). An example of such material is an LDPE polymer which is produced by an extrusion process that creates a directionally biased grain whereby the material is tearable with the direction of the grain, but has a relative resistance to tearing in the direction transverse to the grain. The pull tab 246 may start a tear at a notch in the attachment sheet 241 or 251 that is to be completed along lines 262. The attachment sheets 241, 251 may additionally or alternatively comprise a material such as an LDPE with perforations formed along tear lines 262.

Similar to assembly 100 herein, when the assembly 200 is in a closed configuration and at an open 90 degree configuration as shown in FIG. 7, the elastic sheet 231 is relaxed or unstrained, with the elastic sheet 231 having an unstrained width w3. As the assembly 200 is opened to 180 degrees or up to 360 degrees (e.g. by rotating or pivoting the cover 221 with respect to the base 222), the orthogonal distance increases between lines or areas of attachment 237*a*, 238*a*. When the device 220 is opened, it exerts a separation force between attachment regions defined by attachment lines or areas 237*a*, 238*b* or corresponding attachment areas. The force tensions the elastic sheet 231 creating a strain. Tensioning and imparting a strain on the dressing 230 increases the width between attachment lines or areas 237*a*, 238*a* to width w4. The increase in the width (i.e. width w4 minus width w3) may be a percentage of w3 or a percent strain as described herein. While straining is illustrated as starting when the cover 221 is opened about 90 degrees from the base 222. The dressing 230 may be attached to the cover 221 at a number of locations or in a number of configurations that may vary at which position or configuration the cover 222 may be when the straining begins.

As shown in FIGS. 8 to 8B, the cover 221 and base 222 may be rotated an additional amount, with respect to each other, e.g., up to approximately 360 degrees from the closed configuration prior to applying the dressing 230. According to some variations the assembly is opened to no less than about 180 degrees (minimum angular change) to provide for application of the dressing without interference from the assembly.

Then, once the cover 221 is opened and the adhesive layer 235 is exposed, the adhesive side of the dressing 230 may be place on a skin or wound site using the device 220. The cover 221 and base 222 may be rotated an additional amount, with respect to each other, e.g., up to approximately 360 degrees from the closed configuration prior to applying the dressing 230. The orientation of the cover 221 at which the dressing 230 begins to strain may be varied, e.g. by varying the attachment location of the dressing assembly 210 to the cover 221. A locking mechanism may optionally be provided to lock or secure the device in an open, partially opened or closed position. In some examples, the locking mechanism may comprise magnets, hook-and-loop attachment structures, snaps, latches, clips and the like.

The adhesive layer 235 of the elastic sheet 231 is protected by a release liner 249 before the applicator and tensioning device 220 is opened. The release liner 249 is attached to the inside surface 277 of the cover 221 so that when the cover 221 is opened and is separated from the base 222, (prior to straining the elastic sheet 231) the release liner 249 is pulled away from the elastic sheet 231 exposing the adhesive layer 235 prior. Alternatively, as shown in FIG. 6, a release liner 149*a* may be provided on the adhesive layer 235 that is not attached to the cover 221. When the device 220 is opened, but prior to straining, the release liner 149*a* may be manually removed from the elastic sheet 231 to expose the adhesive layer 235.

After the liner 249 or 149*a* is released and the dressing 231 is strained, the dressing 230 may be applied to a desired location on a subject's skin. The window may be used to visualize proper placement. The user may apply pressure to the back side 229 of the device 220 to activate the adhesive on the dressing 231 and/or to apply compression to a wound. If the cover 221 is rotated to 360 degrees, pressure may be applied to the inside 277 of the cover 221. Once applied to a subject, the dressing 230 may be released from applicator or tensioning device 220 using the release mechanism 250.

The pull tabs 246 of the release mechanism 250 each extend proud of the end 236*a* of elastic sheet 231. Each release pull tab 246 is attached to the dressing assembly 110 in a manner that defines tear paths 262 along which the tabs 246 are pulled to separate the dressing 230 from the device. Notches or perforations may be made in the attachment sheets 241, 251 that facilitate tearing along paths 262.

The dressing 230 is applied to a subject. The dressing 230 may then be released from the device 220 by pulling the tabs 246 to draw the tabs 246 across paths 262 of the attachment sheets 241, 251. The sections 245 of the attachment sheets 241, 251 that bonded to the pull tabs 246 are thereby separated from the attachment sheets thereby separating the sections 265 of the attachment sheets that are attached to the dressing 230 are from the remainder of the attachment sheets 241 and 251 that are attached to the cover 221 and base 222 respectively. Thus, the dressing 230 is released from the remainder of the packaging 100 as shown in FIG. 9. Sections 265 of the attachment sheets 241, 251 may remain on the back surface 239 of the silicone sheet 231 as shown in FIG. 9. Unattached sections 245 of the elastic dressing 230 are unstrained and may be free from the adhesive of the adhesive layer 235 (or may have a reduced amount of adhesive thereon). Thus less stress occurs at the unattached sides or edges defined by sections 245.

Referring to FIGS. 10 to 12B, a dressing and packaging assembly 300 is illustrated. The packaging assembly 300 comprises a packaging device applicator 320 and a dressing assembly 310 including a dressing 330.

The packaging device or applicator 320 is configured to permit transfer of the dressing 330 to the skin of a subject and may also provide for a convenient, expeditious or sterile transfer of an adhesive portion of the skin treatment device to a skin and/or wound site of a subject.

The packaging device or applicator 320 comprises a cover 321 and a bottom element, dressing carrier or base 322, to which dressing assembly 310 is removably coupled or anchored. The cover 321 may be generally planar and include sides 323, 324 with corresponding edges 323*a*, 324*a* defining its length and edges 321*a* at opposing ends. The base 322 may be generally planar and include side 325, 326 with corresponding edges 325*a*, 326*a* defining its length and edges 322*a* at opposing ends.

According to some variations, the cover 321 and base 322 are constructed in part of a relatively inflexible material, e.g., with respect to an attached dressing 330. Such material may comprise, for example, a plastic, paperboard or a laminate of a material, or metal as described herein with reference to cover 121 and base 122. The cover or base may be constructed in a manner as described, for example, with respect to the various applicator, tensioning devices or dressing carriers shown in FIGS. 1 to 22B herein. The cover 321 and base 322 may or may not comprise the same material.

Cover 321 and base 322 may be movably, pivotably, bendably or hingedly coupled at sides 323, 325 and otherwise constructed in a manner similar to that described herein with respect to cover 121 and base 122. The packaging device or applicator 320 may include a window portion 359 through which a wound, incision, or other location may be visualized for accurate placement of the dressing 330 in a manner similar to that described herein with respect to the use of windows 159, 259.

The assembly 300 is constructed including a dressing assembly 310 with a skin dressing device 330. The dressing assembly 310 also includes a dressing release structure or mechanism 350 which may be a release device such as various release and removal structures described herein with reference to FIGS. 1 to 22B. The dressing 330 may comprise a variety of dressing materials, including but not limited to elastic bandages, gauze type bandages, hydrocolloids. The various structures, e.g. the segments and/or the cover and base and coupling elements may provide a structural support for the dressing carrier to be manipulated by a user. Margins between at least a portion of the structural support elements, dressing carrier or backing and the dressing may be provided at or near edges 321a, 323a, 324a, 322a, 325a, and/or 326a, for example as described herein.

When assembled with the packaging device or applicator 320, the dressing 330 is coupled to the base. A length of the dressing 330 adjacent its first side 333 is bonded to a length of the base 322 adjacent its side 324 and outside of release 350. Also a length of the dressing 330 adjacent its second side 334 is coupled to a length of the base 322 adjacent its side 325 and outside of release 350. An attachment sheet similar to sheets 141, 146 or 241, 251 may be used to attach sides 333, 334 of dressing 330 to the base 322. The adhesive layer 335 faces away from the cover 321 and base 322 when the applicator 320 is opened.

According to variation, the dressing 330 is sufficient large with respect to the device 320 so that when applied to the skin, there is relatively less interference by the device 320. According to one example, the width of the strained portion of the dressing may be about 20 mm, about 30 mm, about 40 mm, or about 50 mm According other variations, the distance between each of edges 333a, 334a of the dressing 330 and the edges 325a, 326a of the base 322 respectively (and/or the edges 323a, 324a of the cover 321) is no greater than about 10 mm, 15 mm or 20 mm According to variations the distance between the edges 336a, 336b of the dressing and the edges 322a of the base is no greater than about 10 mm, about 15 mm or about 20 mm.

According to some variations, edges 333, 334, 336a, 336b of the dressing 330 are at least about 3 mm inward of at least a portion of the edges 325a, 326a, and/or 322a of the base 322 so that the edges 325a, 326a, and/or 322a of the base 322 may be gripped by a user with a reduced likelihood of touching the dressing 330 or the adhesive layer 335. According to some variations, the ends 336a, 336b of the dressing 130 have a margin of at least about 3 mm inward of the ends 322a of the base 322. According to some variations the sides 333, 334 and ends 336a, 336b of the dressing 330 have a margin of about 10 mm from the sides 325, 326 and ends 322a of the base respectively. According to some variations the sides 333, 334 and ends 336a, 336b of the dressing 330 have a margin of about 15 mm from the sides 325, 326 and ends 322a of the base respectively. Each of the margins between edges 333,334 or ends 336a, 336b of the dressing 330 and sides 325, 325, and ends 322a of the base 322 may be different. As illustrated in FIG. 3, for example, margins m1 and m2 are about no less than 3 mm and margin m3 is about 15 mm Similar margins may be provided between the dressing 330 and the edges 322a, 325a, and/or 326a of the base 322, Also similar margins may be provided between the dressing 330 and the edges 321a, 323a, and/or 324a of the cover 321, for example if the edges of the cover 321 are used alternatively or additionally to grasp the device 320 or manipulate the dressing 330.

The adhesive layer 335 on the dressing 330 may be protected by a release liner 349 before the packaging device or applicator 320 is opened. The release liner 349 may be attached to the inside surface 377 of cover 321 so that when the cover 321 is opened or is separated from the base 322, the release liner 349 is pulled away from the dressing 330 exposing the adhesive layer 335. The release liner 349 may also be a protective liner that protects or covers the dressing prior to application. For example, the liner may cover a dressing to which a substance or medicament or other agent is applied. One or more hemostatic or coagulative agents may be applied to, or otherwise integrated with dressing to help reduce bleeding. Potential agents include chitosan, calcium-loaded zeolite, microfibrillar collagen, cellulose, anhydrous aluminum sulfate, silver nitrate, potassium alum, titanium oxide, fibrinogen, epinephrine, calcium alginate, poly-N-acetyl glucosamine, thrombin, coagulation factor(s) (e.g. II, VII, VII, X, XIII, Von Willebrand factor), procoagulants (e.g. propyl gallate), antifibrinolytics (e.g. epsilon aminocaproic acid), and the like. In some variations, the agents may be freeze-dried and integrated into the dressing and activated upon contact with blood or other fluid. In some further variations, an activating agent may be applied to the dressing or the treatment site before the dressing is used on the subject. In still other examples, the hemostatic agent may be applied separately and directly to the wound before application of the dressing, or after application to the dressing via a catheter or tube. The devices may also comprise one or more other agents that may be any suitable agent that may be useful in aiding in some aspect of the wound healing process. For example, the active agent may be a pharmaceutical compound, a protein (e.g., a growth factor), a vitamin (e.g., vitamin E), or combinations thereof. Of course, the devices may comprise more than one medicament or agents, and the devices may deliver one or more medicaments or agents. An example of such medicament may include, but is not limited to various antibiotics (including but not limited to cephalosporins, bactitracin, polyxyxin B sulfate, neomycin, polysporin), antiseptics (such as iodine solutions, silver sulfadiazine, chlorhexidine), antifungals (such as nystatin), antiproliferative agents (sirolimus, tacrolimus, zotarolimus, biolimus, paclitaxel), grow factors (such as VEGF) and other treatments (e.g. botulism toxin). The cover 321 may be pulled away or separated in a number of manners. The cover 321 may be opened like a cover of a book. Similar to devices 120 and 220, 420, 520, 620, 720, 820, 920, 1020 herein, the elements 321, 322 may be rotated sufficiently to separate the release liner 349 and up to approximately 360 degrees allowing the exposed adhesive side 335 of the dressing 330 to be place on a skin or wound site using the packaging device or applicator 320. According to some variations the assembly 300 is opened to no less than about 180 degrees (minimum angular change) to provide for application of the dressing without interference of the assembly 300. Alternatively, for example, the cover 321 may be attached to the base 322 by an adhesive and may be peeled off of the dressing 330 or the base 322 to which the dressing 330 is coupled. The cover 321 itself may be a removable, or separable release liner that may be peeled from the base 322. Alternatively, as shown in FIG. 6, a release liner 149a may be provided on the adhesive layer 335 that is not attached to the cover 321. When the device is opened, the release liner 149a may be manually removed from the dressing 330 to expose the adhesive layer 335. In such case, the cover 321 may be omitted. After the device 300 is opened to position shown in FIGS. 11 or 12A and 12B, the dressing 330 may be applied to a desired location on a subject's skin. The window 359 may be used to visualize proper placement. A locking mechanism may optionally be provided to lock or secure the device in an open, partially open, or closed position. In some examples, the locking mechanism may comprise magnets, hook-and-look attachment structures, snaps, latches, clips and the like as well as adhesives, or other adhesive structures. A compressive force may be applied to the back side 378 of base 322 or inside 377 of cover if rotated approximately 360 degrees. Once applied to a subject, the dressing 330 may be released from packaging device or applicator 320 using a release mechanism 350. The release mechanism 350 may include a cutting element or a perforated element as described for example with respect to devices 150 and 250 herein. The release mechanism may further include one more release elements described herein and show in FIGS. 1 to 22B.

Figure 13:
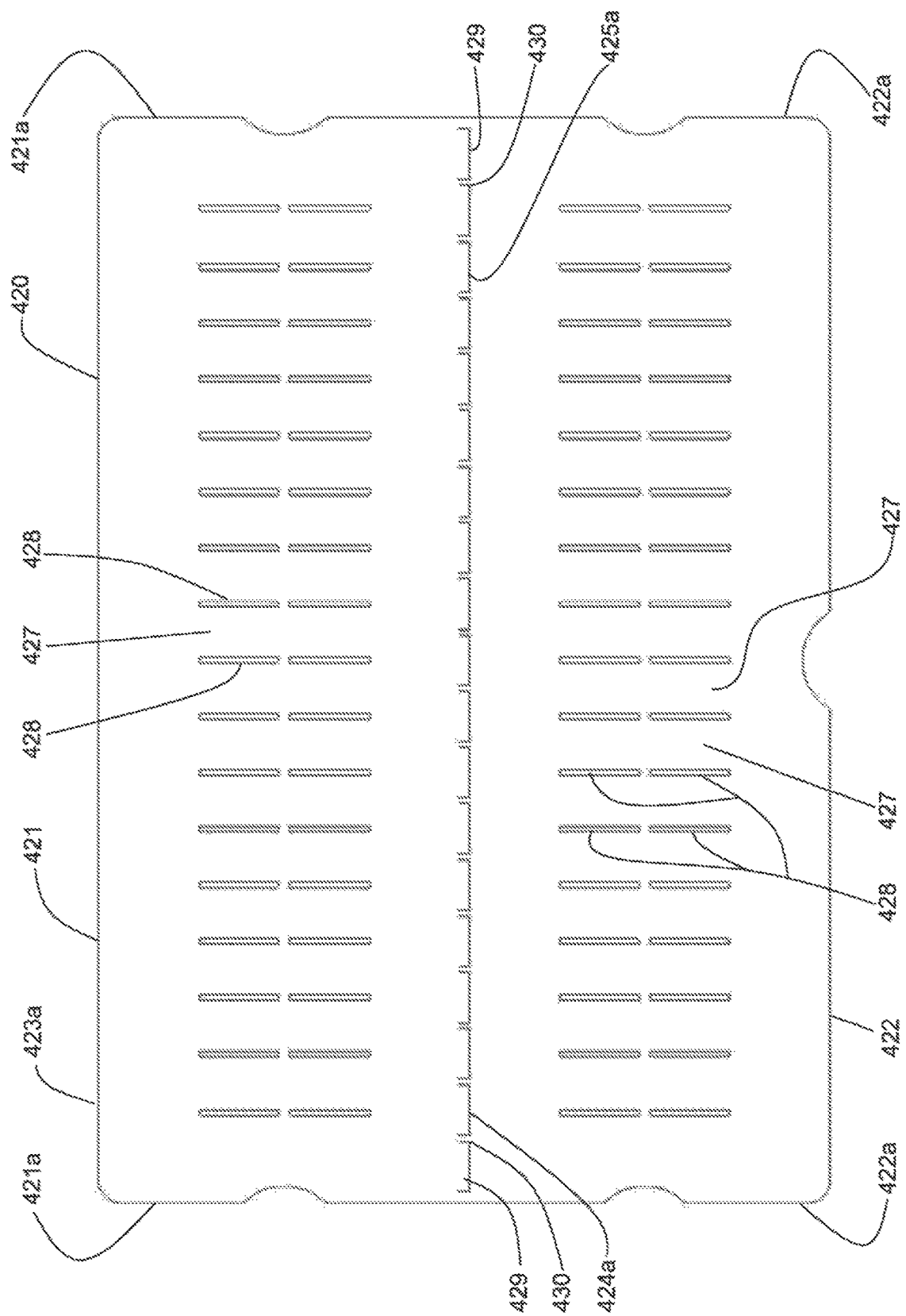
FIG. 13 is a top view of a packaging device in an open configuration.

FIG. 13 illustrates an alternative packaging or applicator 420 that may be used in any of the embodiments herein including device elements or features that may be substituted for device elements or features of devices 120, 220 or 320, 520, 620, 720, 820, 920, 1020, 1120, 1220. FIG. 13 illustrates a cover 421 and a dressing carrier or base 422 that are constructed of a single substrate out of a material such as nylon and/or polyethylene or a metal. The device 420 may be manufactured from a single mold and/or may have portions cut out of the substrate, slots, grooves, scoring or other openings or variations in thickness of the substrate at different locations. The cover 421 and base 422 each comprise slots 428 that form elements such as segments 427. The slots 428 permit flexion of the device 420 allowing it to conform to a subject's body contours where an attached dressing is to be applied. Cover 421 and base 422 are coupled to each other by way of connection features 429 that are formed in the substrate. The cover 421 and base 422 are hingedly or pivotably moveable with respect to each other by virtue of slots 430 that are formed adjacent connection features 429, to permit flexion or movement of the connector features 429 and thus the cover 421 and base 422 with respect to each other. As mentioned with respect to device 100, in other variations, slots 430 may comprise grooves or other structures providing a reduced thickness relative to the cover 421 and base 422. The device 420 may include a release mechanism as described with respect to FIGS. 1A-22B herein. The device 420 may be used in the same manner as the devices described with reference to FIGS. 1A to 22B herein and may attach a dressing in the same manner as described with respect to devices described with reference to FIGS. 1A to 22B herein.

The various structures, e.g. the segments and/or the cover and base and coupling elements, slots and grooves may provide a structural support as well as flexibility for the dressing carrier to be manipulated by a user. Margins between at least a portion of the structural support elements, dressing carrier or backing and an attached dressing may be provided at or near edges 421a, 423a, 424a, 422a, 425a, and/or 426a, for example as described further herein.

Figure 14:
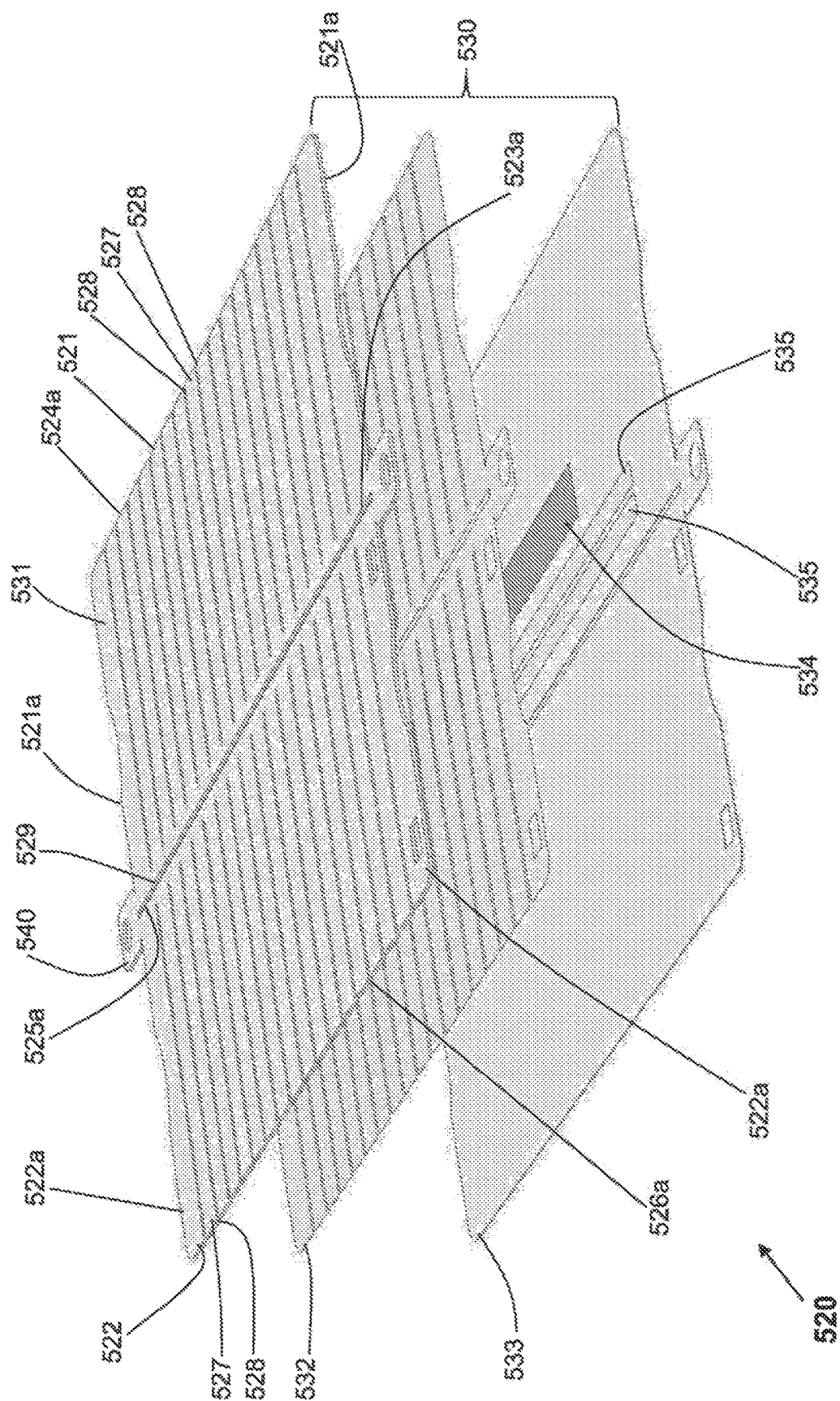
FIG. 14 is an exploded perspective view of a packaging device in an open configuration.

FIG. 14 illustrates an alternative packaging or applicator device 520 that may be used in any of the devices described herein with reference to FIGS. 1A to 22B. A cover portion 521 and a dressing carrier or base portion 522 may be constructed of a laminate structure 530. A first layer 531 of the laminate structure 530 comprises a paperboard or other support material such as a plastic material or metal having slots 528 formed widthwise across each of the cover 521 and base 522. The slots 528 form segments 527 that permit flexion of segments 527 of the device 520 allowing it to conform to a subject's body contours where an attached dressing is to be applied. The first layer 531 further comprises lengthwise slot 529 between the cover 521 and base 522 formed in the first layer 531. The first layer 531 further comprises tabs 540 with openings that are used in assembly of the device 520 and are removed after assembly so that the cover 521 and base 522 are separated by slot 529 and are no longer connected by the first layer 531. The second layer 532 of the laminate comprises an adhesive material such as a PSA acrylic, rubber or silicone adhesive. The second layer 532 may or may not be about 0.001 to 0.006 thick. A flexible strip 534 of material is positioned along the length of the device 520 over the slot 529 and connecting the cover 521 and base 522. The cover 521 and base 522 are flexibly and hingedly or pivotably coupled and moveable with respect to each other by way of the strip 534 of material over the slot 529 to permit flexion or movement of the cover 521 and base 522 with respect to each other. The flexible strip 534 is attached with an adhesive 535 to a third layer 533 that comprises a thin material such as paper or plastic that may have generally a similar outline as the first layer 531 and that holds the structure of the device 520, including segments 527, together.

The device 520 may include a release mechanism, dressing attachment and may be used in the same manner devices and assemblies as described with respect to FIGS. 1A-22B herein.

The various structures, e.g. the segments, adhesive structures, laminate layers and/or the cover and base and coupling elements, slots and grooves may provide structural support as well as flexibility for the dressing carrier, to facilitate manipulation by a user. Margins between at least a portion of the structural support elements, dressing carrier or backing and an attached dressing may be provided at or near edges 521a, 523a, 524a, 522a, 525a, and/or 526a, for example as described further herein.

Referring to FIGS. 15A to 15J, a variation of a dressing and packaging assembly 600 is illustrated. The packaging assembly 600 comprises an applicator and/or tensioning device 620 and a dressing assembly 610 including a dressing 630. The dressing 630 comprises an elastic sheet 631, with one or more adhesive regions comprising a layer of skin adhesive such as described herein.

The features in FIGS. 15A to 15J may be used in any of the variations herein including device elements or features that may being substituted for device elements or features of devices and assemblies shown in FIGS. 1A to 22B.

The packaging assembly 600 applicator, tensioning device 620 and/or dressing assembly 610 may be configured to pre-strain the dressing 630 and/or permit transfer of the pre-strained dressing 630 to the skin of a subject. The applicator or tensioning device 620 may also provide for a convenient sterile transfer of an adhesive portion of the dressing to a skin and/or wound site of a subject.

The device 620 comprises a cover 621 and a base 622. The dressing assembly 610 is removably coupled or anchored to the device 620 which may act as a dressing carrier. The cover 621 may be generally planar and include sides 623, 624 with corresponding edges 623a and 624b defining its length and edges 621a at opposing ends. The base 622 may be generally planar and include sides 625, 626 with corresponding edges 625a and 626a defining its length and edges 622a at opposing ends.

According to some variations, the cover 621 and/or base 622 or elements or segments thereof may be constructed to be sufficiently firm or rigid or less flexible relative to an attached dressing to support an attached dressing until it is applied to a subject as described with respect to the variations herein. The materials and construction of the applicator or tensioning device 620, dressing 630 and packaging 600 may be of similar to the packaging assemblies and/or dressings described in variations herein and shown in FIGS. 1A to 22B.

The cover 621 and base and 622 may be movably, pivotably, bendably or hingedly coupled at sides 623, 624. For example, a layer of material 627 such as silicone, polyurethane, low-density polyethylene or a rubber material may be glued to each of the cover and base, flexibly attaching them together at sides 623, 625. The device 620 may be constructed in a manner similar to that described with respect to other devices herein and shown in FIGS. 1A to 22B and may be constructed in a similar manner as described herein including but not limited to with respect to materials, segmentation, strength and flexibility, visualization, straining mechanisms, and release liners.

The dressing assembly 610 also includes an attachment sheet 641, attachment sheet 651. The attachment sheet 641 has a first side 643 that is attached to the second side 634 of the dressing by way of an adhesive structure 670 such as polyimide film or tape (e.g. KAPTON® by DuPont™) or a peelable adhesive. Adhesive structures herein may include but are not limited to KAPTON® tape or peelable adhesive configured to provide low skin trauma after repeated skin contact or a soft skin adhesive, made of material such as silicone adhesive, silicone gel, or acrylic adhesive. The adhesive structure or KAPTON® tape also comprises a material that is able to adhere to the attachment sheets to impart strain to the dressing when the attachment sheets are separated from each other, while being peelable from a selected dressing material.

As shown in FIG. 15J, the attachment sheet 641 and side 634 of the dressing may be attached on same side 671 of the adhesive structure 670 with the attachment sheet 641 overlapping but unattached to the dressing 631.

The attachment sheet 641 has a second side 644 that is coupled to the cover 621 of the device 620 for example, by bonding with a low surface energy PSA, such as an acrylic adhesive. Attachment sheet 641 may also have a score or perforation 681 between its attachment to the adhesive structure 670 and its attachment to the cover 621. After the dressing has been strained, the perforation 681 is located at the seam between the cover 621 and the base 622, or over the inside surface of the cover 621.

The attachment sheet 651 may be coupled at its side 654 to the back side 698 of the base 622 for example, by bonding with a low surface energy PSA, such as an acrylic adhesive. The side 653 of attachment sheet 651 may be attached to the side 633 of the dressing by way of an adhesive structure 680 such as KAPTON® tape or a peelable adhesive, and in a manner similar to the adhesive structure 670 that attaches the side 654 of the dressing 630 to the attachment sheet 641. The attachment sheet 651 may include a pull tab 688 that is located on the back side 698 of the base adjacent and inside of the attachment zone 655 of the attachment sheet 651 to the back of the base 652.

The cover 621, when opened, exerts a straining force on the dressing 630 through the attachment sheet 641.

According to some variations, the attachment sheets 641, 651 are flexible while being relatively inelastic with respect to the dressing 630 and may be constructed, e.g., out of a low density polyethylene. The attachment sheets 641, 651 may be manufactured to be tearable along the material length while providing tensile strength in other directions, in particular in the tensioning direction of the material of the attachment sheet 641 (direction in which dressing is tensioned, stressed or strained). An example of such material is an LDPE polymer which is produced by an extrusion process that creates an anisotropic or directionally biased grain whereby the material is tearable with the direction of the grain, but has a relative resistance to tearing in the direction transverse to the grain.

Figure 15A:
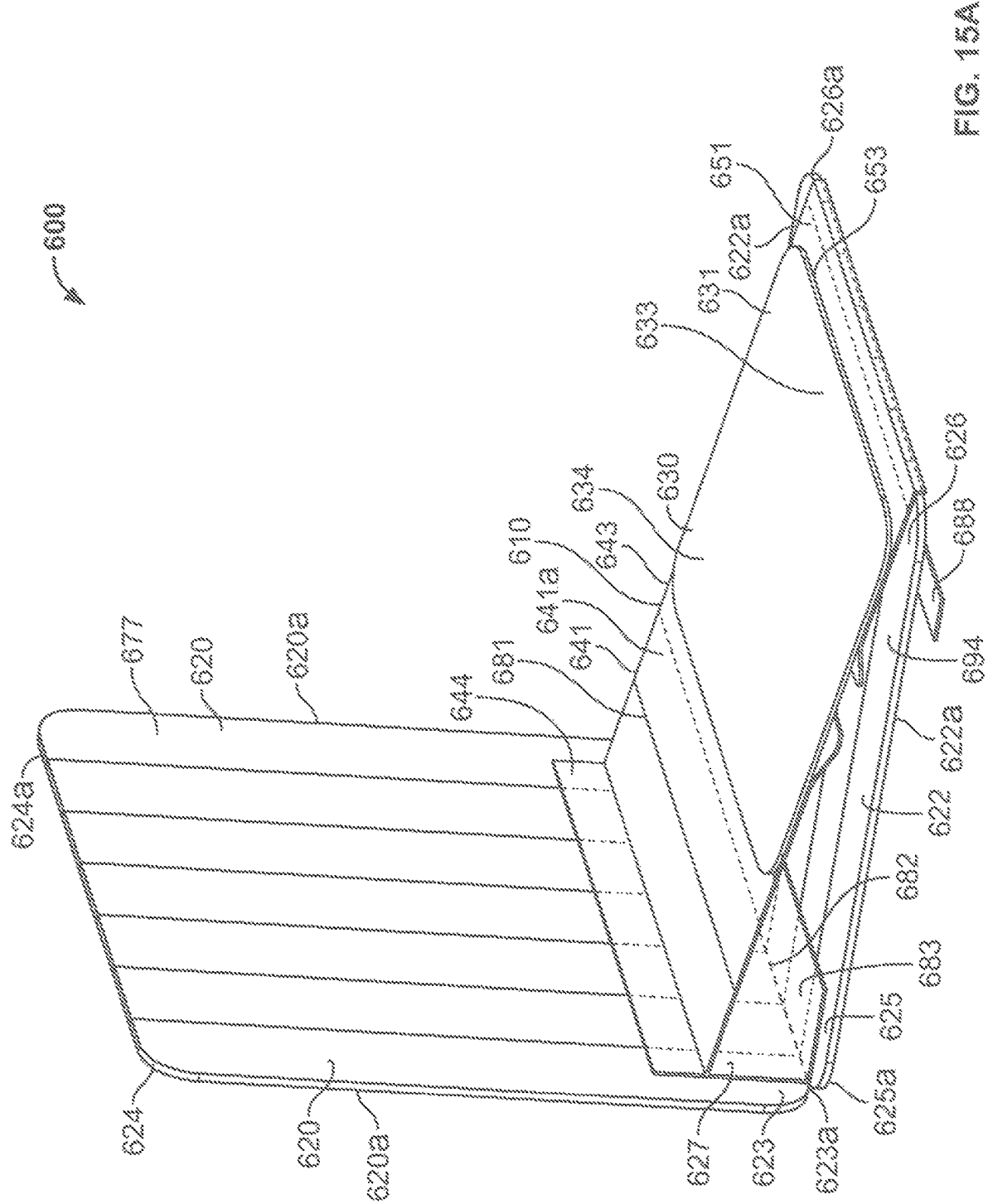
FIG. 15A is a perspective view of a variation of dressing and packaging assembly in an unstrained configuration.

FIG. 15A shows the assembly 600 in an unstrained configuration. An adhesive tape 683 is exposed on the inside surface 694 of the base 622. A skin adhesive layer on the elastic sheet 631 of the dressing 630 may be protected by a release liner similar to release liner 149a herein before the applicator or tensioning device 620 is opened FIG. 15B shows the assembly 600 in an opened and strained configuration. As shown in FIG. 15B, when strained, the perforation 681 on the attachment sheet is aligned with the edges 623a and 625a of the cover 621 and base 622, respectively. A portion 641a of the attachment sheet 641 interfaces with the adhesive tape 683 attaching portion 641a to the base 622 and holding the dressing 630 in the strained configuration. A release liner 645 is attached to the underside of the attachment sheet 641 between the attachment to the cover 621 and the perforation 681. The liner 645 prevents the portion of the attachment sheet 641 that interfaces the cover 621 from adhering to the adhesive tape 683.

The cover 621 and base 622 may be separable from each other by way of, for example, a perforation 682 in the layer 627 that couples the cover 621 to the base 622 and by separation of the sheet 641 along perforation 681. FIG. 15C shows the assembly 600 with the cover 621 separated from the base 622. The strained dressing 630 may be applied to a subject's skin using the base 622 as an applicator.

FIG. 15D illustrates the back side 698 of the base 622 in a position of applying the dressing 630 toward the skin of a subject. As shown, the edge 654 of attachment sheet 651 may be wrapped around from the inside 694 of the base 622 to the back side 698 where it is attached. A tear strip may be attached to the attachment sheet 651 between the attached edge and an unattached middle section. The pull tab 688 or tear strip may be pulled to detach the base 622 from the remainder of the dressing assembly as shown in FIG. 15E. After the tab 688 is pulled, an unattached portion 651a of the attachment sheet 651 is freed from the base 622. After the base is removed, the remaining portions of the attachment sheets 641, 651 may be removed by peeling the KAPTON® tape off of the dressing 630. FIG. 15F shows the dressing 630 after removal of the remainder of the dressing assembly.

FIGS. 15G to 15J illustrate a configuration of the dressing assembly 610 as the KAPTON® tape or adhesive structures 670, 680 and attachment sheets 641, 651 are removed from the dressing 630. FIGS. 15G and 15J show the orientation of the KAPTON® tape or adhesive structures 670, 680 as they are peeled in a direction from inside the dressing 630 towards the sides 633, 634 of the dressing 630, or in a direction of dressing strain. FIG. 15H shows the first structure 670 peeled away from the inside of the dressing across the side 633 of the dressing. FIG. 15I shows the first adhesive structure 670 removed from the dressing 630. The second adhesive structure 680 may be removed in a similar manner.

Figure 16A:
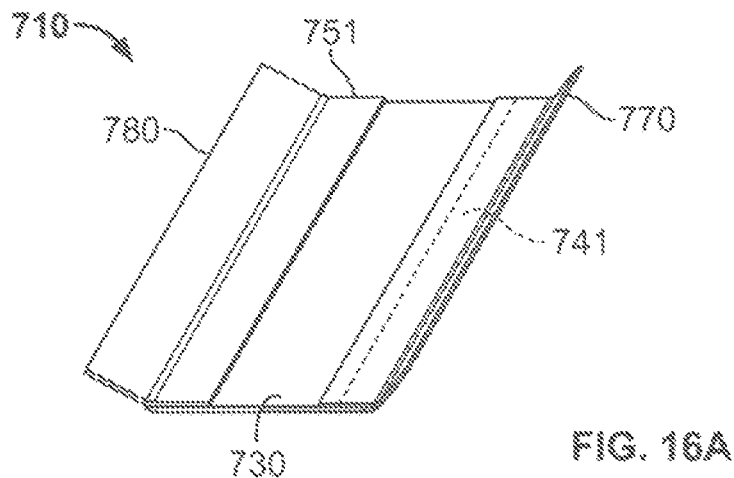
FIG. 16A is a perspective view of a variation of a dressing assembly with removable attachment sheets.
Figure 16B:
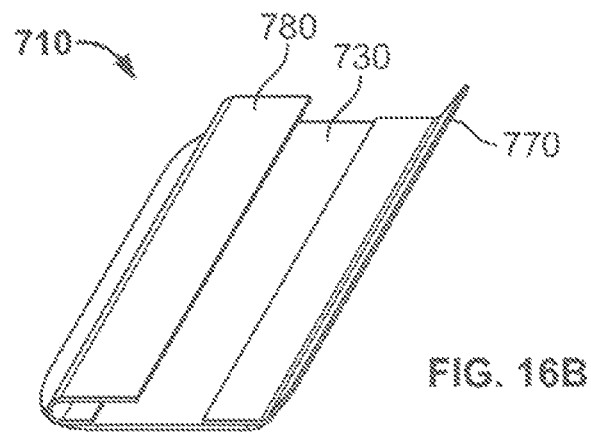
FIG. 16B is a perspective view of the dressing assembly of FIG. 16A with a peeled removable attachment sheet.
Figure 16C:
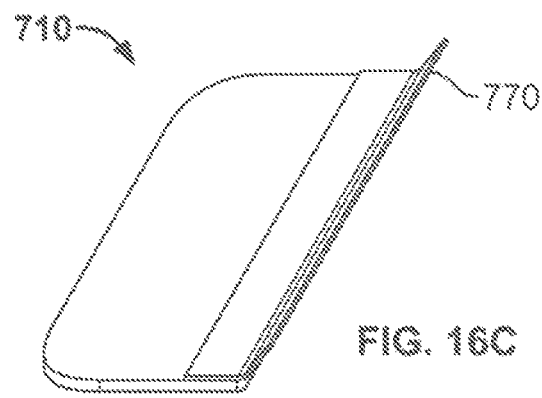
FIG. 16C is a perspective view of the dressing assembly of FIG. 16A with a removed attachment sheet.
Figure 16D:
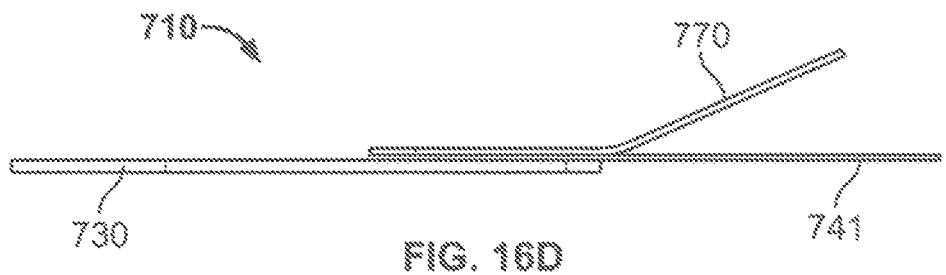
FIG. 16D is a cross section of the dressing assembly with attachment sheets of FIG. 16A

FIGS. 16A to 16D illustrate an alternative dressing assembly 710 in a configuration in which a dressing assembly 710 is separated from the applicator or tensioning device in a manner similar to that described with respect to FIGS. 15A to 15J. FIG. 16A illustrates a first adhesive structure 770 and a second adhesive structure 780, each comprising KAPTON® tape or a peelable adhesive structure used to attach attachment sheets 741, 751 to the dressing 730, As shown in FIG. 16A the unattached ends of the adhesive structures 770, 780 are oriented away from the dressing 730. As shown in FIG. 16B, the second adhesive structure 780 is peeled inwardly and in FIG. 16C, is removed.

FIGS. 17A to 17D illustrate an alternative dressing assembly configuration in which a dressing assembly 810 is separated from the applicator or tensioning device in a manner similar to that described with respect to FIGS. 15A to 15J. FIG. 17D illustrates a first adhesive structure 870 and a second adhesive structure 880, each comprising KAPTON® tape or a peelable adhesive structure used to attach attachment sheets 841, 851 respectively to the dressing 830. As shown in FIGS. 17A and 17D, the adhesive structures 870, 880 are attached to the dressing 830 with adhered length 891. An additional length 892 is wrapped 180 degrees about the adhered length 891. The additional length 892 has an end 893 that extends proud of the dressing 830 for easy access and removal. As shown in FIG. 17B, the first adhesive structure 870 may be pulled using the end 893, in a direction that is in part perpendicular to the direction of strain, to remove the attachment structures 841, 851 and adhesive structure 870 from the dressing 830 as further shown in FIG. 17C.

FIGS. 18A to 18I illustrate a variation of a dressing and packaging assembly 900. The packaging assembly 900 comprises an applicator and/or tensioning device 920 and a dressing assembly 910 including a dressing 930. The device 920 comprises a cover 921 and a base 922. The dressing assembly 910 is removably coupled or anchored to the device 920 which may act as a dressing carrier. The cover 921 may be generally planar and include sides 923, 924 with corresponding edges 923a and 924a defining its length and edges 921a at opposing ends. The base 922 may be generally planar and include sides 925, 926 with corresponding edges 925a and 926a defining its length and edges 922a at opposing ends.

The dressing assembly 910 also includes an attachment sheet 941 and attachment sheet 951. The attachment sheet 941 has a first side 943 that is attached to the second side 934 of the dressing by way of an adhesive structure 970 such as KAPTON® tape or a peelable adhesive. Adhesive structures herein may include but are not limited to KAPTON® tape or peelable adhesive configured to provide low skin trauma after repeated skin contact or a soft skin adhesive, made of material such as silicone adhesive, silicone gel, or acrylic adhesive. The adhesive structure or KAPTON® tape also comprises a material that is able to adhere to the attachment sheets to impart strain to the dressing when the attachment sheets are separated from each other, while being peelable from a selected dressing material.

Figure 18A:
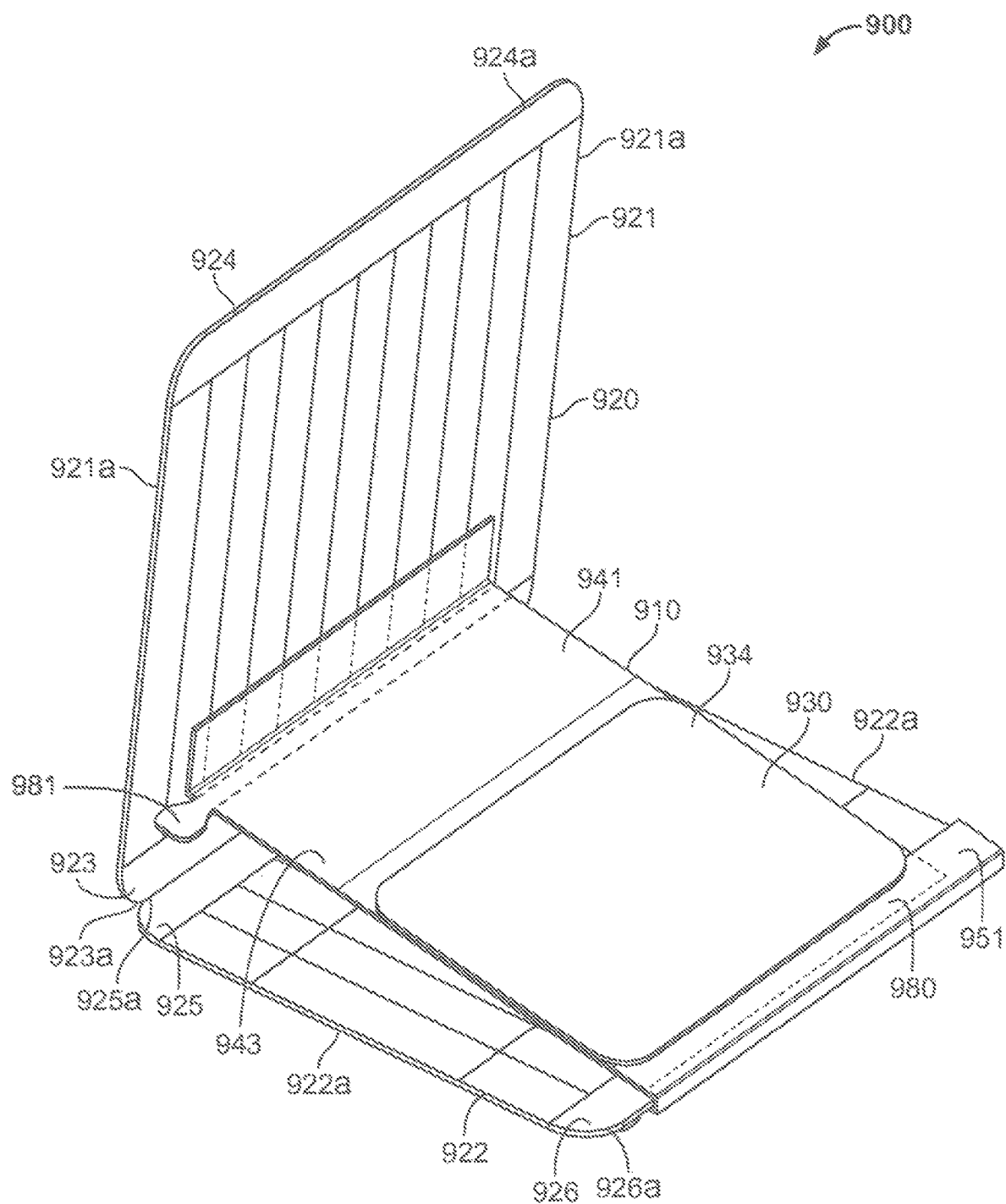
FIG. 18A is a perspective view of a variation of dressing and packaging assembly in an unstrained configuration.
Figure 18B:
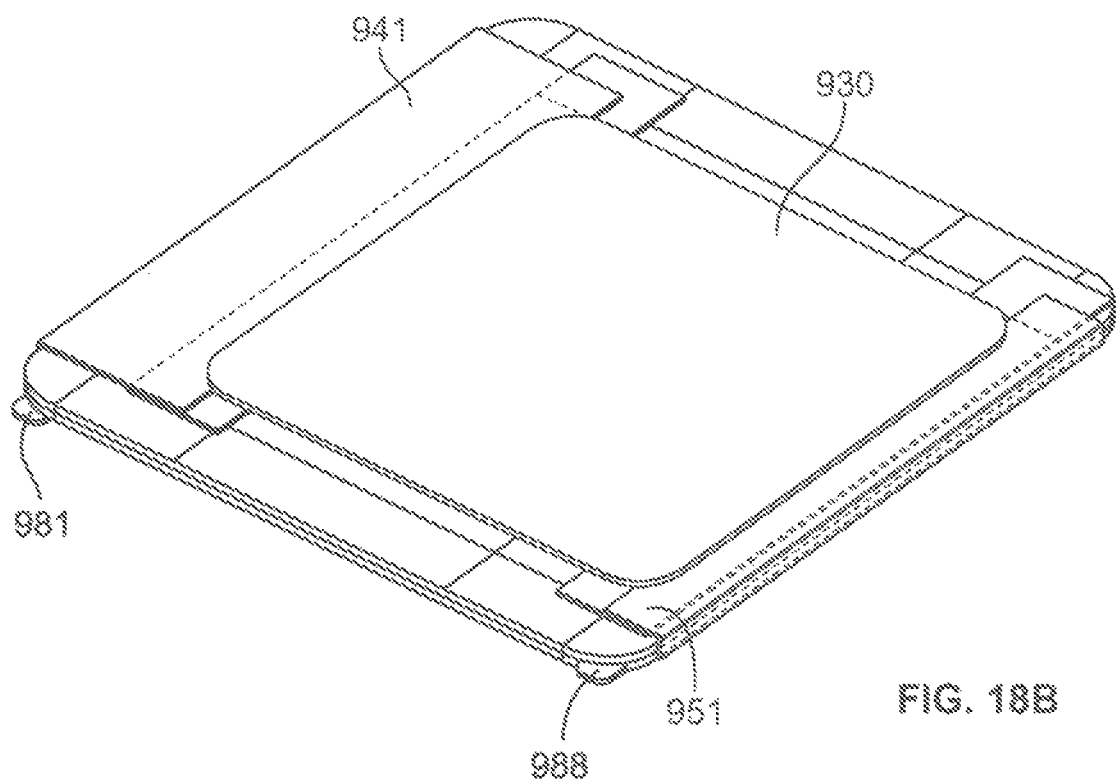
FIG. 18B is a top perspective view of the device of FIG. 18A in a strained and folded configuration.
Figure 18C:
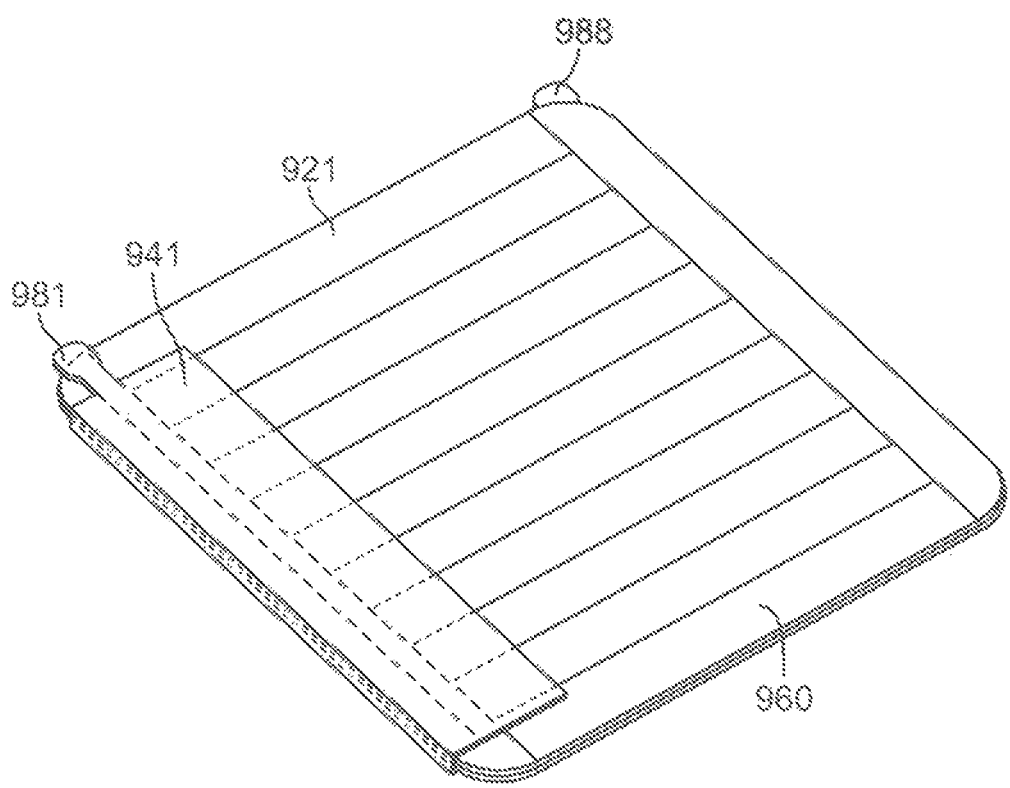
FIG. 18C is a perspective view of the bottom side the device in the strained and folded configuration of FIG. 18B.
Figure 18D:
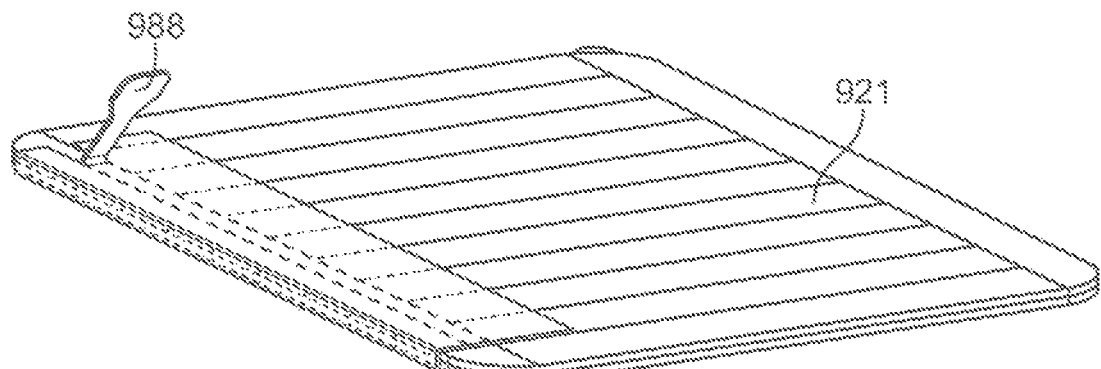
FIG. 18D is a top perspective view of the device of FIG. 18A in a strained and folded configuration while detaching an attachment sheet.
Figure 18E:
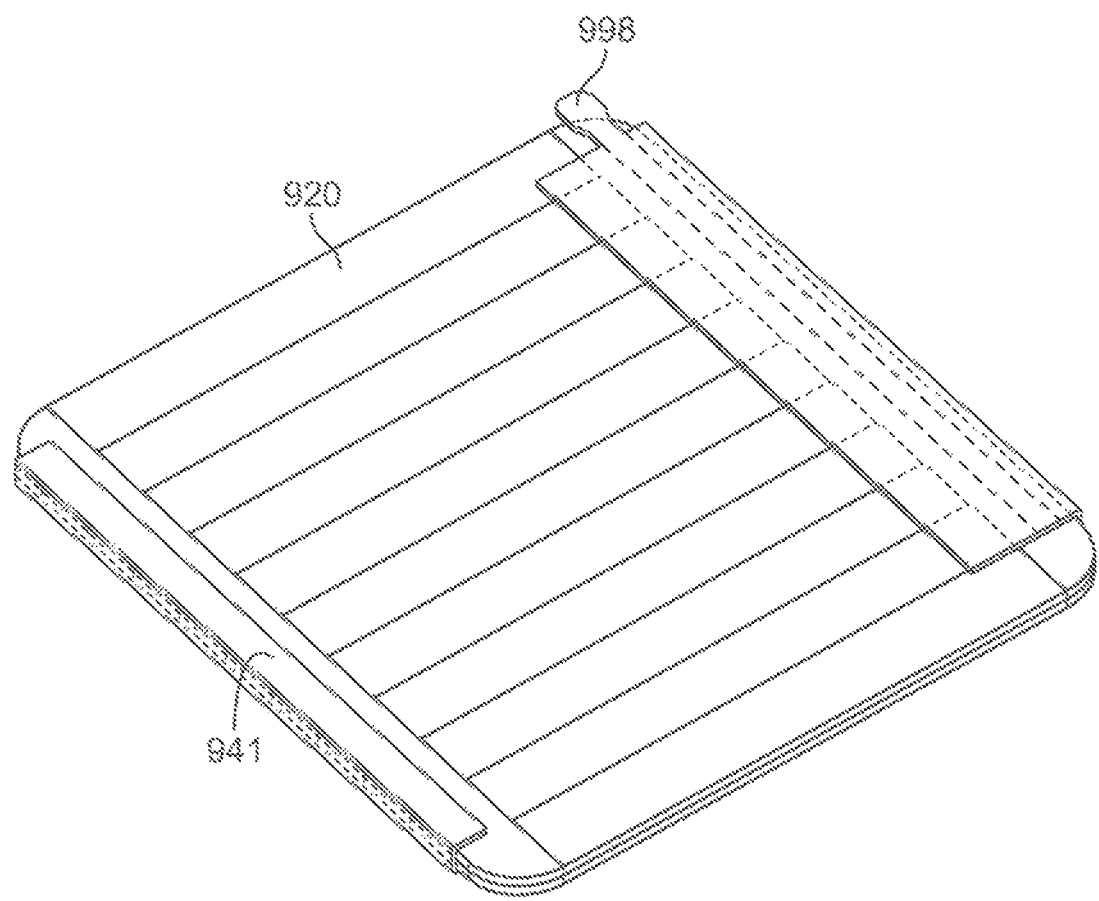
FIG. 18E is a top perspective view of the device of FIG. 18A with a first side of the dressing assembly detached from the carrier and the cover removed.
Figure 18F:
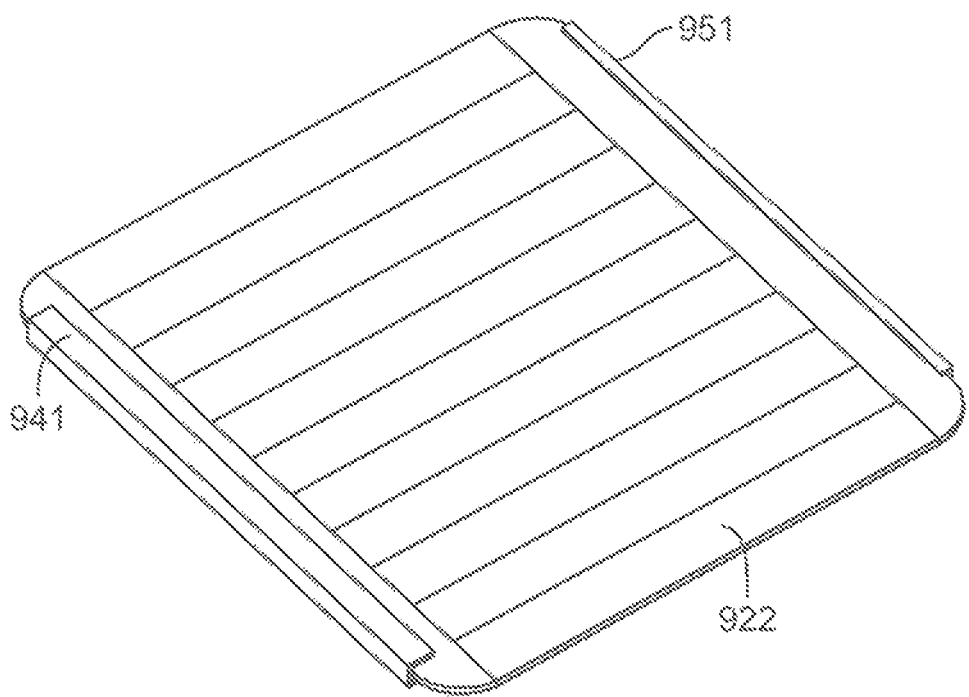
FIG. 18F is a top perspective of the device of FIG. 18A with the dressing assembly detached from the carrier.
Figure 18G:
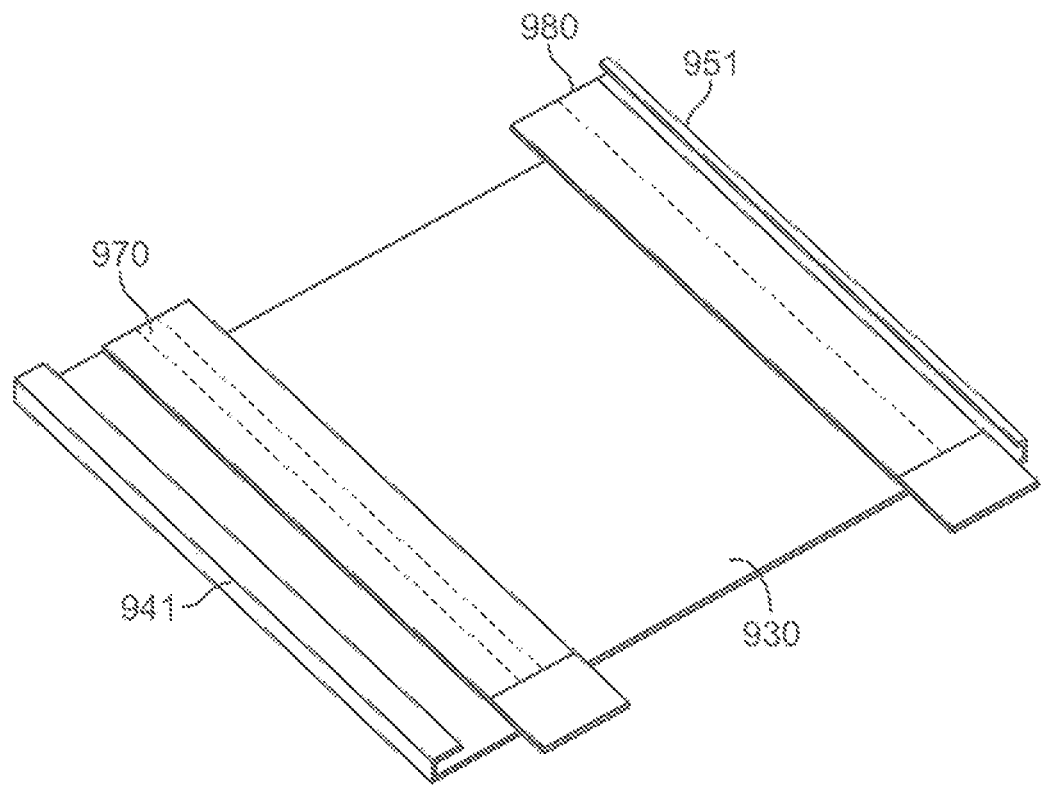
FIG. 18G is a top perspective view of the device of FIG. 18A with the carrier detached and removed.
Figure 18H:
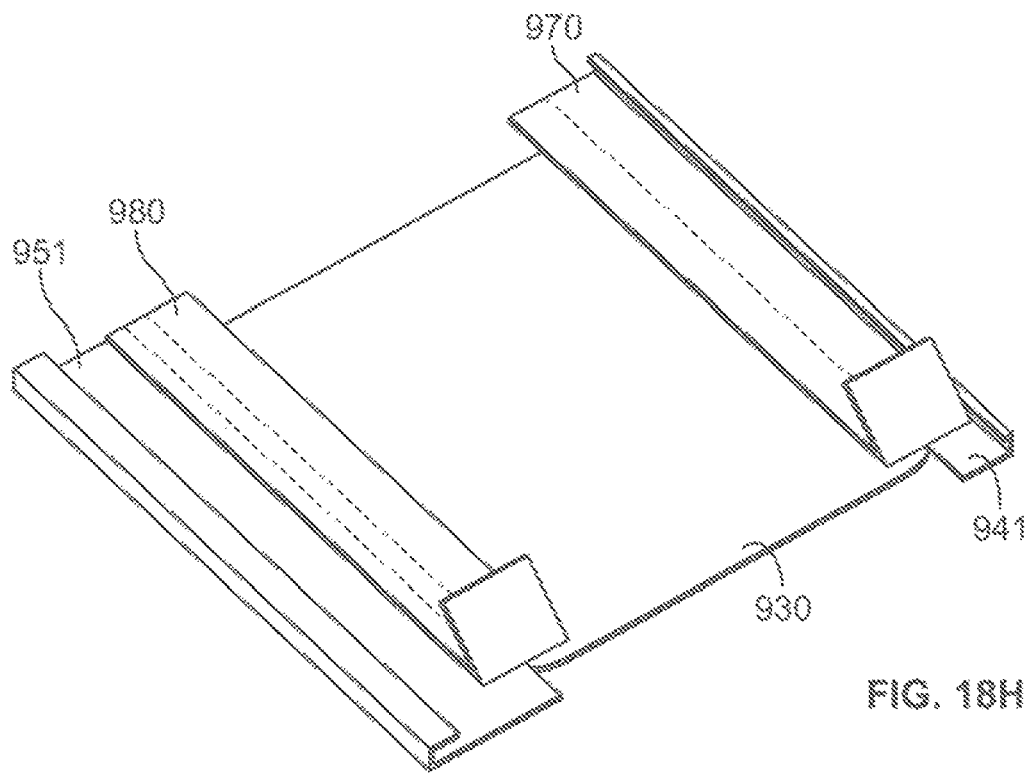
FIG. 18H is a perspective view of the device of FIG. 18A with the dressing being separated from the attachment sheets.
Figure 18I:
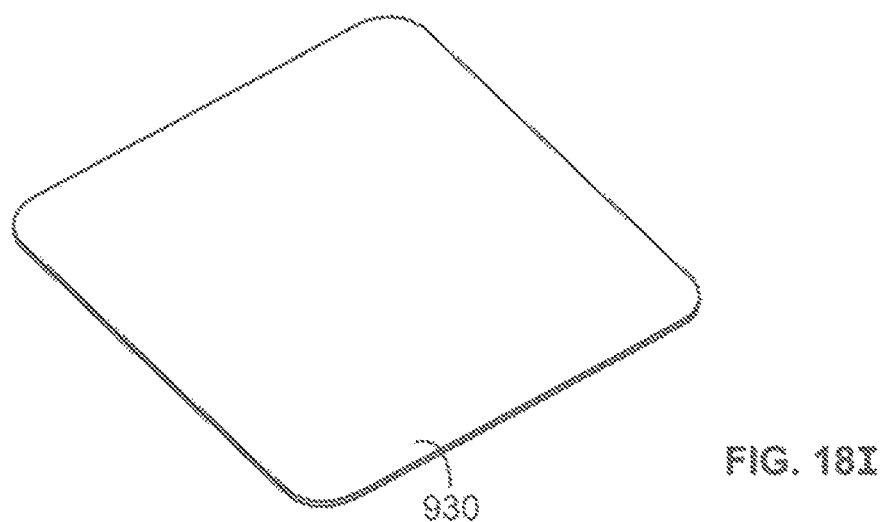
FIG. 18I is a perspective view of the device of FIG. 18A with the dressing separated from the attachment sheets.
Figure 18J:
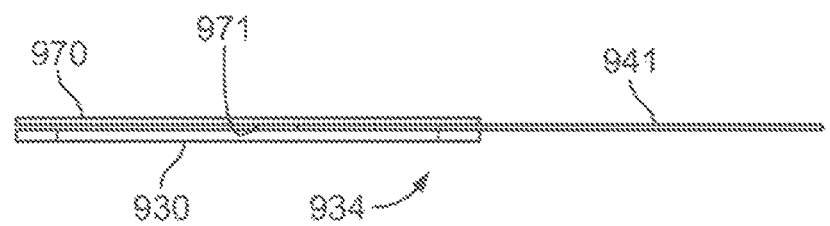
FIG. 18J is a side view of the device of FIG. 18A.

As shown in FIG. 18J, the attachment sheet 941 and side 934 of the dressing are attached on same side 971 of the adhesive structure 970 with the attachment sheet 941 overlapping but unattached to the dressing 931. The attachment sheet 941 has a second side 944 that is coupled to the cover 921 of the device 920 for example, by bonding with a low surface energy PSA such as an acrylic adhesive. Attachment sheet 941 may also have a pull tab 981 in an unattached region between the attachment to the adhesive structure 970 and attachment to the cover 921. After the dressing has been strained, the perforation pull tab 981 is located at the inside surface 960 of the cover 921 or alternatively at the seam between the cover 921 and the base 922.

The attachment sheet 951 is coupled at its side 954 to the back side 998 of the base 922 for example, by bonding with a low surface energy PSA such as an acrylic adhesive. The side 953 of attachment sheet 951 is attached to the side 933 of the dressing 930 by way of an adhesive structure 980 such as KAPTON® tape or a peelable adhesive, and in a manner similar to the adhesive structure 970 that attaches the side 944 of the dressing 930 to the attachment sheet 941. The attachment sheet 951 may include a pull tab 988 that is located on the back side 998 of the base adjacent and inside of the attachment zone 955 of the attachment sheet 951 to the back of the base 952.

According to some variations, the attachment sheets 941, 951 are flexible while being relatively inelastic with respect to the dressing 930 and may be constructed, e.g., out of a LDPE. The attachment sheets 941, 951 may be manufactured to be tearable along the material length while providing tensile strength in other directions, in particular in the tensioning direction of the material of the attachment sheet 941 (direction in which dressing is tensioned, stressed or strained). An example of such material is an LDPE polymer which is produced by an extrusion process that creates an anisotropic or directionally biased grain whereby the material is tearable with the direction of the grain, but has a relative resistance to tearing in the direction transverse to the grain.

The cover 921, when opened, exerts a straining force on the dressing 930 through the attachment sheet 941. FIG. 18A shows the assembly 900 in an unstrained configuration, while FIG. 18B shows the assembly 900 in an opened and strained configuration which may be applied to the skin. As shown in FIG. 18C, when strained, the tab 981 on the attachment sheet 941 is located over the inner surface of the cover 921 (folded back and exposed) and is accessible to a user. After applying the dressing 930, the cover 921 and base 922 may be removed.

The cover 921 and base 922 are separable from each when the tab 988 is pulled. FIG. 18C shows the assembly with the cover positioned with the dressing face down for example as it would be when applied to the skin of a subject. As shown in FIG. 18D the tab 988 is pulled to release the cover 921 from the remaining dressing assembly 910. As shown in FIG. 18E the cover 921 is removed from the remainder of the device 920, exposing the second pull tab 998. As shown in FIG. 18F, the second pulled tab 998 has released the base 922 from the dressing assembly 910 with attachment sheets 941, 951 unattached to the base 922. As shown in FIG. 18G, the base 922 is removed ant the remainder of the attachment sheets 941, 951 and the adhesive structures 970, 980 may be peeled away from the dressing 930 as shown if FIG. 18H with the dressing remaining on the skin in a configuration as shown in FIG. 18I.

Figure 19A:
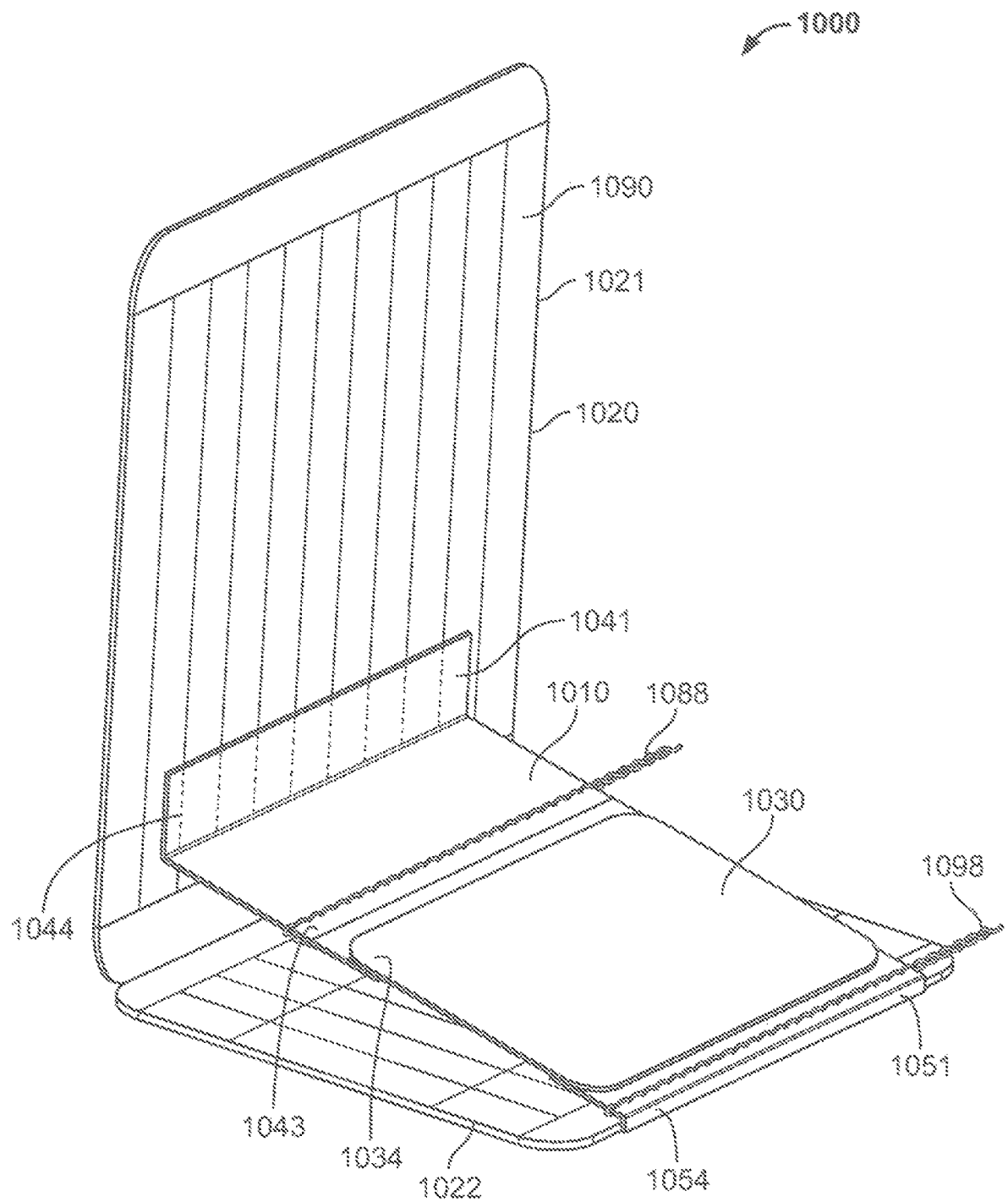
FIG. 19A is a perspective view of a variation of a dressing and packing assembly device.

Referring to FIGS. 19A through 19D, a variation of a dressing and packaging assembly 1000 is illustrated. The packaging assembly 1000 comprises an applicator and/or tensioning device 1020 and a dressing assembly 1010 including a dressing 1030. FIG. 19A shows the dressing assembly 1010 coupled to the applicator or tensioning device 1020. The tensioning member or applicator 1020 may be constructed in a similar manner as the tensioning and applicators described herein and shown in FIGS. 1A to 22B.

The device 1020 comprises a cover 1021 and a base 1022. The dressing assembly 1010 is removably coupled or anchored to the device 1020 which may act as a dressing carrier. The dressing assembly may be attached to the tensioning member or applicator in a manner similar to the assemblies described herein. The dressing assembly 1010 includes an attachment sheet 1041 and attachment sheet 1051. The attachment sheet 1041 has a first side 1043 that is attached to the second side 1034 of the dressing 1030 by way of an adhesive structure 1070 such described with reference to adhesive structures 970, 980. The attachment sheet 1041 has a second side 1044 that is coupled to the cover 1021 of the device 1020 for example, by bonding with a low surface energy PSA such as an acrylic adhesive. Attachment sheet 1041 also has a ripcord 1088 stitched along its length at an unattached portion of the attachment sheet 1041, between its attachment to the adhesive structure 1070 and attachment to the cover 1021. Various types of stitches may be used including but not limited to a chain stitch or a lockstitch. After the dressing has been strained, the ripcord 1088 is located at the exposed inner side 1090 of the cover 1021 or alternatively at the seam between the cover 1021 and the base 1022.

The attachment sheet 1051 is coupled at its side 1054 to the back side of the base 1022 for example, by bonding with a low surface energy PSA such as an acrylic adhesive. The side 1053 of attachment sheet 1051 is attached to the side 1033 of the dressing by way of an adhesive structure 1080 such as KAPTON® tape or a peelable adhesive, and in a manner similar to the adhesive structure 1070 that attaches the side 1034 of the dressing 1030 to the attachment sheet 1041. The attachment sheet 1051 includes a ripcord 1098 that is located between attachment to the adhesive structure 1090 and attachment to the back of the base. The ends of the ripcords 1088, 1098 extend out of the tensioning member 1020 for easy accessibility.

Figure 19B:
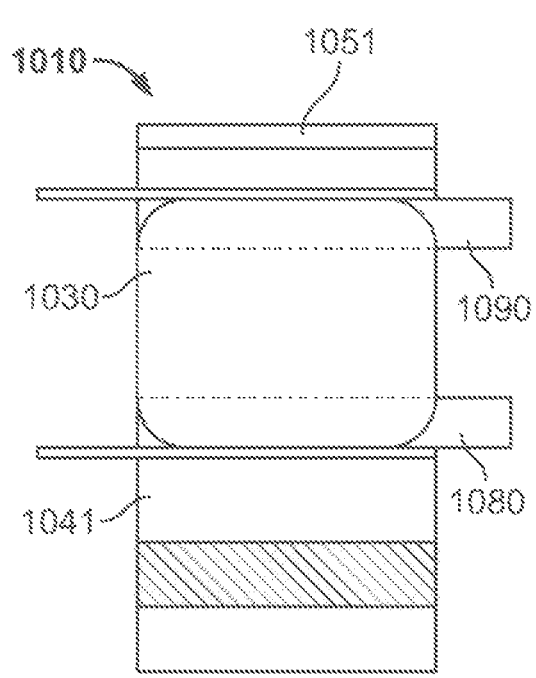
FIG. 19B is a top view of an unstrained configuration of a dressing assembly of FIG. 19A
Figure 19C:
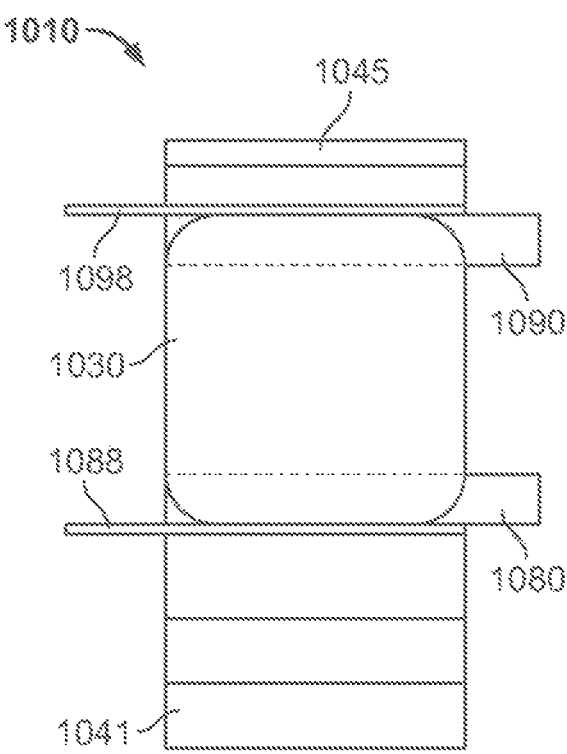
FIG. 19C is a top view of a strained and attached configuration of the dressing assembly of FIG. 19B.

FIGS. 19A and 19B illustrate the dressing assembly 1010 in an unstrained configuration. The cover 1021, when opened, exerts a straining force on the dressing 1030 through the attachment sheet 1041. FIG. 19C illustrates the dressing assembly 1010 in a strained configuration.

Figure 19D:
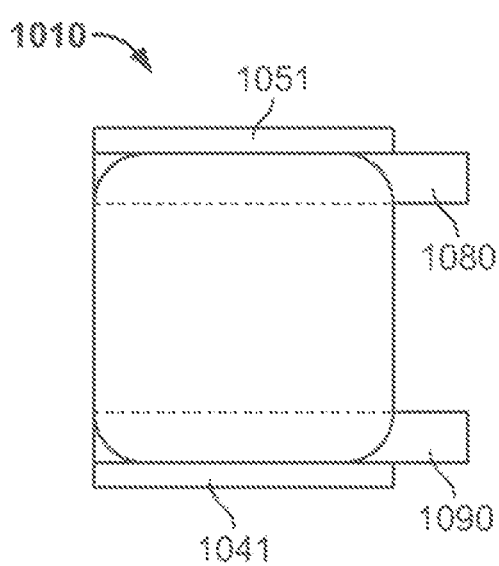
FIG. 19D is a top view of a strained and detached configuration of the dressing assembly of FIG. 19B.
Figure 19E:
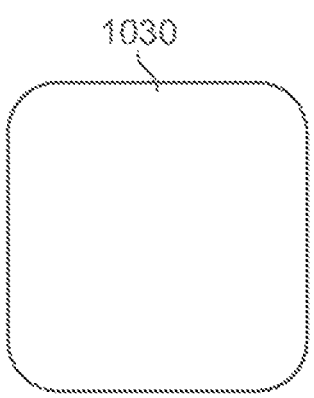
FIG. 19E is a top view of a dressing of FIG. 19B.

After the dressing is strained and applied, the ripcords 1088, 1098 are pulled to separate the portion of the attachment sheets 1041, 1051 attached to the tensioning device 1020 from the portions of the attachment sheets 1041, 1051 attached to the dressing 1030. The applicator or tensioning device 1020 may then be removed as shown in FIG. 19D. The adhesive structures 1080, 1090 may then be peeled away to remove the remaining portion of the dressing assembly 1010 and attachment sheets 1041, 1051, from the dressing as shown in FIG. 19E.

Figure 20A:
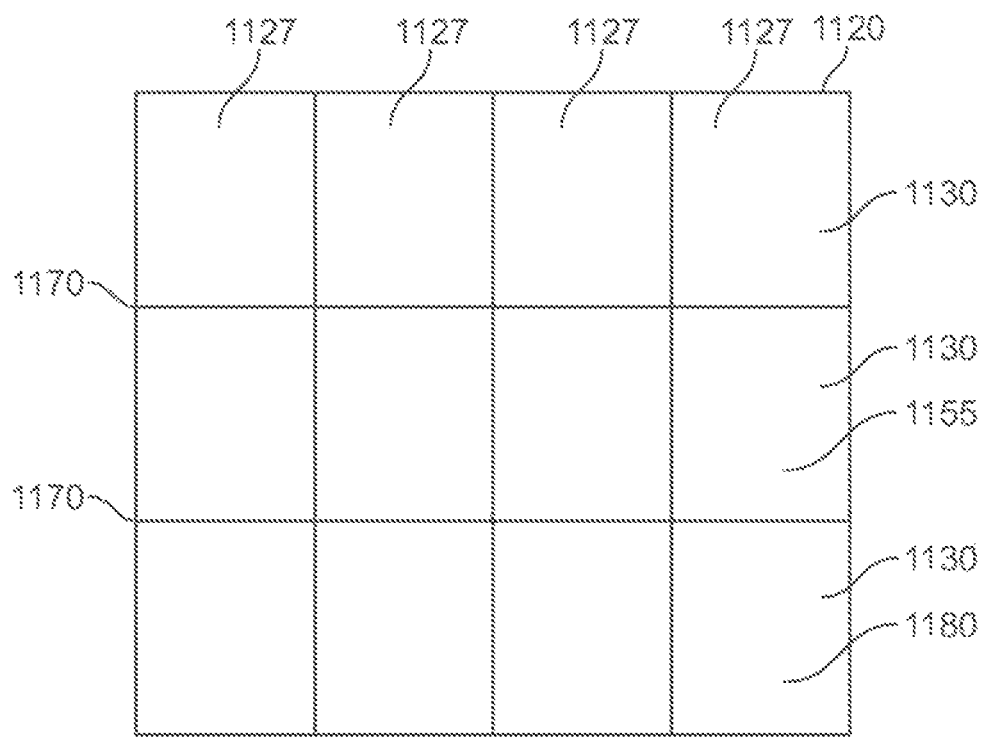
FIG. 20A is a top view of a variation of a dressing carrier, support, base tensioning device or applicator.
Figure 20B:
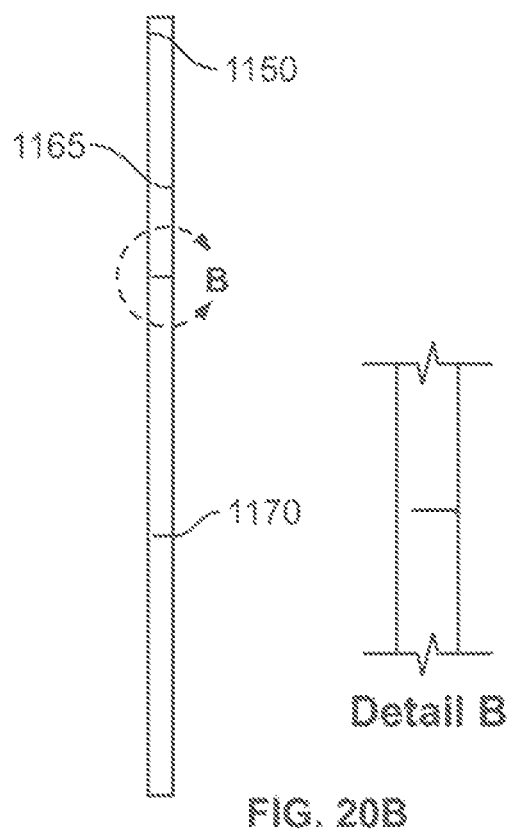
FIG. 20B is a side view of the dressing carrier, support, base tensioning device or applicator of FIG. 20A in a first configuration.
Figure 20C:
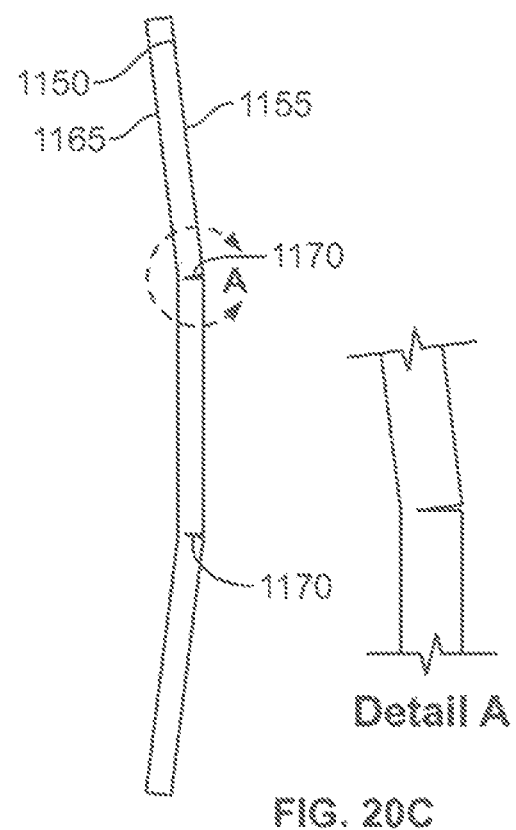
FIG. 20C is a side view of the dressing carrier, support, base tensioning device or applicator of FIG. 20A in a second configuration.
Figure 21A:
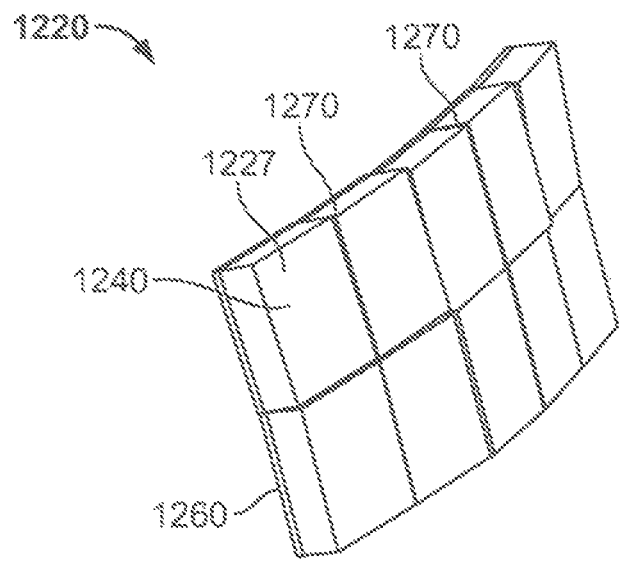
FIG. 21A is a perspective view of a variation of a dressing carrier, support, base tensioning device or applicator
Figure 21B:
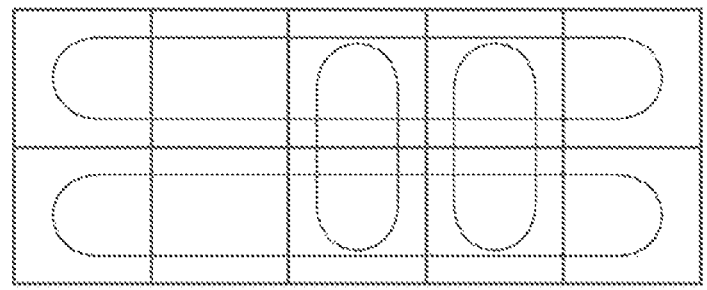
FIG. 21B is a top view of the dressing carrier, support, base tensioning device or applicator of FIG. 21A.
Figure 21C:
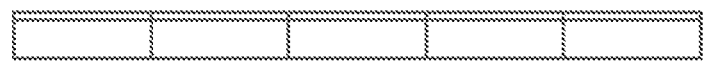
FIG. 21C is a side view of dressing carrier, support, base tensioning device or applicator of FIG. 21A.
Figure 21D:
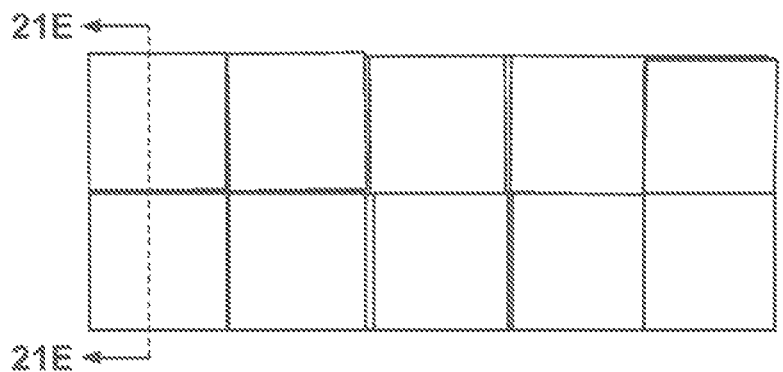
FIG. 21D is a top view of the dressing carrier, support, base tensioning device or applicator of FIG. 21A in a flexed configuration.
Figure 21E:
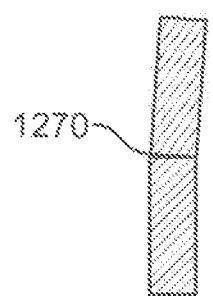
FIG. 21E is a cross-section of FIG. 21D along the lines A-A

Referring to FIGS. 20A to 20C, a variation is shown of a dressing carrier, tensioning device or applicator 1120. The device 1120 comprises a plurality of segments 1130 formed by scoring a substrate 1150 on one side 1155 of a planar surface. The scores 1170 may be formed in one or more directions or having one or more shapes, curved or straight. Additionally the scores may be formed on both sides permitting both convex and concave shaping of a device. As illustrated, the scores 1170 permit shaping of the device or an attached dressing. The scores 1170 as illustrated are formed on a first side 1155 of a planar surface of the device while the second side 1165 is not scored. When a force is applied to the second side 1165, the substrate bends. When a force is applied to the first side 1155, the substrate 1150 the device does not flex at the scores 1170. The remaining substrate at the scores 1170 may act as flexion limiter while the scores 1170 act as a flex element.

When a convex dressing shape is desired for a concave surface, the dressing may be attached on the first side 1155 so that when the substrate is bent, the dressing forms a convex shape to match a concave contour where the device is to be applied. When a concave dressing shape is desired for a convex body contour, the dressing may be positioned on the second side 1165 of the substrate 1150. So that when the substrate is bent, the dressing forms a concave shape to match a convex body contour where the device is to be applied. Various dressing backings may be provided for different body locations or contours.

According to variations, the score may be orthogonal or have orthogonal components with respect to the segments 1127 of the carrier, applicator or tensioning device. The segments 1127 may be similar to segments shown in FIGS. 1A to 22B.

Referring to FIGS. 21A to 21D, a variation is shown of a dressing carrier, tensioning device or applicator 1220. The device 1220 comprises a plurality of foam cells 1240 coupled by and adhesive backing 1260. The foam cells 1240 form a plurality of segments 1227 that permit flexing in multiple directions so that the device conforms to a curvature, profile or shape of a subject where the dressing is to be applied. The foam may be sufficiently thick to generally provide added column strength for straining a dressing, i.e. a resistance to bending. A backing or support may be provided for straining a dressing, for example constructed of a material with an elastic modulus and appropriate thickness that will, at minimum, counteract the force created by straining the dressing. The dressing strain may be fixed, for example, using an adhesive on the back of a portion of the dressing assembly or attachment sheet. After the dressing is fixed, the backing or support may be removed permitting increased manipulation of the shape of the strained dressing to conform to a greater degree to the shape of the patient's body contours where the dressing is to be applied.

As illustrated, the separations 1270 between the foam sections permit shaping of the device. The separations 1270 as illustrated are formed on a first side 1255 of a planar surface of the device while the second side 1265 is not scored. When a force is applied to the first side 1255, the substrate bends. When a force is applied to the second side 1265, the substrate 1250 the device does not flex at the separations. The remaining substrate at the separations may act as flexion limiter while the scores act as a flex element.

When a convex dressing shape is desired for a concave surface, the dressing may be attached on the first side 1255 so that when the substrate is bent, the dressing forms a convex shape to match a concave contour where the device is to be applied. When a concave dressing shape is desired for a convex body contour, the dressing may be positioned on the second side 1265 of the substrate 1250. So that when the substrate is bent, the dressing forms a concave shape to match a convex body contour where the device is to be applied. Various dressing backings may be provided for different body locations or contours.

Figure 22B:
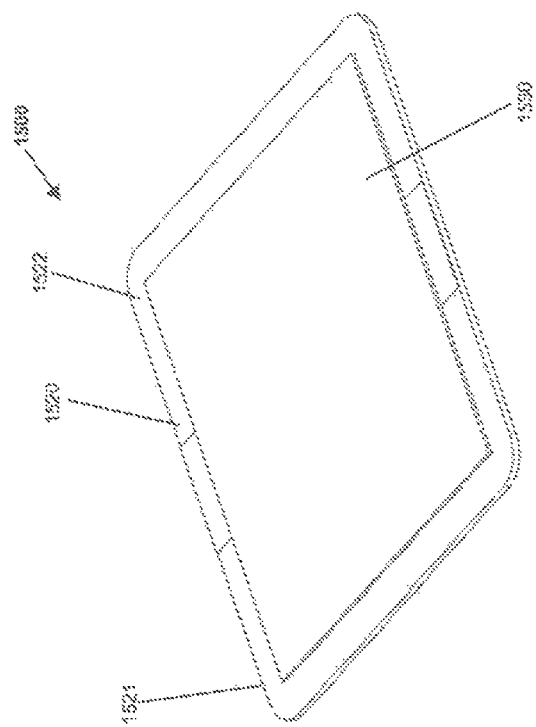
FIG. 22B is a perspective view of a variation of a dressing and packaging device in a strained configuration.
Figure 22A:
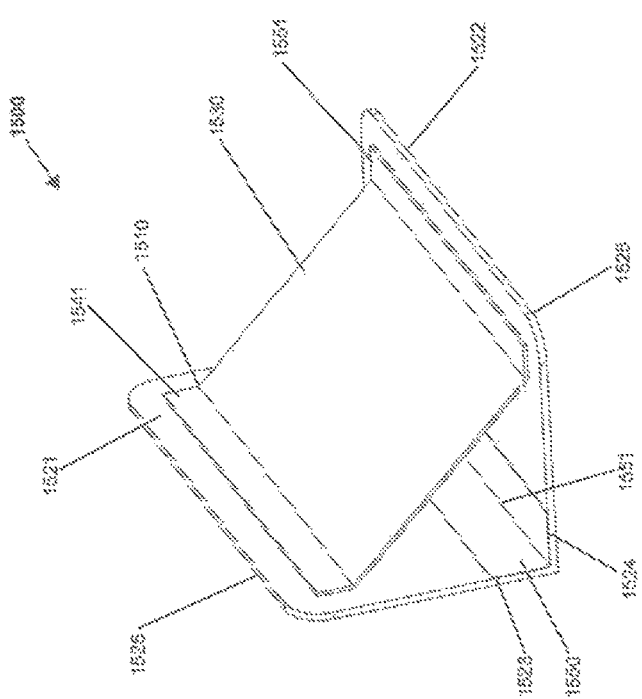
FIG. 22A is a perspective view of a variation of a dressing and packaging assembly in an unstrained configuration.

Referring to FIGS. 22A and 22B, a variation of a dressing and packaging assembly 1500 is illustrated. The packaging assembly 1500 comprises an applicator and/or tensioning device 1520 and a dressing assembly 1510 including a dressing 1530. The packaging assembly 1500, applicator or tensioning device 1520, and/or dressing assembly 1510 may be configured to pre-strain the dressing 1530 and/or permit transfer of the pre-strained dressing 1530 to the skin of a subject.

The device 1520 may comprise a cover 1521 and a base 1522. The dressing assembly 1510 is removably coupled or anchored to the device 1520, and may serve as a dressing carrier. The cover 1521 and base 1522 are movably, pivotably, bendably or hingedly coupled at sides 1523, 1524 and may be constructed in a manner similar to that described with respect to covers and bases described in FIGS. 1A to 22B. Attachment regions 1541, 1551 of the dressing assembly 1510 are attached near free sides 1525, 1526 of cover 1521, 1522 respectively, for example by way of a peelable adhesive or removable adhesive structures. However an attachment sheet or attachment structure described with respect FIGS. 1A to 22B herein may be used. The attachment regions 1541, 1551 and or positioning of the dressing 1530 on the device 1520, may be symmetric with respect to a line defined by attachment of sides 1523, 1524 of the cover 1521 and base 1522 respectively. As shown in FIG. 22B, the dressing 1530 is strained with the cover 1521 and base 1522 are opened. The dressing 1530 may then be applied to the skin of a subject and the device 1520 may be peeled away from the dressing 1530. In addition or alternatively, the cover 1521 and base 1522 may be separated by way of a perforation formed in the substrate of the device 1520 or a perforation 1551 formed in an attachment structure 1550 such as a tape or layer of material that attaches sides 1523 and 1524 of the cover 1521 and base 1522 respectively.

In some variations, the device 1520 may optionally comprise an adhesive coating or adhesive tape on the cover 1521 and/or base 1522 which may adhere to the dressing 1530 when the dressing 1530 is tensioned and the dressing comes in further contact with the cover 1521 and base 1522. In some variations, the adhesive is configured to maintain the dressing 1530 in a tensioned state and/or against the cover 1521 and/or base 1522. The adhesive coating or adhesive tape may be located along the side regions 1523, 1524 of the cover 1521 and/or base 1522, but many also be provided adjacent to the attachment regions 1541, 1551. Release liners may also be provided to reduce inadvertent adhesion of the dressing or other structures to the adhesive until activation of the device 1520 is desired.

According to variations the various assemblies or devices described herein may provide a temporary wound dressing that may be applied before a wound is closed. The assembly may be configured to apply a dressing to a wound and to use the packaging or applicator to apply pressure to the wound before removing or separating the applicator, tensioning device or dressing carrier, base or support from the dressing. According to this variation which may be provided with any of the embodiments described below, the packaging or applicator has sufficient rigidity to distribute a relatively even or firm force to a wound by applying pressure to the packaging or applicator when and/or after the dressing is applied to a wound. According to a variation, such dressing may include a coagulation agent or other agent or medicament, for example as described herein. According to another variation, margins as described herein, are provided on such a device between a dressing and edges used to manipulate the device.

The assemblies or devices described herein may also form a dressing support structure. For example, the dressing support structure may comprise of a plurality of segments of the base structures. The dressing support structure may comprise at least 3 segments that extend at least from a first side of the dressing to a second side of the dressing. The dressing support structure may comprise a plurality of segments such as segments described in FIGS. 1A to 22B that are coupled or formed together. The plurality of segments of a cover described herein may also provide support to a dressing when the cover is folded over 360 degrees with respect to the corresponding base structure.

In other examples, the strained dressing may be provided to the user as pre-strained dressing that is strained at the point-of-manufacture, rather than at the point-of-use. Referring to FIGS. 23A to 23I, preparation of a pre-strained assembly 2351 that includes a pre-strained dressing is illustrated. A tensioning device 2341 used to prestrain the dressing is shown in use in FIGS. 23A to 23D. Various features and stages of preparing prestrained assembly 2351 are further shown in FIGS. 23E to 23I.

The pre-strained assembly 2351 may comprise a dressing assembly 2308 and strain maintaining structure or support structure 2330. (See FIG. 23I) The pre-strained assembly 2351 may be stored for a period of time prior to use.

The dressing assembly 2308 may include a dressing 2310 comprising a relatively planar elastic sheet 2360 defining a plane. The elastic sheet 2360 may comprise a silicone sheet or other elastic material, for example, as described herein. The dressing assembly 2308 may further comprise an attachment sheet 2304, tensioning sheet 2307, a pre-strained assembly release 2352 and a dressing release 2319.

The attachment sheet 2304 may be configured to attach the dressing 2310 to a support structure 2330 by way of engaging element 2322. The attachment sheet 2304 of the dressing assembly 2308 may include a first engaging wall or element 2322 extending downward with respect to the plane of the dressing 2310 and including an inwardly extending hook 2323. Engaging element 2322 may be attached to the attachment sheet 2304, for example, with an adhesive. The tensioning sheet 2307 of the dressing assembly 2308 may include a second engaging element 2324 extending downward with respect to the plane of the dressing 2310 and including an inwardly extending hook 2325. The tensioning sheet 2307 may be configured to attach the dressing 2310 to the support structure 2330 by way of engaging element 2324. Engaging element 2324 may be attached to tensioning sheet 2307, for example, with an adhesive. The tensioning sheet 2307 may also be configured to translate tension from the tensioning device 2341 to the dressing 2310 to strain the dressing 2310.

Figure 23A:
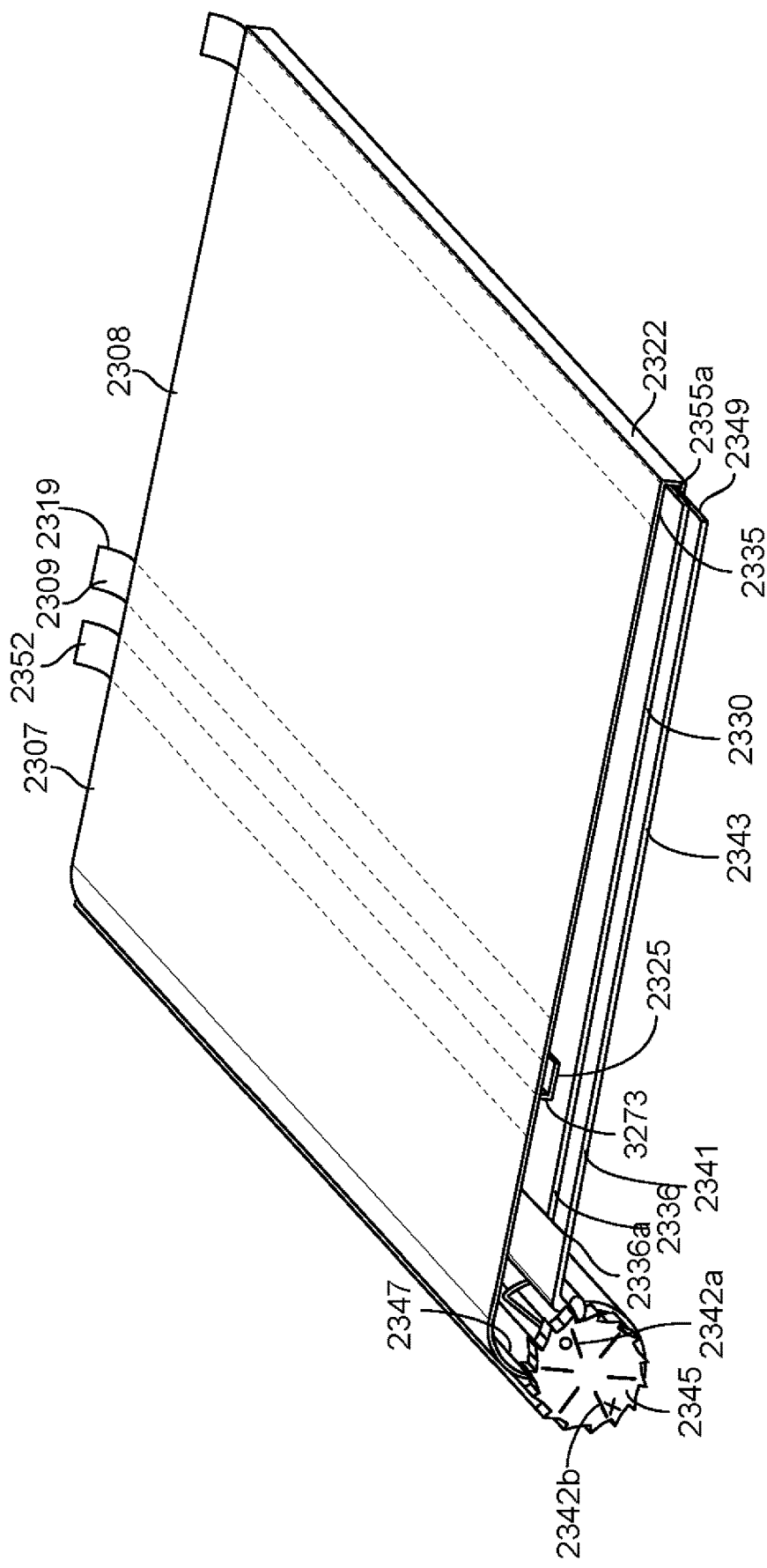
FIG. 23A is a top perspective view of the dressing assembly, support structure, and tensioning device in a relatively unstrained configuration.
Figure 23B:
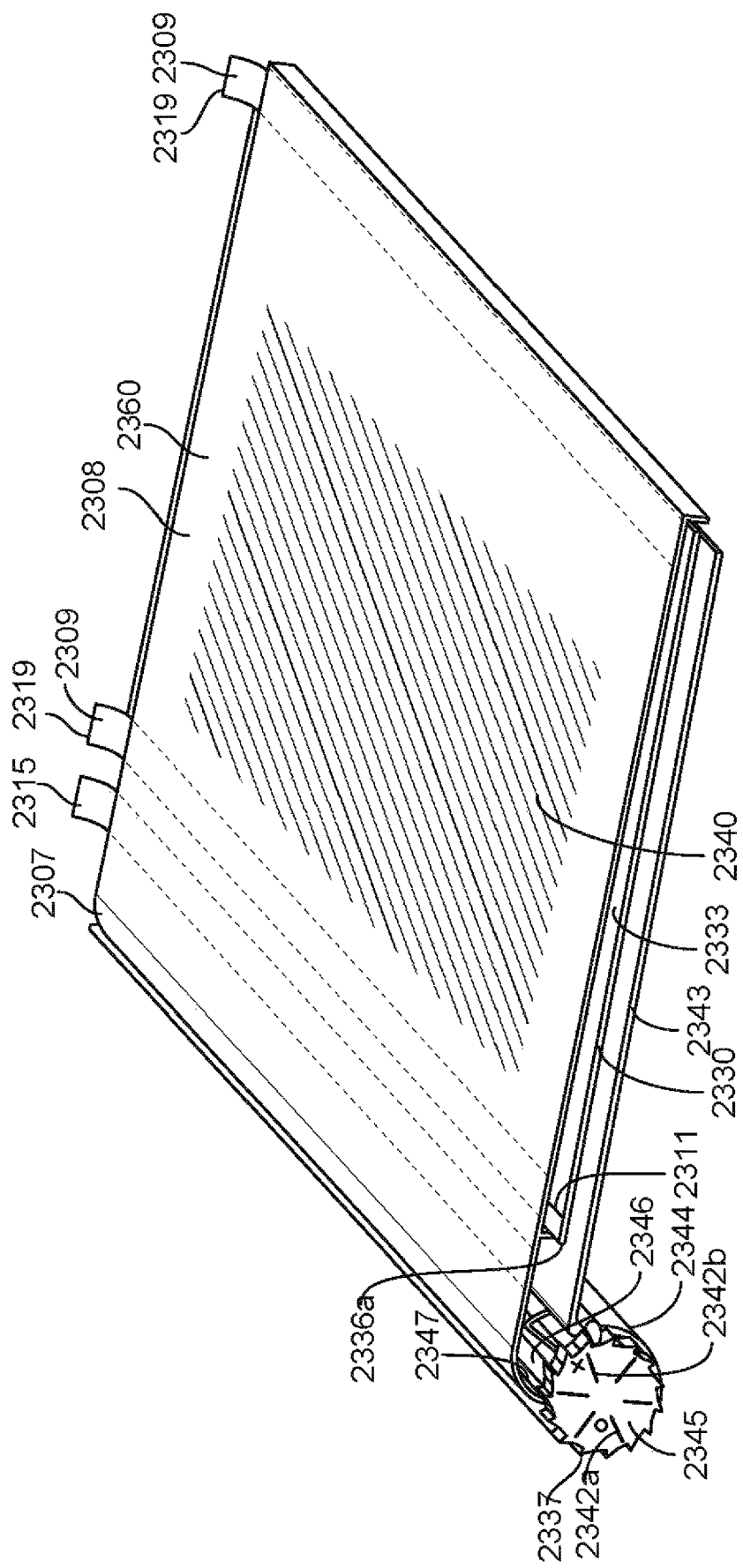
FIG. 23B is a top perspective view of the dressing assembly, support structure, and tensioning device in a pre-strained configuration.
Figure 23C:
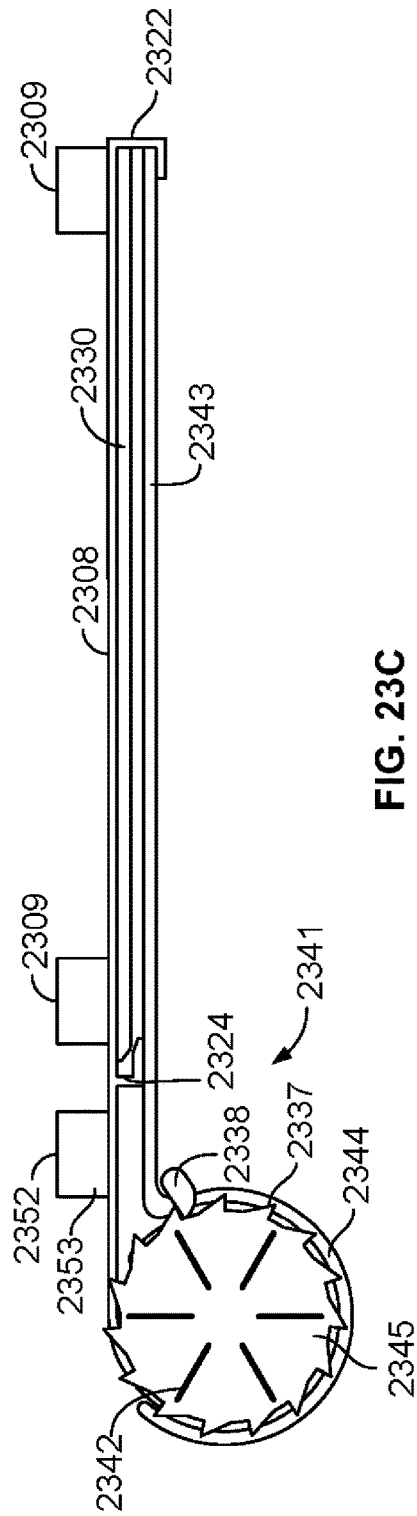
FIG. 23C is a schematic side view of the dressing assembly, support structure and tensioning device of FIG. 23B.
Figure 23D:
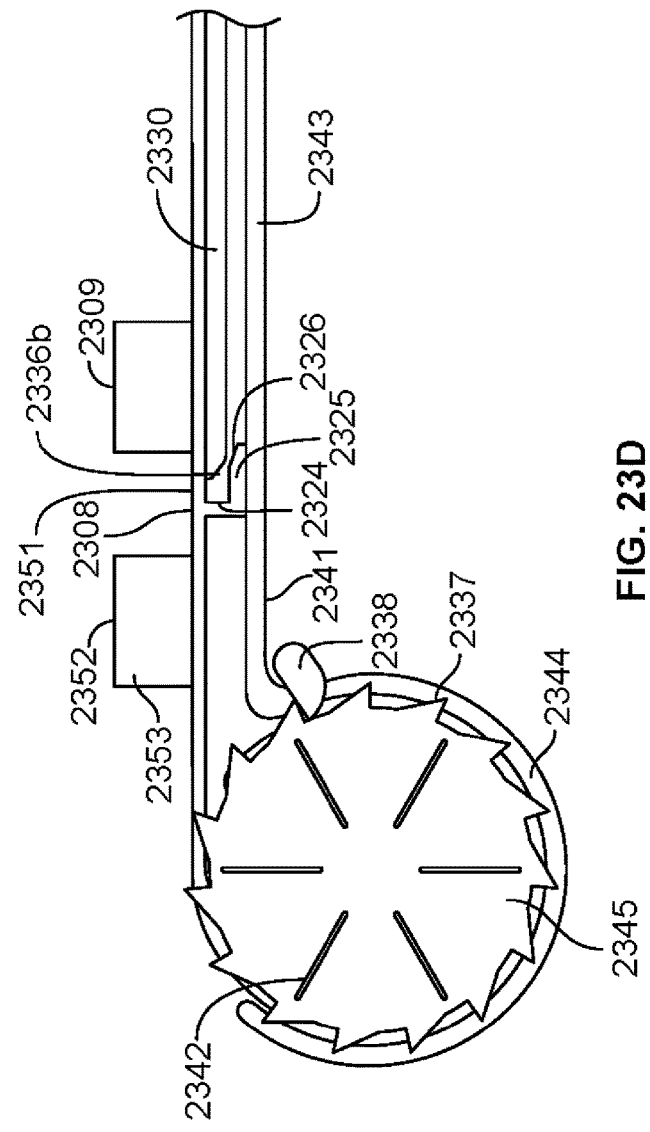
FIG. 23D is an enlarged schematic side sectional view of the dressing assembly, support structure, and tensioning device of FIG. 23C.
Figure 23E:
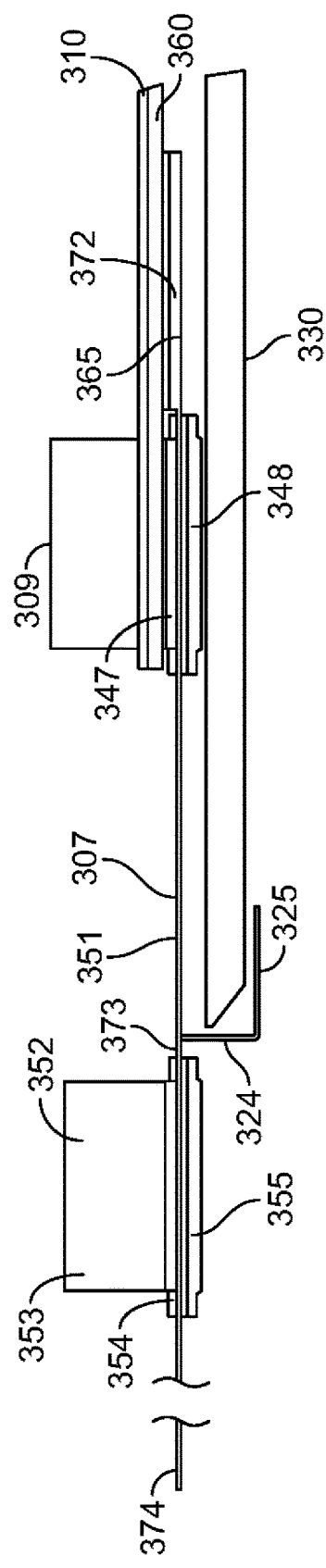
FIG. 23E is an enlarged, schematic, detailed side view of a portion of the dressing and support structure of FIG. 23D.
Figure 23F:
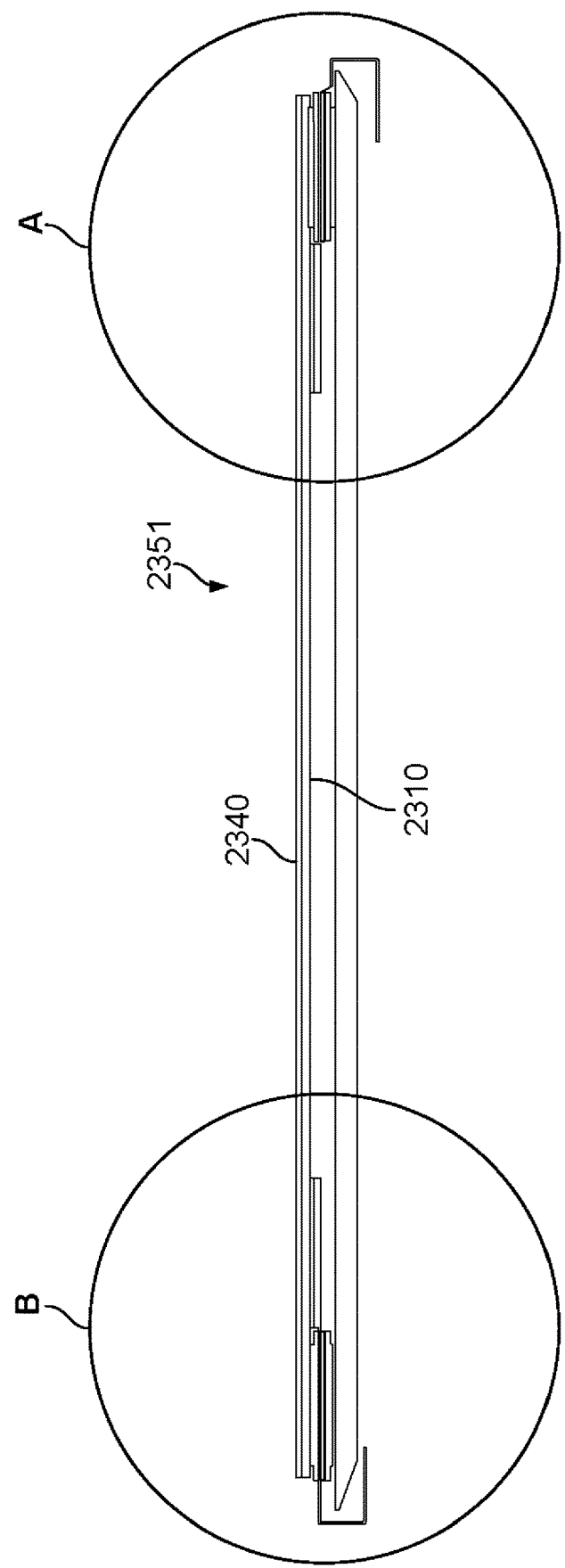
FIG. 23F is a schematic side view of the dressing assembly and support structure in a pre-strained configuration.
Figure 23G:
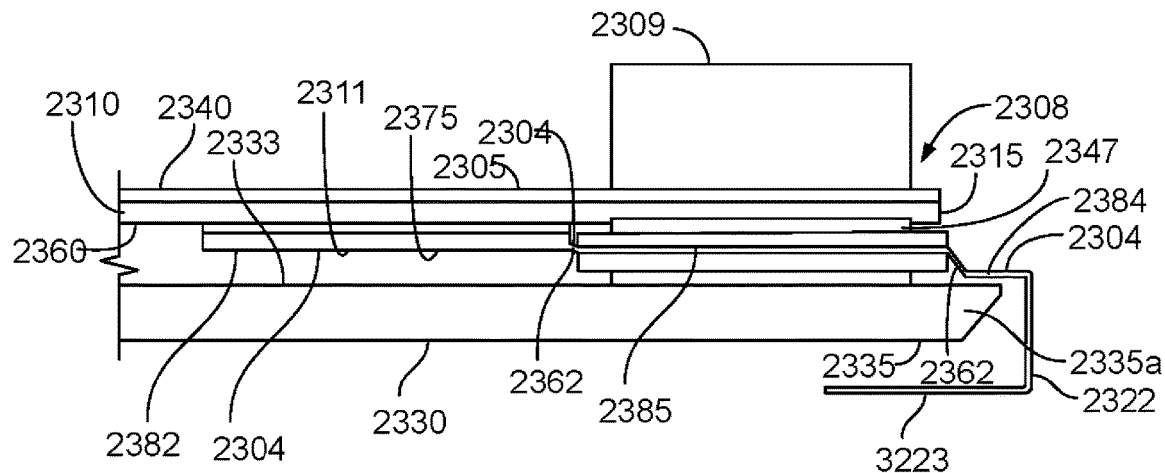
FIG. 23G is an enlarged side view of the dressing assembly and support structure of Section A of FIG. 23F
Figure 23H:
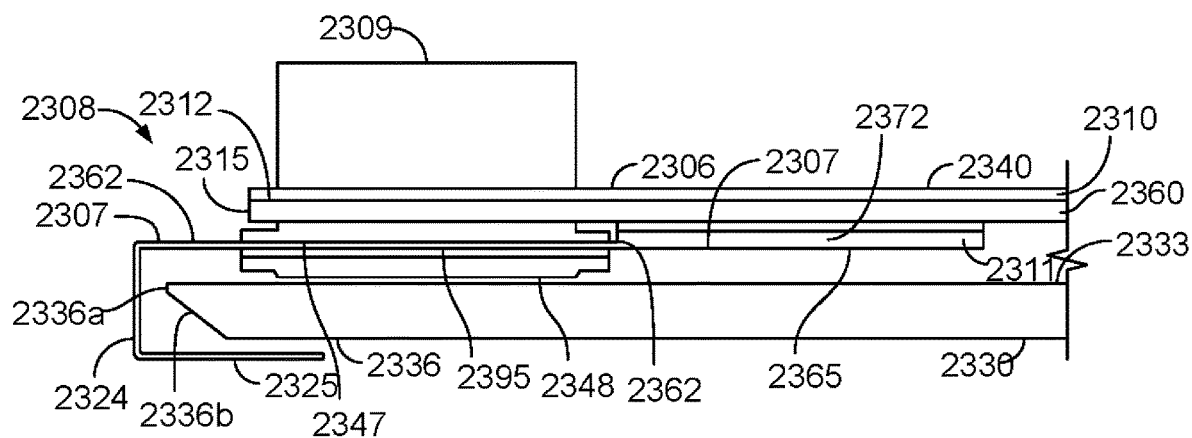
FIG. 23H is an enlarged side view of the dressing assembly and support structure of Section B of FIG. 23F.
Figure 23I:
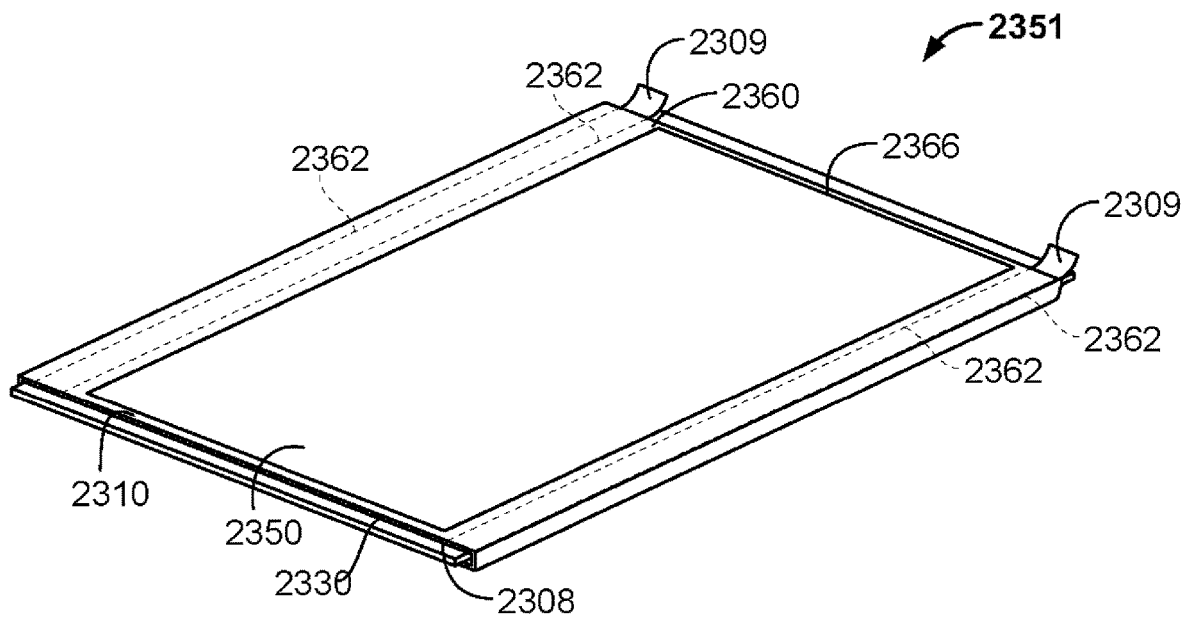
FIG. 23I is a top perspective view of a pre-strained assembly including remaining elements of a dressing assembly and a support structure.

The pre-strained assembly release 2352 may be configured to release the pre-strained assembly 2351 (the dressing 2310 and support structure 2330) from the tensioning device 2341 (see, e.g., FIGS. 23E and 23I). The dressing release mechanism 2319 may be configured to release the dressing 2310 from the engaging elements 2322, 2324 (including hooks 2323, 2325) and thus from the support structure 2330. The dressing release mechanism 2319 may be configured to release the dressing 2310 after the dressing 2310 is applied to a subject.

The dressing 2310 of the dressing assembly 2308 may have a first edge or side 2305 having a length, and a second edge or side 2306 having a length. The dressing 2310 may be coupled at a first edge or side 2305 to the attachment sheet 2304 which may be flexible yet relatively less elastic or in-elastic than the dressing 2310. The attachment sheet 2304 may have a first side 2382 and a second side 2384. When assembled, the attachment sheet 2304 may be bonded to the elastic sheet 2360 of the dressing 2310 at section 2375 of attachment sheet 2304 at or near the side 2382 of the attachment sheet 2304, for example, using a combination of a silicone PSA/acrylic PSA. The attachment sheet 2304 may be coupled at its side 2384 to engaging element 2322 and hook 2323, for example, by bonding with an adhesive material, e.g., using a combination of a silicone PSA/acrylic PSA. The attachment sheet 2304 may couple the dressing 2310 by way of engaging element 2322 and hook 2323, to the support 2330 near the first side 2305 of the dressing 2310. The dressing 2310 may be coupled at its second edge or side 2306 to the tensioning sheet 2307 which may be flexible yet non-elastic or less elastic than the dressing 2310. The tensioning sheet 2307 may have a first side 2372 a middle location 2373 and a second side 2374. When assembled, the tensioning sheet 2307 may be bonded to the elastic sheet 2360 of the dressing 2310 at section 365 of tensioning sheet 2307 at or near the side 2372 of the tensioning sheet 2307, for example, using a combination of a silicone PSA/acrylic PSA. The tensioning sheet 2307 may be coupled at a middle location 2373 to side wall 2324 and hook 2325, for example, by bonding with an adhesive material, for example, using a combination of a silicone PSA/acrylic PSA. When assembled into the pre-strained assembly 2351, the tensioning sheet 2307 may couple the dressing 2310 by way of side wall 2324 and hook 2325 to the support structure 2330 near the second side 2306 of the dressing 2310. The tensioning sheet 2307 may be loaded onto the tensioning device 2341 at the second side 2374 as described in more detail herein. According to some variations, the attachment sheet 2304 or tensioning sheet 2307 may be constructed, e.g., out of a low density polyethylene.

The dressing assembly 2308 is shown in FIG. 23A, positioned over a support structure 2330 to which it may be removably attached when or after the dressing 2310 is pre-strained to form the pre-strained assembly 2351. The support 2330 may be generally planar and include sides 2335, 2336 with corresponding edges 2335a and 2336a defining its length. Other support elements, support structures and/or strain maintaining elements may be used, for example, the sides of the dressing 2310 or dressing assembly 2308 may be clamped and a desired distance maintained between the clamps, e.g., using a separating element.

The dressing 2310 of the dressing assembly 2308 may be strained, for example, with a tensioning device 2341 as shown in FIGS. 23A to 23D. The pre-strained dressing 2310 may then be stored in a pre-strained configuration for a period of time prior to use. The tensioning device 2341 may be used at a point of manufacture, by an intermediary, or by an end user. The tensioning device 2341 may comprise a planar portion 2343 and a circular portion 2344 configured to contain a rotating element 2345. The rotating element 2345 may have a middle section 2346 with a slot 2347 to receive and engage the tensioning sheet 2307 of the dressing assembly 2308.

In FIG. 23A the dressing assembly 2308 may be shown in a first configuration on the tensioning device 2341 where it is relatively unstrained. The dressing assembly 2308 may be positioned over support structure 2330. This support structure 2330 may be positioned over the tensioning device 2341 with the upper surface 2333 of the support structure 2330 interfacing the back side 2311 of the dressing 2310. A first edge 2335a of the support structure 2330 and a first side or edge 2349 of the planar portion 2343 of the tensioning device 2341 may be engaged and held by engaging wall 2322 and hook 2323. The second end 2336 and edge 2336a of the support 2330 may initially be free from engagement with but is in a position interfacing the dressing 2310. This may permit the dressing 2308 to be strained to a desired degree without interference of the support structure 2330.

In use, the end 2374 of the tensioning sheet 2307 may be inserted into the slot 2347 in the middle section 2346 of the rotating element 2345 of the tensioning device 2341. Then the rotating element 2345 may be rotated until the tensioning sheet 2307 is engaged. Initially the tensioning sheet 2307 and dressing 2310 may be in an unstrained configuration but with minimal slack, when attached to the tensioning device 2341. As the rotating element 2345 is rotated, the dressing 2310 may be strained as the tensioning sheet 2307 is pulled in a tensile straining direction with respect to the dressing 2310 by the rotating element 2345.

The dressing 2310 may be strained by turning the rotating element 2345 as shown in FIGS. 23A-23D. Once the tensioning sheet is loaded as the rotating element 2345 is turned, the tensioning sheet 2307 may wrap around the rotating element 2345 thereby shortening the distance between the rotating element 2345 and the dressing 2310, to stretch or strain the dressing 2310. A locking mechanism comprising ratchets 2337 on the rotating element 2345 and a pawl 2338 on the circular portion 2344 may be used to lock the dressing 2310 in a strained configuration as shown in FIGS. 23B to 23D. When the tensioning sheet 2307 is pulled in a tensile straining direction towards the circular portion 2344 of the tensioning device 2341, the engaging element 2324 and hook 2325 may also move in the tensile straining direction. The edges 2336a of the support comprises a ramp 2336b that may engage with a ramp 2326 on the hook 2325 to guide the edge 2336a of the support 2330 into engagement with the hook 2325 as the hook 2325 moves towards the circular portion 2344 of the tensioning device. (See FIGS. 23C to 23H). The strain of the pre-strained dressing 2310 may be controlled or determined using measurement elements or marks 2342 on the rotating element 2345 the distance between each of which may correspond to an increment of increased strain or distance. Once a dressing assembly 2308 is loaded on the tensioning device 2341, the strain may be determined by the amount the rotating element 2345 rotates. Each mark 2342 may correspond to a percentage strain or a distance. A 0% strain may be identified as the position in which the dressing assembly 2308 is loaded onto the tensioning device 2341 with no slack and minimal strain or tension. As shown in FIG. 23A the 0% position may be shown where mark 2342a is aligned with the pawl 2338. As the rotary element 2345 is rotated, the identified 0% mark 2342a may rotate a certain degree which corresponds to a percent strain. Mark 2342b as shown in FIG. 23B is aligned with the pawl 2338 when the dressing is strained to a desired amount x indicated by mark 2342b.

The support structure 2330 may maintain the dressing 2310 in its strained configuration as shown in FIGS. 23B to 23I during storage where the engaging elements 2322, 2324 and hooks 2323, 2325 engaging the support structure 2330, prevent movement of the dressing 2310 or loss of strain. One or more adhesive regions comprising a layer of skin adhesive 2340 may be applied to the top surface 2312 of the dressing 2310. The adhesive 2340 used may be, for example, a suitable pressure activated adhesive (PSA), or a non-pressure sensitive adhesive. The adhesive 2340 is shown on a dressing 2310 in an unstrained configuration. However, the adhesive may be applied to the dressing 2310 after the dressing 2310 has been strained. A removable liner 2350 may be placed over the adhesive layer 2340. The liner 2350 may further be selected to maintain the strain in the dressing 2310. Such liner may comprise rigid or semi-rigid material, for example, ultra-high molecular weight polyethylene (UHMWPE) with a release coating or layer, e.g., a fluoropolymer such as perfluoroalkoxy (PFA), fluorinated ethylene propylene (FEP), polytetrafluoroethylene (PTFE) or expanded PTFE (ePTFE). Other hard plastics or resins that may be used include melamine, fiberglass, acrylonitrile butadiene styrene (ABS) or polyvinyl chloride (PVC). In other variations, the rigid liner may be a composite structure comprising a flexible liner with a rigid frame or rigid struts, which may comprise, for example, a metal (e.g. stainless steel), or a hard plastic/resin.

Once the dressing 2310 is strained and the dressing assembly 2308 may be secured in engagement with the support structure 2330, the dressing assembly 2308 and support structure 2330 may be separated from the tensioning device 2341 to form the pre-strained assembly 2351 that may be used immediately or stored for a period of time.

The pre-strained assembly release 2352 may comprise a tear strip 2353 that is attached to the tensioning sheet 2307 between the middle location 2373 and the second side 2374 with upper and lower portions 2354, 2355 respectively (See FIG. 23E). The tear strip 2353 may act to separate the pre-strained assembly 2351 from the tensioning device 2341 by tearing across the tensioning sheet 2307 between the pre-strained assembly 2351 and the tensioning device 2341.

In use, after the liner 2350 is released, the dressing 2310 may be applied to a desired location on a subject's skin. The user may apply pressure to the back side 2333 of the support 2330 to activate the adhesive on the dressing 2310 and/or to apply compression to a wound. Once applied to a subject, the dressing 2310 may be released from the support 2330 using the release mechanism 2319.

The release mechanism 2319 may comprise tear strips 2309. The tear strips 2309 of the release mechanism 2319 may each extend proud of the end 2366 of elastic sheet 2360. The tear strips 2309 may each be coupled to the dressing assembly 2308. A tear strip 2309 may be coupled to the attachment sheet 2304 of the dressing assembly 308 in a manner that defines tear path 2362 along which the tear strip 2309 is pulled to separate the dressing 2310 from the support 2330. A tear strip 2309 may be coupled to the tensioning sheet 2307 of the dressing assembly 2308 in a manner that defines tear path 2362 along which the tear strip 2309 is pulled to separate the dressing 2310 from the support 2330. Each tear strip 2309 may comprise a top section 2347 and bottom section 2348. The bottom sections 2348 may be unattached or free from the support 2330 as illustrated. The top sections 2347 of each tear strip 2309 may be adjacent but unattached to the dressing 2310. The tensioning sheet 2307 and attachment sheet 2304 may be manufactured to be tearable along the material length while providing tensile strength in other directions, in particular in the tensioning direction of the material of the tensioning sheet 2307 (direction in which dressing is tensioned, stressed or strained) An example of such material is an LDPE polymer which is produced by an extrusion process that creates a directionally biased grain whereby the material is tearable with the direction of the grain, but has a relative resistance to tearing in the direction transverse to the grain. Notches may be made in the tensioning sheet 2307 and attachment sheet 2304 that facilitate tearing along paths 2362. The tensioning sheet 2307 and attachment sheet 2304 may additionally or alternatively comprise a material such as a low-density polyethylene (LDPE) with perforations formed along tear lines 2362.

The dressing 2310 may be released from the support 2330 by pulling the tear strips 2309 to draw the tear strips across paths 2362 of the tensioning sheet 2307 and attachment sheet 2304. Sections 2365 and 2375 respectively of the tensioning sheet 2307 and attachment sheet 2304 may remain on the back side 2311 of the elastic sheet 2360. The sections 2385, 2395 respectively, of the attachment sheet 2304 and tear sheet 2307 bonded to the tear strips 2309 may thereby be separated from the tensioning sheet 2307 and attachment sheet 2304. The sections 2365 and 2375 respectively of the tensioning sheet 2307 and attachment sheet 2304 that are attached to the dressing 2310 may thereby be separated from the remainder of the tensioning sheet 2307 and attachment sheet 2304 that are attached to the support structure 2330 at its ends 2305 and 2306. Thus, the dressing 2310 may be released from the remainder of the support structure 2330.

The dressing 2310 may have unattached portions or edges 2315 at its sides 2305, 2306 where the elastic sheet 2360 is free from the tensioning sheet 2307 and attachment sheets 2304 respectively. Accordingly, the dressing 2310 may be unstrained at unattached portions 2315. Unattached sections 2315 of the elastic dressing 2310 may be unstrained and may be free from the adhesive of the adhesive layer 340 (or may have a reduced amount of adhesive thereon). Thus less stress may occur at the unattached sides or edges defined by sections 2315.

In use, the adhesive liner 2350 may be removed and the dressing 2310 applied to the surface of a subject's skin. Tear strips 2309 on each side of the dressing at tear lines may be pulled to separate the dressing 2310 from the support structure 2330, attachment sheet 2304 and tensioning sheet 2307, after the dressing is applied to the surface of skin of a subject. When the support structure 2330, attachment sheet 2304 and tensioning sheet 2307 are removed from the dressing 2310, the stress or strain of the dressing 2310 may apply a (tangential) compressive force to the skin to thereby treat the skin.

Figure 24:
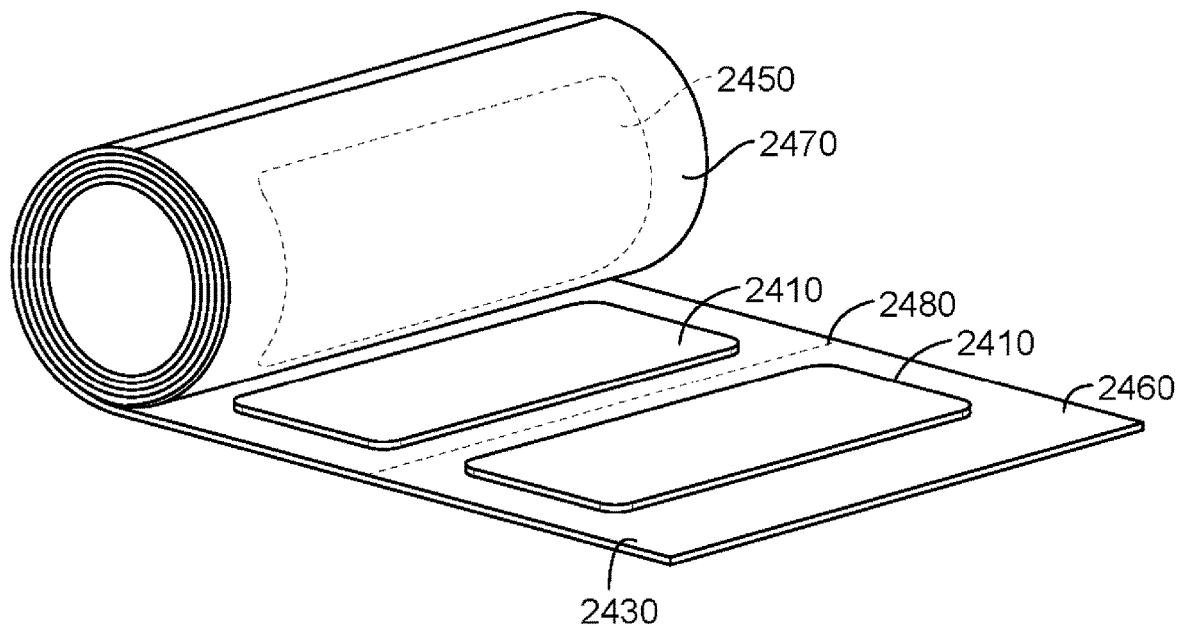
FIG. 24 is a perspective view of a plurality of pre-strained dressings on a support element.
Figure 25:
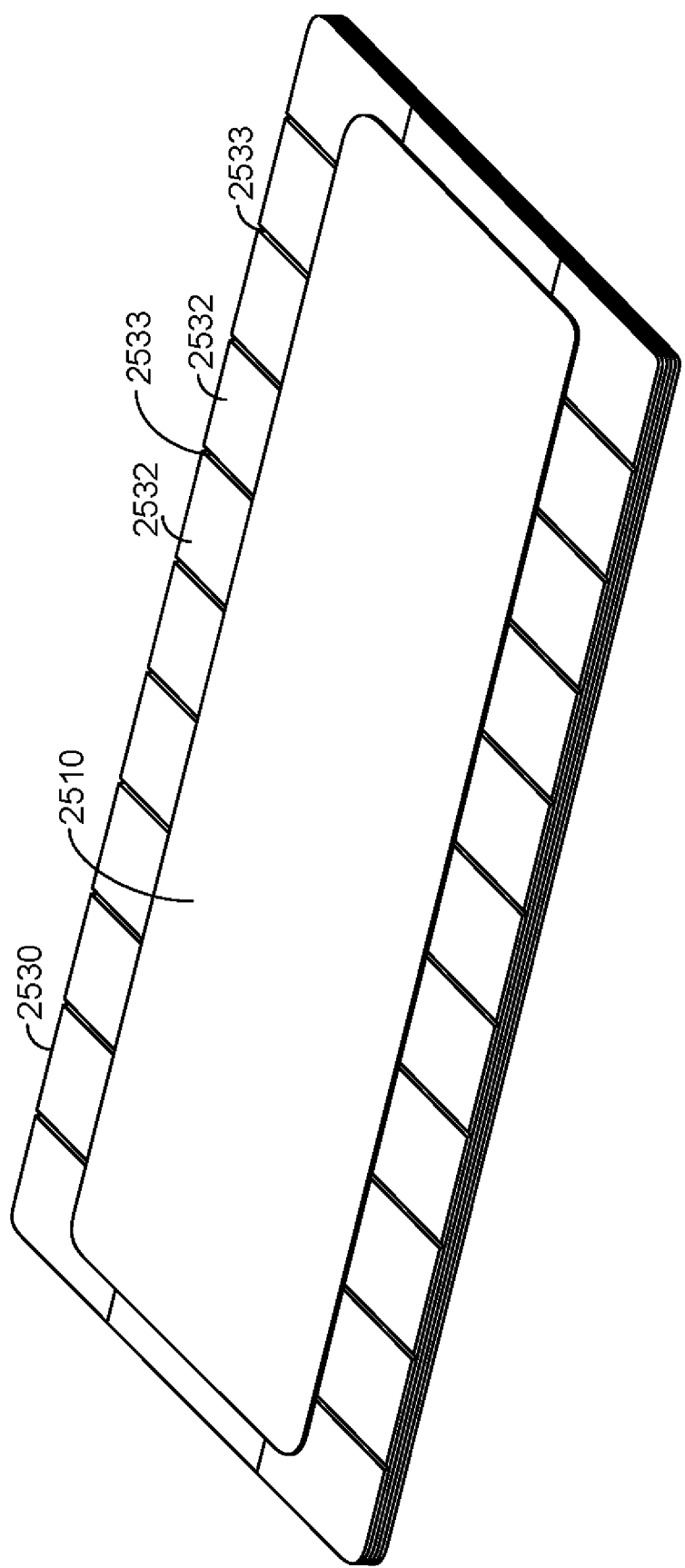
FIG. 25 illustrates a pre-strained dressing and support structure.
Figure 26:
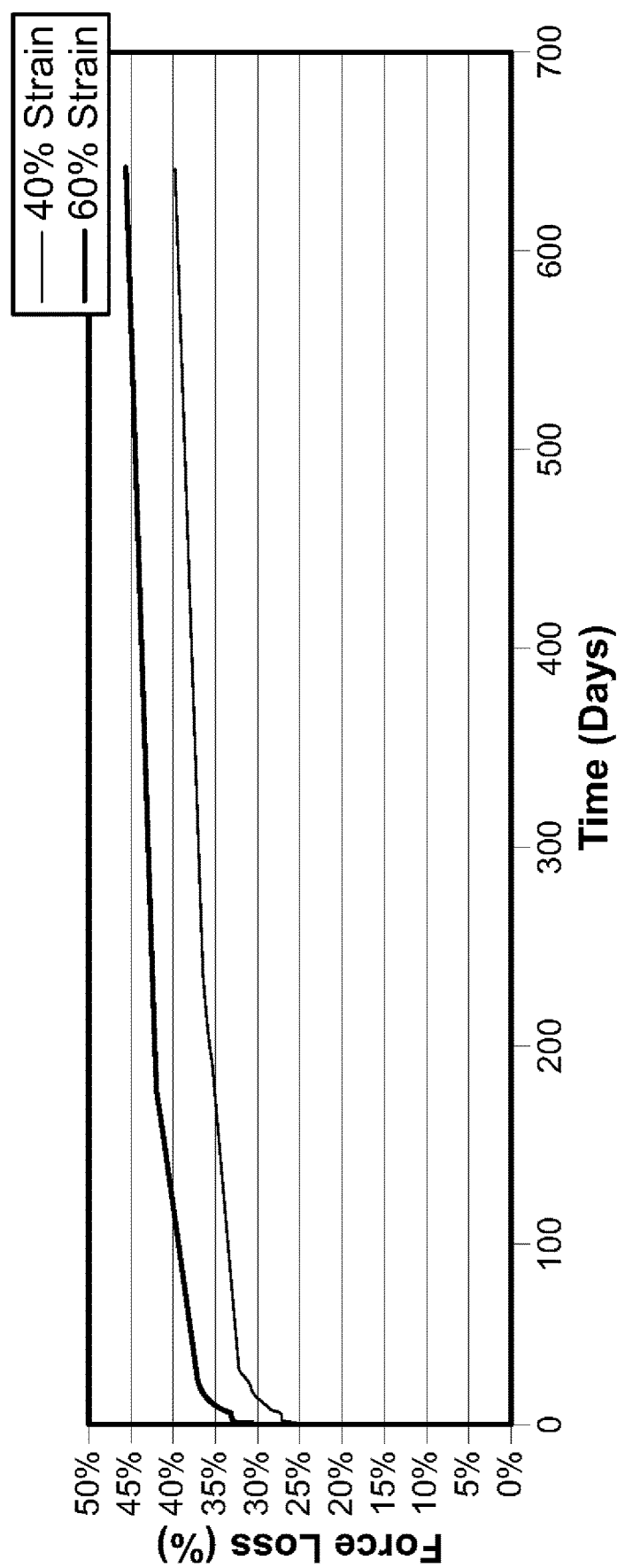
FIG. 26 illustrates the percent loss of force over time for elastic dressing material as describe in Example I.
Figure 27:
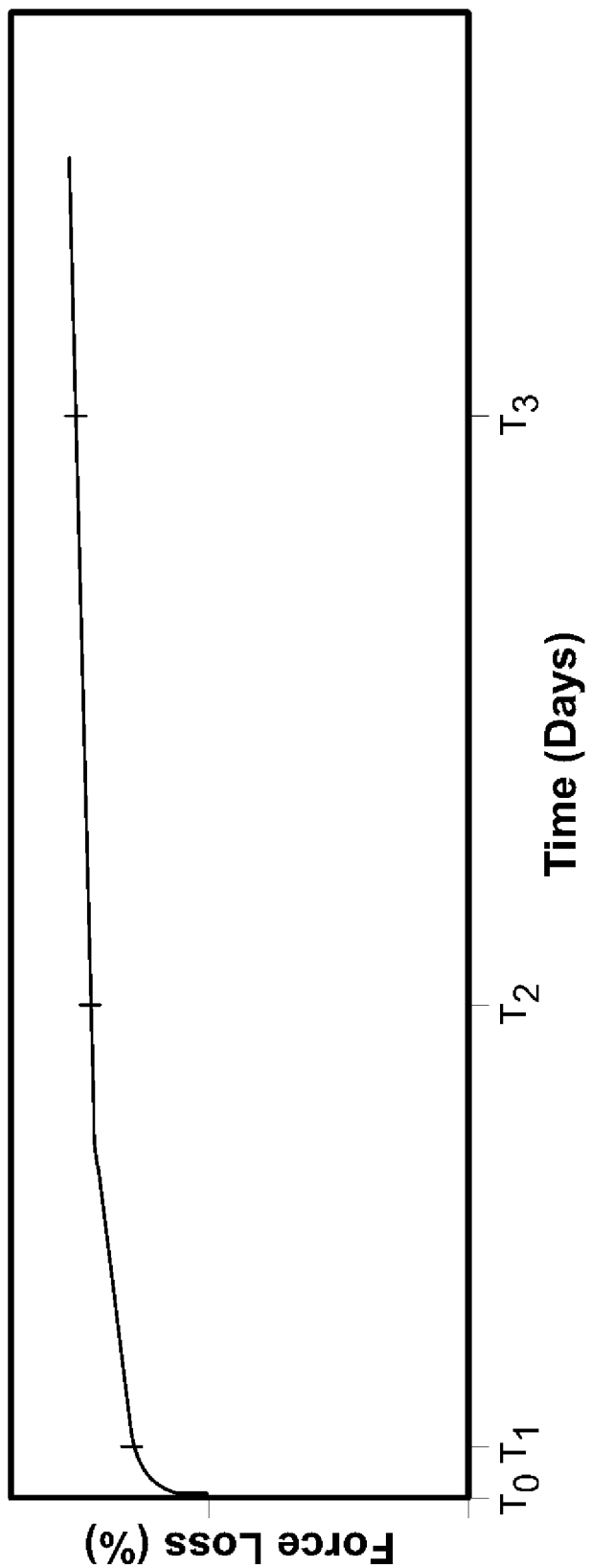
FIG. 27 is a schematic illustration of percent force loss over time for a pre-strained elastic material component of a dressing.
Figure 28:
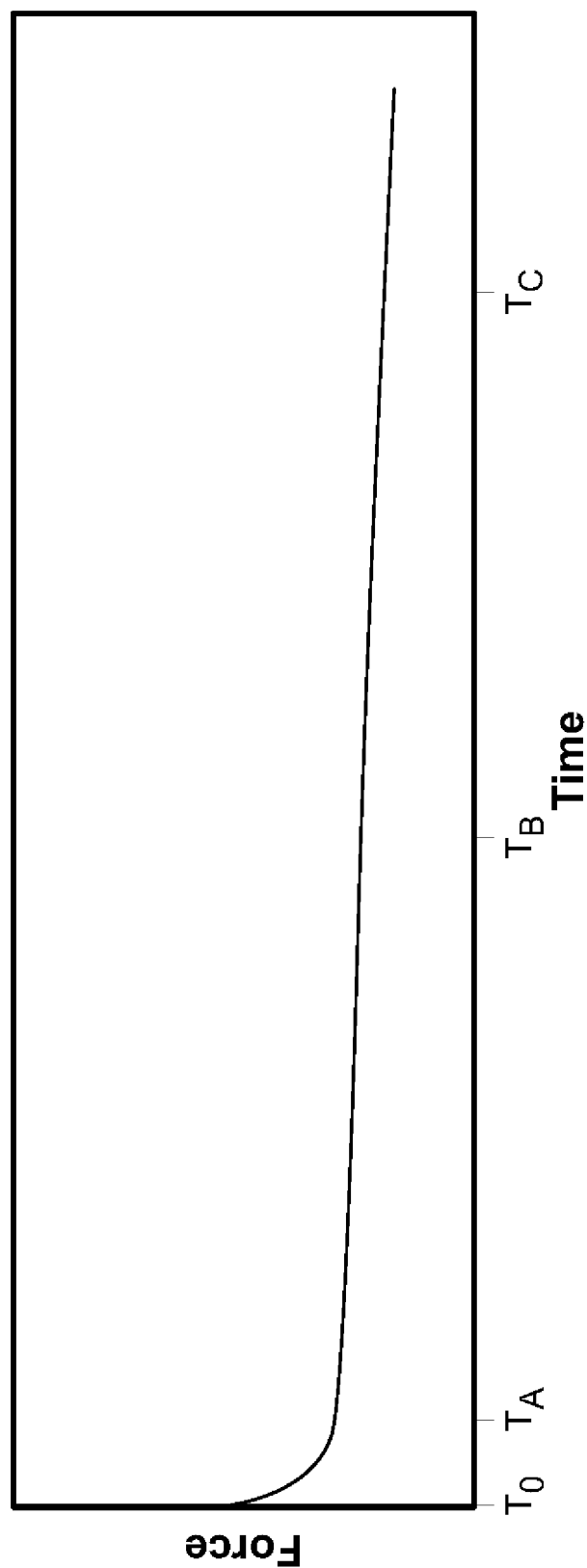
FIG. 28 is a schematic illustration of tensile force over time for a pre-strained elastic material component of a dressing.
Figure 29:
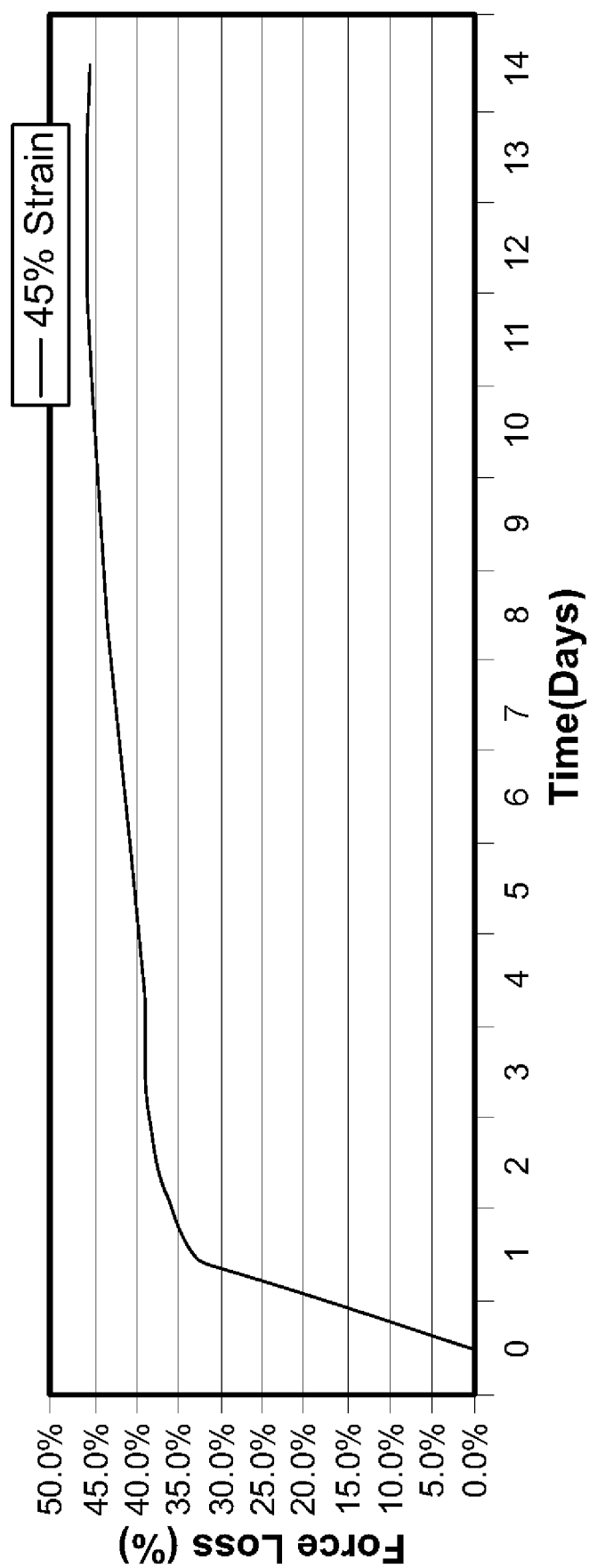
FIG. 29 illustrates the percent loss of force over time for elastic dressing material as describe in Example II.

Referring to FIG. 24, a plurality of strained dressings 2410 may be strained in a manner similar to dressing 2310 and then may each be attached to a first surface 2460 of single support 2430 which is rolled and stored in a rolled configuration for dispensing as shown in FIG. 24. The strained dressings 2410 may be coupled to the first surface 2460 of the single support 2430 by an adhesive, such as, e.g., a high tack/low peel PSA, which maintains the dressings 2410 in a strained configuration. Liners 2450 may be placed on a second and opposite side 2470 of the support 2430 and are positioned so that when the support 2430 is rolled, they are over a skin adhesive on the top of the dressings 2410. The adhesive liner 2450 may also help minimize creep properties of the strained dressings 2410. The support 2430 may be rolled to store the dressings 2410. When the support 2430 is unrolled, the adhesive liner 2450 positioned on the second side 2470 and opposing a dressing 2410 may release from the dressing 2410. Dressings 2410 may be separated by a perforation 2480 so that they may be individually used.

In some variations, the dressing may be used for the treatment of chronic injection sites or catheter sites that are required for a variety of conditions, including but not limited diabetes, cancer, immune disorders such as severe combined immunodeficiency disease, and the like. It is hypothesized that treatment of skin injection/infusion sites may not only reduce the development of scar tissue or other hyperproliferative disorders associated with frequent injections or chronic infusions, but may have other mechanical effects on pharmacokinetics, that may improve drug dispersion in the tissue, reduce drug leakage, increase the depth of effect, reduce pain at the injection/infusion site, reduce site infection risk, reduce risk of line/pump occlusion at an infusion site, improve analyte or drug level variability, reduce inflammatory layer thickness or depth, reduce dosing level. For diabetes patients, the skin treatment may result in fewer glycemic excursions, improved time-in-range as measured by multiple daily fingerstick or continuous glucose monitoring (CGM), increased insulin bolus volume and/or area in the subcutaneous tissue.

In other variations, the tensioned tissue treatments described herein may be also be used to treat subdermal or subcutaneous tissue conditions, which may result from injection, infusions or implants. In one example, the tensioned tissue treatment system may be applied to the insertion site of a drug-eluting oral contraceptive implant, such as the NEXPLANON® etonogestrel implant (Merck, Whitehouse Station, NJ). This implant is a radiopaque, soft, flexible progestin eluting implant that consists of ethylene vinyl acetate (EVA) copolymer core that has been doped with barium sulfate to provide radio-opacity, with 68 mg of progestin etonogestrel that is released for up to three years. Difficulties or complications with the removal of the implant have been reported in 1.5% of cases, with encasement of the implant in fibrotic tissue being the most common cause. It is believed that treatment of insertion site and final implant location with a tensioned tissue treatment system may reduce the development of fibrotic tissue surrounding the implant, which may reduce the complication rate during the explantation procedure. Fat atrophy at the subdermal contraceptive implant site has been known to lead to loss of contour, with a significant aesthetic impact. Fat atrophy local to subdermal contraceptive may be due to any of the components in the implant acting directly on surrounding fat cells or by means of foreign body type reaction. Injection site nodule formation in the subcutaneous layer is another common reaction to diabetes drug treatment injections such as GLP-1 (i.e. exenatide) agonist therapy used by T2D patients. Paresthesias, pain, and blot clot risk at the implantation site may also be reduced during the three-year treatment period with the implant whether or not fibrotic tissue development is reduced. In some variations, the tensioned tissue treatment device may be applied to the implantation site for the entire duration of the implantation, but in other variations, tensioned tissue treatment may be applied for a period of time in the range of 4 to 6 weeks, 4 to 8 weeks, 6 to 8 weeks, 6 to 12 weeks after implantation, or following explantation. In some further variations, treatment may be applied to the proposed implantation site 4 to 6 weeks, 4 to 8 weeks, 6 to 8 weeks, 6 to 12 weeks prior to implantation. This may reduce or break up existing fibrosis or otherwise cause the tissue to remodel pre-implantation, and facilitate the implantation procedure and facilitate promote post-implantation healing and other tissue responses. An initial limited period of treatment may be sufficient to alter or slow the initial tissue remodeling process or inflammation to reduce the adverse reactions associated with the implantation. The user may be instructed to place the tensioned dressing to cover the skin area that is at least 1 cm, 2 cm, or 3 cm or more surrounding the implant. The direction of tension of the dressing may be oriented along or transverse to the longitudinal axis of the implant.

The implant may also be an injectable material, such as a depo formulation of an injectable contraceptive like DEPO-PROVERA® (Pfizer, New York, NY), a medroxyprogesterone acetate formulation with a polyethylene glycol and polysorbate carrier that is injected every three months. Drug levels peak 3 weeks after injection and become undetectable between 120 to 200 days post-injection.

Another depo injection is SUBLOCADE® (INDIVIOR, North Chesterfield, VA), a monthly depo formulation of buprenorphine for the treatment of opioid use disorder for patients who are undergoing treatment with another buprenorphine product. SUBLOCADE® is intended to be injected subcutaneously at a rotating abdominal site, free of skin conditions, between the transpyloric and transtubercular plane of the abdomen. Phase 3 studies of SUBLOCADE® found a 16.5% rate of injection site reactions, which included, pain, itching, redness, bruising, swelling, induration, cellulitis and other discomfort.

In another example, an injectable oncology therapy agent may also be treated. For example PHESGO® (Genentech, South San Francisco, CA), a combination therapy of pertuzumab and trastuzumab monoclonal antibodies with recombinant human hyaluronidase for the treatment of HER2+ breast cancer. PHESGO® may be used in conjunction with a tensioned skin dressing, to modulate drug levels and/or to reduce injection site reactions such as pain, itching.

In still other variations, the tensioned tissue treatment system may be used in conjunction with injectable therapies for autoimmune or inflammatory disorders, including but not limited rheumatoid arthritis, psoriasis, lupus, and the like. Subcutaneous injections may include disease-modifying anti-rheumatic drugs (DMARDs) such as methotrexate, weekly subcutaneous injectable ACTEMRA® (tocilizumab) (Genentech, South San Francisco, CA) for treatment of rheumatoid arthritis, giant cell arteritis, cytokine release syndrome, juvenile idiopathic arthritis and systemic sclerosis-associated interstitial lung disease, ever four week subcutaneously injectable ILARIS® (Canakinumab)(Novartis, East Hanover, NJ) for treatment of periodic fever syndrome, TNF receptor associated periodic fever, hyperimmunoglobulin D syndrome (RIDS)/mevalonate kinase deficiency, Still's disease, and juvenile idiopathic arthritis, every two weeks subcutaneous injectable KEVZARA® (IL-6 receptor agonist)(Sanofi, Bridgewater, NJ) in combination with methotrexate or other convention disease-modifying anti-rheumatic drug for the treatment of severe rheumatoid arthritis, Treatment with a tensioned skin dressing may be provided continuously during use of the depo injections above, or for a limited period of time following each injection, e.g. 3 to 5 days, 3 to 7 days, 5 to 10 days, or 7 to 14 days post-injection. The dressing may contain apertures to facilitate a rotational injection patterns with therapeutic agents require multiple serial injections.

Although the particular example above involves a drug eluting device, in other variations, the implant may be a non-drug eluting implant, e.g. cosmetic body modifications including but not limited to dermal or subdermal beads, rods or horns, or therapeutic implants such as a hyoid bone implant for treatment of obstructive sleep apnea. For implants intended for extended or undefined treatment durations, tensioned tissue treatment may be applied for a period of time in the range of 4 to 6 weeks, 4 to 8 weeks, 6 to 8 weeks, 6 to 12 weeks after implantation. Fibrous capsule formation may occur around implants during the end-stage healing response. Eventually, atrophy may occur due to diminished blood supply. It is hypothesized that the tensioned dressing may have an effect on the fibrous capsulation. This may include a reduction in the final size and/or the pliability, compared to untreated controls.

The injectable material may also be an autologous fat, or a cosmetic fillers such as JUVEDERM® (Allergan Aesthetics, Madison, NJ), RADIESSE® (Merz, Franksville, WI), RESTYLANE® (Galderma, Fort Worth, TX), whether injections are performed using a needle or a flexible blunt-tipped microcannula, such as the DERMASCULPT MICROCANNULA® by CosmoFrance (Miami, FL), PIX'L cannula by Thiebaud (Paris, France) and Merz cannulas by TSK Labs (Tochigi, Japan). Use of a tensioned skin dressing over the injection site(s) may reduce the swelling and/or bruising that may occur. Tensioned skin dressing may be applied for 3 to 5 days, 5 to 7 days, 7 to 10 days, 3 to 7 days, or 7 to 14 days post injection, with the tensioned skin dressing reapplied with each injection of the treatment regimen. In some variations, the tensioned dressing may be indicated only with the onset of the local size adverse reactions, or may be applied preventatively, to reduce the risk or rate of onset of such adverse reactions. Treatment of dermal filler injection at the subcutaneous junction via threading or tunneling techniques may reduce visibility of the injection tract by reducing scar formation along the tract and/or migration of the filler location. Treatment with cosmetic fillers with a tensioned skin dressing may be provided for a limited period of time following each injection, e.g. 3 to 5 days, 3 to 7 days, 5 to 10 days, or 7 to 14 days post-injection. The tensioned skin dressing may be sized to ensure coverage of the injection area(s) by at least a 1 cm, 2 cm or 3 cm margin. In some variations, the direction of tension in the skin dressing may be selected to be generally transverse to the direction or average directions of the threading or tunneling injection paths. It is hypothesized that the tensioned tissue treatment may reduce the chance of ecchymosis that may result from increased tissue resistance during insertion of microcannulas, when the tension off-loading dressing therapy is used prior to injections and existing fibrosis has been pre-treated and/or reduced. Additionally, tolerability of the procedure and treatment compliance may increase if the patient's discomfort level has decreased due to reduced scar tissue build-up. Patients have reported discomfort from insertions in scar tissue causing pain and noise of a blunt cannula passing through hard dense scar tissue.

In other variations, tensioned tissue treatment described herein may be provided for, or used with, a variety of infusion devices that may be used for various therapeutic and/or diagnostic procedures. These include intradermal infusion devices, subcutaneous infusion devices, and intravascular implantable infusion ports. These infusion devices may be used, for example, to provide insulin infusion for the treatment of diabetes, intravenous immune globin or subcutaneous immune globin infusion for the treatment of immune deficiency syndromes, chemotherapy infusions for the treatment of a variety of cancers, and the like. In some of the embodiments described below, the tensioned tissue treatment system may be integrated with or specifically tailored to the infusion device, but in other variations, the tensioned tissue treatment device may be applied in between infusions or injections, or for a specific period of time after each infusion or injection. As described in greater detail below, the use of tensioned tissue treatment may reduce, slow or prevent the development of intradermal scar tissue, which may improve or slow the rate of change in absorption or diffusion kinetics of any intradermal or subcutaneous injections or infusions, and/or may reduce the development of chronic pain or paresthesias resulting from repeated tissue trauma from the injection or infusion. Examples of such devices include the SAF-Q and OPTIFLOW infusion sets and SCIG60 infusion pumps by EMED Technologies (El Dorado Hills, CA), the PORT-A-CATH® implantable venous access systems by Smiths Medical (Dublin, OH), the INSUFLON multi-injection subcutaneous catheter by Unomedical (Roskilde, Denmark), and the I-PORT ADVANCE injection port by Medtronic MiniMed (Northridge, CA). Tensioned tissue treatment may be applied for a period of time in the range of 4 to 6 weeks, 4 to 8 weeks, 6 to 8 weeks, 6 to 12 weeks after implantation of such devices, and/or for 3 to 5 days, 5 to 7 days, 7 to 10 days, 3 to 7 days, or 7 to 14 days after each injection. For infusion systems adhered to the skin, the tensioned tissue treatment systems described herein may be applied first, and then the infusion system is inserted through an aperture in the tensioned tissue treatment device. Use of the tensioned tissue treatment system may improve, reduce and/or prevent the risk of catheter or port erosion through the skin, catheter occlusion, device migration or rotation, device extravasation, fibrin sheath formation, injection, inflammation, necrosis or hyperpigmentation over the implant area, pain at the port pocket site, catheter tip malposition or retraction, insertion vessel erosion, and/or vascular thrombosis.

In another embodiment, the tensioned tissue treatment system is used in conjunction with hemodialysis procedures and applied to the needle insertion sites of the dialysis graft or fistula. In some variations, a single tensioned tissue treatment device may be applied, covering both needle insertion sites, while in other variations, two tensioned tissue treatment devices are used, one for each needle insertion site. In these embodiments, the direction of the tension applied to the arm of the hemodialysis patient may be along the longitudinal or the transverse direction of the arm. It is hypothesized that the use of tensioned tissue treatment at the hemodialysis needle insertion sites may reduce the risk of developing pain, ulceration and/or tissue calcification in the dermal and/or subcutaneous tissue overlying the graft or fistula. In another example, use of tensioned tissue treatment on patients that are not eligible for an AV fistula due to excessive scar tissue build up from previous IV, blood work, or medication, may remodel tissue sufficiently to allow for the fistulization procedure. In some further variations, the tensioned tissue treatment may even reduce the rate of thrombosis of a fistula by reducing short-term inflammation at the insertion site, or mechanical stresses in the graft that may activate local clotting pathways. Therapy will be typically applied between hemodialysis visits, e.g. 48 to 72 hours each application following hemodialysis. The tensioned tissue therapy may also be provided along the implantation site of a new hemodialysis graft or AV fistula formation surgery or AV fistula revision procedure. For AV fistulas, treatment with tensioned tissue devices may be 1 to 2 weeks, 2 to 4 week, 4 to 8 weeks, 8 to 12 weeks, or the entire maturation time from the surgery to the first use of the fistula. For AV grafts, treatment with tensioned tissue devices may be in the range of 1 to 2 weeks, 2 to 3 weeks, or 2 to 4 weeks, for example.

In still other embodiments, the tensioned tissue treatment devices may be used to treat the post-implantation site of a pacemaker housing, implantable cardioverter defibrillator (ICD), or implantable pulse generator of a neuromodulation system, and the subcutaneous implantation site of a neuromodulation electrode. The neuromodulation systems may be used to perform spinal cord stimulation (SCS) to treat low back pain, such as the SPECTRA WAVEWRITER and PRECISION SCS systems by Boston Scientific (Marlborough, MA), the INTELLIS and RESTORE neurostimulator system by Medtronic (Minneapolis, MN), the SENZA OMNIA system by Nevro (Redwood City, CA) and the PROCLAIM and PRODIGY SCS systems by Abbott (Austin, TX). Treatment may reduce or prevent implantation site pain, paresthesia, paralysis, spinal cord compression, swelling, inflammation, ulceration or erosion, capsular fibrosis, tissue ingrowth and/or implant migration. In some instances, firm fibrotic capsules form around the implant and begin to squeeze the implant or capsular contracture, causing tenderness and pain. This effect may be reduced with treating using a tensioned tissue treatment device.

In other examples, the tensioned tissue treatment devices may be used to directly treat diseases that involve subcutaneous tissue or structures. These may include autoimmune diseases, metabolic diseases, endocrine diseases, genetic diseases, inflammatory diseases, oncologic diseases, infectious diseases, and the like. For example, certain disease may result in the development of subcutaneous calcifications in the dermis or subcutaneous tissues, often as a result of inflammation from a variety of etiologies. It is believed that symptomatic treatment of calcifications visualized on medical imaging may reduce pain or progression of calcifications with the application of tensioned tissue treatment devices as described herein. Such diseases may include autoimmune diseases such as dermatomyositis and scleroderma, metabolic disease such as hyperparathyroidism, and inflammatory conditions such as sarcoidosis, as well as calciphylaxis of the subcutaneous vasculature associated with end-stage renal disease, multiple myeloma, rheumatoid arthritis, and liver cirrhosis. Calcifications with associated tissue erosion may also be treated. Symptomatic treatment with tensioned tissue treatment devices may be applied for 1 to 2 weeks, 2 to 4 week, 4 to 8 weeks, 8 to 12 weeks, for example, to dermal or subcutaneous calcifications.

In other examples, the tensioned tissue treatment devices may be used to treat livedo reticularis or livedo racemosa, or other vascular diseases of the medium size blood vessels found in the subcutaneous tissue. These disease phenomena are characterized by blotchy, net-like colored patterns of the skin, which are thought to originate from alterations in blood flow, vaso spasm, venodilation, thrombosis or increased blood viscosity. The tensioned tissue treatment devices may be used alone or in conjunction with systemic therapy directed to the underlying cause of the skin condition. Causes may include, for example, vasculitis, polyarteritis nodosa, temporal arteritis, Takayasu arteritis, lupus erythematosus, Still's disease, rheumatic fever, endocarditis, hepatitis, anti-phospholipid syndrome, cryoglobulinemia, deep vein thrombosis, thrombotic thrombocytopenic purpura, hemolytic uremic syndrome, and the like. Medication-induced vascular changes may also be treated. Treatment periods with the tensioned tissue treatment devices may be in the range of 1 to 2 weeks, 2 to 4 week, 4 to 8 weeks, 8 to 12 weeks, as needed. Treatment may also temporarily improve the cosmesis of congenital vascular malformations, which may persist for hours, days or weeks following temporary treatment.

In some other embodiments, tensioned tissue treatment devices may be used in conjunction with body sculpting or contouring procedures. Treatment combined with these procedures may accelerate healing post-procedure or improve the contouring effect by reducing subcutaneous tissue inflammation during the healing process. Such procedures may include invasive energy-based, cooling-based or mechanical-based lipolysis or septae disruption, as well as non-invasive vacuum and massage therapies that may be combined with invasive body sculpting procedures or used alone. Use of invasive lipolysis procedures has been associated with development of subcutaneous fibrosis, which may be the result of inadequate removal of disrupted subcutaneous cells or connective tissues. In some examples, tensioned tissue treatment systems may be applied after an invasive body sculpting procedure, or between an invasive and a non-invasive body sculpting procedure, or between treatments of a multiple treatment regimen. Treatment after an invasive body sculpting procedure may be performed for 1 week to 3 months, or 2 weeks to 6 weeks, or 4 weeks to 12 weeks, for example, while treatments between multi-treatment regimens will vary depending on the treatment schedule, which could be as above, or in the range of 3 to 5 days, 5 to 7 days, 7 to 10 days, 3 to 7 days, or 7 to 14 days after each procedure of the regimen or treatment schedule.

Figure 30A:
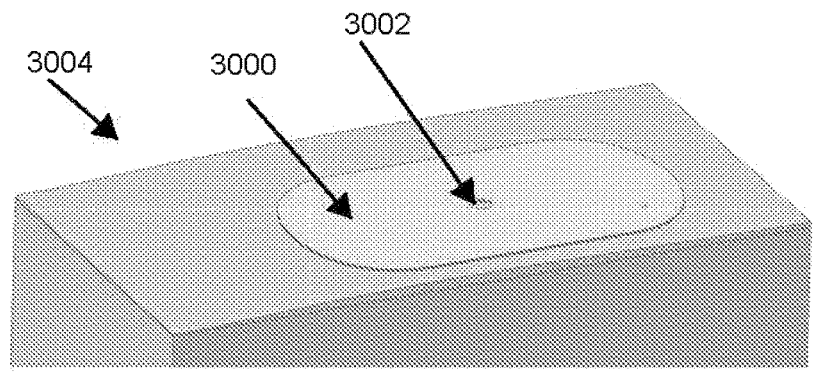
FIGS. 30A to 30C depict the use of a strained dressing with an exemplary infusion set.
Figure 30B:
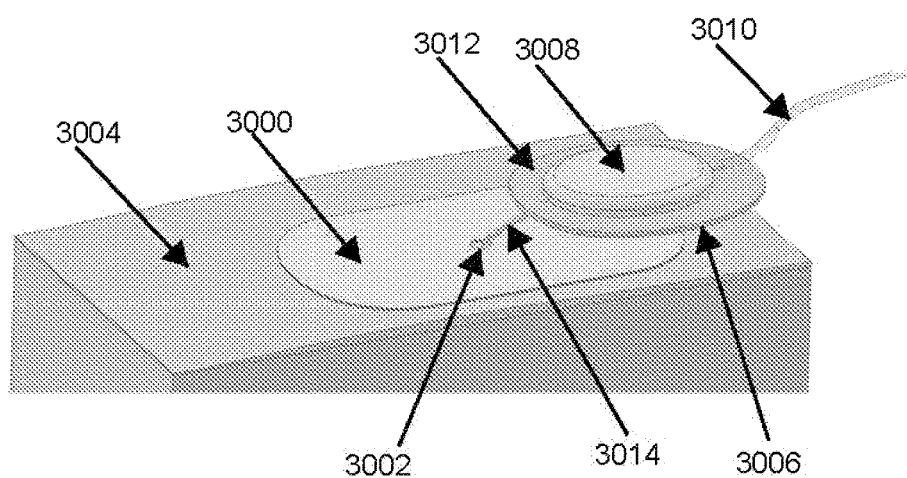
Figure 30C:
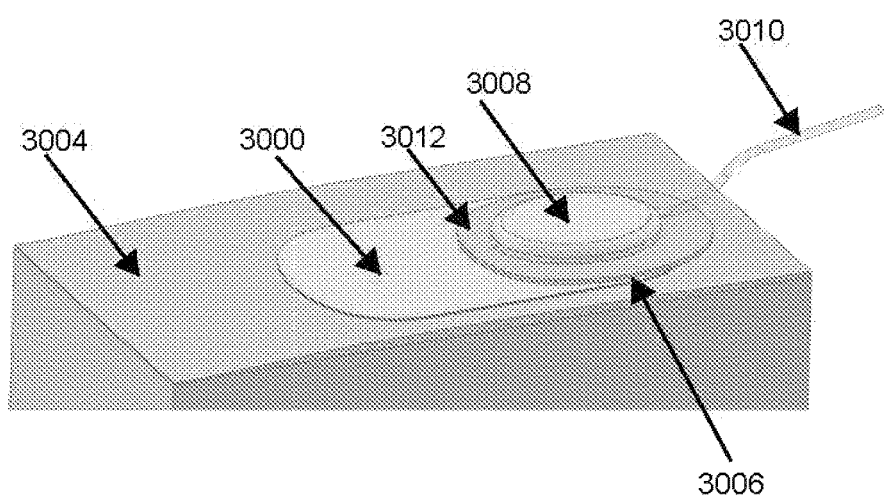
Figure 30D:
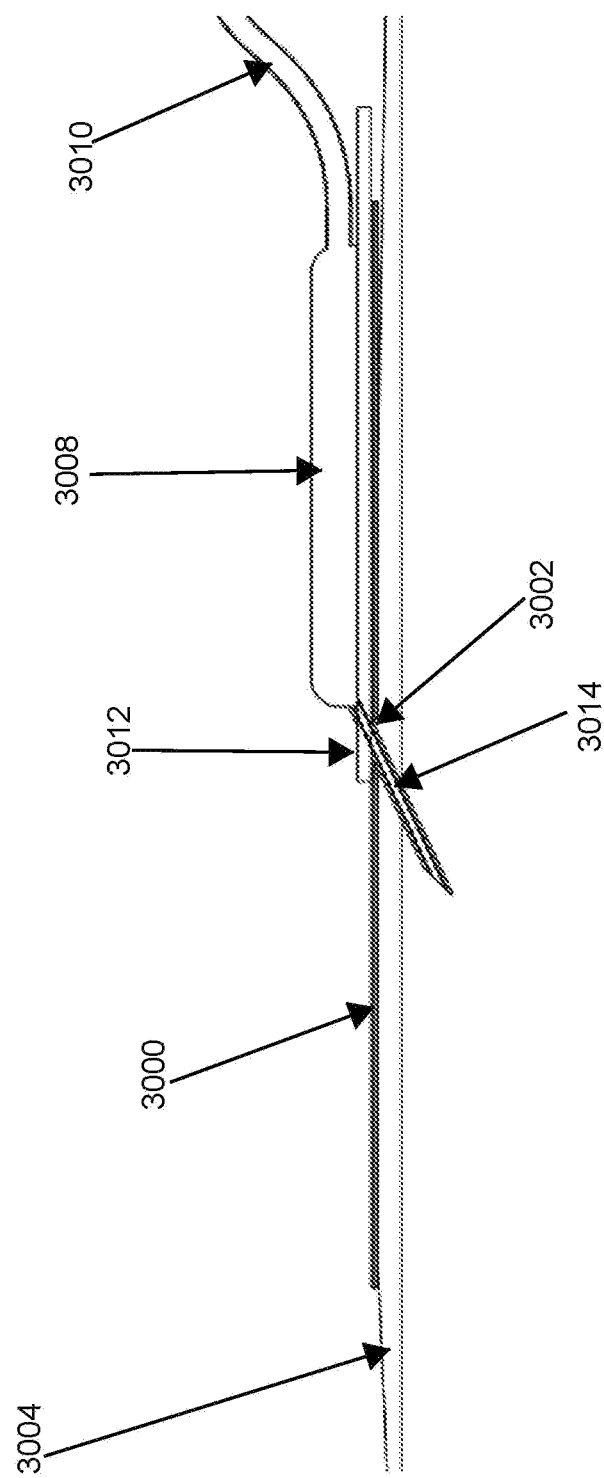
FIG. 30D is a cross sectional view of the strained dressing and infusion set in FIG. 30C.

In some examples, the dressing, and optionally one or more structures of the dressing support structure, may comprise one or more openings that may facilitate the use of the strained dressing with an indwelling catheter, cannula or sensor that is inserted into the tissue. In other examples, the device used with the dressing may be transiently inserted through the dressing, e.g. a needle for a blood draw, or needle biopsy tool. FIG. 30A depict one embodiment of the strained dressing 3000 with an opening 3002 that has been applied to a target site 3004 and released from its applicator (not shown) to transfer stress from the dressing 3000 to de-tension the treatment site 3004. An indwelling device, such as an infusion set for an insulin pump system or an indwelling sensor system, may then be placed through the access aperture 3002 and into the skin or subcutaneous tissue at the treatment site. In this particular example depicted in FIGS. 30B to 30D, an infusion set 3006 for use with a medication pump comprises a housing 3008, connector tubing 3010, a support layer 3012 for an adhesive layer, and a needle 3014. In this particular embodiment, the needle has an acute angle orientation relative to the plane of the support layer 3012, but in other examples, the needle may have an orthogonal orientation, or may be in the same plane or otherwise parallel to the plane of the housing or support layer. The needle length may or may not extend beyond the peripheral boundaries of the housing or support layer. The needle sheath (not shown) and/or adhesive protection layer (not shown) of the infusion set 3006 is removed. The needle 3014 is then aligned with the opening 3002, as shown in FIG. 30B, until the needle 3014 is fully inserted into the target site 3004 and the adhesive of the support layer 3012 is adhered to the dressing 3000 and/or target site 3004. In some further variations, a protective dressing may be partially or completed applied over the strained dressing and infusion set. In some variations, the direction of strain in the dressing may be parallel or preferably transverse to the direction of the needle insertion into the target site, or parallel or preferably transverse to the length of the dressing.

Figure 31A:
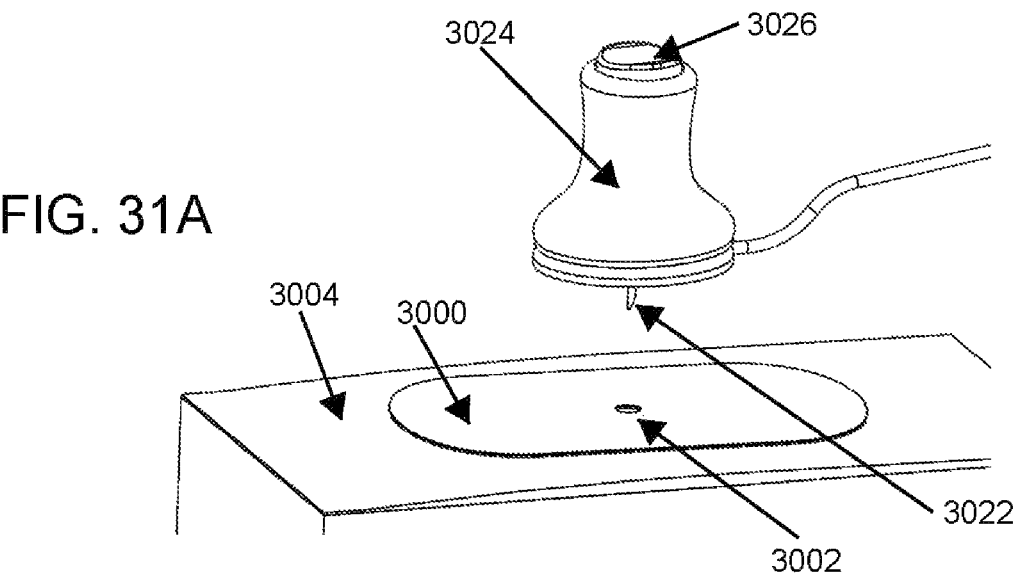
FIGS. 31A to 31C depict the method of use of a strained dressing with an infusion set delivery device.
Figure 31B:
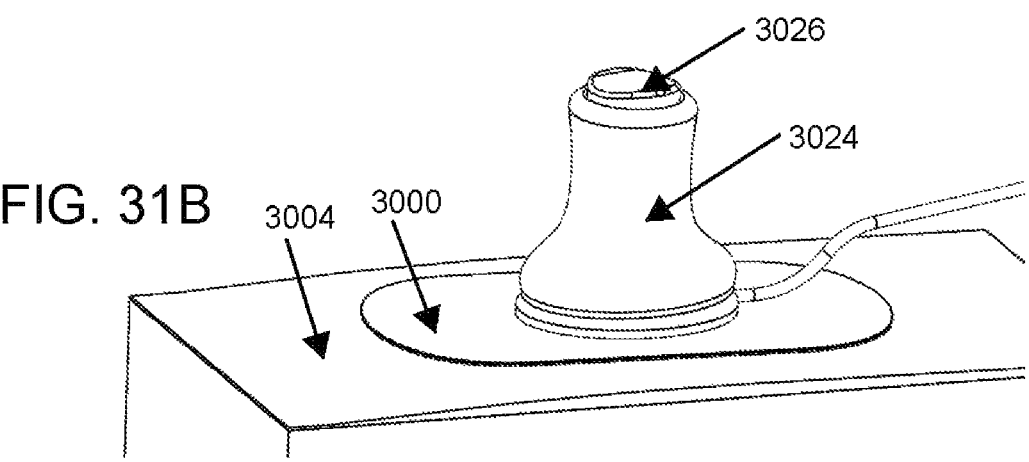
Figure 31C:
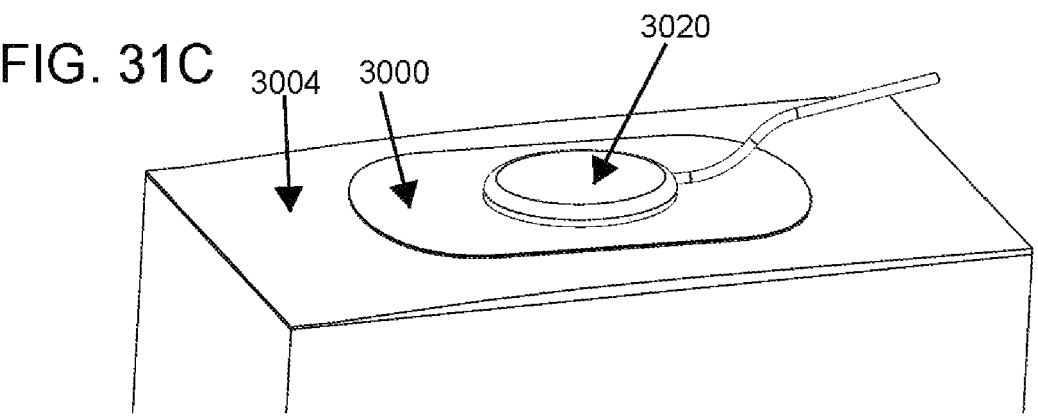
Figure 31D:
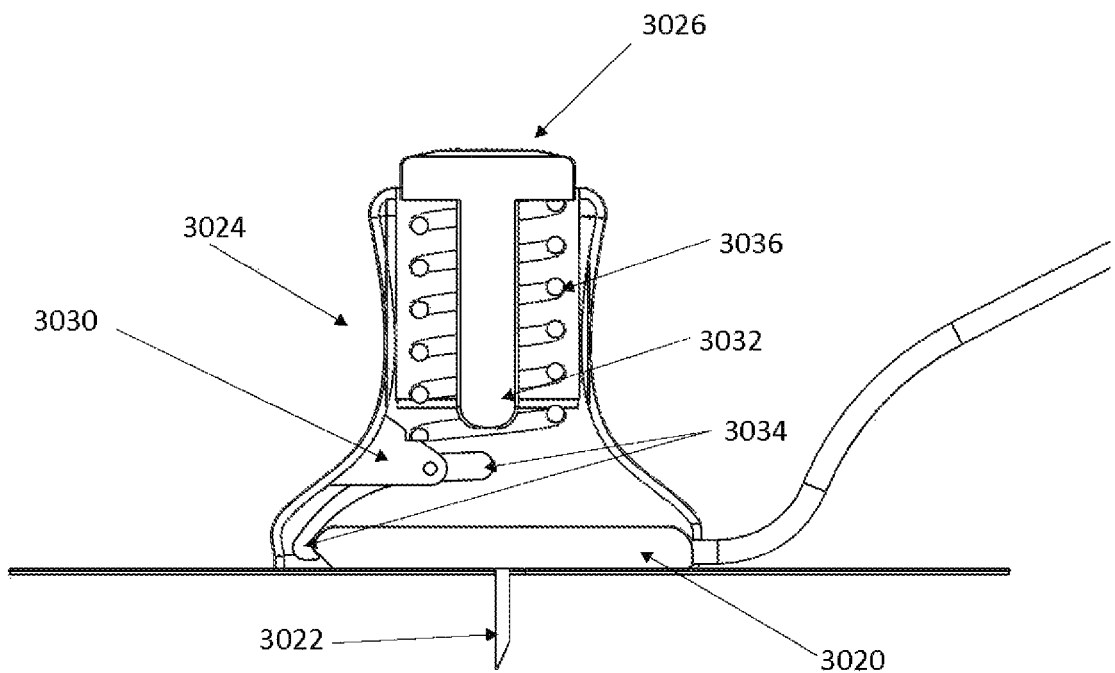
FIGS. 31D and 31E are cross sectional views of the method of use.
Figure 31E:
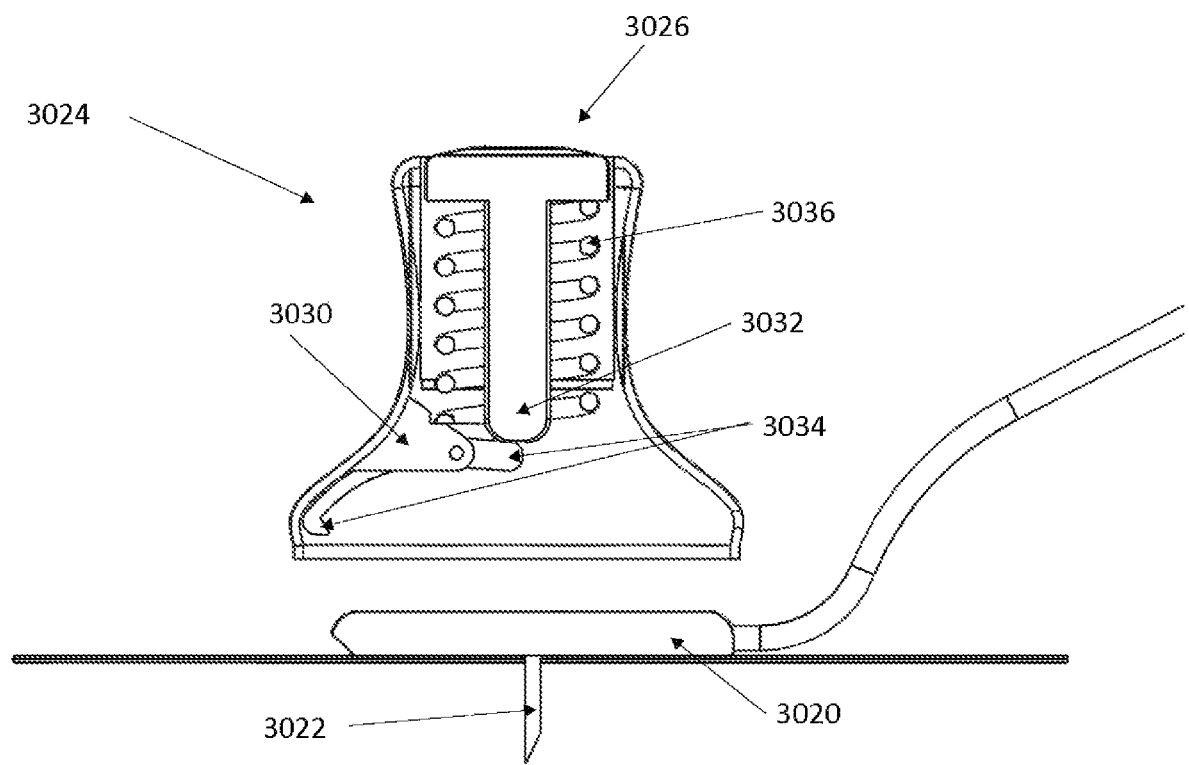

In addition to the manual insertion of the needle of an infusion set or indwelling device through an aperture of the dressing, in some variations, the infusion set or indwelling device may comprise a delivery tool or system to facilitate the insertion or placement of the infusion set or indwelling device. The delivery tool may be easier or otherwise require less dexterity to grip than the smaller infusion set, or may hide the delivery needle from the user and/or may automatically insert and/or withdraw the delivery needle during the insertion procedure, which may improve compliance or other aspects of the user experience. In FIGS. 31A to 31C, for example, the dressing 3000 with aperture 3002 may be placed at the target site 3004, but where the infusion set 3020 comprises an exposed orthogonal needle 3022 is releasably coupled to a larger delivery device or device 3024. The delivery device 3024 and/or needle 3022 is aligned with the dressing 3000 and/or aperture 3002, as shown in FIG. 31A, and then place against the dressing 3000, as shown in FIG. 31B. The actuator 3026 on the device 3024 is then activated to separate the pod 3024 from the infusion set 3020. In this particular embodiment, the infusion set 3020 does not have an adhesive support layer that extends beyond the peripheral boundary of the infusion set housing 3021. Instead, the adhesive may be provided directly on the inferior surface of the housing 3021, with or without any support layer therebetween. FIGS. 31D and 31E are cross-sectional views depicting the actuation mechanism of the delivery device 3024 and the detachment of the delivery device 3024 from the infusion housing 3021. The infusion housing 3021 may be mechanically attached to the delivery device 3024 by friction and/or by one or more mechanical interlocks 3030. To release the infusion device 3020, the actuator 3026 is depressed and plunger tip 3032 engages catch lever 3034 to release infusion housing 3021. The actuator 3026 and the plunger tip 3032 are maintained in the non-engaged position by a spring 3036. In another variation, the infusion housing may be releasably attached using an adhesive such as a gel that temporarily adheres the plunger tip to the superior surface of the infusion housing.

Although the exemplary dressings above comprise a single circular aperture that is centrally located, in other examples, the apertures may have other shapes, sizes and/or eccentric locations, and may comprise other markings or indicia. The markings or indicia may be used to differentiate between different openings, and/or to facilitate alignment of the dressing with the target location and/or inserted device. Some variations may also include more than one aperture, e.g. two, three, four, five or more apertures. In still other examples, a dressing may be provided without an aperture, and the needle of the infusion set, syringe or insertion device is used to pierce the dressing and then inserted through the skin or tissue.

Figure 32A:
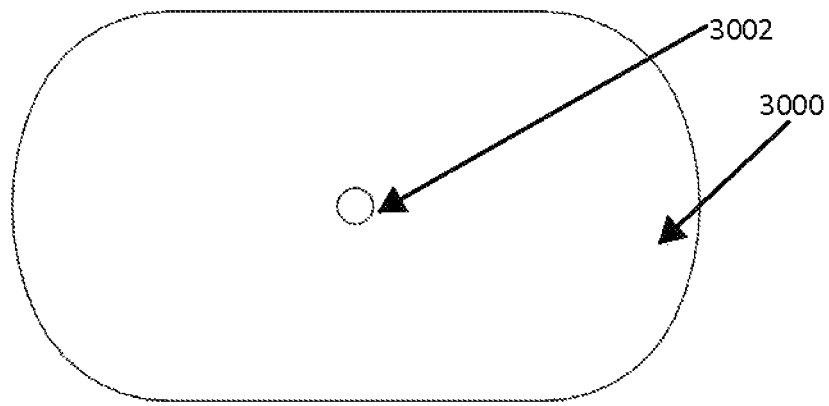
FIGS. 32A to 32E depict various exemplary aperture configurations for the dressing.

FIG. 32A depicts the exemplary embodiment of the dressing 3000 in FIGS. 30A to 31C. The dressing 3000 comprises an oblong shape with rounded corners and a centrally located circular opening 3002. The opening 3002 may have a diameter of about 0.10" to 0.30", or 0.05" to 0.20". The dressing 3000 has a longitudinal length that is greater than its transverse width, but in other examples, the dressing may be radially symmetrical. The length and/or width of the dressing may be in the range of 4 cm to 16 cm, or 2.5 cm to 5 cm, or have a surface area of 9 cm$^2$ to 19 cm$^2$, or 46 cm$^2$ to 70 cm$^2$.

Figure 32B:
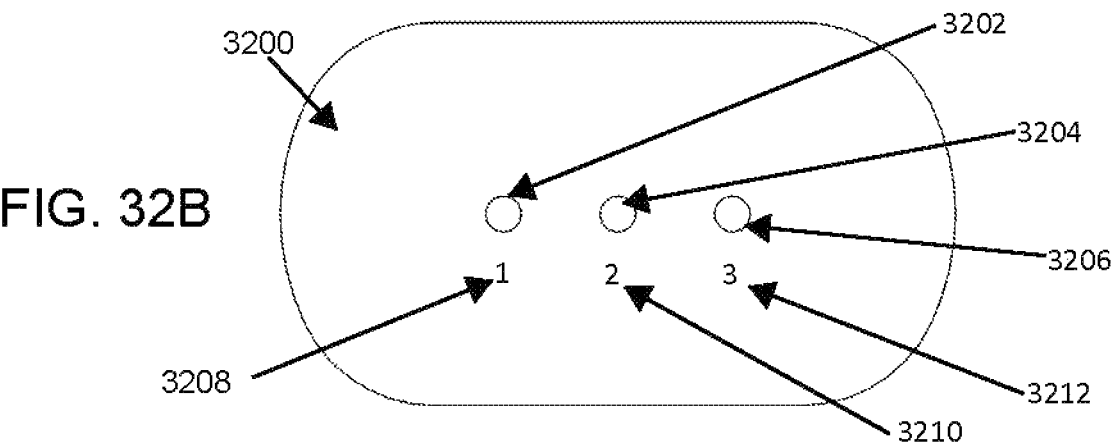
Figure 33:
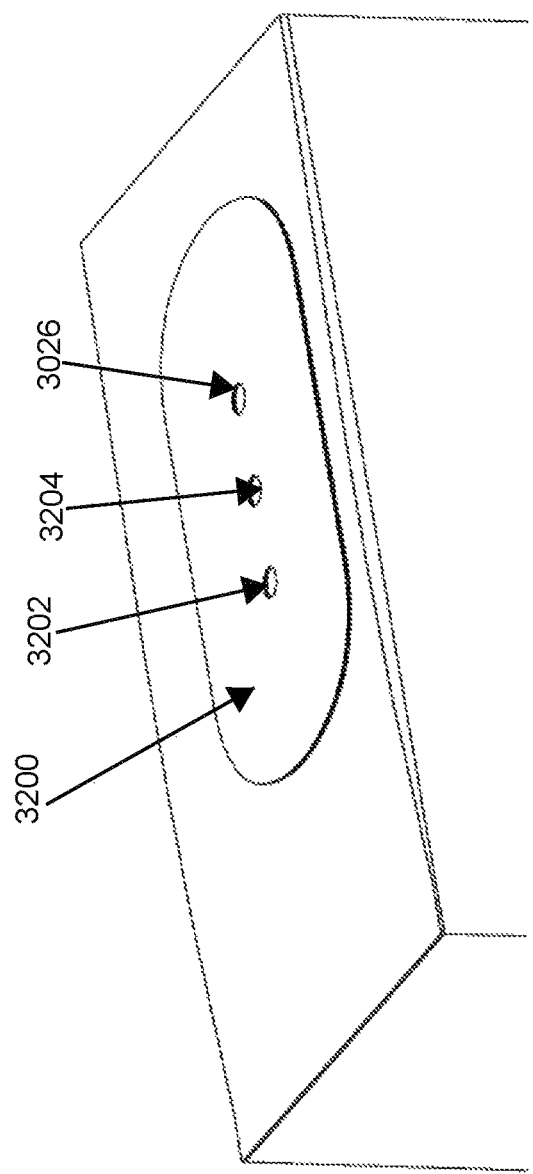
FIG. 33 depicts the placement of a three-aperture dressing onto an injection location.

FIG. 32B depicts another exemplary embodiment of a dressing 3200, comprising multiple openings 3202, 3204, 3206. In this particular embodiment, the openings 3202, 3204, 3206 are linearly aligned with each other, and optionally linearly aligned along the central longitudinal axis of the dressing 3200, as shown in FIG. 32B. Optional indicia 3208, 3210, 3212 may be provided to facilitate changing of the insertion location during a single use of the dressing 3200. FIG. 33 depicts dressing 3200 placed against a skin location.

Figure 32C:
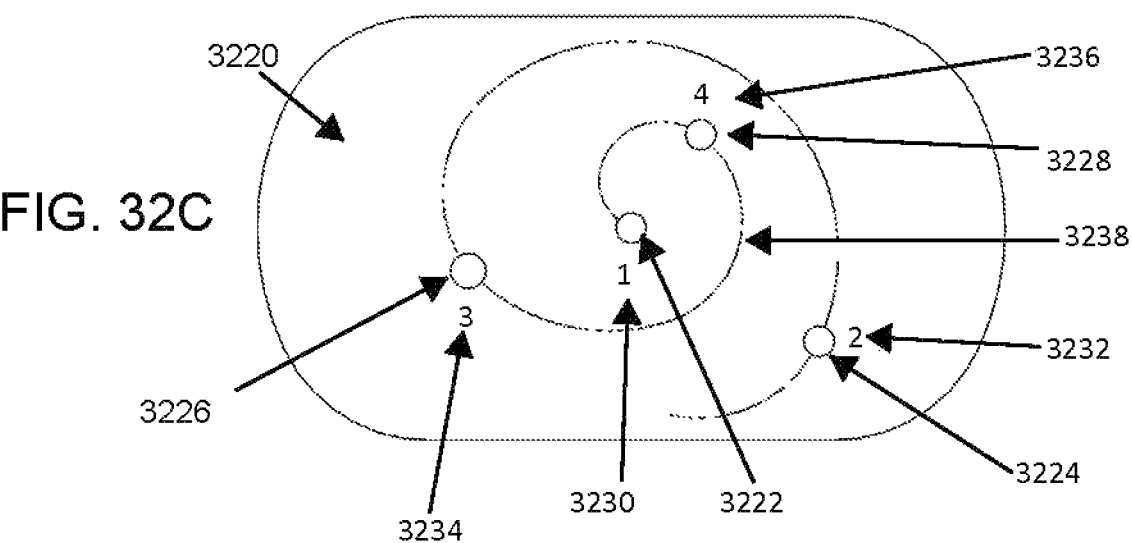

FIG. 32C depicts another exemplary embodiment of a dressing 3220, comprising multiple openings 3222, 3224, 3226, 3228. In this example, one opening 3222 is centrally located, but the other three openings 3224, 3226, 3228 are eccentrically located and no three openings are linearly arranged. In other examples, all of the openings may be eccentrically located. Indicia 3230, 3232, 3234 and 3236 may optionally be provided for each opening 3222, 3224, 3226, 3228, along with other optional indicia such as the spiral lines 3238, which may be used to indicate relative locations.

Figure 32D:
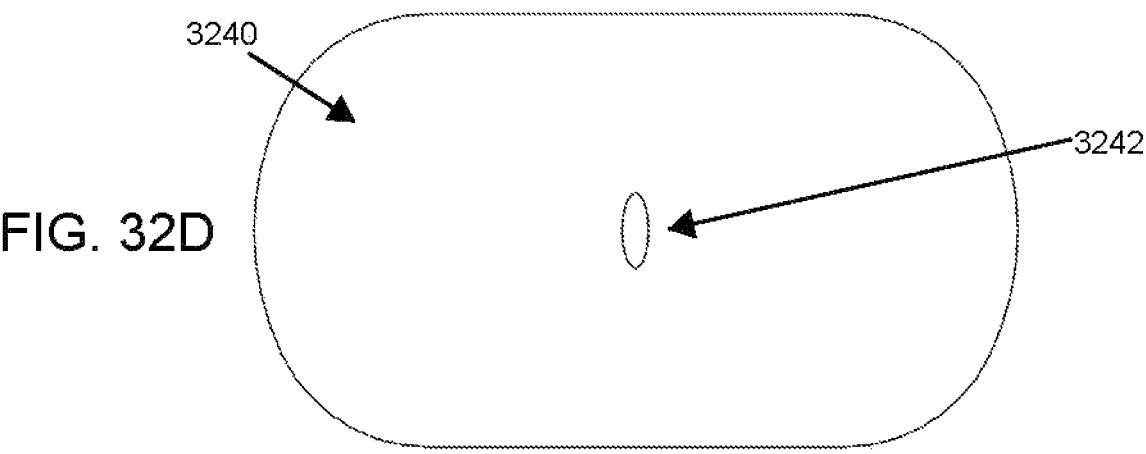
Figure 32E:
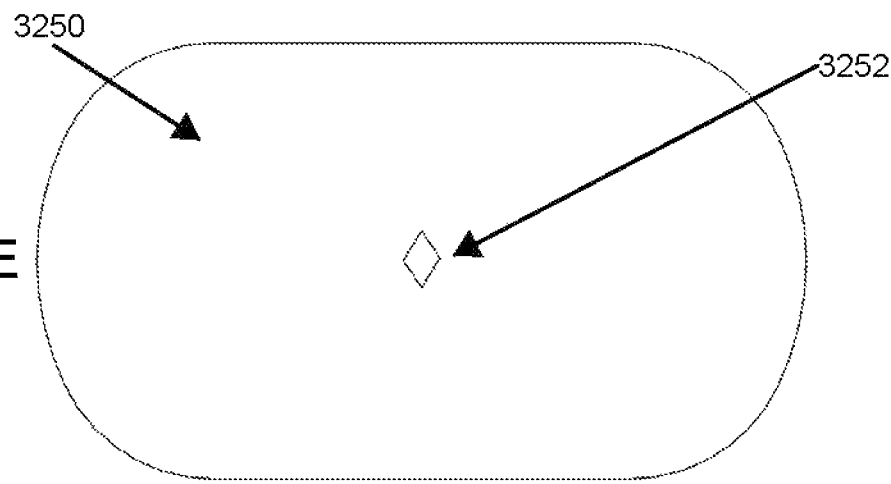

Other exemplary dressings may include dressings with one or more opening shapes that are non-circular. FIG. 32D, for example, depicts a dressing 3240 with an oval opening 3242, and FIG. 32E depicts a dressing 3250 with a diamond shaped or parallelogram shaped opening 3252.

FIG. 57A to 57D depicts another embodiment of a tensioned tissue treatment system 5700, comprising a dressing 5702 and one or more removably attachable injection templates 5704a-c. The templates 5704a-c (a subset of three of five exemplary templates are depicted) are temporarily applied to the dressing in order to indicate to the user where to inject, while being removable so that bulkiness or discomfort of the tensioned tissue treatment system is reduced between injections. As with many of the exemplary embodiments depicted herein, the dressing 5702 is depicted schematically without an applicator or tension applicator that are described elsewhere herein for simplicity. Each of the templates 5704a-c have the same size and shape but includes a plurality of injection openings 5706a-c, 5708a-c, 5710a-c, 5712a-c, each at a different location on the template 5704a-c relative to the other templates 5704a-c. Thus, each template 5704 is used on a different day to assist the user to rotate injection sites with each injection every day. Indicia 5714a-c may also be provided on the template 5704a-c to help the user or caretaker with identifying which template 5704a-c to use for each time period. The indicia 5714a-c preferably comprises a set of ordinal indicia or words indicating a numerical or alphabetic series, but in other variations may comprise other sets of indicia that may be non-ordinal. Although the injection openings 5706a-c, 5708a-c, 5710a-c, 5712a-c of each template 5704a-c are grouped or clustered together in different areas of each template 5704a-c, in other variations, the injection openings on each template may be located at different locations relative to the other templates, but not clustered such that the perimeter of the shape defined by the openings on each template may overlap or intersect the perimeter of the shape provided on other templates of the same set. This exemplary template also comprises four injection openings 5706a-c, 5708a-c, 5710a-c, 5712a-c, but in other variations, two, three, five or six openings may be provided for each set or group of injection openings for each template. In another embodiment, the injection template is a transparent thin film polymer (e.g. polyethylene terephthalate, polycarbonate, or similar) and may be printed with an outline of the dressing shape to visually align over. Because of the materials, the thin polymer film may cling and temporarily adhere to the silicone dressing without the need for an adhesive or other attachment mechanism. Once the template 5704a-c is aligned and attached to the dressing 5702. The template openings 5714a-c, 5706a-c, 5708a-c, 5710a-c will be generally coaxially aligned with one of the corresponding groups of dressing openings 5724a-e of the dressing 5702, to facilitate or permit injections through the template openings 5714a-c, 5706a-c, 5708a-c, 5710a-c and the groups of dressing openings 5724a-e. Some variations in alignment of the template openings 5714a-c, 5706a-c, 5708a-c, 5710a-c and the dressing openings 5724a-e may occur due to variations in the tensioned size of the dressing 5702. In other variations, however, dressing openings of the embodiments herein are not provided and a needle may be passed through the template opening and then pierces through the dressing for the injection.

To facilitate the reproducible alignment of the injection templates 5704a-c to the dressing 5702, one or more complementary alignment structures 5720, 5722, 5716a-c, 5718a-c may be provided on the dressing 5702 and templates 5704a-c. In this particular example, flat but raised alignment structures 5720, 5722 are bonded, heat melded or welded to the upper surface of each end of the dressing 5702. In other examples, the alignment structures may be apertures in the dressing which may be aligned with raised alignment structures on lower surface of the templates. Complementary alignment structures or openings 5716a-c and 5718a-c are arranged on the template 5704a, which can form interfit or interlock with the alignment structures 5720, 5722. In some variations the geometric shapes of the alignment structure 5720, 5722 are different, e.g. square and triangle, so as to limit the orientations of the injection template 5704a-c when attached to the dressing 5702. Other shapes that may be used include rectangles, slots, circles, ovals or other polygonal shapes. The shapes may be configured with a tolerance that allows alignment when the dressing is stretched or contracted in along the orientation direction between the alignment structures. For example, the raised alignment structures 5720, 5722 may be slightly undersized when compared to the complimentary alignment structures or openings 5716a-c and 5718a-c on the template(s) 5704a-c, to accommodate variations in the length of the dressing when it is adhered to the skin, from movement and/or positioning. In some further embodiments, the complementary alignment structures may be further configured to provide a removable snapfit between the dressing and template, to resist inadvertent misalignment or unintended separation. The template may be manufactured a single layer or multi-layer structure, comprising woven or a non-woven structure, and include materials such as polyimide, polyester, polyethylene, paperboard, and the like. Any indicia on the template may be ink printed, silk-screened, embossed, die-cut, stamped or laser etched on the surface of the template. In still other variations, the template(s) may comprise an elastic material that accommodate variations in the stretched length and/or width of the dressing when it is adhered to the skin. With an elastic template, the elastic material may comprise a force per millimeter width that is lower than the force per millimeter width of the dressing itself, e.g. 50% or less, 40% or less, 30% or less 20% or less, or 10% or less, so that the tension in underlying tissue and the dressing is no substantially altered by the temporary attachment of the template.

The size of the injection openings 5706a-c, 5708a-c, 5710a-c, 5712a-c may vary, with a diameter or maximum transverse dimension in the range of about 3 mm to 20 mm, 5 mm to 15 mm, or 8 mm to 12 mm. The size of the injection openings may be sufficiently large so that the user can adequate clean the injection site with an alcohol swab prior to injection, and/or for adequate visibility by patients with poor vision, e.g. diabetic retinopathy. The perimeter of the injection openings may be optionally raised to provide tactile feedback to facilitate positioning of a needle, which may assist users with poor vision or color blindness.

Figure 58:
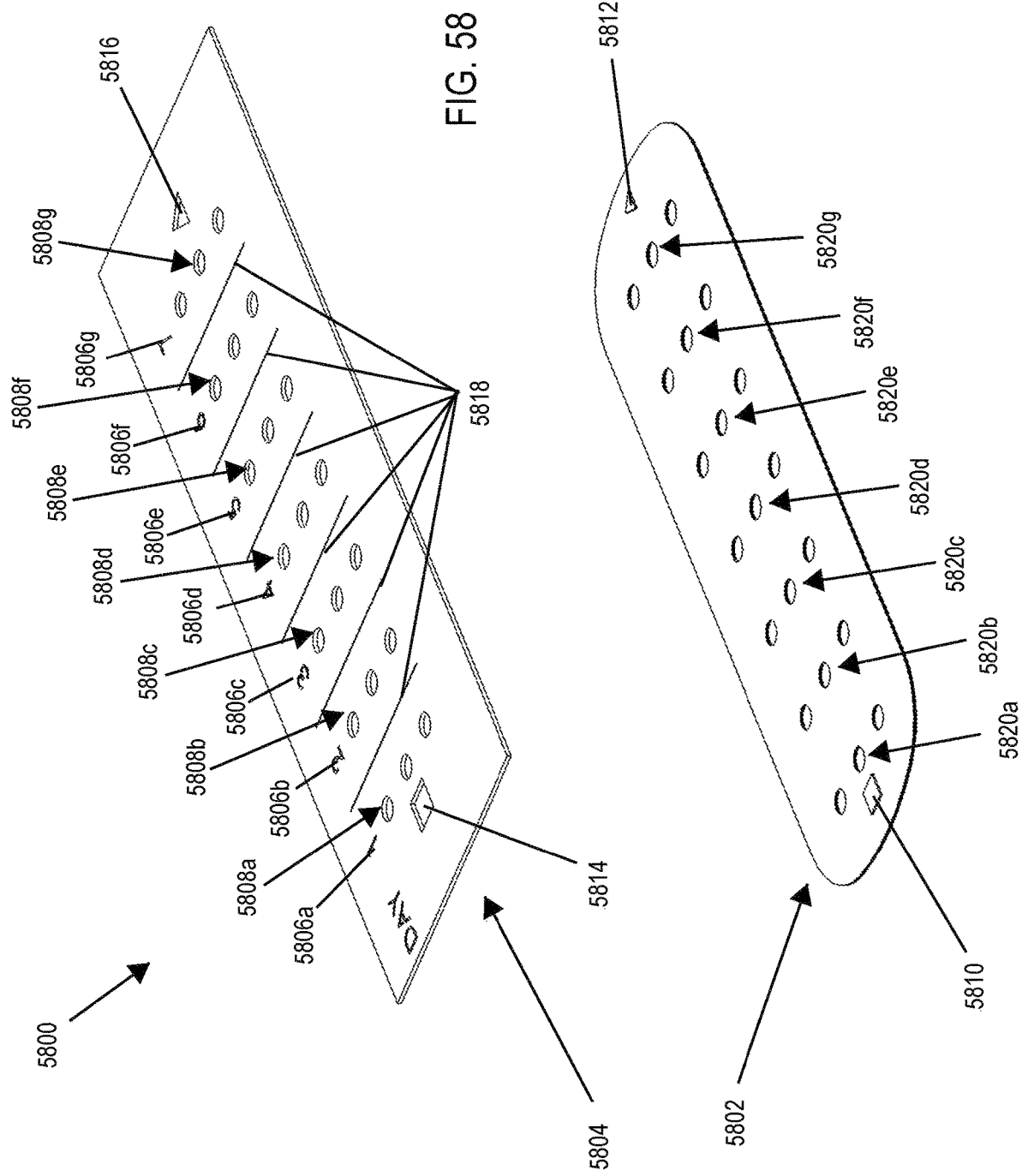
FIG. 58 is a perspective view of another exemplary tensioned skin treatment system comprising a multi-day removable injection template
Figure 59A:
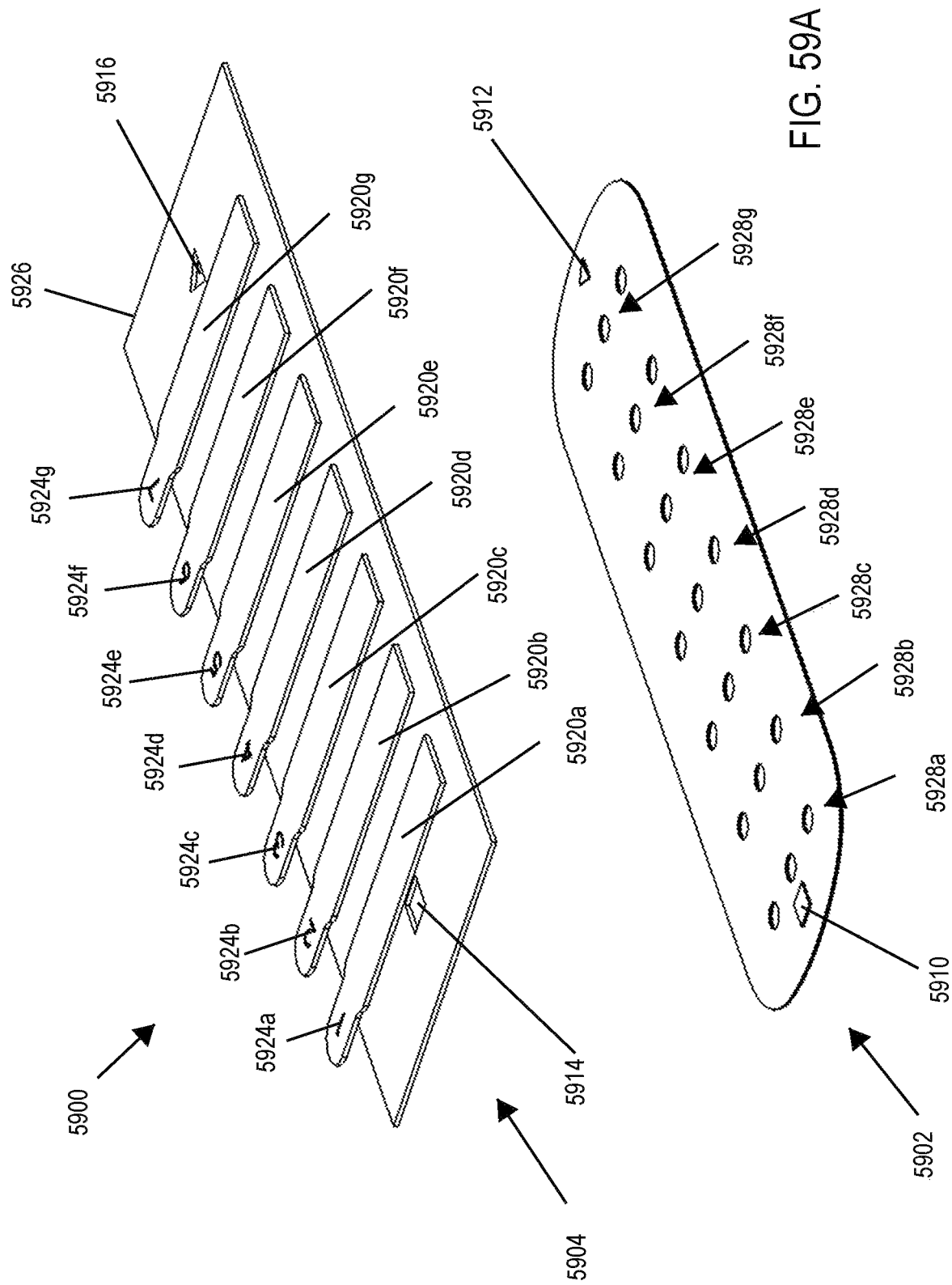
FIG. 59A is a perspective view of another exemplary tensioned skin treatment system comprising a weekly removable injection template with removable indicator strips.

While the tensioned tissue treatment system 5700 in FIGS. 57A to 57D comprises a plurality of different templates 5704a-c, each for use with a different time period, e.g. one day, in other examples, a treatment system may include a template configured with injection openings for multiple time periods. In FIG. 58, for example, the tensioned tissue treatment system 5800 comprises a dressing 5802 that is similar to dressing 5702 from FIGS. 57A, but wherein the template 5804 is configured with multiple groups of injection openings 5808a-g, each group optionally labeled by its own indicia 5806a-g and/or separated by separation indicia 5818. During use, the template 5804 is attached to the dressing 5802 via the alignment structures 5810, 5812, 5816, 5818. Once attached, the groups of injection openings 5808a-g of the template 5804 will be generally or coaxially aligned with the corresponding groups of injection openings 5820a-g of the dressing 5802. This facilitates or permits injections through the injection openings 5820a-g of the template 5804 and through the groups of injection openings 5820a-g of the dressing 5802. As noted elsewhere, some variations in alignment of groups of injection openings 5820a-g and the groups of injection openings 5820a-g of the dressing 5802 may occur due to variations in the tensioned size of the dressing 5802. The user then identifies which set of openings 5808a-g to be used, and then, based on the time of day or meal, identifies which of the injection openings for that set of openings 5808a-g to be used for the injection used. The example system 5800, illustrated in FIG. 58, includes three injection openings per group 5808a-g, but noted elsewhere herein, while in other variations, two, four, five or six openings may be provided per group. Each group 5808a-g has a linear arrangement of openings that is transverse to the long axis of the template 5804, but in other variations may have a cluster arrangement equally spaced around a central point to ensure proper injection rotation, without overlap between groups 5080a-g. The other features of the system 5800 may otherwise be similar to the range of features as described for system 5700.

FIGS. 59A to 59E depict another variation of a tensioned tissue treatment system 5900. The system 5900 comprises a dressing 5902 with a multi-time period template 5904 similar to the system 5800 in FIG. 58, but wherein each subgroup of template openings 5908a-g is covered by a single removable adhesive cover 5920a-g. The first openings of each group 5908a-g is aligned with first openings of the other groups with respect to the longitudinal axis of the template 5904, as is each of the subsequent openings of each subgroup with the corresponding openings of the other subgroups. This results in the subgroup of openings 5908a-g forming a rectangular grid of openings. In other variations, however, the arrangement and alignments of the subgroups may be different, as will be described for other exemplary embodiments below. Each cover 5920a-g has a shape and size sufficient to cover all the corresponding openings in a group of openings 5908a-g, and further configured to extend beyond the outer edge 5926 of the template 5904, to facilitate grasping and removal of each cover 5920a-g by a user. Each cover 5908a-g optionally further comprises different indicia 5924a-g to assist the user to identify which group of openings 5908a-g to use each day. The indicia 5924a-g may comprise ordinal numbers, letters or words, or may comprise symbols. Although the covers 5924a-g depicted in FIGS. 59A-59E are configured to extend beyond the same side of the edge 5926 of the dressing and are arranged consecutively from one end of the template 5904 to the other end, in other variations, the covers may be arranged to extend from either of the two sides of the template, e.g. in an alternating fashion, and/or in a non-consecutive arrangement. The latter may be beneficial to provide greater spacing between the groups of openings based on the order in which the covers and groups of openings are removed per the indicia on the covers. With the indicia 5924a-g located on the covers 5920a-g, other indicia, like the ordinal indicia 5806a-g or the separation indicia 5814 found in the system 5800 in FIG. 58, may or may not be provided. The covers may comprise a flexible polymeric or paper material, and the adhesive adhering the cover 5920a-g to the template 5904 may be a pressure sensitive adhesive, e.g., polyacrylate-based, polyisobutylene-based, silicone-based pressure sensitive adhesives, synthetic rubber, acrylic, and polyisobutylene (PIB), hydrocolloid, and the like. Preferably, the t-peel force of the cover adhesive is significantly lower than the t-peel force provided on the dressing 5902, so that the dressing 5902 or the template 5904 is not pulled off during use if the template 5904 is attached to the dressing 5902 before the cover 5920a-g is removed. The alignment structures 5910, 5912, 5914, 5916 of the dressing 5902 and template 5904 may otherwise be similar to systems 5700, 5800 described previously, or the other variants described elsewhere herein. Once aligned, the subgroups of template openings 5908a-g are aligned with corresponding subgroups of dressing openings 5928a-g of the dressing 5902.

In use, the system 5900 involves the removal of any dressing 5902 that was previously applied. Depending on the type of adhesive provided on the dressing, water or an alcohol or emollient adhesive remover may be used to avoid or reduce the risk of medical adhesive related skin injury. The new injection area is identified and cleaned, and then the new dressing 5902 of the system 5900 is applied to the new injection area. The template 5904 is then grasped, and the first or the next consecutive cover 5908a-g is grasped and peeled away from the template 5904 and removably attached to the dressing via the alignment structures 5910, 5912, 5914, 5916. If the group of openings 5908a-g to be used already been removed earlier in the day or time period, the user may use an alcohol swab to wipe the exposed group of openings 5908a-g prior to attachment to the dressing 5902. The user then prepares the injection and selects the opening in the group of openings 5908a-g based on the time of day or meal time, and injects the therapeutic agents through the selected opening. After the injection is completed, the template 5904. This procedure is repeated several times per day until the dressing is replaced, as shown in FIGS. 59B to 59E, illustrating Days 1-3 of a newly applied system 5900.

FIGS. 60A to 60D depicts another variation of a tensioned tissue treatment system 6000, which is similar to system 5700 and its variants, except that instead of one attachment shape located at each end of the dressing and template(s), with the shapes being different, the attachment shapes are each the same size and shape, but there are different numbers of them at each end. In the example in FIGS. 60A to 60D, one end of the dressing 6002 comprises a single circular shape 6012a, while the other end comprises two circular shapes 6014a, 6016a. Likewise the complementary attachment structures on the templates 6004a-c comprise a single complementary circular opening 6012a-c at one end of the templates 6004a-c and two complementary circular openings 6014a-c, 6016a-c at the other end. The difference in the number of shapes at each end specifies the relative orientation of dressing 6002 and template 6004a-c. Once the template 6004a-c is aligned and attached to the dressing 6002. The groups of template openings 6020a-c will be generally coaxially aligned with one of the corresponding groups of dressing openings 6024a-e of the dressing 6002. This facilitates or permits injections through the groups of template openings 6020a-c and the groups of dressing openings 6024a-e. In still further variations, other shapes besides circles may be provided, and even in embodiments where different shapes are provided, the number of shapes may still be different and/or different sizes of the same shape may be included. The number of shapes on each end may be in the range of one to five, one to four, one to three or one to two. The shapes may be arranged linearly or may be clustered around a common center point. In still other variations, instead of a different size openings on the templates that form a complementary interfit with protruding shapes on the dressing, hook-and-loop applicators, adhesives, and/or magnetic attachment structures may be used to removably couple the dressing and templates.

Figure 61A:
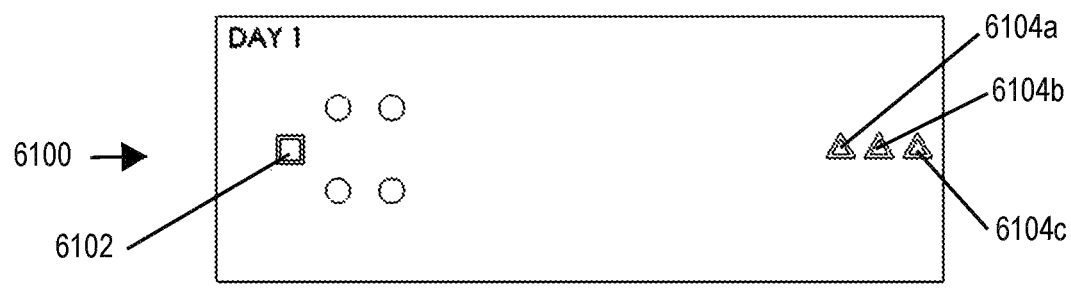
FIGS. 61A to 61D are top views of injection templates comprising a variable alignment structure.
Figure 61B:
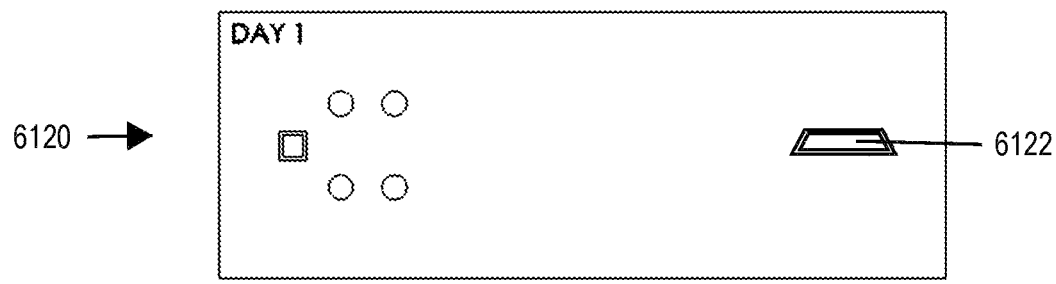
Figure 61C:
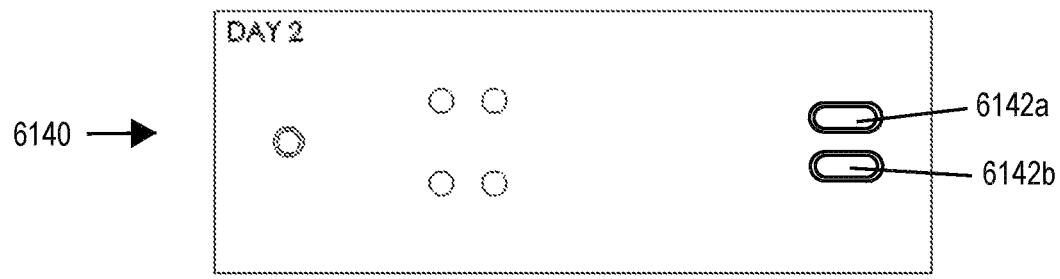
Figure 61D:
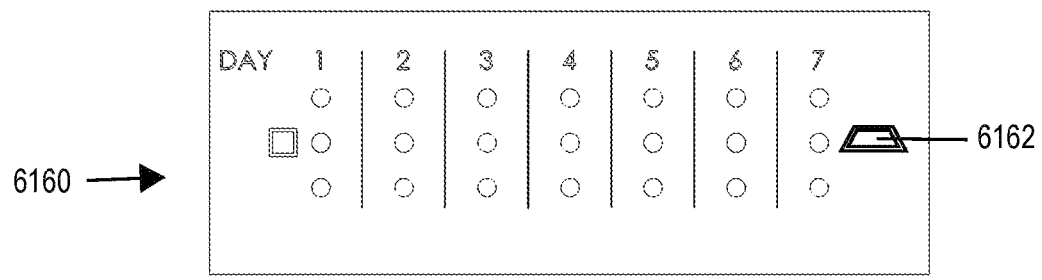

Due to variations in the equilibrium state between a tensioned tissue treatment device and the underlying tissue, the resting size, and therefore the distance between the attachment structures on the dressing component of the system may vary. To accommodate these variations during template attachment and the injection of the therapeutic agent, a linear set of attachment structures may be provided, or a modified opening may be provided wherein the opening is configured to form an interfit with the attachment structure of the dressing across a transverse axis of the template, but permits longitudinally variable positions along the longitudinal axis. FIG. 61A depicts an example of an alternate template 6104 that may be used with the system 5700 in FIGS. 57A to 57D. This template 6100 comprising a single attachment opening 6102 at one end, and a plurality of openings 6104a-c at the other end. During use one single attachment opening 6102 is first attached to the dressing, then the opening 6104a-c of best fit to attach to the corresponding attachment structure on the dressing is selected to minimize any fold or ruffles, or excessive stretching in the template 6104 or dressing. FIG. 61B depicts an embodiment of an alternate template 6120 that may be used with system 5700 in wherein instead of triangular attachment opening, a trapezoidal attachment opening 6122 which is configured to form an interlock with a triangular attachment structure of a dressing anywhere along the length of the trapezoidal opening 6122. The trapezoidal opening 6122 is oriented along the longitudinal length of the template, so as accommodate variable dressing lengths and therefore variable dressing attachment structure positions. FIG. 61C depicts an exemplary alternate template 6140 that may be used with the system 6000 in FIGS. 60A to 60D, comprising two oval openings 6142a, 6142b that are oriented along the longitudinal length of the template, to accommodate variable positions of the two circular openings of the dressing 6002 of system 6000. FIG. 61D depicts an exemplary alternate template 6160 that may be used with systems 5800 or 5900, also with a trapezoidal opening 6162 to accommodate the variable position of a triangular attachment structure of a corresponding dressing. In each of the templates 6100, 6120, 6140, 6160, the attachment opening may be larger than the corresponding attachment structure(s) 6104a-c, 6122, 6142a-b, 6162, to accommodate variable dressing lengths and therefore variable dressing attachment structure positions. In each of the templates 6100, 6120, 6140, 6160, the attachment opening on the right of the template was configured to accommodate the variable attachment position, but in other variations, the attachment opening on the left side of the template may be configured as such.

Figure 62A:
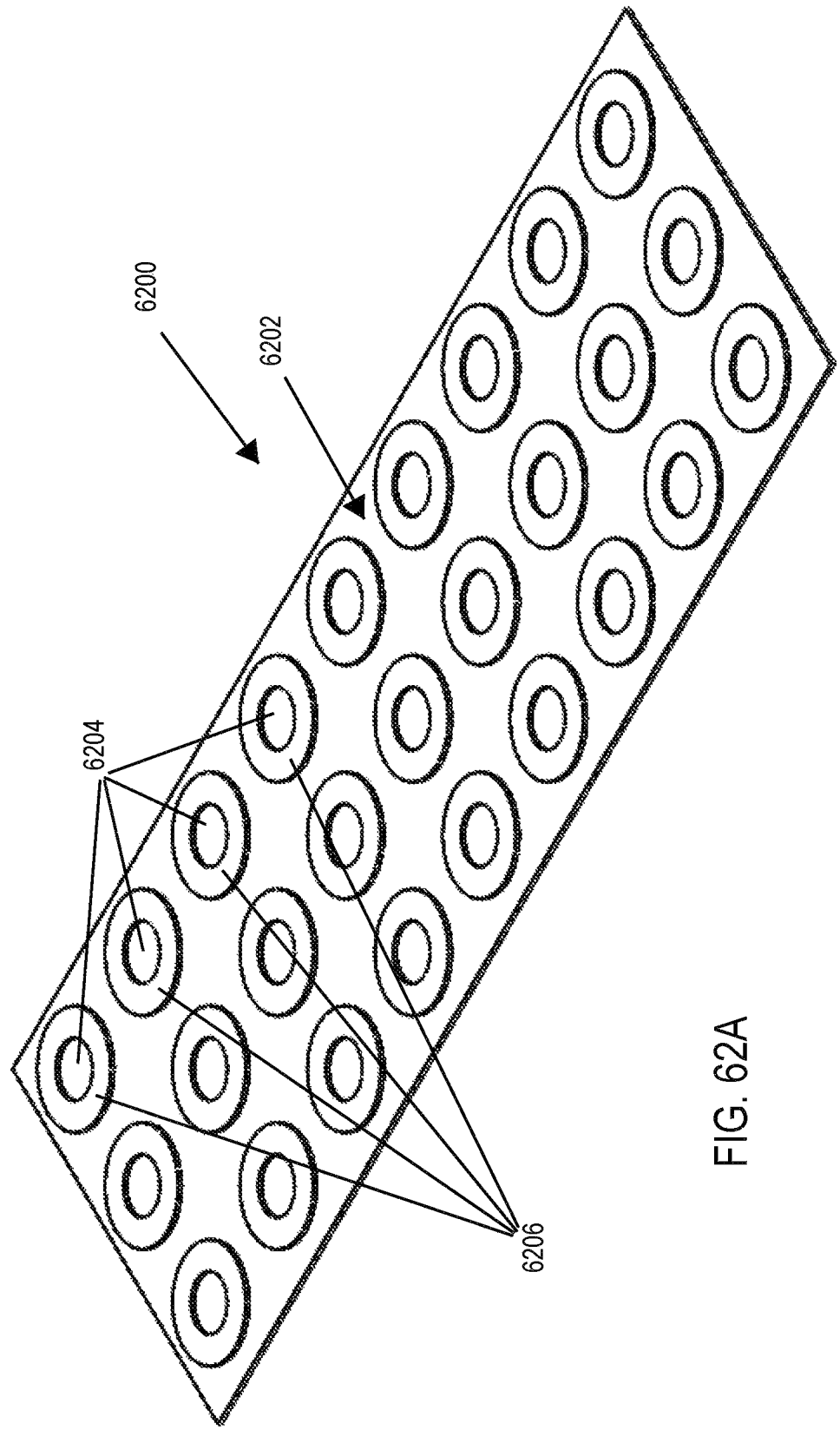
FIG. 62A is a perspective view of another tensioned skin treatment system comprising removable rings.
Figure 62D:
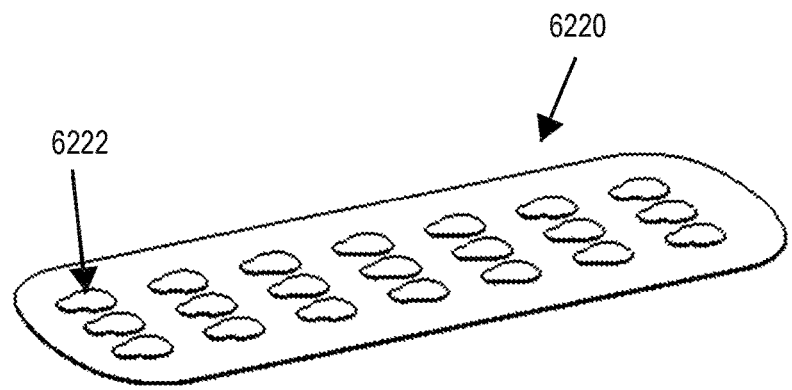
FIGS. 62D to 62G depicts the use of the exemplary system in FIG. 62B.
Figure 62E:
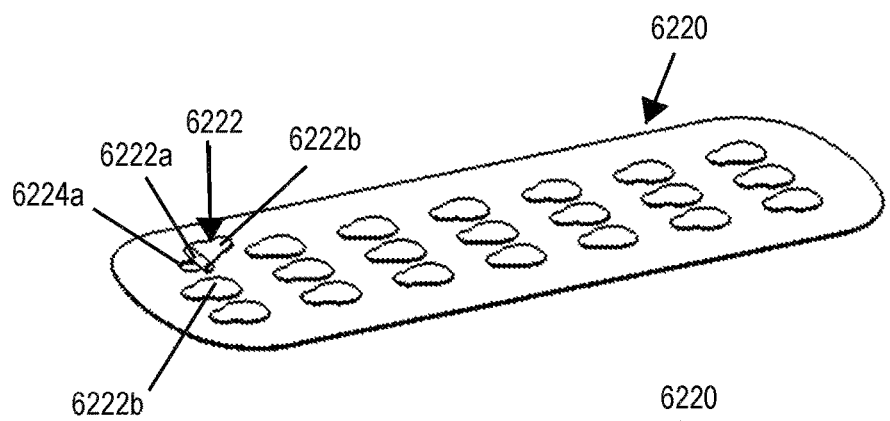
Figure 62F:
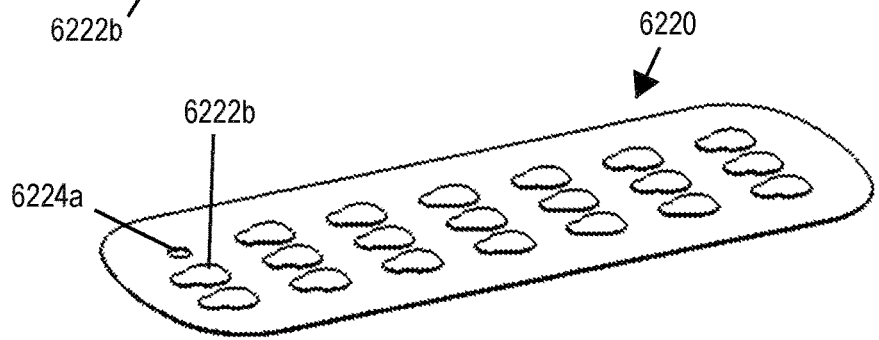
Figure 62G:
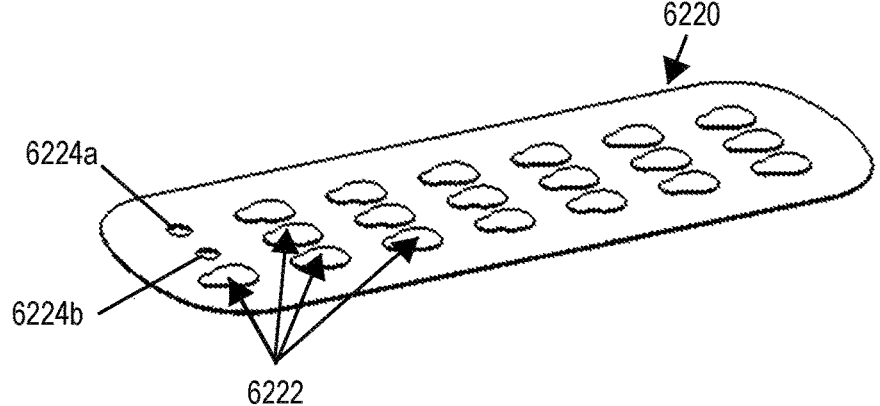

FIG. 62A depicts another embodiment of a tensioned tissue treatment system 6200, comprising a dressing 6202 without any template. Instead, the plurality of openings 6204 are surrounded by a plurality of adhesive removable rings 6206. The rings 6206 are preferably made of a soft foam. As each opening 6204 is used, the foam ring 6206 may be removed or peeled off from the dressing 6202 to indicate its usage. In this particular embodiment, no indicia or groups are necessarily provided, and the user may be instructed to use any previously unused opening 6202 s indicated by the remaining or existing foam rings 6204, and may or may not be instructed to use the openings 6202 in any particular order or manner, e.g. across the each row or column of the grid of openings 6202, and to the another row or column, whether adjacent or not FIGS. 62B and 62C depict other exemplary embodiments of tensioned tissue treatment dressings 6220, 6240 which are not used with templates. In these particular embodiments, each dressing 6220, 6240 comprises individual adhesive covers 6222 for each dressing opening (not shown). Each cover includes a main body 6222a that is adhered to the dressing surrounding each dressing opening. A smaller flap 6222b is also included. The flap 6222b may be non-adhesive to the dressing surface, to facilitate grasping of the cover 6222 for peeling off the main body 6222a. Dressing 6240 in FIG. 62C is similar to dressing 6220 in FIG. 62B, except that each of the covers 6242 also includes an indicia 6242c, in addition to the adhesive main body 6242a and non-adhesive flap 6242b. The indicia 6242c on each cover 6242 may be arranged in groups 6244a-g to facilitate the order of use by day or other time period. In this particular example, the indicia 6242*c* of each group 6244*a-g* may be identical, but in other variations, each indicia 6242*c* may be different. As noted for other embodiments, the indicia 6242*c* may be ordinal numbers or letters, or may comprise other symbols indicating a time of day or meal, e.g. sunrise, moon, food symbols. Referring to FIGS. 62D to 62G, the use of dressing 6220 depicts its initial use with the removal of a first cover 6222 via the flap 6222*b*, to peel away the adhesive body 6222*a*, to expose the underlying dressing opening 6224*a*. The covers 6222 may be removed in order using the next closest adjacent cover 6222, as depicted in FIG. 62G, but in other variations, any unused cover 6222 on the dressing 6220 may be selected for use.

Figure 63:
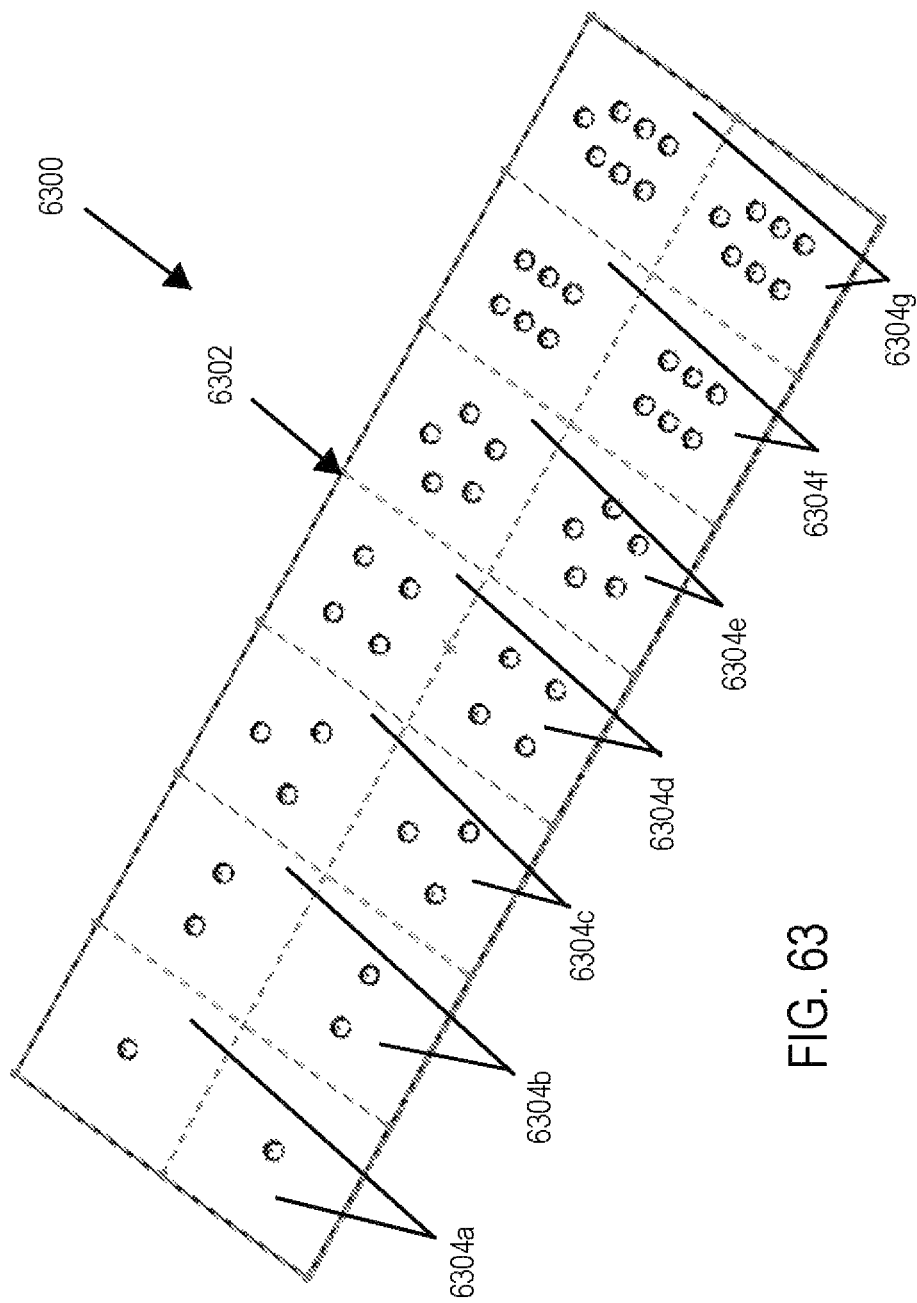
FIG. 63 is a perspective view of another tensioned skin treatment system.

FIG. 63 depicts another embodiment of a tensioned tissue treatment system 6300 comprising a dressing 6302 with a plurality of removable tabs or covers 6304*a-g*. In this particular embodiment, the covers 6304*a-g* are detachable from the dressing 6302 to expose the injection opening (not shown). Each cover 6304*a-g*, however, has one or more raised bumps or protrusions, so that limited sight users, e.g. those with diabetic retinopathy or other visual impairment, can identify unused openings of the dressing 6302, remove the cover 6304*a-g* and perform the injection. The bumps on each cover 6304*a-g* may comprise a sequentially incremented number of bumps to indicate the time period of use, as shown in FIG. 63, but in other variations, the bumps may be braille alphabet or numbers to indicated sequential letters or numbers to indicate or to track the order of use.

Figure 64A:
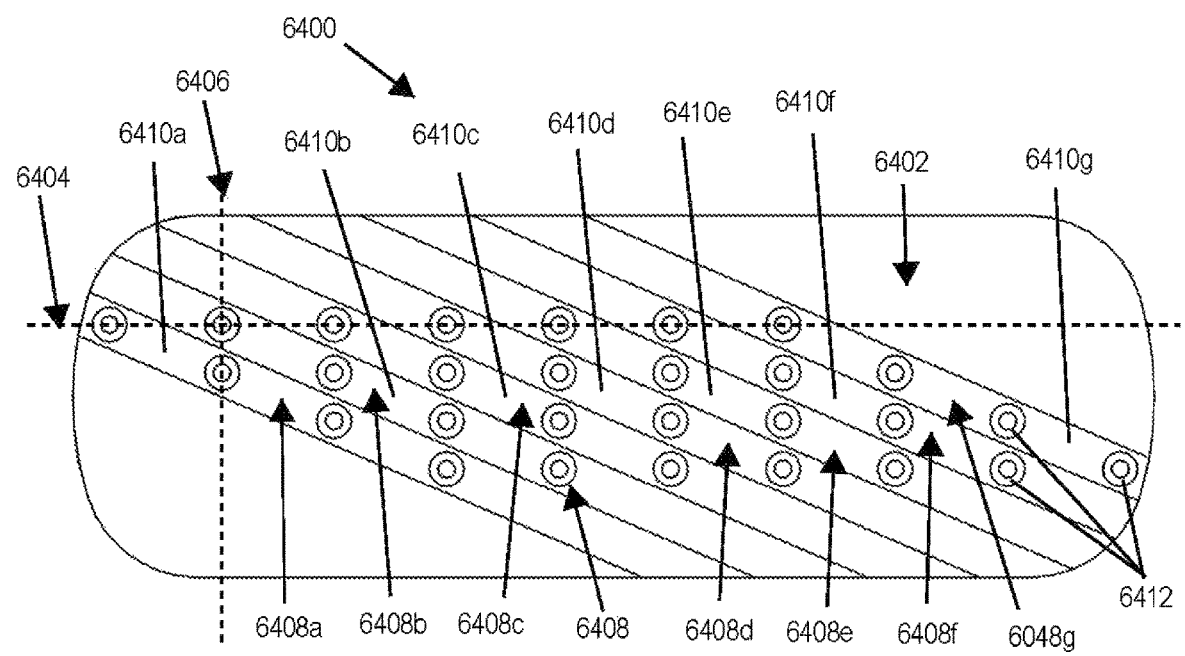
FIG. 64A is a top view of another embodiment of a tensioned skin treatment system comprising removable strip ring markers.
Figure 64B:
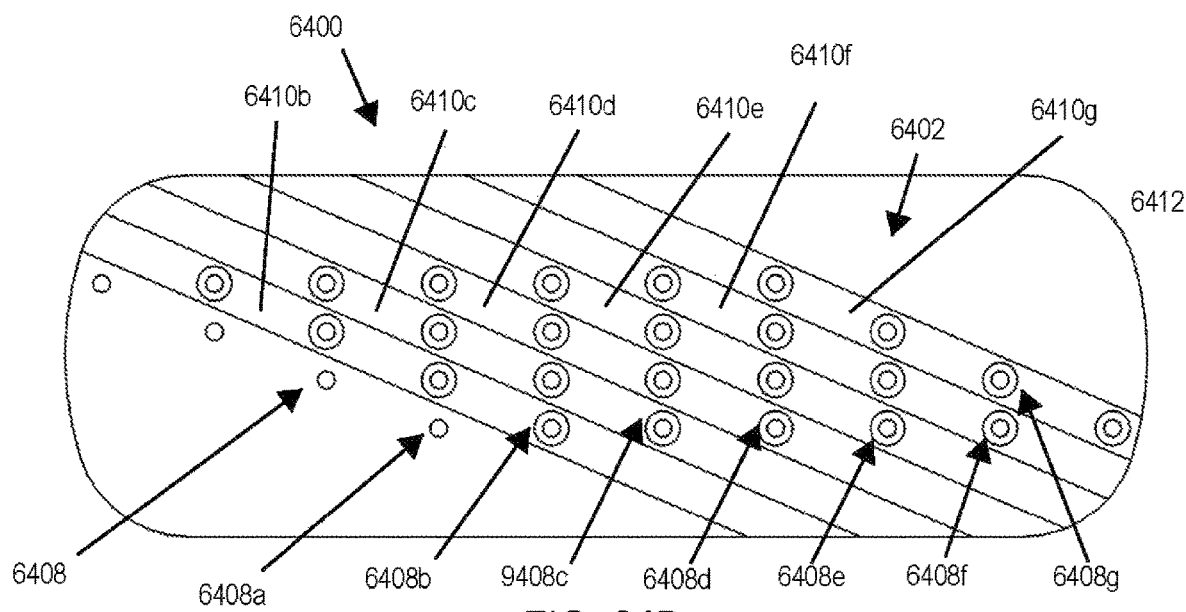
FIG. 64B is a top of the system in FIG. 64A with one strip ring marker removed.
Figure 65A:
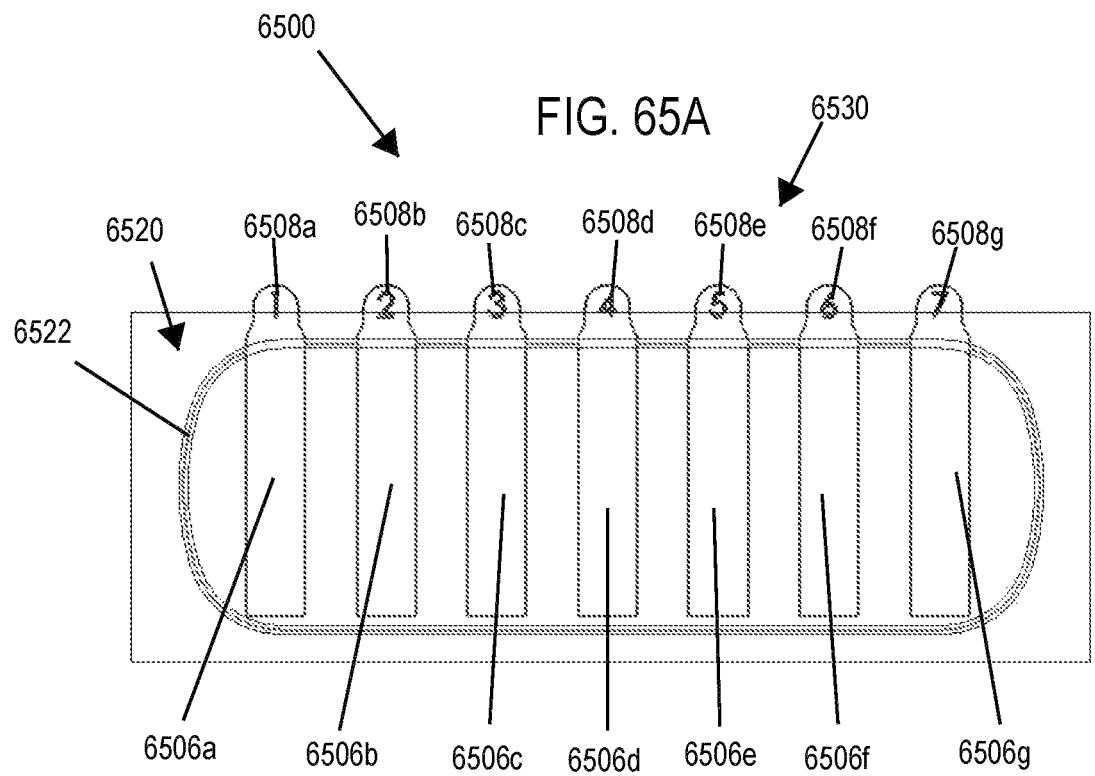
FIG. 65A is a top plan view of another embodiment of a tensioned skin treatment system, comprising an adhesive set of injection guides and covers, with an applicator.
Figure 65B:
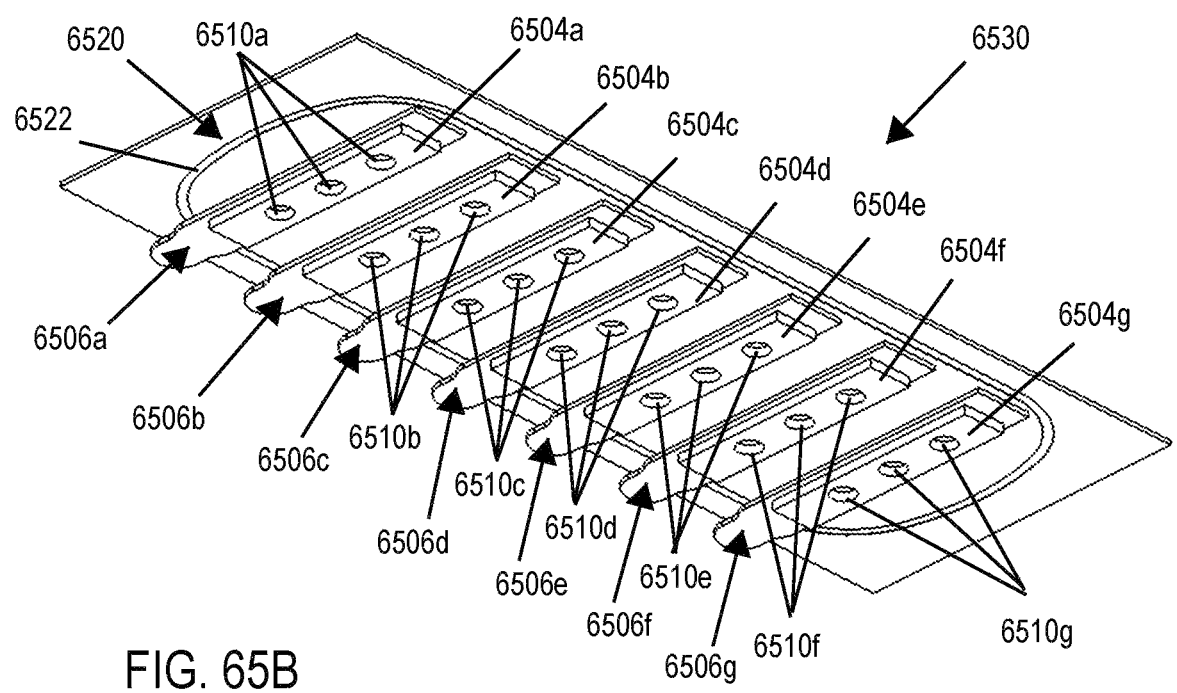
FIG. 65B is a bottom plan view of the system in FIG. 65A, with the release liner removed.
Figure 65C:
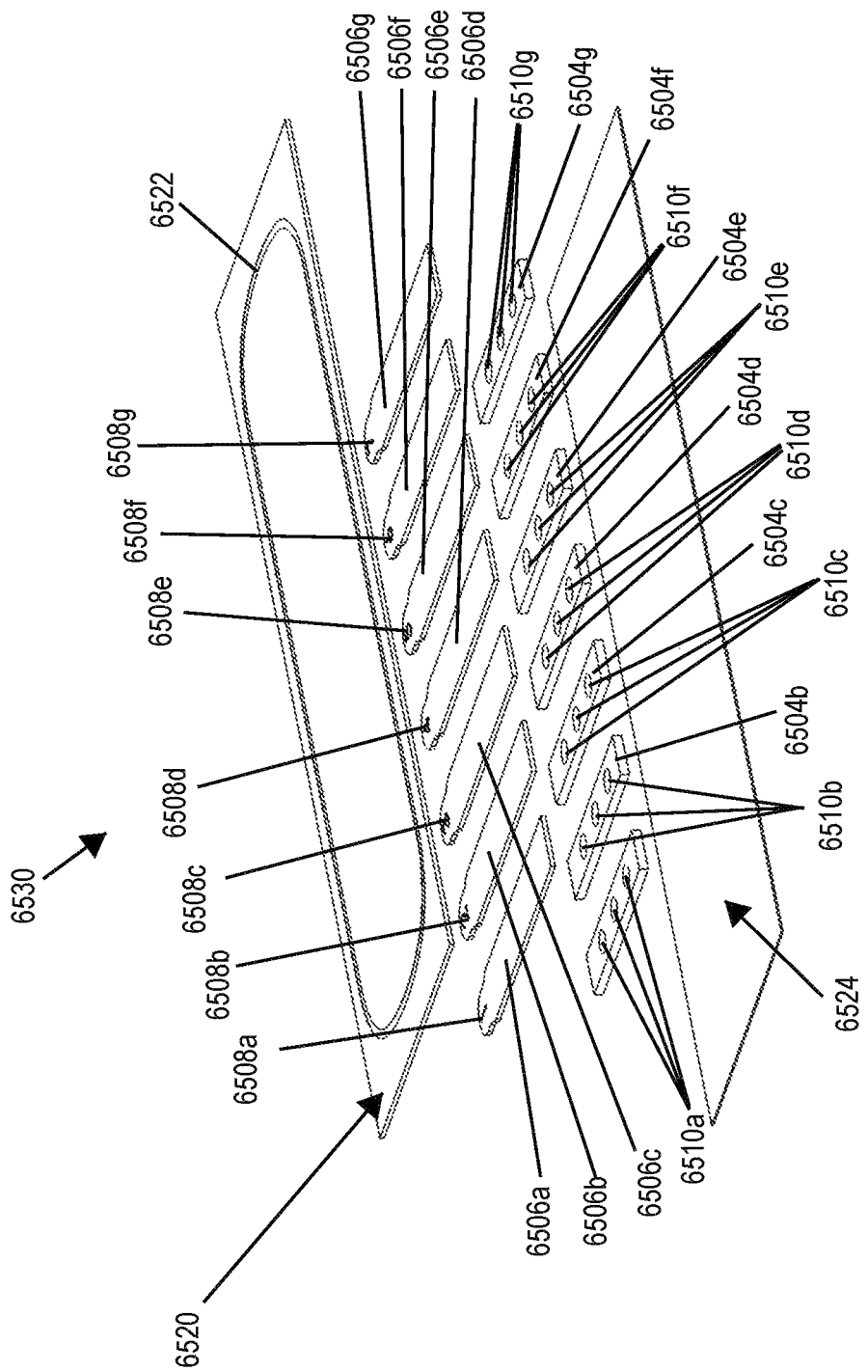
FIG. 65C is an exploded view of the system in FIG. 65A.
Figure 65E:
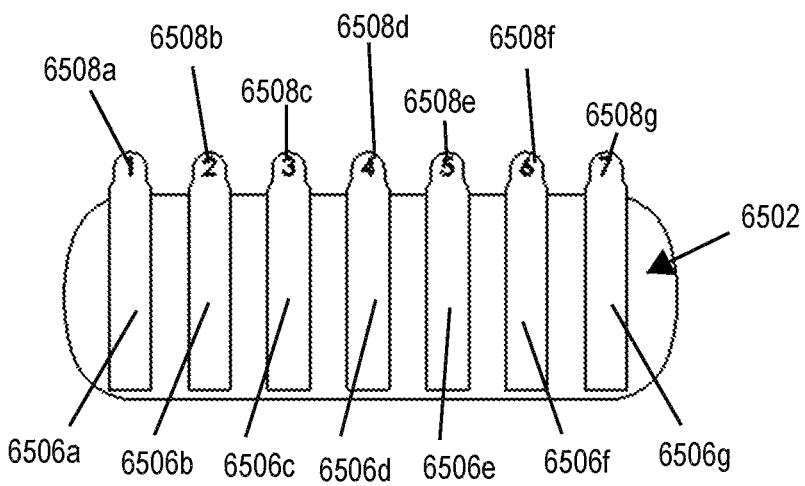
FIG. 65E to 65G depicts the initial use of the system adhered to a dressing.
Figure 65F:
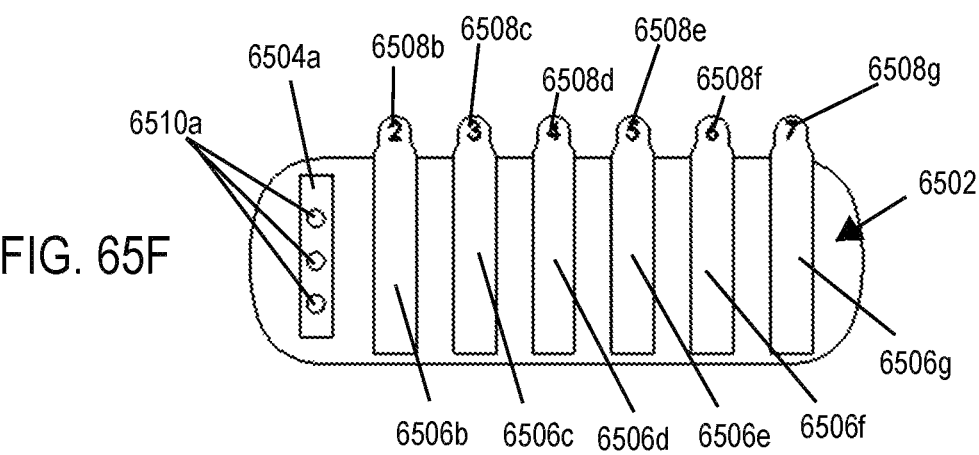
Figure 65G:
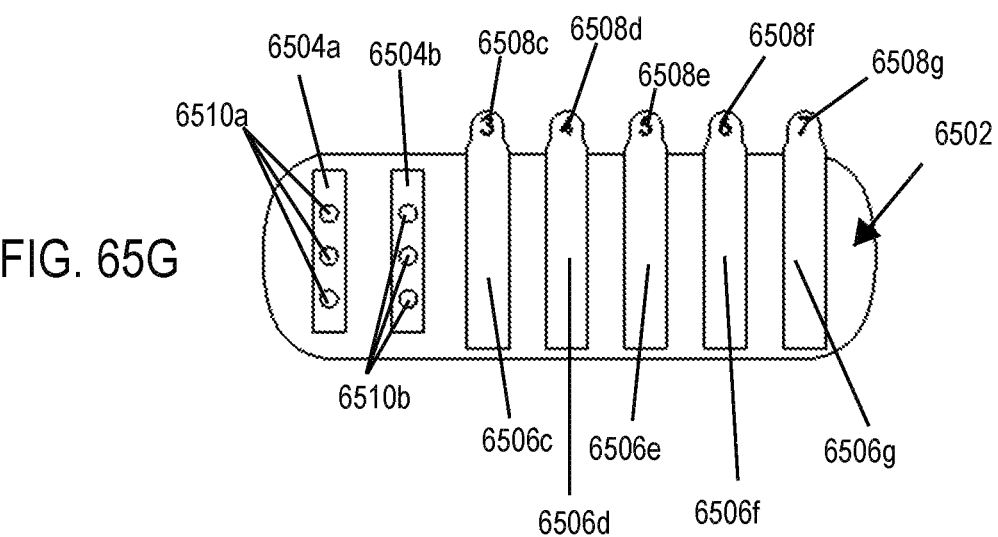

FIGS. 64A and 64B depict another variation of a tensioned tissue treatment system 6400, comprising a dressing 6402 with a longitudinal axis 6404 and a transverse axis 6406, and a plurality of openings 6408, which in turn comprise subgroups of openings 6408*a-g*, where each subgroup of opening are covered an adhesive removable cover strip 6410*a-g*. in system 6400, however, the plurality of openings 6408 have an optionally transversely staggered arrangement, wherein the first openings of each subgroup 6208 *a-g* is aligned longitudinally with first openings of the other subgroups 6408 *a-g*, but each sequential opening of a subgroup 6408 *b-g* is transversely offset from the earlier opening within each subgroup and optionally aligned with the earlier opening of the next adjacent subgroup 6408 *b-g*. This results in subgroups 6408 *a-g* that are linearly arranged but oriented at an angle to both the longitudinal and transverse axes of the dressing 6400, as depicted in FIG. 64A, as are the adhesive cover strips 6410*a-g*. In the particular example in FIG. 64A, the plurality of openings 6408 comprise seven subgroups 6408*a-g*, each with four openings, and a cover strip 6410*a-g* for each of the subgroups. Each of the adhesive cover strips further comprise optional removable foam rings 6412 around each of the openings. As each injection hole is used, the foam ring 6412 associated with the injection opening is removed. This indicates to the user that the opening has already been used and not to use it again for the duration of the dressing application. In other variations, the foam rings around each dressing are not removable from its strip 6410*a-g*, but the strip 6410*a-g* is removed, as illustrated in FIG. 64B for strip 6410*a*, to indicate usage for each day or time period.

It is hypothesized that the staggered arrangement of openings and subgroups of openings in system 6200 may provide a greater separation distance between the injections performed each day while still grouping the openings in a manner to provide for multi-day or weekly use for each dressing or system. In the particular example in FIGS. 64A and 64B, the longitudinal spacing between adjacent openings of adjacent subgroups may be about 0.49", or in the range of 0.4" to 0.6", 0.3" to 0.5", and the transverse spacing between adjacent openings of adjacent subgroups may be about 0.21", or in the range of 0.15" to 0.3", or 0.12" to 0.35". The resulting distance between adjacent openings of the same subgroup would be about 0.533", or in the range of 0.5" to 0.6", 0.45" to 0.7".

In other embodiments, instead of temporarily attaching and then removing an injection template, a set of injection guides may be provided permanently on the dressing. While the injection guides may be pre-attached to the dressing during the manufacturing processes, in other variations, the injection guides may be adhered to the dressing after the dressing has been attached and after the dressing tension has been released to offload the tension in the tissue. FIGS. 65A to 65G, depicts an injection guide system 6500 comprising a plurality of separate adhesive injection guides 6504*a-g*, which are removably covered by a plurality of guide covers 6506*a-g*. The plurality of adhesive injection guides 6504*a-g* are arranged or configured to align with a plurality of pre-formed dressing openings of a dressing, with subgroups 6512*a-g* of the dressing openings in alignment with the openings 6510*a-g* of the injection guides 6504*a-g*. By providing a plurality of separate injection guides 6504*a-g*, the dressing 6502 is able to stretch and bend between the guides 6504*a-g* in comparison a single unibody template. Being less rigid, this allows the guides 6504*a-g* to remain on the dressing 6502 during the entire use of the dressing 6502, rather than temporary attachment used during injections. Once attached to the dressing 6502, the openings 6510*a-g* of the injection guides 6504 are aligned with the subgroups 6512*a-g* of dressing openings 6512 of the dressing 6502 to permit injections through guide openings 6510*a-g* and the corresponding groups of dressing openings 6512*a-g*. To protect unused subgroups 6512*a-g* of dressing openings the unused injection guides 6504*a-g* are covered by removable guide covers 6506*a-g*. Each guide cover 6506*a-g* comprises a flexible strip of material that covers and is removably adhered to the injection guide 6504*a-g*, with a portion of the strip material lacking adhesive and extending beyond the perimeter or edge of the injection guide 6504*a-g* to facilitate its grasping and removal. Optional cover indicia 6508*a-g* may be provided, to indicate the order of use. The surface of the injection guide 6504*a-g* may be coated to facilitate removal of the guide covers 6506*a-g*.

As noted previously, the injection guides and guide covers may be pre-attached to the dressing during the manufacturing process, but in the embodiment depicted in FIGS. 65A to 65G, the guides 6504*a-g* and guide covers 6512*a-g* may be provided separately from the dressing 6502 and are adhered or attached to the dressing 6502 at the point-of-use or post-manufacturing. To facilitate their attachment to the dressing, the guides 6504*a-g* and covers 6506*a-g* may be pre-arranged on a carrier sheet 6520 with a low-tack adhesive, with the guides 6504*a-g* spaced apart, oriented and aligned in a manner to match the corresponding subgroups of dressing openings 6512*a-g* with the plurality of guides 6504*a-g*. The carrier sheet 6520 may comprise a flexible or semi-rigid, but non-elastic polymeric sheet which may be transparent to facilitate visual alignment of the carrier sheet 6520 and the dressing 6502. To further facilitate alignment, graphical indicia 6522 may be provided on the carrier sheet which corresponds to the edges of the dressing and/or aperture locations on the dressings, or other indicia on the dressing that are specifically complementary to the carrier sheet or the plurality of guides 6504*a-g*. For more precise alignment, the graphical indicia 6522 may include complementary checkerboard patterns or other optical interference patterns corresponding to complementary graphical indicia on the dressing. In alternate embodiments, the carrier sheet may comprise a transparent window and an opaque outer frame, wherein the boundary of the window and frame forms a shape corresponding to the dressing. In addition to the carrier structure or sheet 6520, a release liner 6524 may be provided to releasably protect the adhesive on the underside of the plurality of injection guides 6504*a-g* until the user is ready to attach the guides 6504*a-g* to dressing 6502. Together, these structures may comprise a guide applicator 6530.

In use, the selected tissue site for injections is cleaned in preparation for the application of the tensioned dressing 6502. The dressing 6502 is applied as described elsewhere herein. Next, the guide applicator 6530 is prepared by the removal of the release liner 6524, to expose the plurality of adhesive injection guides 6504*a-g* that are adhered in a predetermined arrangement or configuration on the adhesive underside of the carrier sheet 6520, via the corresponding guide covers 6506*a-g*. The user then views the dressing 6502 through the carrier sheet 6520, using the indicia 6522 on the carrier sheet 6520 to align the guides 6504*a-g* to the openings on the dressing 6502. Once the desired visual alignment is achieved, the user applies pressure to guides 6504*a-g* through the carrier sheet 6520 to maximize adhesion of the guides 6504*a-g* to the dressing 6502. The carrier sheet 6520 is then peeled away from the guide covers 6506*a-g* to expose and leave the guides 6504*a-g* and covers 6506*a-g* on the dressing 6502. The first cover 6506*a* is grasped and pulled away, to expose the openings of the first injection guide 6504*a*. The opening and skin/tissue surface exposed in the opening are then sterilized with an alcohol pad or other sterilization procedure, and then the injectable therapeutic agent is prepared and injected through the sterilized opening of the guide. The same sterilization of remaining openings of the injection guide 6504*a* is performed for subsequent injections, and the next cover 6506*b-g* is removed when access to the next injection guide 6504*b-g* is needed.

As may be noted from the procedure above, the application of the injection guides 6504*a-g* and covers 6506*a-g* to the dressing 6502 involves a multi-layered adhesive combination of structure where the adhered layers are preferentially separated at different stages of the procedure. To facilitate this, different adhesives with different peel force removal values are used. The strongest or highest peel force adhesive is provided on the adhesive layer of the dressing for adherence to the skin, and the injection guide to the dressing. This reduces the risk of inadvertent peeling or removal of the dressing from the skin, or the injection guide from the dressing, when the guide covers are being peeled off. The next highest relative adhesive is the adhesive used to adhere the guide covers to the injection guides. This reduces the risk that the covers may be inadvertently removed or peeled away when the carrier sheet is removed during the application procedure. The next highest adhesive is the one on the underside of the carrier sheet or applicator template, which is pulled away after the injection guides are adhered to the dressing. The lowest peel force is the one between the release liner and the injection guides. As noted earlier, since the adhesive on the injection guides needs to have the highest relative strength to avoid inadvertent removal when a guide cover is removed, to achieve a lower peel force of the release liner from the injection guides, the release liner may comprise a fluorosilicone or silicone liner, e.g. FRA-310 (Fox River Associates; Geneva, Illinois), 3M 9744 or 3M 5051 (3M; St. Paul, MN), and the like, to permit ease of separation of the liner from the strong adhesive provided on the injection guides.

The injection guides may comprise an adhesive foam tape or strip material, such as Adhesive Applications BW1125-1 or 1008-1 (Adhesive Applications; Easthampton, MA). The carrier sheet may comprise a transparent polymeric rigid or semi-rigid sheet material, which may be covered by a low-tack adhesive carrier or protective film known in the art, such as Pregis 1614C (Pregis; Deerfield, IL). The guide covers may comprise a flexible polymeric material coated with a removable acrylic adhesive, such as A5000 by Adhesive Applications.

Figure 34:
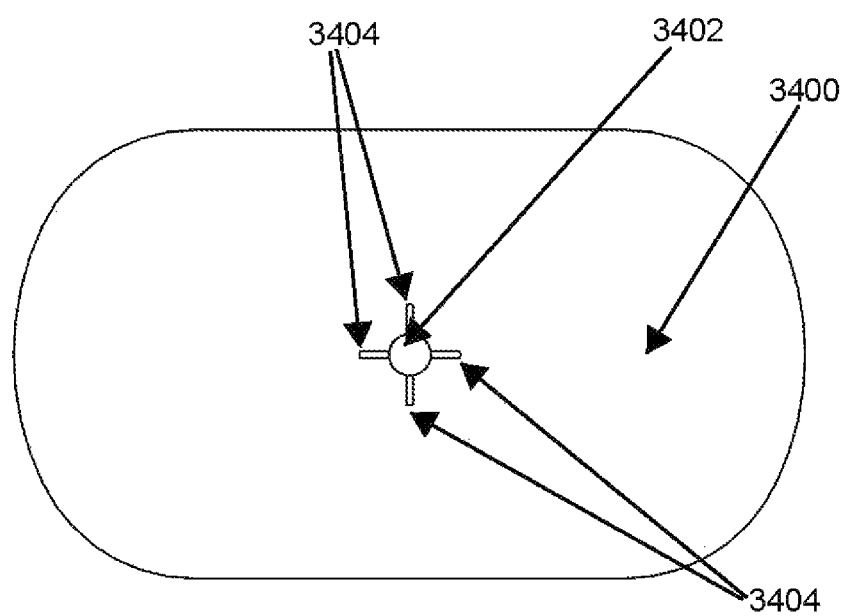
FIG. 34 depicts an exemplary dressing comprising an aperture and various alignment indicia.
Figure 35:
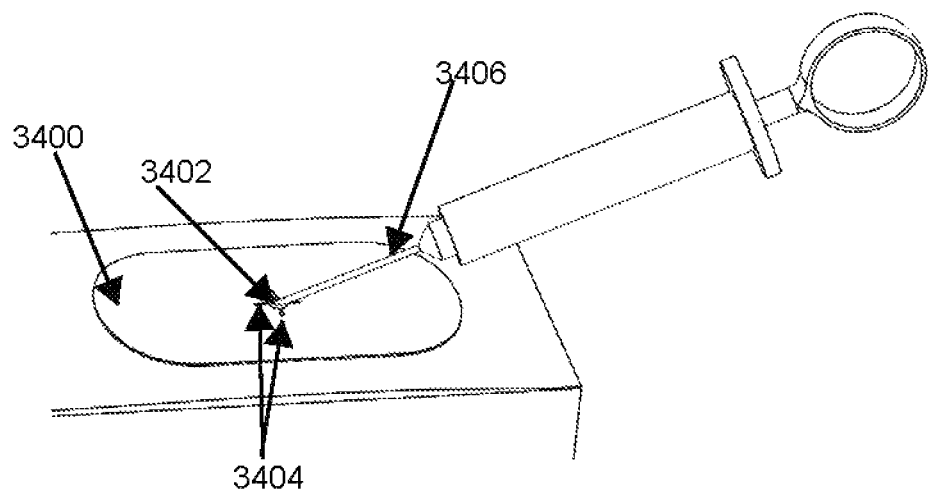
FIG. 35 depicts the use of the exemplary dressing in FIG. 34 with a delivery syringe.

FIG. 34 depicts another variation of a dressing 3400 comprising indicia 3404 to facilitate identification and/or alignment with the dressing opening 3402. In this particular embodiment, the indicia 3404 are provided in four orthogonal directions from the opening 3402. These indicia may be helpful for identifying the location of the opening 3402, especially in circumstances where the dressing 3400 comprises a clear material and wherein the underlying skin may be mottled or has extensive markings from scarring or skin damage, which may make identification of the opening 3402 more difficult. The indicia may be laser etched or printed onto the dressing surface. FIG. 35 depicts the placement of a strained dressing 3400 onto a skin location and then released from its applicator (not shown). Once adhered to the skin location, the indicia 3404 may be used to facilitate the insertion of a syringe needle 3406 or other access device, while the strain transferred from the dressing 3400 may reduce the tissue response from the needle insertion to form scar tissue or to induce lipohypertrophy. Although the indicia 3404 in FIGS. 34 and 35 are in contact or otherwise close proximity to the opening 3402, in other examples, the indicia may be providing along the periphery of the dressing, or span the dressing area between the opening and edges of the dressing. This may be useful for aligning larger devices that may obscure the opening of the dressing once positioned over the dressing. Alternatively, the material of dressing 3400 may be opaque and/or colored to provide contrast with the dressing and the dressing opening 3402. In still other examples, a dressing may be provided without an aperture, and the needle of the infusion set, syringe or insertion device is used to pierce the dressing and then inserted through the skin or tissue.

Figure 36:
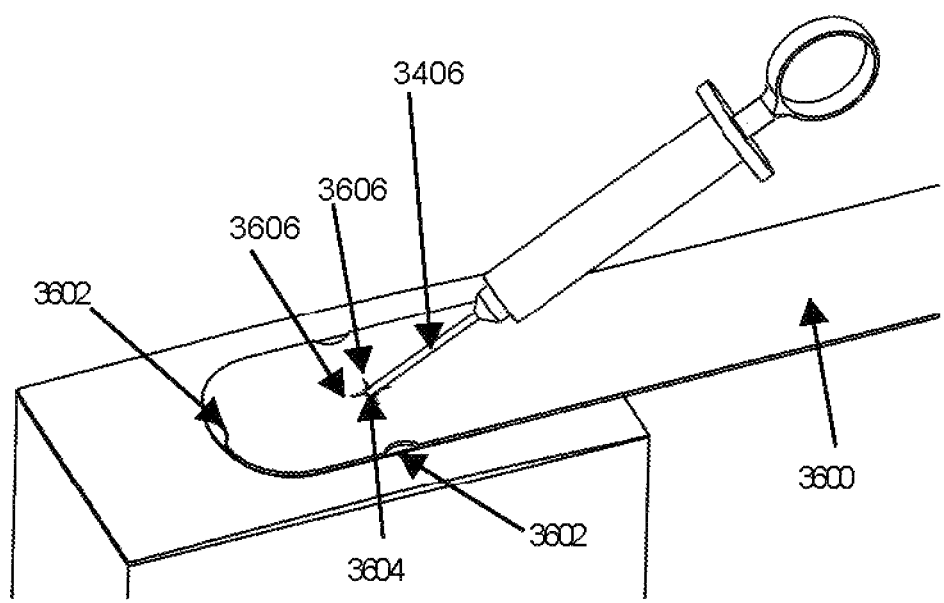
FIG. 36 depicts the use of a dressing and a visual guide tool with the delivery syringe.

In other examples as depicted in FIG. 36, a visual guide tool 3600 may be optionally provided or used to facilitate alignment of the syringe needle 3406 with the dressing opening 3402. The visual guide tool 3600 includes peripheral indentations 3602 or openings that may facilitate alignment of the visual guide tool 3600 with the peripheral edges of the dressing 3400. The dressing 3400 may also be provided with optional indicia or markings to facilitate alignment with the guide tool indentations 3602. By aligning the peripheral edge of the guide tool 3600 with the peripheral edge of the dressing 3400, the opening 3402 of the dressing 3400 may then be secondarily aligned with the opening 3604 of the guide tool 3600. The opening 3604 of the guide tool 3600 preferably may be smaller than the opening 3402 of the dressing 3400, but in other examples may be larger or the same size. The visual guide tool 3600 may also include indicia 3606 around its opening 3604, and may or may not comprise an opaque material, which may make it easier to visualize the opening 3604. The undersurface of the visual guide tool may comprise an adhesive to facilitate maintaining the position of the tool 3600 during use. The tool 3600 may comprise an elongate body with the opening 3604 at the distal end, with the proximal end used to grasp and manipulate the tool 3600 during the procedure.

In one exemplary procedure, the user will clean and prepare skin site with isopropyl alcohol wipes or other sterile preparations. The dressing is then strained using an applicator, if the dressing is not a pre-strained dressing, and then placed onto the desired site. The applicator is then removed to transfer the strain to the skin. If a visual guide is not needed, the patient can insert the needle into the orifice in the dressing and administer the infusion. If a visual guide is required, place guide on top of dressing and insert the needle through the visual target and administer the infusion. For where there is a preexisting dressing with multiple openings, subsequent injection can follow a rotational sequence and inject in site #1, followed by #2, followed by #3, etc. In some variations, depending on skin conditions, a dressing may last up to 10 days and injections using the dressing may take place at frequencies of 3 per day. The dressing is removed and replaced with a new dressing at the end of the wear period (average 7-10 days).

Figures 37A, 37B:
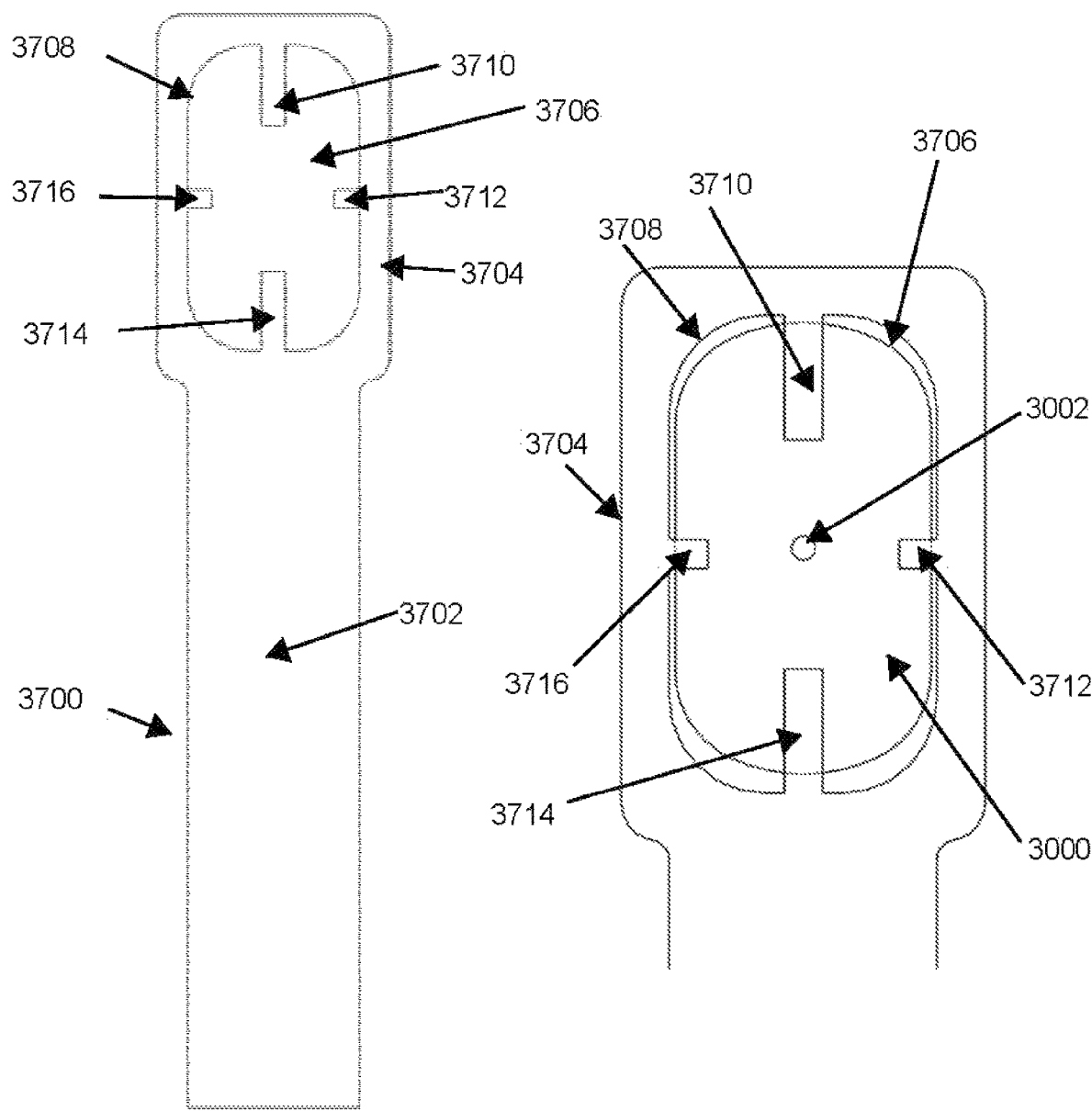
FIG. 37A depicts another exemplary embodiment of a visual guide tool comprising distal opening and one or more inward projections.
FIG. 37B depicts the visual guide tool of FIG. 37A overlaid on a dressing.
Figure 38A:
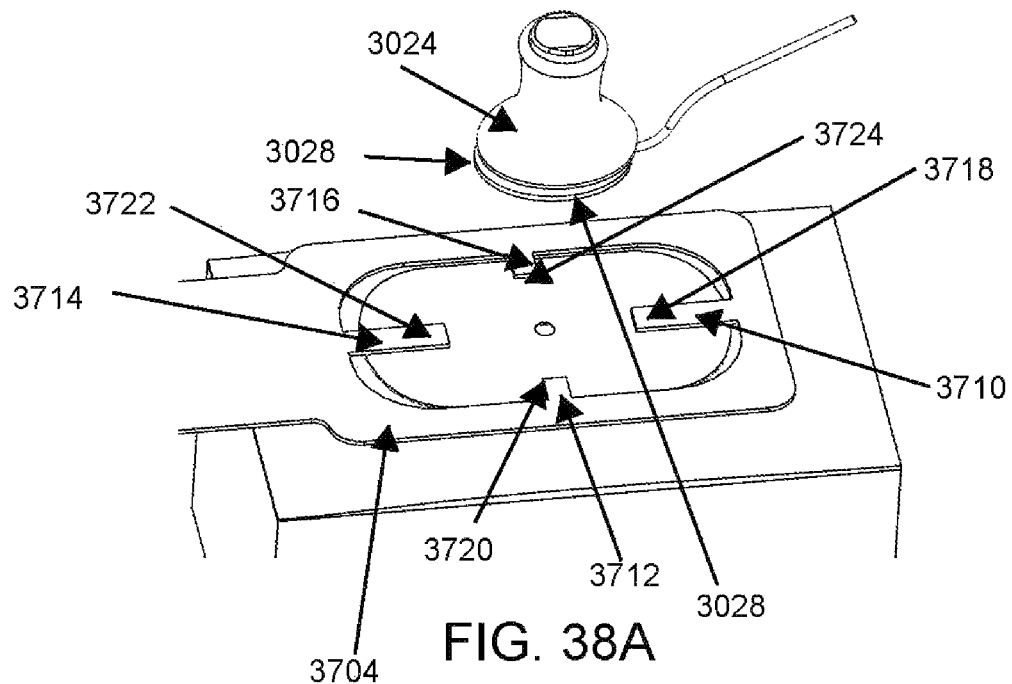
FIGS. 38A and 38B depict the use of the visual guide tool in FIGS. 37A and 37B with an infusion set delivery tool.
Figure 38B:
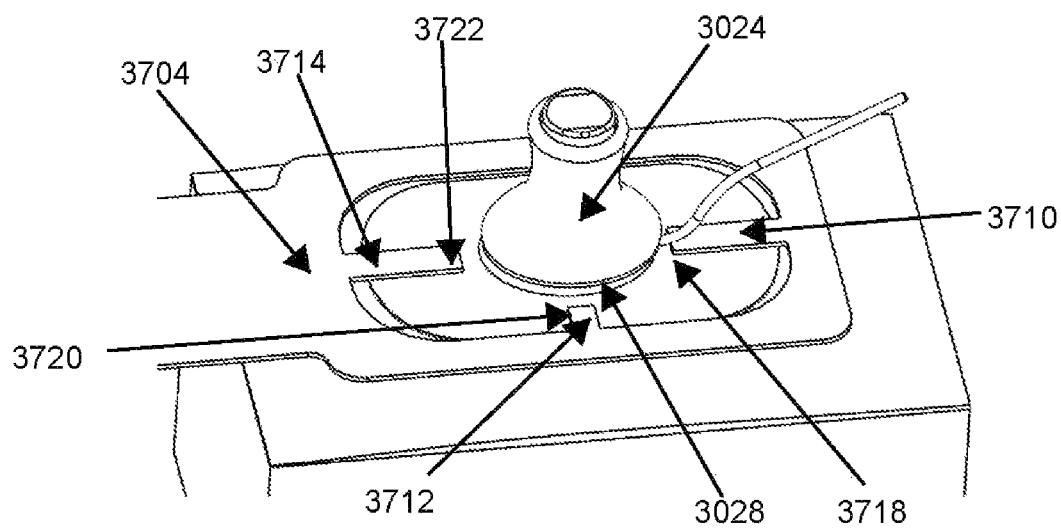
Figure 39A:
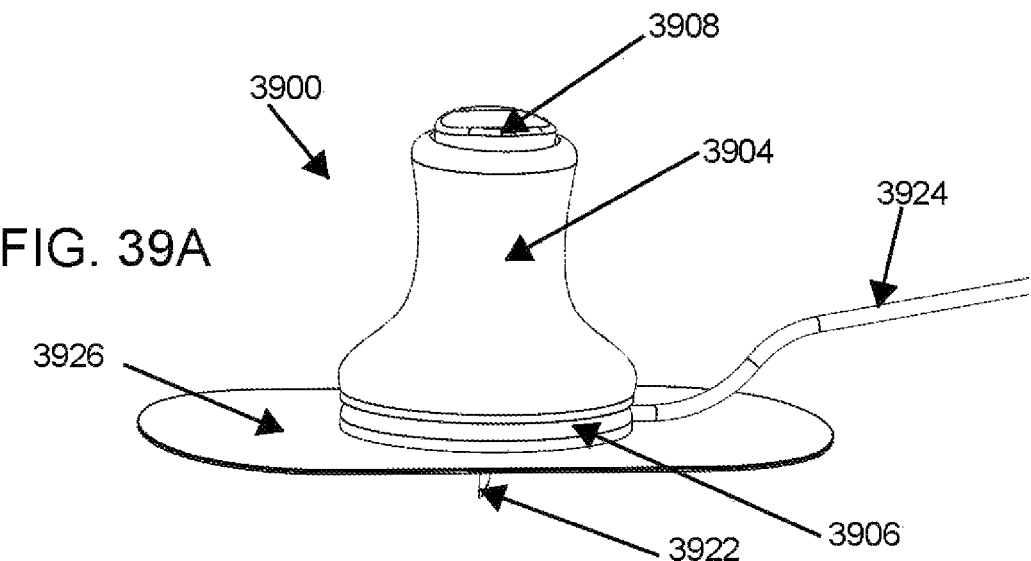
FIG. 39A is a perspective view of an exemplary infusion set delivery system that includes a pre-attached pre-strained dressing.
Figure 39B:
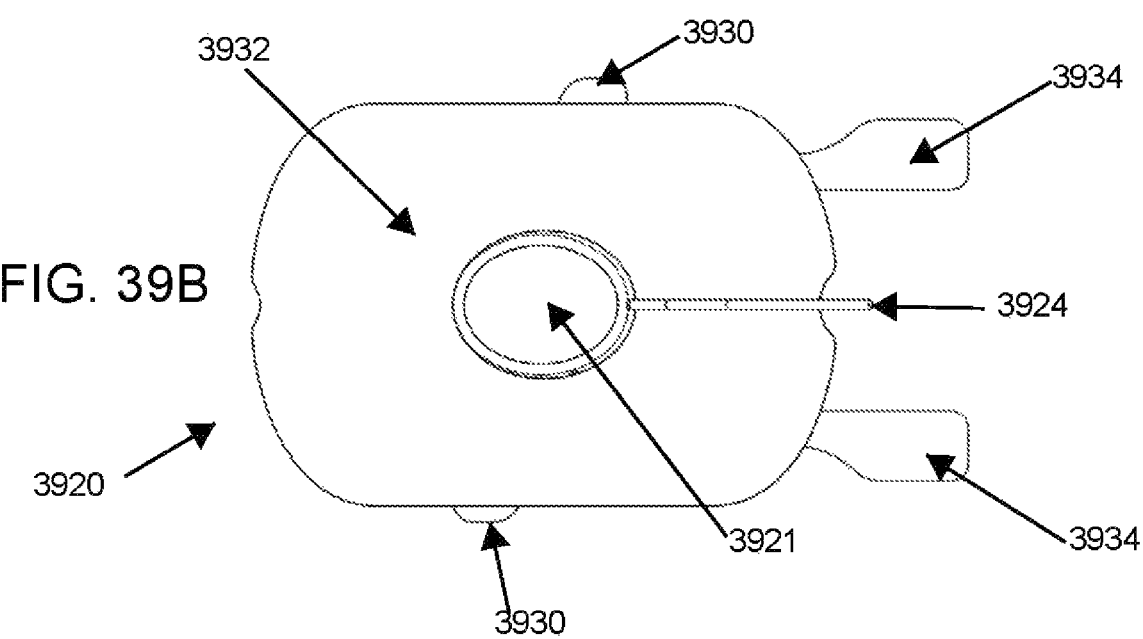
FIG. 39B to 39D are top, side and bottom views of the system in FIG. 39A.
Figure 39C:
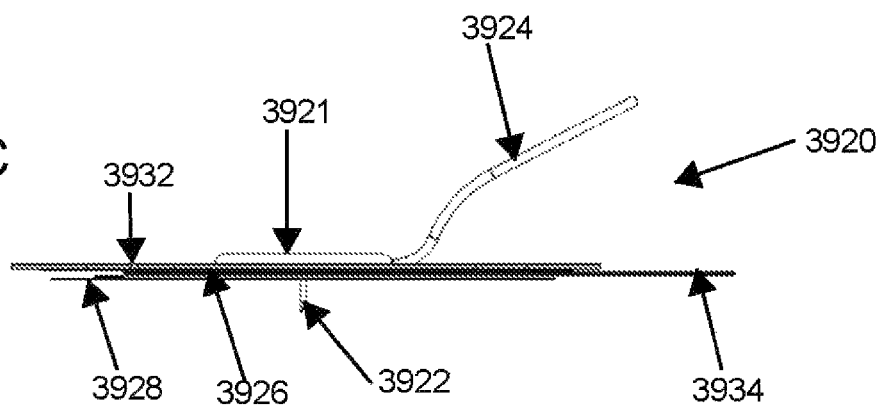
Figure 39D:
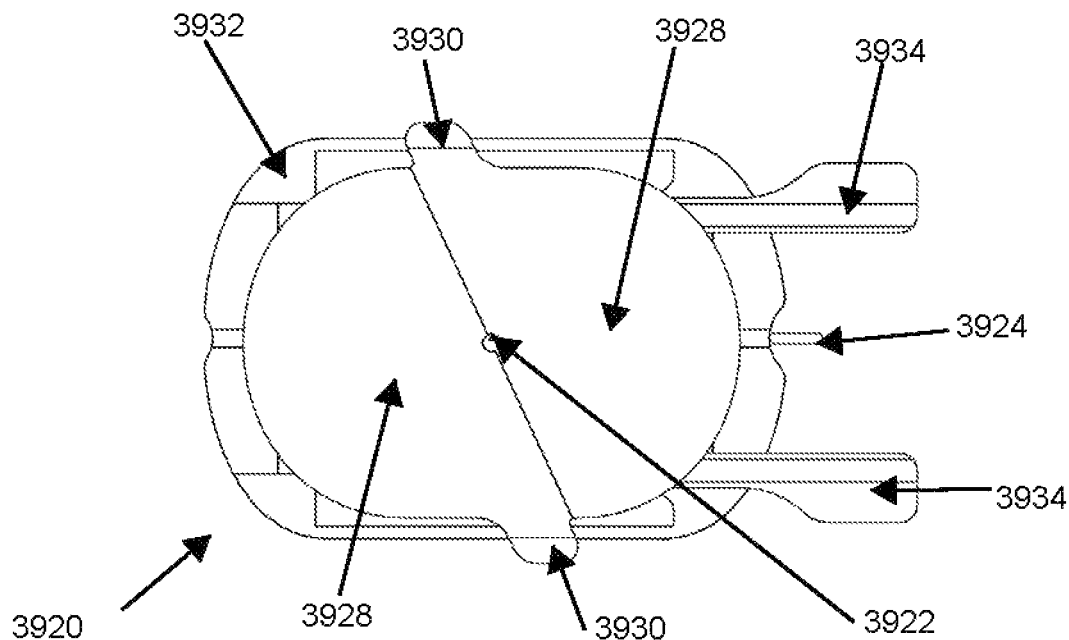
Figure 39E:
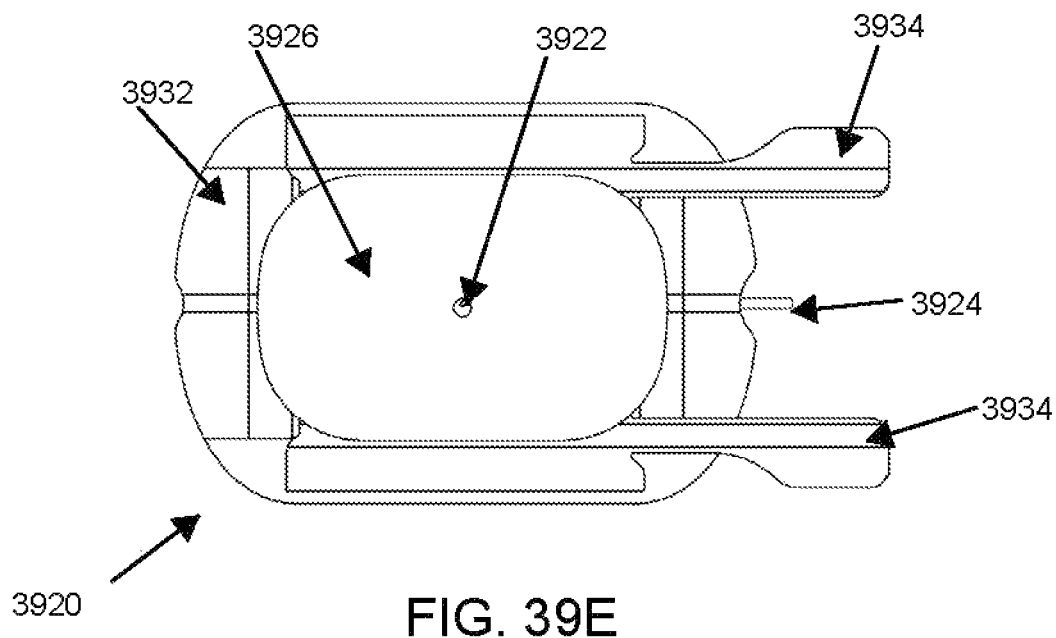
FIG. 39E is a bottom view of the system with its adhesive protective liners removed.

FIGS. 37A and 38B depict another example of a visual guide tool 3700. In this example, the tool 3700 comprises an elongate body 3702 with an enlarged distal end 3704 and a large distal opening 3706. The distal opening 3706 may be configured with boundary edge 3708 that permits visualization of the outer edge of the dressing 3000, excluding the radially inward projections 3710, 3712, 3714, and 3716. These radially inward projections 3710, 3712, 3714, and 3716 may help to point to the location of the dressing opening 3002 when the tool opening 3706 is positioned to surround the dressing 3000. Although four projections 3710, 3712, 3714, and 3716 are depicted in FIGS. 37A and 37B, in other examples, a different number of projections may be provided and at other locations along the boundary edge 3708 of the opening 3706, and may be different shapes, sizes, and lengths than the four orthogonal projections 3710, 3712, 3714, and 3716 in FIGS. 37A and 37B, e.g. the projections may comprise arrowhead shapes.

As depicted in FIGS. 38A and 38B, in some variations, the projections 3710, 3712, 3714, and 3716 may be configured to facilitate positioning of a delivery device or pod, such as the delivery device 3024 from FIGS. 31A to 31B. In this example, the lengths of the projections 3710, 3712, 3714, and 3716 are configured so that the ends 3718, 3720, 3722, 3724 of the projections 3710, 3712, 3714, and 3716 are each on contact with or equally spaced from the perimeter edge 3028 of the delivery device 3024 when the pod 3024 is properly aligned with the projections 3710, 3712, 3714, and 3716 of the tool 3700. Thus, the configuration of the radially inward projections 3710, 3712, 3714, and 3716 may facilitate alignment and positioning of the pod 3024 during use.

In another variation, depicted in FIGS. 39A to 39E, the strainable or strained dressing 3926 may be a pre-strained at the point of manufacture to an infusion set 3921 or assembly, as depicted in FIGS. 39A to 39E. The system may optionally include a delivery device 3900 with a body 3904, a lower edge 3906 and an actuator 3908. Releasably attached to the bottom of the body 3904 is an infusion housing 3921 of the infusion set 3920, and includes a needle 3922, connector tubing 3924 and a tension dressing layer 3926 that extends beyond the lower edge 3906 of the delivery device 3900 and housing 3921. The tension dressing layer 3926 further comprises a skin adhesive on its lower surface, which is removably covered by one or more adhesive protective liners 3928. The liners 3928 may comprise a liner tab 3930 that extends further from the liner 3928 to facilitate removal of the liner 3928 from the adhesive on the tension dressing layer 3926. The tension dressing layer 3926 is maintained in a stressed configuration by a rigid applicator or tension support structure 3932 that includes one or more pull tabs 3934 to facilitate the separation of the tension dressing layer 3926 from the tension support structure 3932 during use. The pull tabs 3934 attach the dressing layer 3926 and support structure 3932 together, but comprises perforations or adhesives that facilitate separation of the dressing layer 3926 and support structure 3932 when the pull tabs 3934 are pulled away from the device. The tension support structure 3932 or applicator may be removed from around the infusion housing 3921 by passing the structure 3932 over the connector tubing 3924, or by tearing the structure 3932 away from the housing 3921.

Figure 40A:
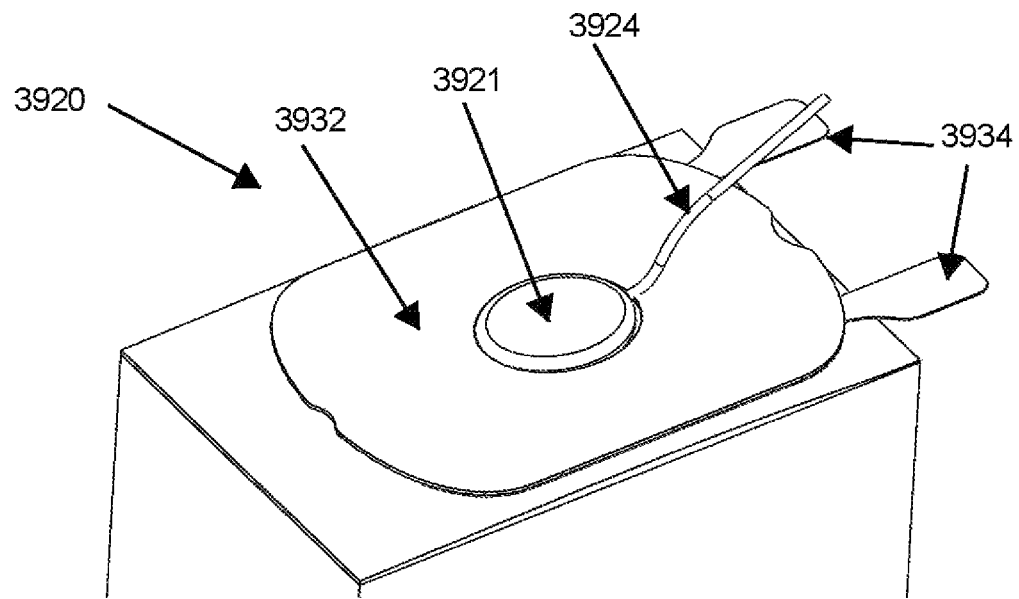
FIG. 40A depicts the placement of the delivery system in FIG. 39E onto a treatment site.

In one exemplary implantation procedure for the integrated infusion set 3920, a skin insertion site is selected and prepared with isopropyl alcohol wipes or other sterile preparation. The protective needle sheath (not shown) is first removed from the needle 3922 of the integrated infusion set 3920 as it is engaged to the delivery system 3900. Next, the adhesive protective liners 3928 are removed to expose the adhesive on the inferior surface of the prestrained tension dressing layer 3926. In other examples, however, the needle cover may be integrated with a liner, such that removal of the needle sheath concurrently removes the protective liners or vice versa. The delivery system 3900 and infusion set 3920 is then positioned at the desired insertion site and the needle is advanced into the skin, either manually or via a needle advancement mechanism. Once inserted, the system 3900 may be used to push the infusion set 3920 against the skin or otherwise held in place to facilitate bonding between the adhesive and the skin tissue surrounding the needle 3922. The actuator 3908 on the system 3900 is then actuated to release the infusion set housing 3920 so that the delivery system 3900 may be removed, as depicted in FIG. 40A. In other examples, the infusion set 3920 with integrated dressing may be inserted without the use of the delivery system 3900.

Figure 40B:
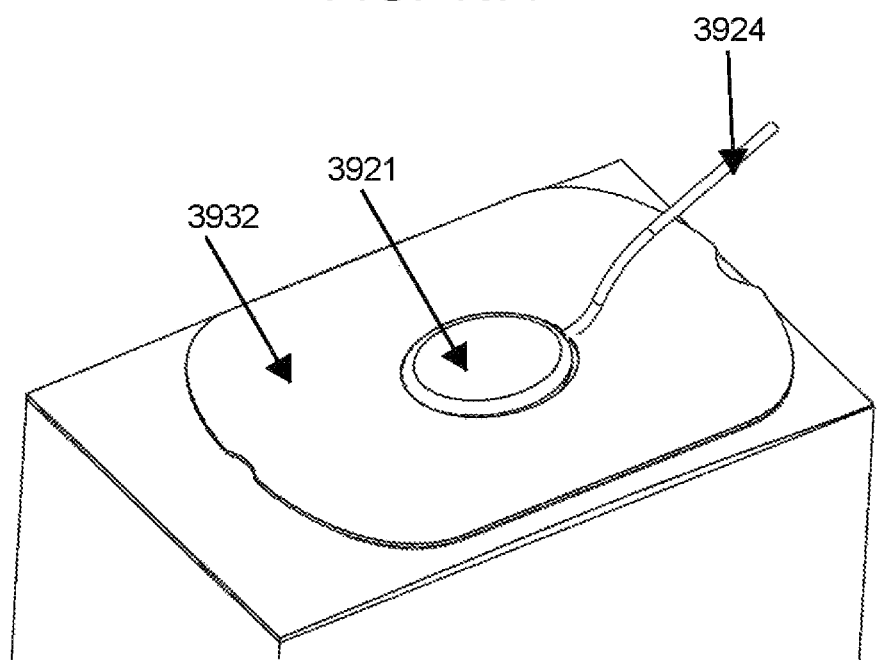
FIG. 40B depicts the infusion set and pre-attached dressing in FIG. 40A with the pull tabs removed.
Figure 40C:
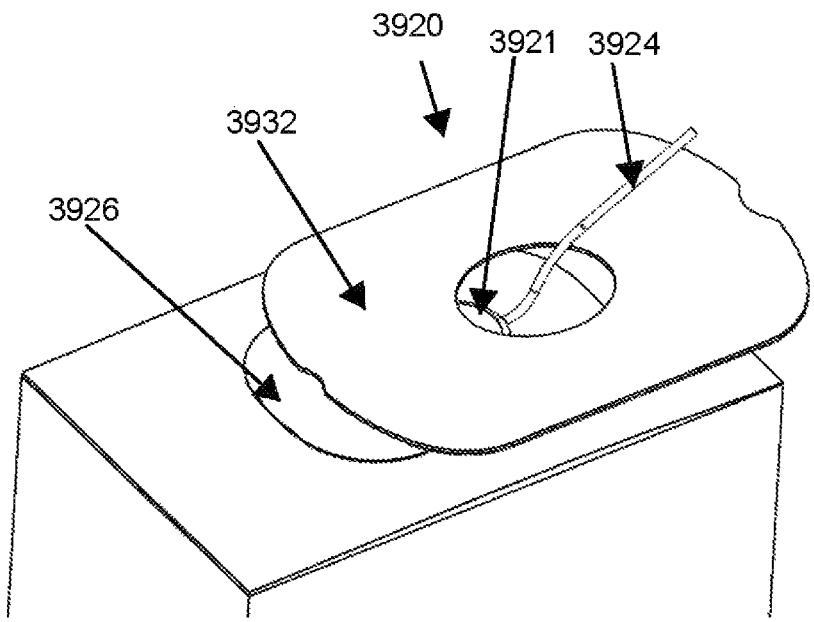
FIG. 40C depicts the infusion set in FIG. 40B with the dressing support separated from the dressing and withdrawal over the infusion set tubing.
Figure 40D:
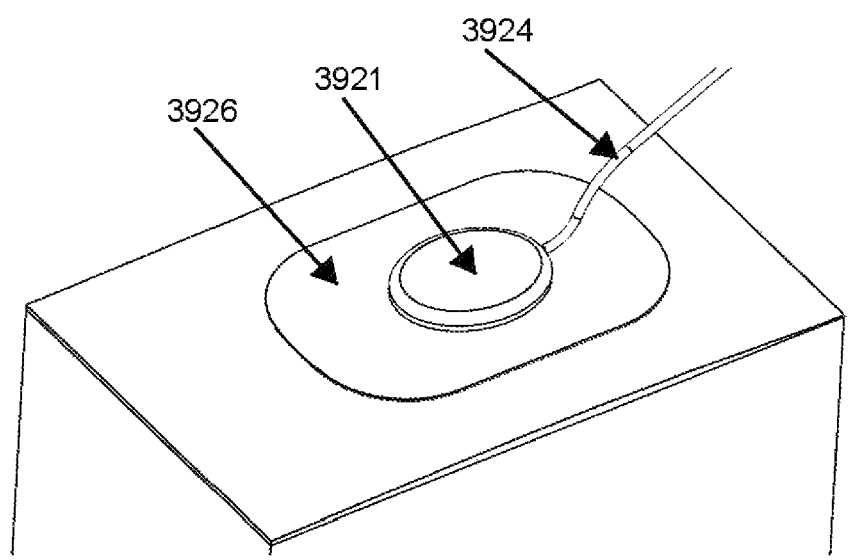
FIG. 40D depicts the infusion set and pre-attached dressing.
Figure 40E:
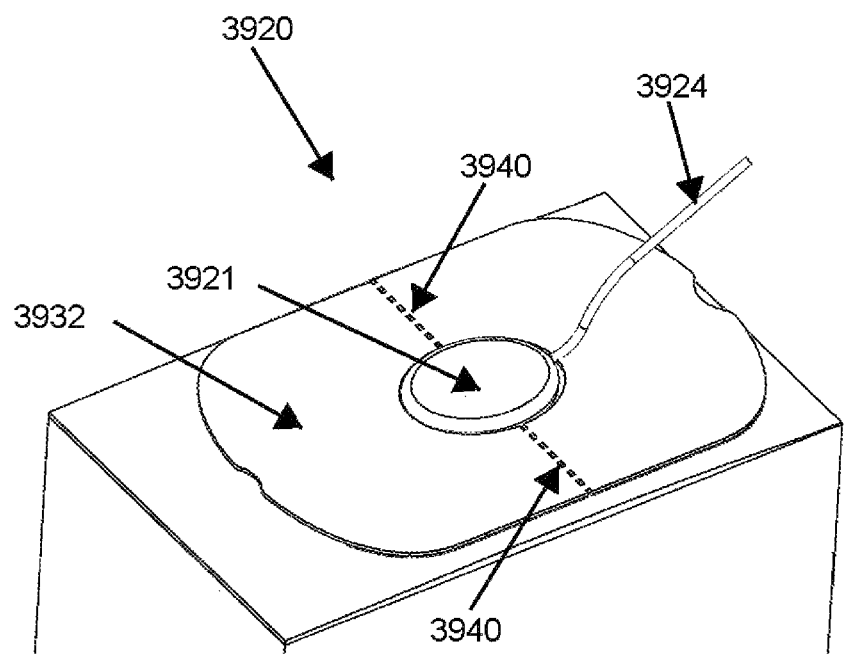
FIG. 40E depicts the infusion set with the dressing support comprising tearable perforations.

Next, the pull tabs 3934 are removed from the infusion set 3920, which allows the strained dressing layer 3926 to decouple from the tension support structure 3932, thereby allowing strained dressing layer 3926 to transfer its tensile stress to a compressive force acting on the tissue surrounding the needle 3922, as shown in FIG. 40B. In some variations, the tension support structure 3932 may be left in place after the pull tabs are removed, but in other examples, the tension support structure 3932 may be removed, to decrease the bulk and/or rigidity of the indwelling infusion set 3920. In some variations, the tension support structure 3932 may be removed by passing the tension support structure 3932 over the connector tubing 3924, as depicted in FIG. 40C, if the connector tubing 3924 is not yet coupled to the infusion pump, leaving the infusion set 3920 with the dressing layer 3926 transferring compression to the underlying skin tissue, as shown in FIG. 40D. In other variations, as depicted in FIG. 40E, the tension support structure 3932 may comprise a slit or perforations 3940, which may allow the tension support structure 3932 to be pulled away or torn away, from the infusion set housing 3921 or the connector tubing 3924, whether the connector tubing 3924 has been attached or not. The infusion set 3920 is ready for use, and may be removed and a new infusion set may be placed at the end of the use period, which may be in the range of 7 to 10 days, but may be replaced earlier if occluded or damaged.

In some other examples, rather than visual indicia or markings, one or more physical alignment structures may be provided on the dressing to facilitate alignment. In FIGS. 49A to 49E, a pre-strained elastic member or dressing 4900 with a pre-attached removable alignment structure 4902 is provided that is configured to align an infusion set with access opening 4926 of the dressing 4900. This alignment structure 4902 is configured for use with the MINIMED™ QUICK-SERTER™ (Medtronic, Fridley, MN) infusion set applicator 4904, but one of skill in the art understands that the alignment structure may be tailored to the shape and function of any other infusion set applicator or delivery device. The pre-strained dressing 4900 is maintained in a pre-strained configuration by semi-rigid or rigid strain support 4906 attached or adhered to the top surface of the dressing 4900, and surrounding the alignment structure 4902. The strain support may be configured to have some flexibility in at least one direction in order to contour the dressing to the tissue surface. In some variations, the direction of flexibility may be orthogonal to the direction of strain of the dressing. The shear bond strength between the strain support and the strained elastic member is greater than the force produced by the straining of the elastic member. The attachment of the support 4906 to the dressing 4900 may be achieved with an adhesive, or may be heat staked to the dressing 4900, depending on the materials selected for the dressing 4900. For example, if a polyurethane is used for the dressing 4900, the support 4906 may comprise PETG and can be heat staked to the dressing 4900. For example, a heat stake may be used to bond the strained elastic member to the strain support. The heat stake may have a width of about 1 mm, 2 mm or 5 mm, for example. The bond provides adequate shear force without creep in the direction of strain while also allowing the support structure to be peeled away from the elastic member. The strain support may also comprise perforations to facilitate the splitting of the strain support and its separation and removal from the elastic member, and optionally tabs to facilitate grasping and tearing of the perforations. Alternate embodiments of the device may also include the perforations and pull tabs separation mechanism as described for dressing 3926 in FIGS. 39A to 39E may also be adapted to this embodiment.

This particular alignment structure 4902 comprises a unibody structure with three interconnected alignment flanges 4908, 4910, 4912 along a base 4914 and base opening 4916. The opening 4916 is sized and shaped to form a mechanical interfit with the applicator 4904, and may be oval, circular, polygonal or other custom shape complementary to the perimeter of the applicator 4904. The base 4914 may also comprise a lip to increase the surface of area of attachment to the dressing 4900. Although interconnected along the base 4914, in other examples, the flanges may be separate from each other. In some further examples, the flanges 4908, 4910, 4912 and/or base 4914 may be integrally formed with eat strain support 4906. In still other examples, the alignment structure 4902 may be provided separately and is attached to the strain support 4906 at the point-of-use. The alignment structure 4902 may also be selected from a plurality of different alignment structures, each configured for use with a different available infusion set applicator. The selected alignment structure is then attached to the strain support prior to use.

The attachment of the alignment structure 4902 may vary depending on the material used for the structure 4902 and the rigid support 4906. The alignment flanges 4910 and 4912 are configured to provide a recess 4918 accommodate the infusion set tubing 4920, and one or more of the alignment flanges 4908 may comprise a gripping structures to facilitate handling of the dressing 4900, such as finger grips, recesses or ridges 4922. The alignment flanges 4910 and 4912 may be further configured to be pulled apart to facilitate removal of the alignment structure 4902 from the tubing 4920. After or concomitantly with the removal of the alignment structure 4902, the strain support 4906 is removed to permit the dressing 4900 to contract from the strained configuration to its less strained configuration. In this particular configuration of the alignment structure 4902, the height of the flanges 4908, 4910, 4912 may be in the range of about 1-10 mm, 2-8 mm, or 3-6 mm, for example. The inner surfaces of the flanges 4908, 4910, 4912 may be comprise an orthogonal orientation or may comprise a slight obtuse angle, e.g. 91-95 degrees, 91-100 degrees or 91-105 degrees, so that the initial placement of the applicator 4904 itself does not require precise alignment but guides the applicator 4904 to a more precise location with further insertion. The spacing of the flanges 4908, 4910 and 4912, in addition to accommodating the tubing 4920, may also be configured to provide access to the sides of the applicator 4904, which may also have finger grips 4936, so that the actuator 4924 of the applicator 4904 is not used to position the applicator 4904.

The shape of the dressing 4900 may be any of a variety of shapes, including but not limited to an oval, circular or polygonal shape. Likewise, the access opening 4926 may also comprise an oval, circular or polygonal shape, and sized to accommodate the catheter of the infusion set. The access opening 4926 may comprise a diameter or transverse dimension in the range of 1-20 mm, 2-10 mm, or 3-5 mm, for example. The alignment structure 4902 may comprise a polymeric material that may be thermoformed or injection molded, 3D printed or CNC machined.

The skin adhesive on the dressing configured to attach to the skin or tissue may be the same or different adhesive used to attach the strain support to the dressing. In some examples, the skin adhesive may be selected with a greater T-peel force than the adhesive used to attach the support. In other examples, the adhesive used to attach the support may have a higher T-peel force. A higher T-peel force may be selected where the predetermined strain in the dressing is needed to resist strain loss during storage of a pre-strained device. A protective or adhesive release sheet may be applied to the skin adhesive to protect the skin adhesive against unintentional adhesion during storage or application. Coatings on the release sheet and the dressing may also be provided to facilitate peeling or removal of the release sheet and the strain support during use.

Figure 50A:
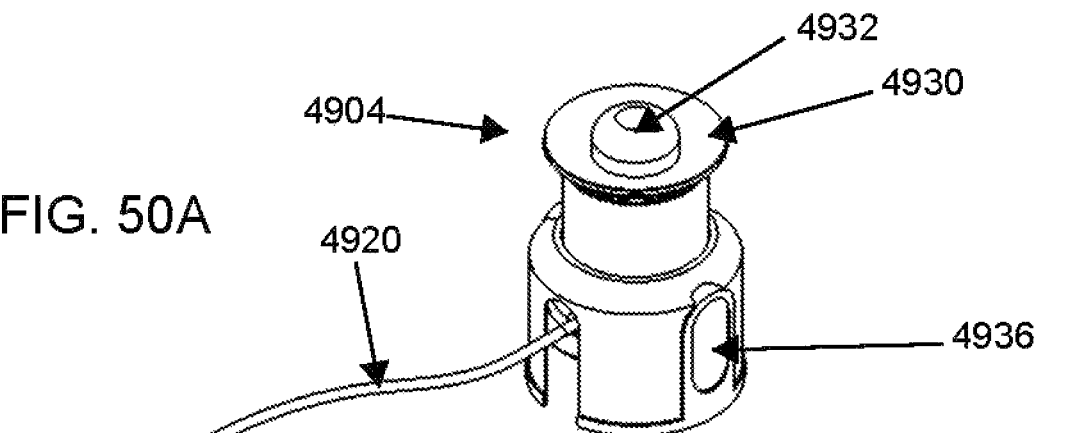
FIGS. 50A to 50E depicts the use of the skin tensioning device in FIGS. 49A to 49E with an infusion set delivery system.
Figure 50B:
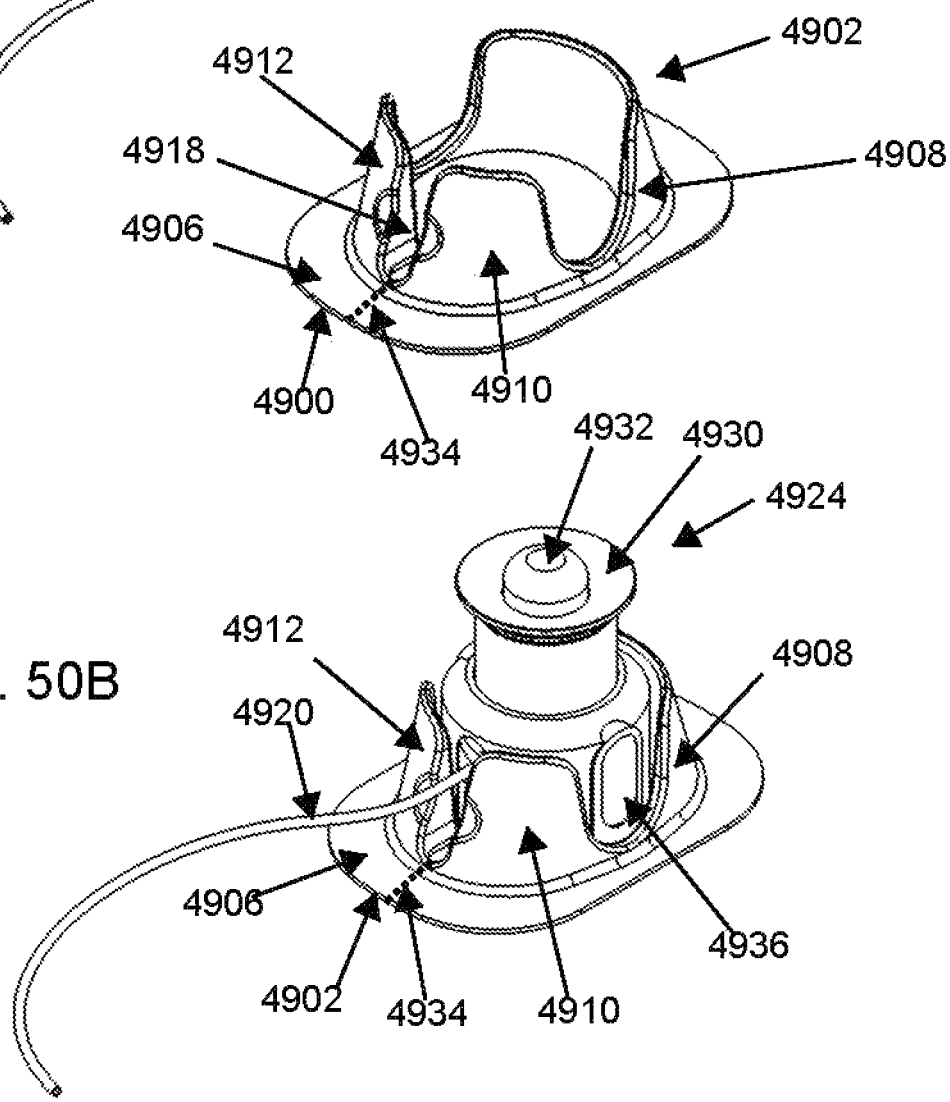
Figure 50C:
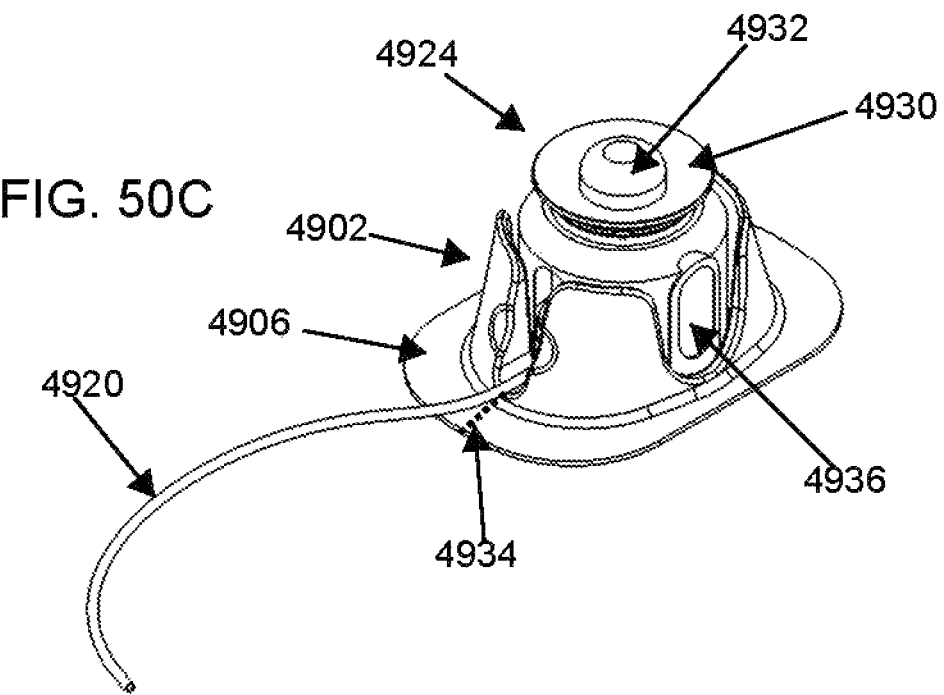
Figure 50D:
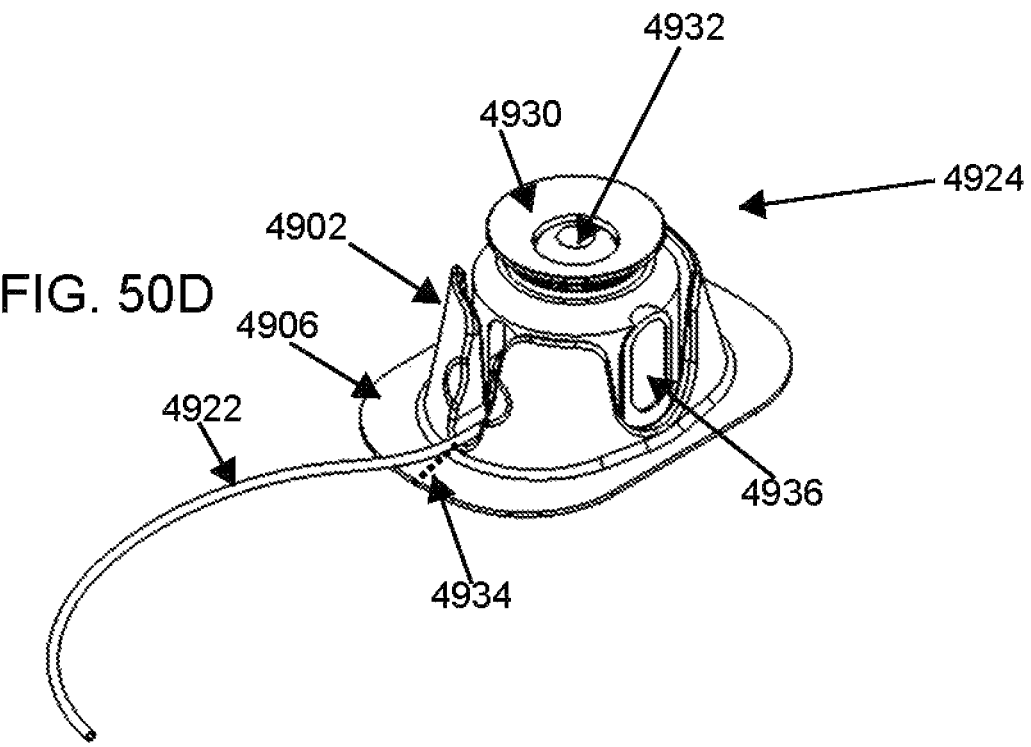
Figure 50E:
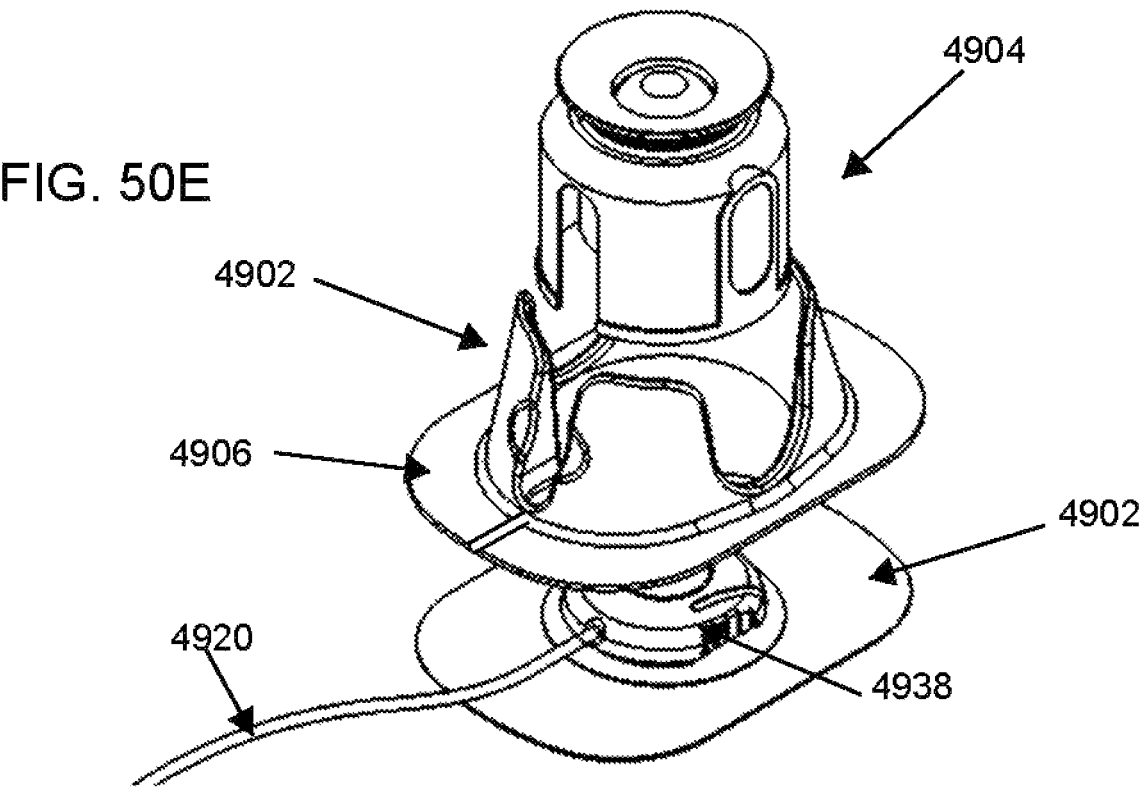

Referring to FIG. 50A, the dressing 4900 and alignment structure 4902 is applied and adhered to the selected target site. The adhesive liner of the infusion set held by the applicator 4904 is removed and the applicator 4904 is aligned with alignment structure 4902, with the tubing 4920 and the finger grips 4922 of the infusion correctly oriented to the recesses. The applicator 4904 is then inserted into the opening of the alignment structure 4902 until it is fully seated, as illustrated in FIG. 50B. In some variations, visual indicia on the alignment structure 4902, tactile feedback may be provided to confirm to the user that the applicator 4904 is fully seated. In FIG. 50C, the actuator 4924 of the applicator 4904 is depressed to insert the needle/cannula of the infusion set through the opening of the dressing 4900 and into the skin. In FIG. 50D, the actuator 4924 is then activated a second time to decouple the applicator from the infusion set hub 4938, as shown in FIG. 50E. In this particular example, the actuator 4924 comprises an outer annular button 4930 and an inner button 4932 to separately deploy the needle/cannula and to decouple but not yet separate the applicator 4904.

Figure 51:
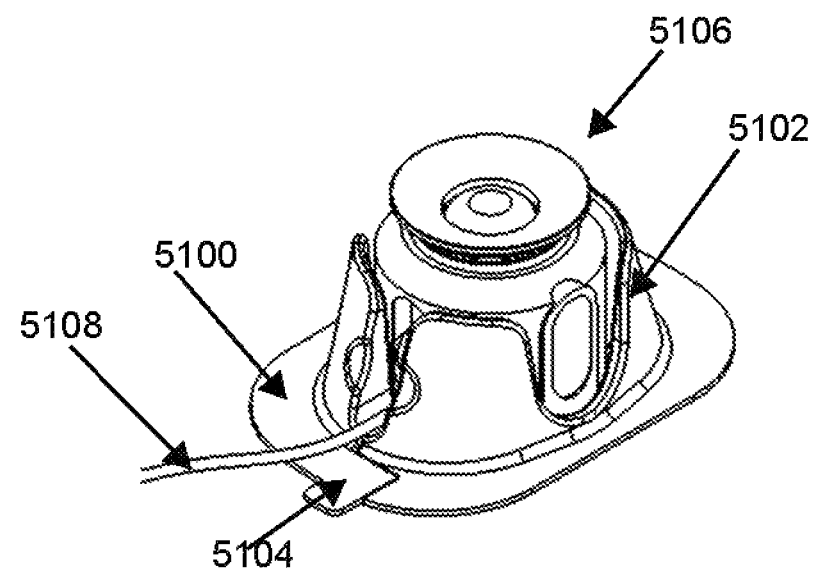
FIG. 51 is a front perspective view of an alternate support structure for the skin tensioning device depicted in FIGS. 49A to 49E.

Next, the alignment structure 4902 and the dressing support 4906 are removed from the dressing 4900 by applying downward pressure on the released applicator 4904 as the alignment structure 4902 and support 4906 are pulled away. To facilitate their removal, the support 4906 may comprise a perforation 4934 that can be torn so that the alignment structure 4902 and support 4906 may be peeled or pulled off, so that the dressing 4900 can contract from its strained configuration, In other variations, as shown in FIG. 51, the support 5100 of the alignment structure 5102 may comprise an arcuate configuration with a tabbed end 5104 that may be grasped and used to pull out the support 5100 and alignment structure 5102 from the periphery of the applicator 5106 and the tubing 5108. This then separates the infusion hub 4938 from the applicator 4904, and the rigid support 4906 from the dressing 4902, which allows the dressing 4902 to contract from its pre-strained configuration.

FIGS. 48A to 48E depict example of an infusion system 4800 with a delivery device 4802 that releasably holds an infusion hub 4804 with a pre-attached radially pre-strained skin tensioning device 4806. The delivery device 4802 comprises a body 4808 and actuator 4810, similar to the delivery system 3900 in FIG. 39A. The pre-attached radially pre-strained skin tensioning device 4806 comprise a radially outward strained adhesive elastic layer 4812 that is maintained in the pre-strained state by a semi-rigid strain support 4814a, 4814b that may comprise a semi-rigid or rigid card stock or polymer layer that is adhered to the top surface of the elastic layer. Although this particular embodiment comprises a strain support with two sections 4814a and 4814b, in other examples, a single support may be provided, or a 3, 4 or 5 part support may be provided.

Figure 48A:
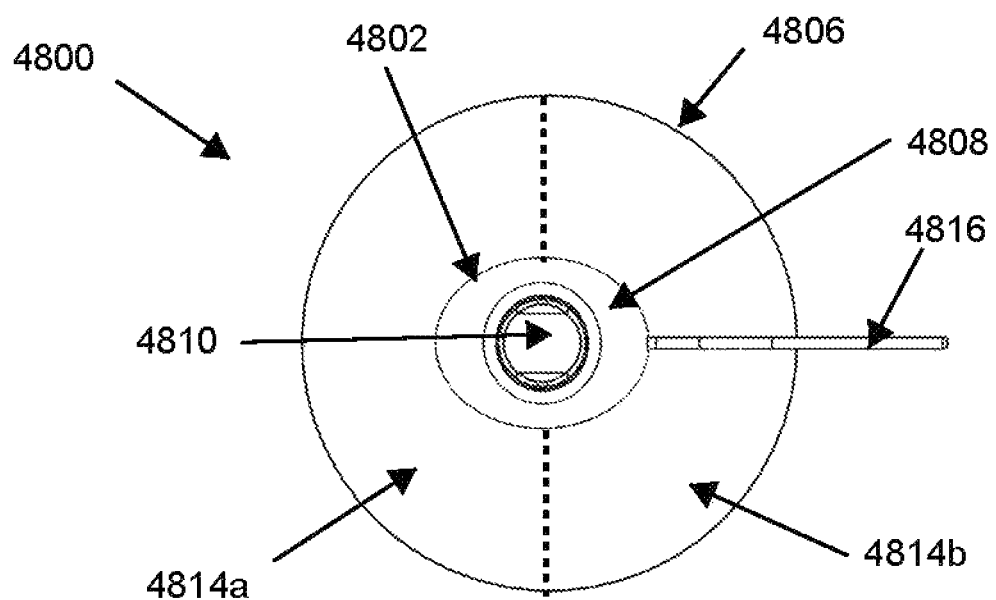
FIGS. 48A and 48B are superior plan and inferior perspective views of another exemplary infusion set delivery system with a pre-attached radially pre-strained skin tensioning device.
Figure 48B:
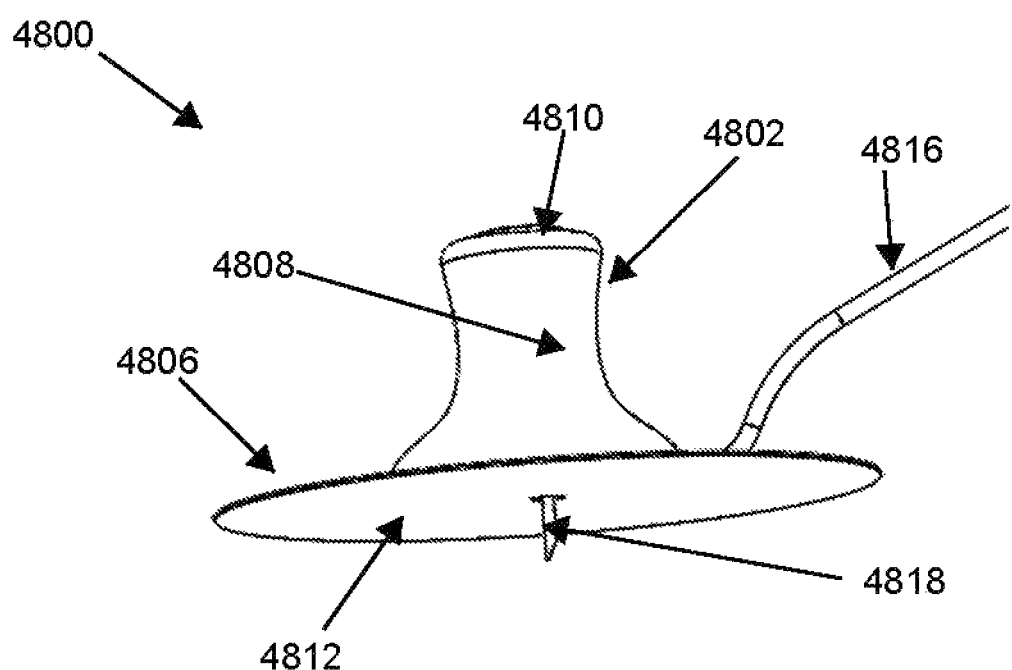
Figure 48C:
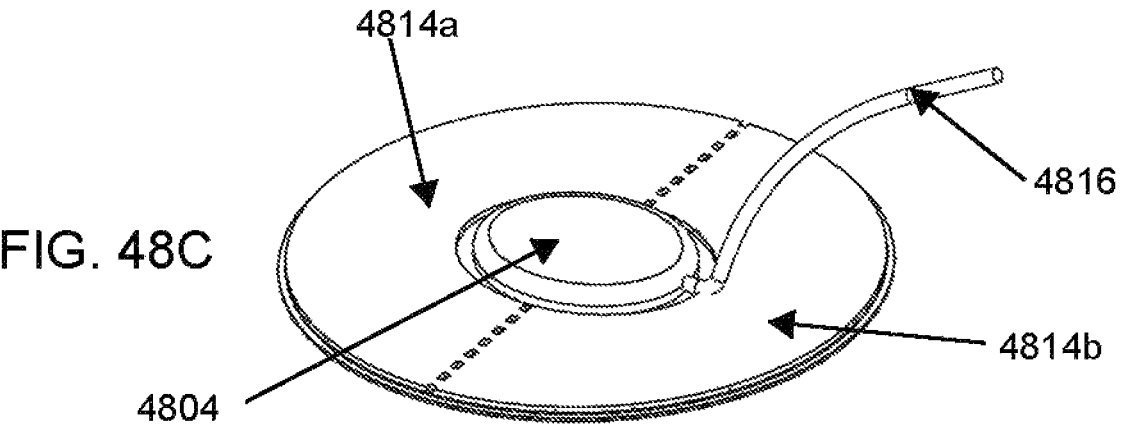
FIGS. 48C to 48E depicts the placement and release of the pre-strained skin tensioning device.
Figure 48D:
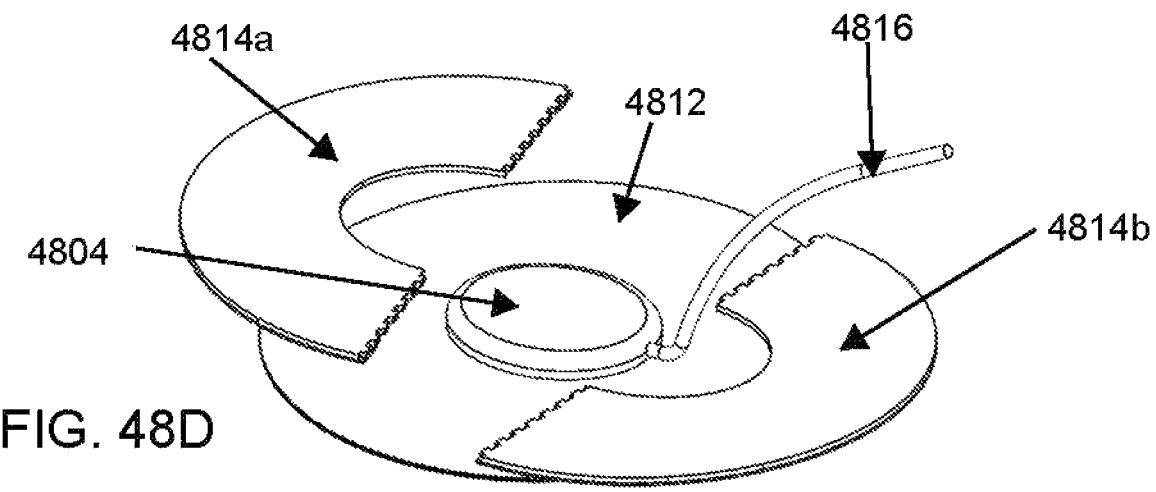
Figure 48E:
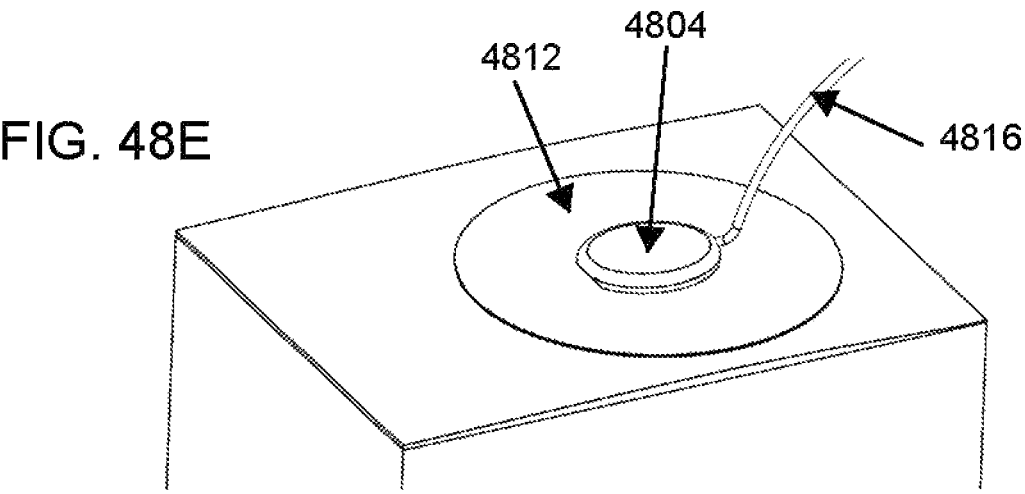

After the infusion system 4800 is applied to the desired anatomical location, and the actuator 4810 is activated, the infusion hub 4804 is released and can be separated from the delivery body 4808, leaving the infusion hub 4804 and skin tensioning device 4806 attached to the anatomical location, as illustrated in FIG. 48E. The function and patency of the infusion tubing 4816, hub 4804 and catheter 4818 may be checked. If functioning correctly, the strain support 4814a and 4814b may be removed or separated from the elastic layer 4812, which will then radially compress the adhered skin or tissue toward the center of the elastic layer 4812 around the hub 4804 and catheter 4818. The function and patency of the infusion tubing 4816, hub 4804 and catheter 4818 is then rechecked before initiating therapy. In some variations, a radially strained skin tensioning device may reduce the risk or rate of kinking or occlusion of the catheter 4818 in comparison to skin tensioning devices strain along a single strain axis. The shape of the elastic layer 4812 may be circular as depicted in FIGS. 48A to 48E, but in other examples, the elastic layer may be oval, oblong, square, rectangular, star or other shape. An oval or oblong shape may be used when the catheter is not orthogonally inserted into the tissue, but rather inserted along an acute angle to the treatment site, where the forces acting on the catheter or infusion hub may not be radially symmetrical.

In an embodiment, a dressing with an integrated infusion set is provided. The device may be used, for example, to treat, minimize, or slow the progression of subcutaneous growth or lipohypertrophy in subjects provided with infusion therapy as described in more detail herein. The infusion set is removable from the dressing. After a period of time, for example, after the infusion set life cycle has finished, the infusion set may be detached from the dressing. The tensioned dressing substrate may then remain attached to the subject for an additional period of time without the catheter indwelling in skin.

In an embodiment, the integrated infusion pump and dressing include a dressing substrate with a dressing attachment structure with attachment features that allow the infusion set to be attached, for example, during manufacture or assembly, and may be provide for user separation of the infusion hub, or a portion thereof, of an infusion set, from the dressing with the release structure. The device may provide for permanent removal of an infusion hub to prevent reuse of the infusion set or infusion hub with the dressing. All or a portion of the attachment structure or structures may remain on the dressing when the infusion hub is separated.

Attachment structures may include for example a dressing attachment structure attached to a dressing substrate. A dressing attachment structure may be, for example, a physical structure that may or may not, in whole or in part be removed from a dressing when release structures are used to release the infusion hub. The attachment sheets or structures, and related features thereof, may be the same or similar as those described for FIGS. 1A to 22B, including but not limited to the attachment sheets used for dressing assemblies 100, 210, 320, 610, 810, 910 and 1000.

Release structures or releasable attachment structures may include but are not limited to pockets and tabs, hook and loop mechanism, hooks, angled bars, pivoting, rolling, rocking or sliding features associated with or coupled to attachment structures, adhesives, removable adhesives, adhesive tapes or other adhesive devices, pegs, rip string, towel bar configurations, sliding pins, friction locks, cam locks, vacuum or suction devices, snap connectors, carpet tack, press fit connections or other connections, levers, latches, locking members, spring members, for example, or other mechanisms such as cutters or rip string or other structures or features to facilitate tearing, cutting or separation of attachment structures or elements perforated or otherwise severable structures, that permit removal of dressing from the applicator, packaging, other portions of the dressing assembly and/or attachment structures, features, elements or portions They may be self-releasing latches or spring members. The release assembly may be integrated in the dressing assembly and/or applicator, or may be provided separately to be used with the dressing assembly. They may be actuated when a pressure member is applied to a skin treatment device prior to removing the applicator. They may be manually actuated.

The dressing and infusion set may comprise an infusion hub that is configured to receive an infusion housing or connector. The infusion set may additionally include the infusion housing or connector. These treatment systems may be all-in one infusions sets integrated into the dressing. They may be manufactured together, rather than assembled by the clinician at the point-of-use, as described for other embodiments herein.

Referring to FIGS. 66A to 66H, a system 6600 is illustrated comprising a dressing 6610 and an infusion set 6650. The infusion set 6650 includes an infusion set housing or connector 6660 with infusion tubing 6661 and release elements 6662 for releasing the housing 6660 from an infusion hub 6670 and attached catheter 6680. By actuating or squeezing the release elements 6662, the housing 6660 may be unlatched from the hub 6670, or the friction between the housing 6660 and hub 6670 may be reduced to facilitate removal and separation. Fluid communication between the lumen of the tubing 6661 may be provided via an opening or channel in the hub 6670, which may include a seal therebetween.

The dressing 6610 includes a substrate 6620, an attachment element 6630 and an opening 6640 in the dressing 6610 for receiving the catheter 6680. The attachment element 6630 is attached on opposing sides 6632*a*, 6632*b* to the substrate 6620, for example with an adhesive, bond or other attachment mechanism. The attachment sheet, structure or element 6630 further includes a removable portion or element 6633 having a release or decoupling element, for example, a pull tab 6634 and tear structures or elements 6635 (e.g., tear lines, weakened sections, perforations or other tear elements) extending through the attachment element 6630 adjacent sides 6632. In some variations, the removable portion or element 6633 may lack any attachment to the underlying dressing substrate 6620. In other variations, the removable portion or element 6633 may be attached to the surface of the dressing substrate via non-adhesive static forces or Van der Waals forces, or with a differential adhesive, such as a hybrid or compound silicone/acrylic adhesive. The hub 6670 of the infusion set is attached to the removable element 6633 for example by way of an adhesive, bond, mount or attachment element.

Figure 66A:
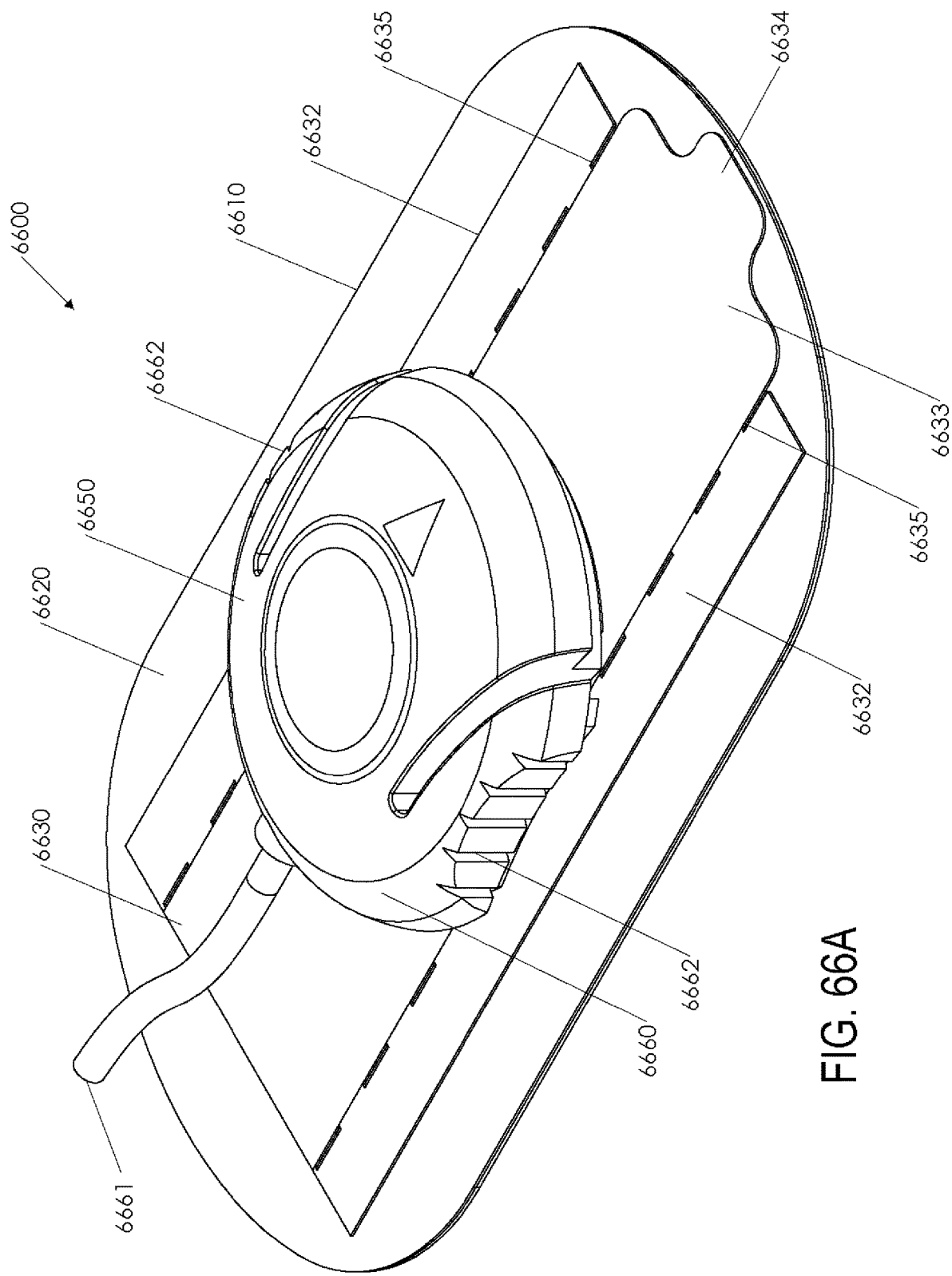
FIG. 66A is a superior perspective view of an embodiment of a treatment system, including a dressing with an integrated, separable or removable infusion set.
Figure 66B:
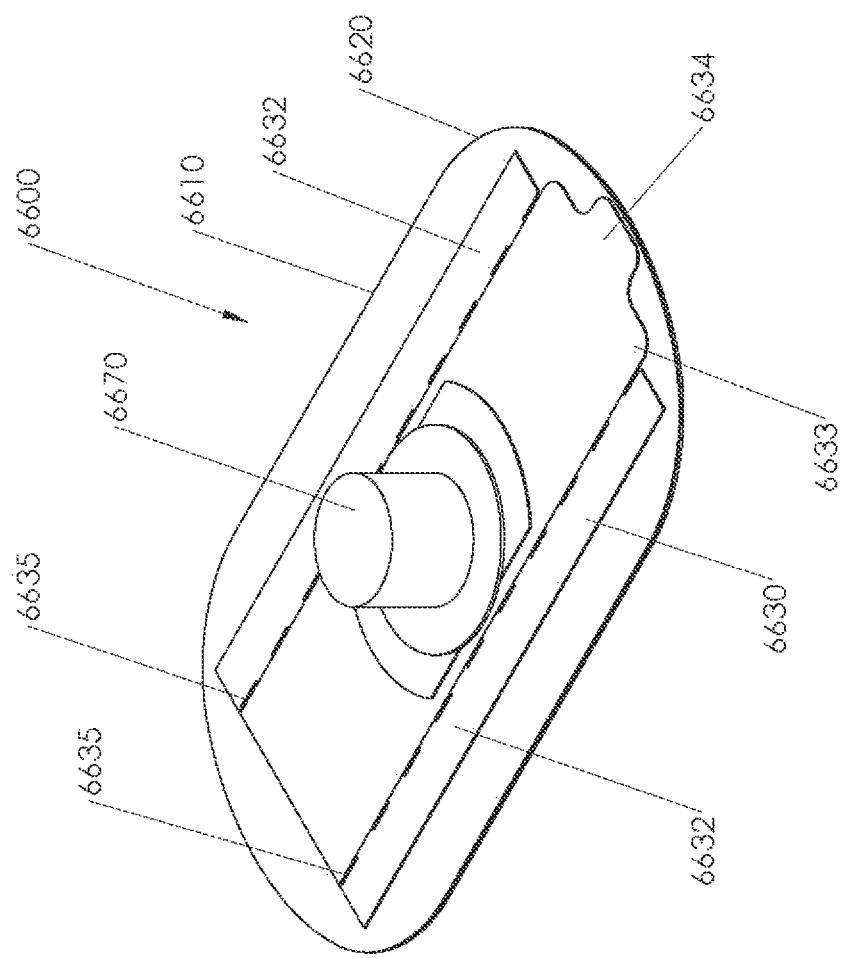
FIG. 66B is a superior perspective view of the system in FIG. 66A, with the infusion set connector and tubing removed.
Figure 66C:
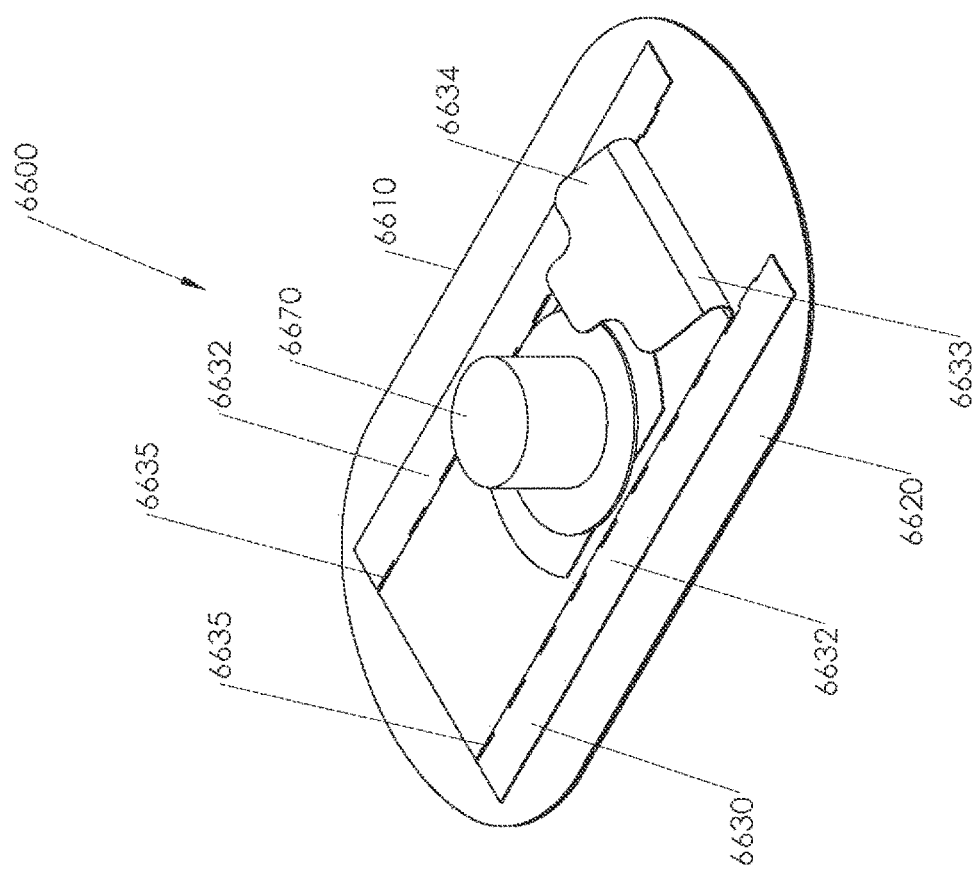
FIG. 66C is a superior perspective view of the system in FIGS. 66A and 66B with the infusion set connector and tubing removed and the infusion hub and infusion catheter in the process of being removed.
Figure 66D:
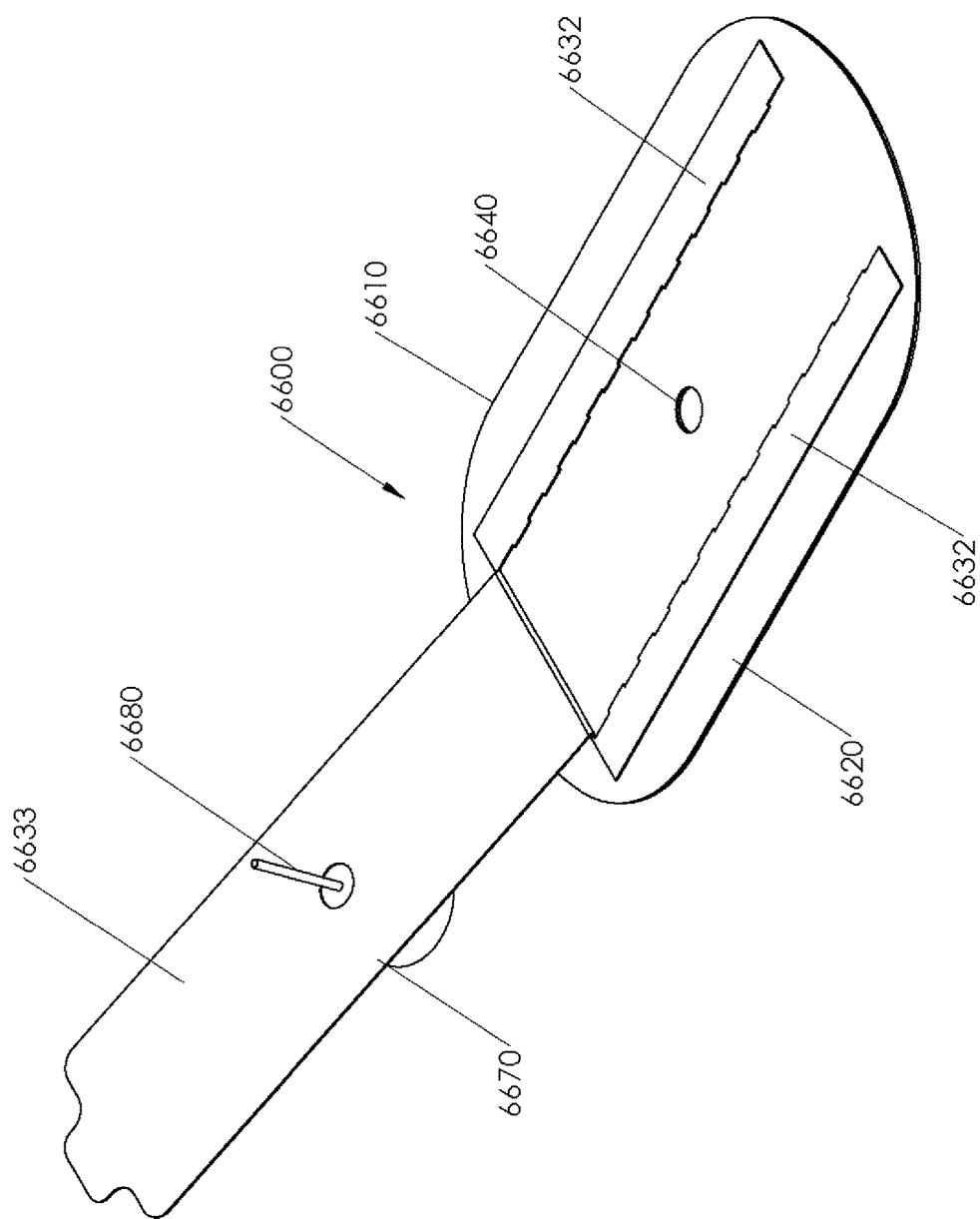
FIG. 66D is superior perspective view of the system in FIG. 66A to 66C, with the infusion hub and infusion catheter removed from the dressing.

FIGS. 66C to 66H illustrate the use of the system 6600. As shown in FIG. 66E, the dressing 6610 is placed on and attached or adhered to a subject with the infusion set 6650 attached to the dressing 6610 and the catheter 6680 extending through the opening 6640 in place in a subject. The dressing substrate 6620 may be attached, for example, by way of a skin adhesive, to the skin of a subject and may be removed by peeling from the skin when desired. When it is desirable to do so, the infusion set housing 6660 may be removed by actuating the release elements 6662. The infusion hub 6670 and catheter 6680 may remain attached to the subject with the dressing 6610. The same or a different infusion set housing 6660 may be reattached to the hub 6670 if additional infusion treatment is desired. As shown in FIGS. 66C and 66G, when the infusion set is to be permanently removed, the hub 6670 is removed by grasping and pulling the pull tab 6634 and tearing the removable element 6633 along tear elements or lines 6635. As shown in FIGS. 66D and 66H, the pull tab 6634 is pulled or actuated until the removable element 6633 is separated by way of tear structures 6635, e.g., the perforations or tear lines 6635 from the dressing substrate 6620. The dressing substrate 6620 may then remain attached to the subject for an additional period of time without the infusion set indwelling in skin.

Figure 67A:
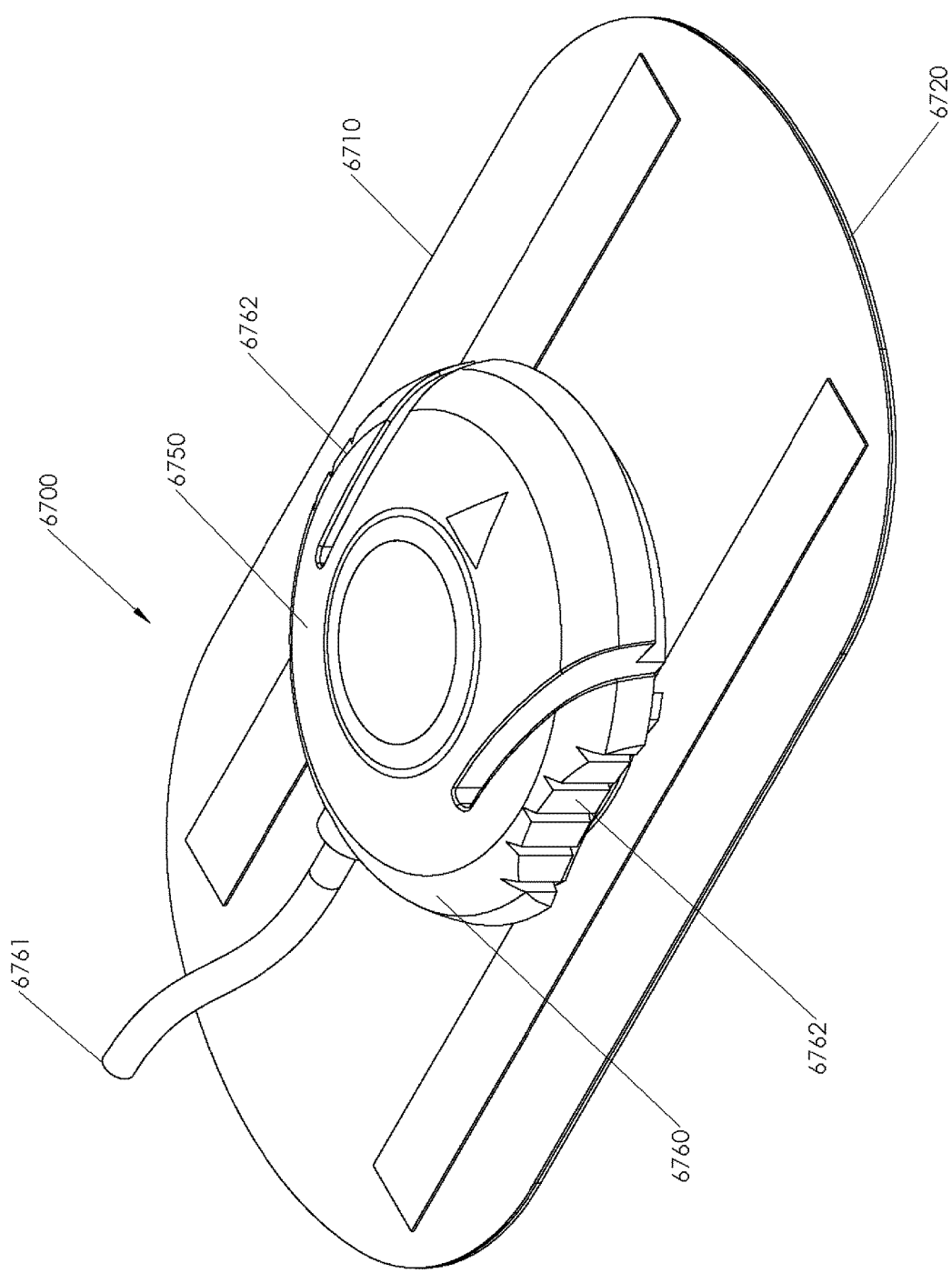
FIG. 67A is a superior perspective view of an embodiment of a treatment system, including a dressing with an integrated, separable or removeable infusion set.
Figure 67B:
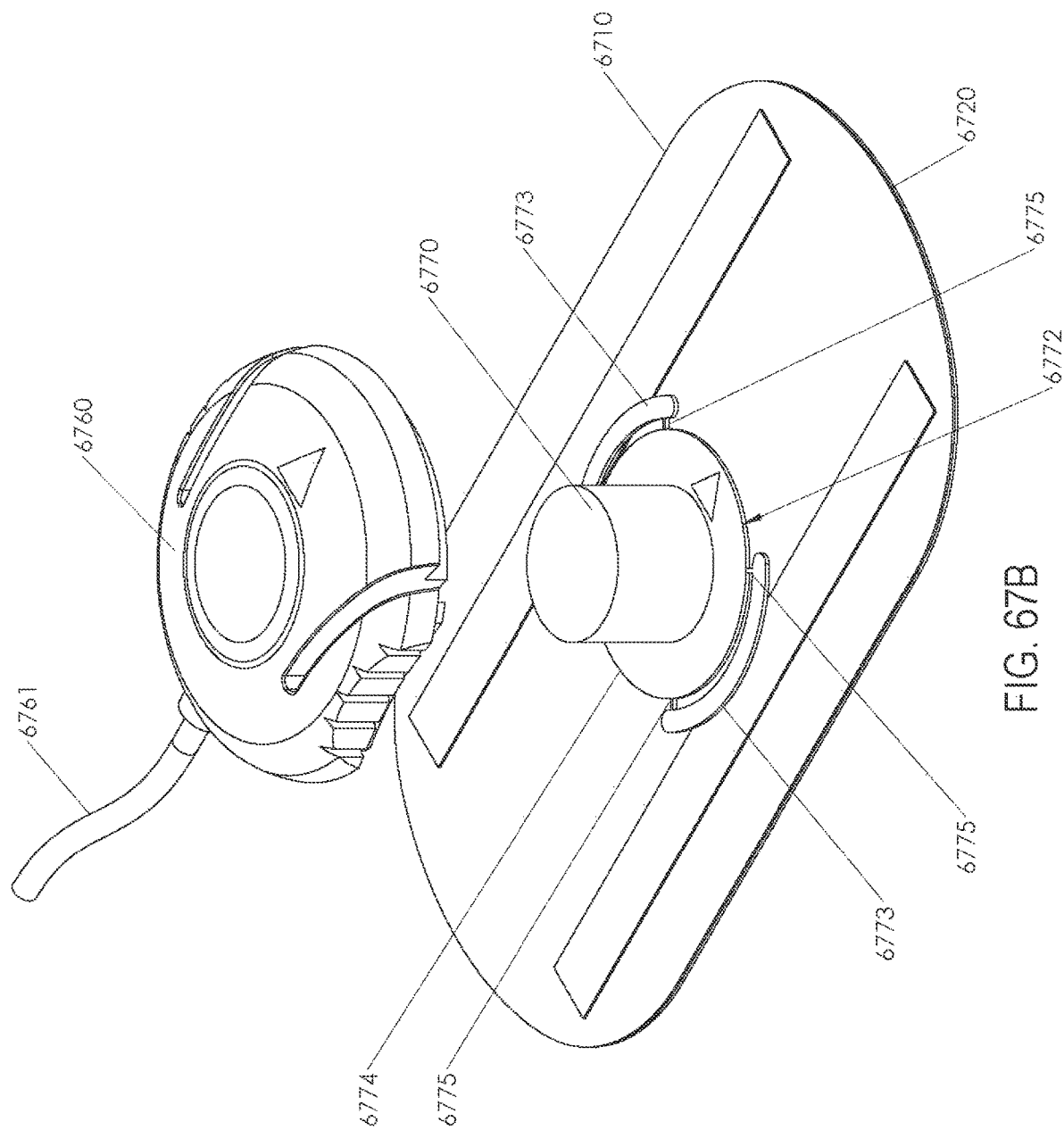
FIG. 67B is a superior perspective view of the system in FIG. 67A, showing the infusion set connector and tubing as it is removed.
Figure 67C:
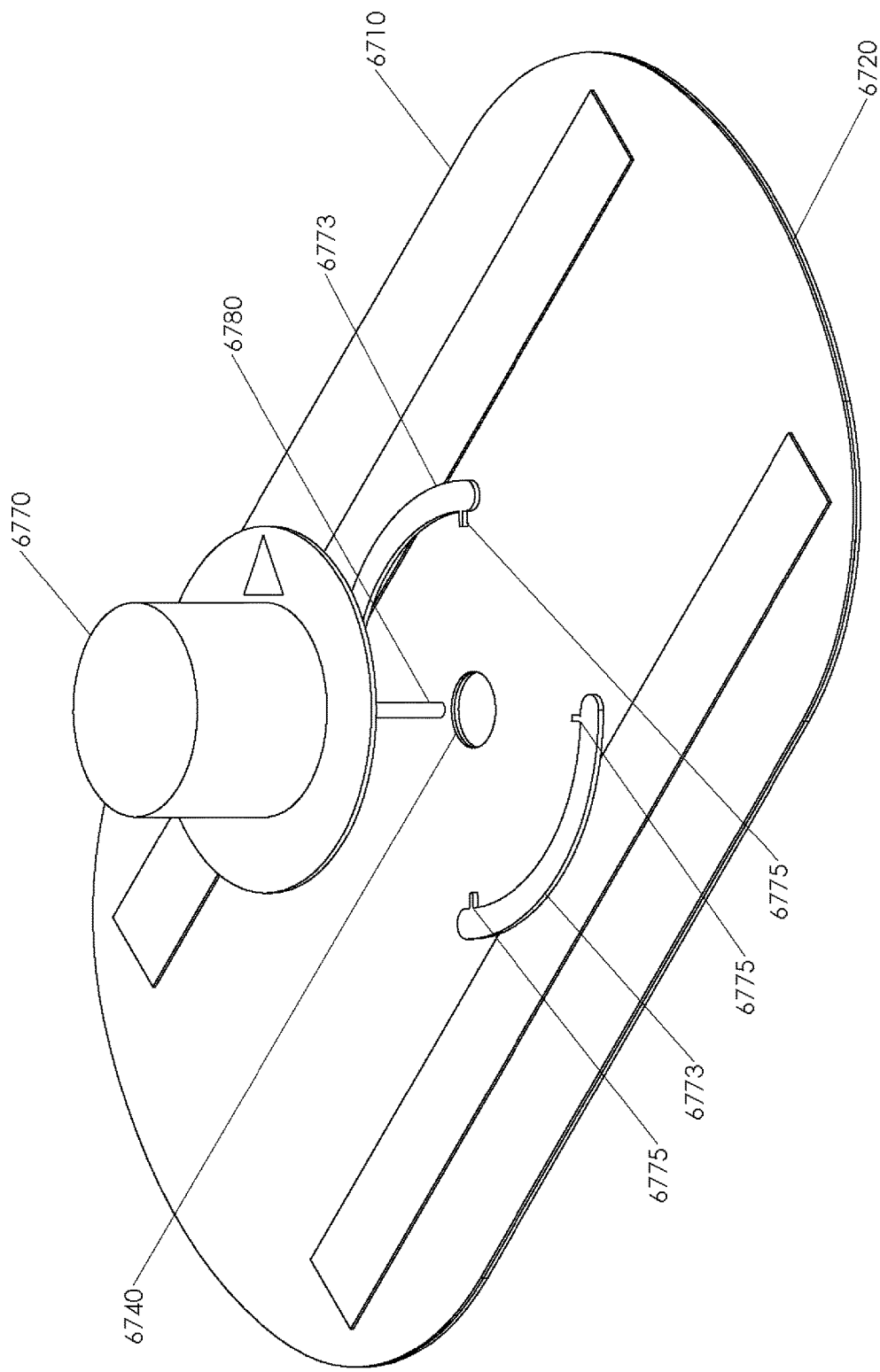
FIG. 67C is a superior perspective view of the system in FIGS. 67A and 67B showing the infusion set hub and catheter as they are removed.

Referring to FIGS. 67A to 67C, a system 6700 is illustrated comprising a dressing 6710 and an infusion set 6750. The infusion set 6750 includes an infusion set housing or connector 6760 with infusion tubing 6761 and release elements 6762 for releasing the housing 6760 from an infusion hub 6770 and attached infusion conduit, e.g. needle or catheter 6780. The dressing 6710 includes a substrate 6720, and an opening 6740 in the dressing 6710 for receiving the catheter 6780.

The infusion hub 6770 of the infusion set 6750 is configured to receive the infusion set housing 6760 and to provide fluid communication between the tubing 6761 of the infusion housing 6760 and the infusion conduit 6780. The device 6700 further includes an attachment structure 6772 for attaching the infusion hub 6770 to the dressing substrate 6720.

The attachment structure 6772 may include one or more substrate attachment sections 6773 attached to the substrate 6720, for example with an adhesive, chemically bonded, heat welded, or other attachment mechanism. The attachment structure may further include release elements or release structures. For example, the attachment structure 6772 further includes a removable section 6774 coupled to or integral with the infusion hub 6770. The attachment structure 6772 further includes tear elements 6775 (e.g., tear lines, breakable elements, weakened sections, perforations or other detachment elements) coupling the removable section 6774 to the one or more substrate attachment sections 6773. The attachment structure's substrate attachment sections 6773, removable section 6774, tear elements 6775 may be constructed of a single unibody material.

The attachment structure 6772 may comprise a split ring attachment structure that allows the dressing to apply compression to the insertion area. The split ring attachment structure may be made of a soft plastic to reduce rigidity of the dressing and reduce interference with a subject's clothing and to minimize discomfort when wearing a large rigid element on skin. The removable section 6774 may be a circular flange formed with or attached to the infusion hub 6770. The substrate attachment elements 6773 may be arced elements attached to the circular flange with frangible, breakable or tear elements 6775.

In use, the dressing 6710 is placed on and attached or adhered to a subject with the infusion set 6750 attached to the dressing 6710 and the catheter 6780 extending through the opening 6740 in place in a subject, as depicted in FIG. 67A. The dressing substrate 6720 may be attached, for example, by way of a skin adhesive as described elsewhere herein, to the skin of a subject and may be removed by peeling from the skin when desired.

As illustrated in FIG. 67B, during use of the infusion set 6750, the infusion set housing 6760 may be placed on or removed from the infusion hub 6770 for example actuating the release elements 6762 As shown in FIG. 67C, when the infusion set 6750 is to be permanently or entirely removed, the hub 6770 is removed by twisting the hub 6770 and breaking the tear elements 6775. The removable section 6774 including catheter 6778 may then be separated from the attachment sections 6773. The dressing substrate 6720 may then remain attached to the subject for an additional period of time without the catheter indwelling in skin.

Referring to FIGS. 68A to 68F, a system 6800 is illustrated comprising a dressing 6810 and an infusion set 6850. The infusion set 6850 includes an infusion set housing or connector 6860 with infusion tubing 6861 and release elements 6862 for releasing the housing 6860 from an infusion hub 6870 and attached catheter 6880.

The dressing 6810 includes a substrate 6820, an attachment element 6830 and an opening 6840 in the dressing 6810 and aligned opening 6837 in the attachment structure 6830, for receiving the catheter 6880. The attachment element 6830 is attached on opposing sides 6832 to the substrate 6820, for example with an adhesive, bond or other attachment mechanism. The attachment element 6830 further includes a release element, for example, a circular perforation or tear section 6835 (e.g., having tear lines, weakened sections, perforations or other tear elements) around the opening 6837. The circular tear section 6835 generally aligns with the circumference 6877 of the infusion hub 6870 where the infusion hub is attached to the attachment element 6830, e.g., with an adhesive, glue, bond or other securing structure 6834.

Figure 68A:
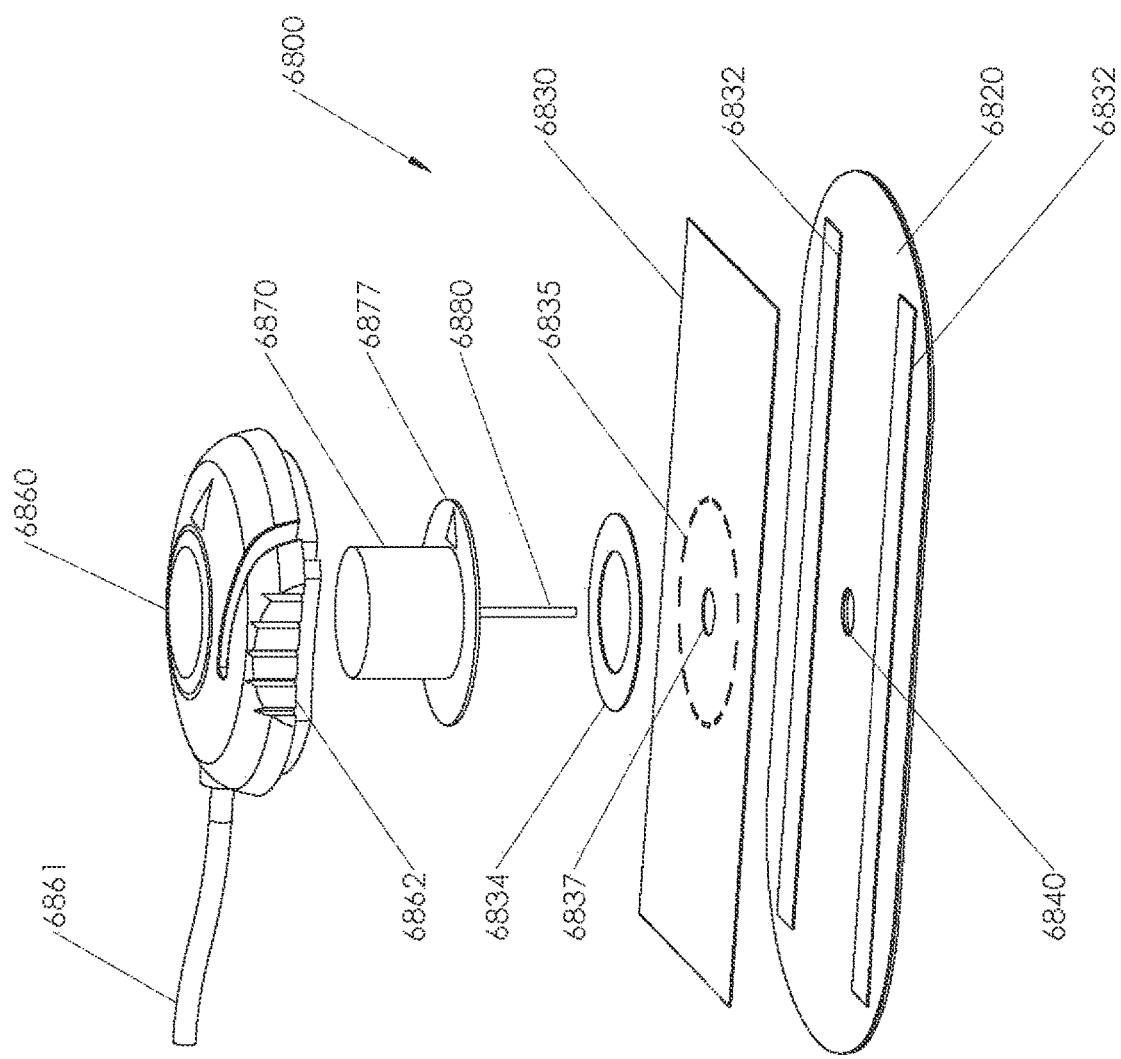
FIG. 68A is an exploded superior perspective view of an embodiment of a treatment system including a dressing with an integrated separable or removeable infusion set.

Referring to FIG. 68A, in use, the dressing 6810 is placed on and attached or adhered to a subject with the infusion set 6850 attached to the dressing 6810, and the catheter 6880 extending through the opening 6840 and in place in a subject. The dressing substrate 6820 may be attached, for example, by way of a skin adhesive, to the skin of a subject and may be removed by peeling from the skin when desired.

Figure 68E:
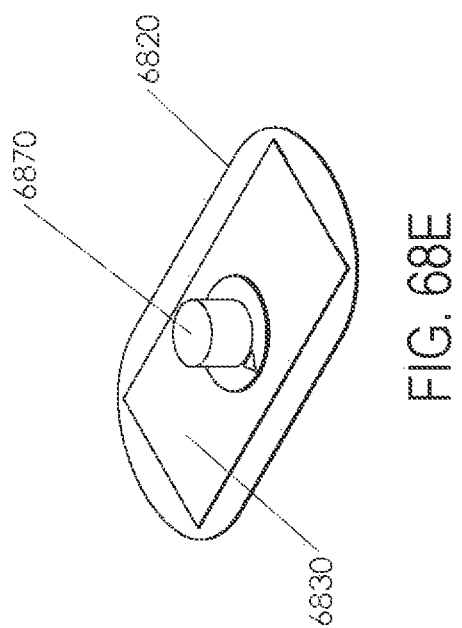
Figure 68F:
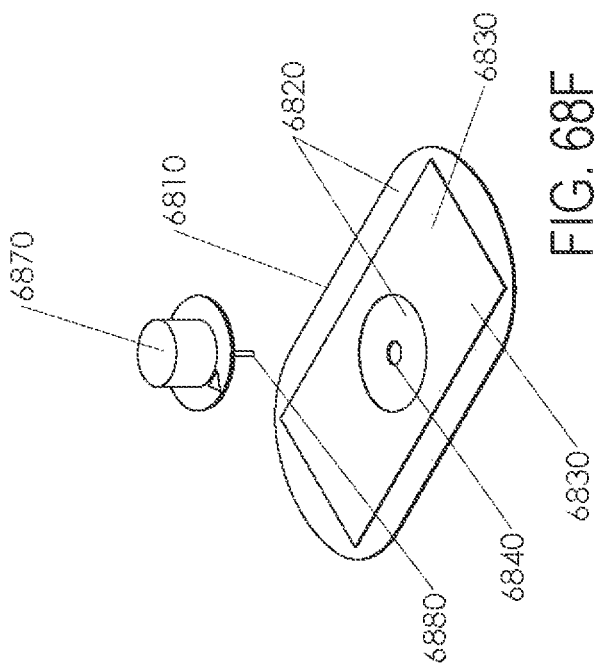

During use of the infusion set 6850, the infusion set housing 6860 may be placed on or removed from the infusion hub 6870, for example, by actuating the release elements 6862. As shown in FIGS. 68C and 68D, the infusion set housing 6860 is removed. In FIG. 68E, when the infusion set 6850 is to be permanently or entirely removed, the hub 6870 is removed by twisting the hub 6870 and separating the hub 6870 at the perforations 6875. The hub 6870 including catheter 6880 may then be separated from the dressing substrate 6820 and remaining portions of the attachment element 6830, as depicted in FIG. 68F. The dressing substrate 6820 may then remain attached to the subject for an additional period of time without the catheter indwelling in skin.

Referring to FIGS. 69A to 69K, a system 6900 is illustrated comprising a dressing 6910 and an infusion set 6950. The infusion set 6950 includes an infusion set housing 6960 with infusion tubing 6961 and release elements 6962 for releasing the housing 6960 from an infusion hub 6970 with attached catheter 6980. The dressing 6910 includes a substrate 6920, and an opening 6940 in the dressing 6910 for receiving the catheter 6980. A dressing connector 6925 is attached to the dressing 6910 and is configured to releasably couple the infusion hub 6970 to the dressing 6910.

The infusion hub 6970 of the infusion set 6950 is configured to reversibly receive the infusion set housing 6960 and provide fluid communication between the tubing 6961 of the infusion housing 6960 and the infusion conduit 6980. Tubing 6961 is fluidically joined to a lumen 6963 of the housing 6960 which terminates inwardly at a fluid seal 6963, e.g. a silicone seal or grommet. When the infusion housing 6960 is coupled to the infusion hub 6970, the fluid seal 6963 is configured to align and seal with the fluid seal 6963 of the lumen 6982 of the hub 6970. This lumen 6982 communicates with the infusion conduit 6980. In embodiments wherein the infusion conduit 6980 comprises a soft cannula or catheter, an additional needle lumen 6982 and self-sealing needle seal 6983 may be provided to allow a solid needle or trocar (not shown) of an applicator to provide mechanical support and ability to pierce tissue, in order to facilitate insertion of the infusion conduit. The needle lumen 6982 may be oriented to provide a linear insertion and withdrawal path of the solid needle or trocar through the infusion conduit 6980. The solid needle or trocar is then withdrawn from the infusion conduit 6980 with the applicator once insertion of the conduit 6980 is completed. A complementary mechanical interfit between the interior cavity shape of the infusion housing 6960 and the outer shape of the hub 6970 may be provided to facilitate alignment of the fluid seals and lumens. In some other variations, a sealed circumferential recess or channel may be provided on the interior surface of the housing and/or the outer surface of the hub with seals, to allow fluid communication between the housing and hub that is independent of the angular orientation of the housing, and therefore not require angular alignment. These various fluid channel configurations may be adapted to provide fluid communications with the other infusion sets described herein that have separable infusion housings and hubs, including systems 6600, 6700, 6800 and 7000.

The infusion hub 6970 includes an attachment structure 6972 for attaching the infusion hub 6970 to the dressing connector 6925. The infusion hub 6970 further includes a release element, for example, a removable attachment section 6974 coupled to or integral with the engagement element 6971. The attachment structure 6972 may comprise a flange 6975 having bendable arms 6973 with extension tabs 6976 configured to engage the dressing connector 6925. The dressing connector 6925 may include one or more connector sections 6926 attached to the substrate 6920, for example with an adhesive, bond or other attachment mechanism 6927. The dressing connector 6925 may comprise a split ring attachment structure that allows the dressing 6910 to apply compression to the insertion area. The split ring attachment structure may be made of a soft plastic to reduce rigidity of the dressing and reduce interference with a subject's clothing.

The connector sections 6926 comprise recesses or cutouts 6929 configured to receive extension tabs 6976 of the infusion hub 6970 along an orthogonal direction to the treatment surface. Cutouts 6929 are in communication with transverse slots 6928 for rotatably receiving extension tabs 6976. Cutouts 6929 at the end of the slots 6928 are configured to lock the extension tabs 6976 in place.

Figure 69A:
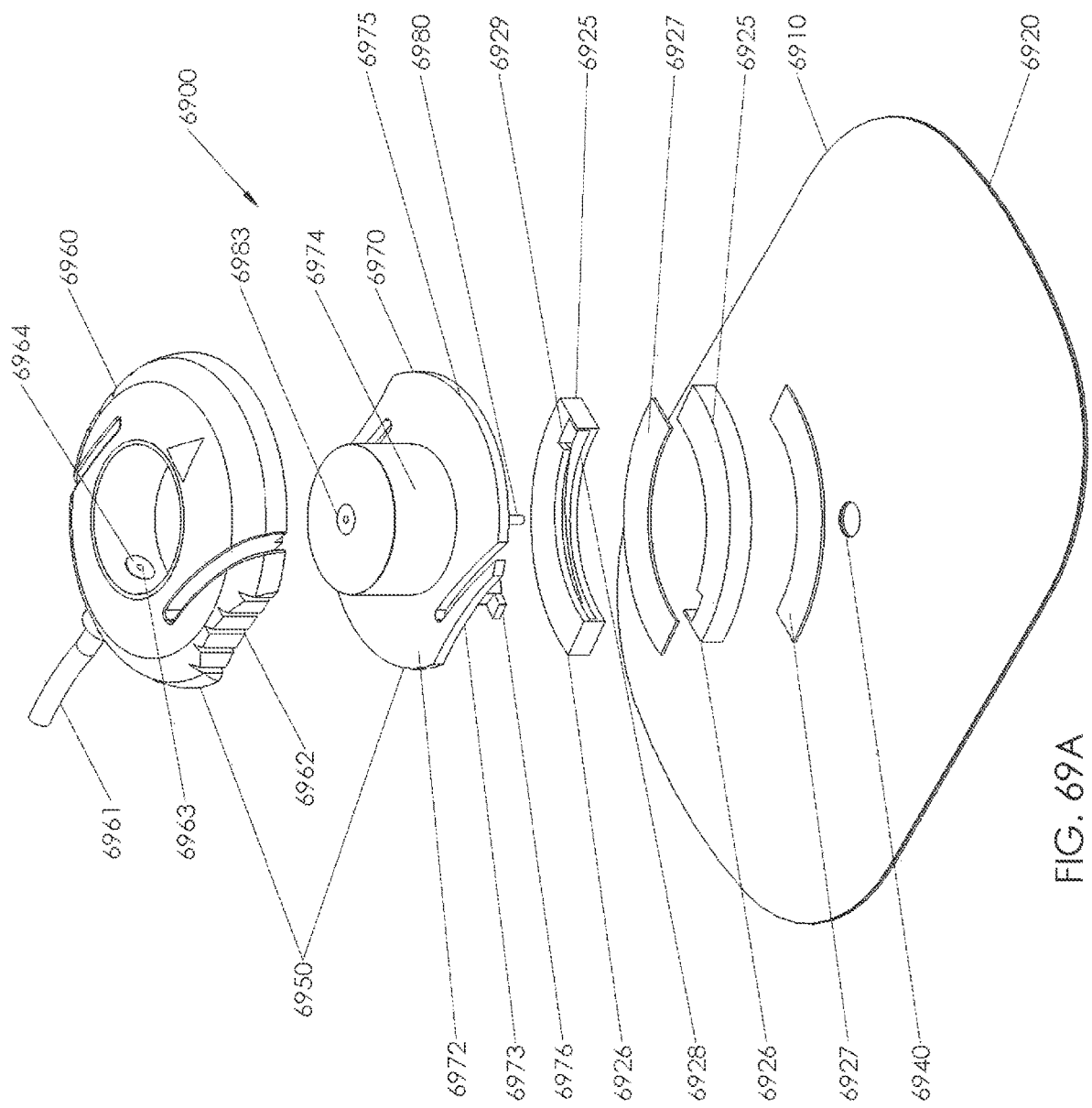
FIG. 69A is an exploded superior perspective view of an embodiment of a treatment system including a dressing with an integrated separable or removeable infusion set.

As shown in FIGS. 69A and 69B, in use, the dressing 6910 is placed on and attached or adhered to a subject with the infusion set 6950 attached to the dressing 6910 and the catheter 6980 extending through the opening 6940 in place in a subject. The dressing substrate 6920 may be attached, for example, by way of a skin adhesive, to the skin of a subject and may be removed by peeling from the skin when desired.

In FIG. 69C, during use of the infusion set 6950, the infusion set housing 6960 may be placed on or removed from the infusion hub 6970 for example actuating the release elements 6962. When the infusion set 6950 is to be permanently or entirely removed, the hub 6970 is removed by a) depressing the bendable arms 6973 to release the extension tabs 6976 from the cutouts 6929, b) twisting or turning the hub 6970 to move the extension tabs 6976 through the slots 6928 to openings 6927, and c) lifting the hub 6970 to detach it from the dressing connector 6925 and dressing 6910, per FIG. 69E. The dressing substrate 6920 may then remain attached to the subject for an additional period of time without the catheter indwelling in skin, as in FIG. 69F.

FIG. 69K depicts an exemplary configuration of fluid channels providing fluid communication between the catheter tubing 6961 and the fluid conduit 6980, for providing insulin therapy or other infused therapy. Seals, such as silicone rings 6963 and Referring to FIGS. 70A to 70K, a system 7000 is illustrated comprising a dressing 7010 and an infusion set 7050. The infusion set 7050 includes an infusion set housing 7060 with infusion tubing 7061 and release elements 7062 for releasing the housing 7060 from an infusion hub 7070 with attached catheter 7080. The dressing 7010 includes a substrate 7020, and an opening 7040 in the dressing 7010 for receiving the catheter 7080. A dressing connector 7025 is attached to the dressing 7010 and is configured to releasably couple the infusion hub 7070 to the dressing 7010.

The infusion hub 7070 further includes: an outer engagement hub 7071; tool receptacles 7072 from the superior side through the inferior side of the infusion hub 7070; and a central section 7073. The central section 7073 includes an opening 7074 through which infusion fluid is delivered from infusion tubing 7061 to the catheter 7080. The central section 7073 also includes spring arms 7076 with connector tabs 7077 extending into and through tool receptacles 7072. An inner wall of the outer engagement hub 7071 includes a cut out edge section 7079 of the hub for attaching a removal tool 7090 tool to the infusion hub 7070.

The dressing connector 7025 includes a hub receptacle opening 7026 for receiving the central section 7073 (including connector tabs 7077) of the infusion hub 7070. The hub receptacle opening 7026 is in communication with a catheter opening 7027 for receiving the catheter 7080. The openings 7026, 7027, and 7074 are further aligned with the opening 7040 in the dressing substrate 7020, so that when the system is assembled, the catheter 7080 extends through opening 7040 in dressing 7010. The attachment structure may comprise a dressing connector 7025 further includes engagement tabs 7028 that receive connector tabs 7077 at the ends of the spring biased arms 7076 when the infusion hub 7070 is attached with the dressing connector 7025 to the dressing 7010.

Figure 70A:
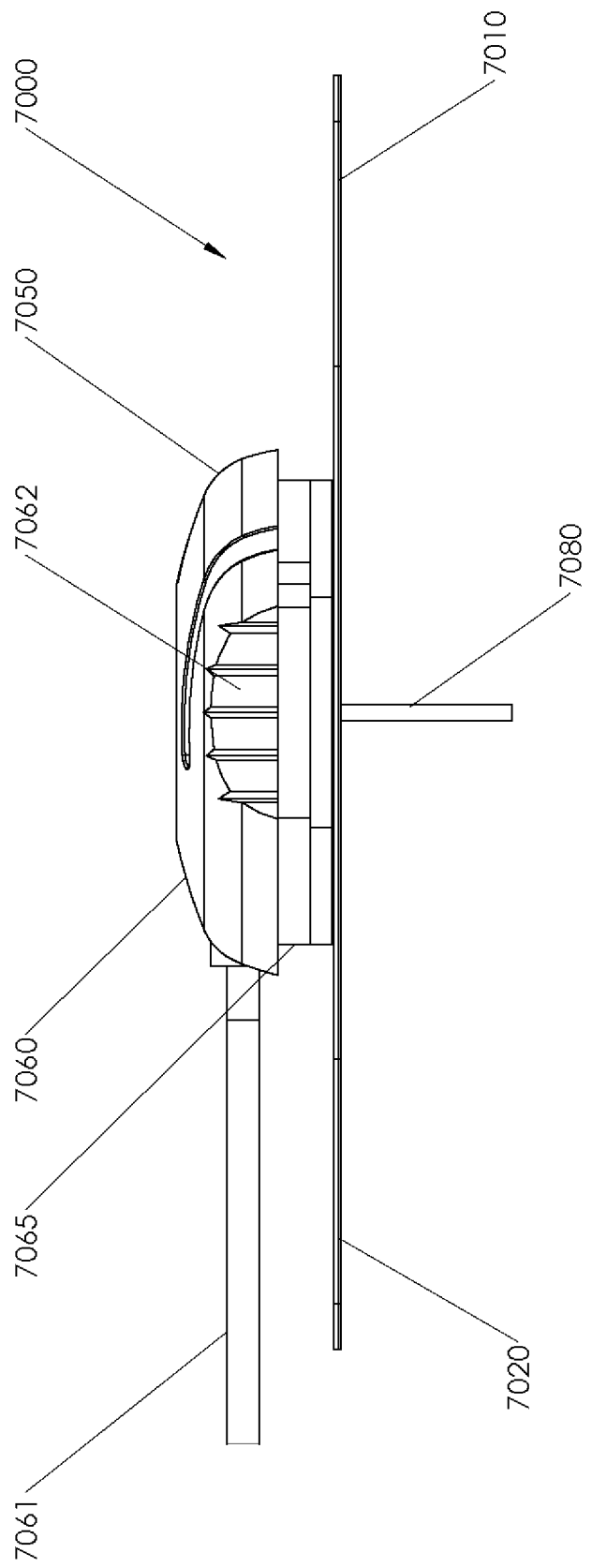
FIG. 70A is a side view of an embodiment of a treatment system including a dressing with an integrated separable or removable infusion set.

The dressing 7010 with integrated infusion set 7050 is shown assembled in FIG. 70A. The infusion set housing 7060 is coupled by way of engagement hub 7071 to the infusion hub 7070 and is released using release elements 7062. The infusion hub 7070 is attached to the dressing 7010 by way of the dressing connector 7025. The catheter 7080 is placed through openings 7027 and 7040 respectively in the hub 7070 and dressing 7010. The central portion 7073, spring arms 7076 with tabs connector tabs 7077 are positioned through the opening 7026. The spring arms 7076 are biased outward so that the connector tabs 7077 engage the engagement tabs 7028 when the arms 7076 are pushed into the opening 7026.

In use, the dressing 7010 is placed on and attached or adhered to a subject with the infusion set 7050 attached to the dressing 7010 and the catheter 7080 extending through the opening 7080 in place in a subject, as shown in FIG. 70A. The dressing substrate 7020 may be attached, for example, by way of a skin adhesive, to the skin of a subject and may be removed by peeling from the skin when desired.

Figure 70B:
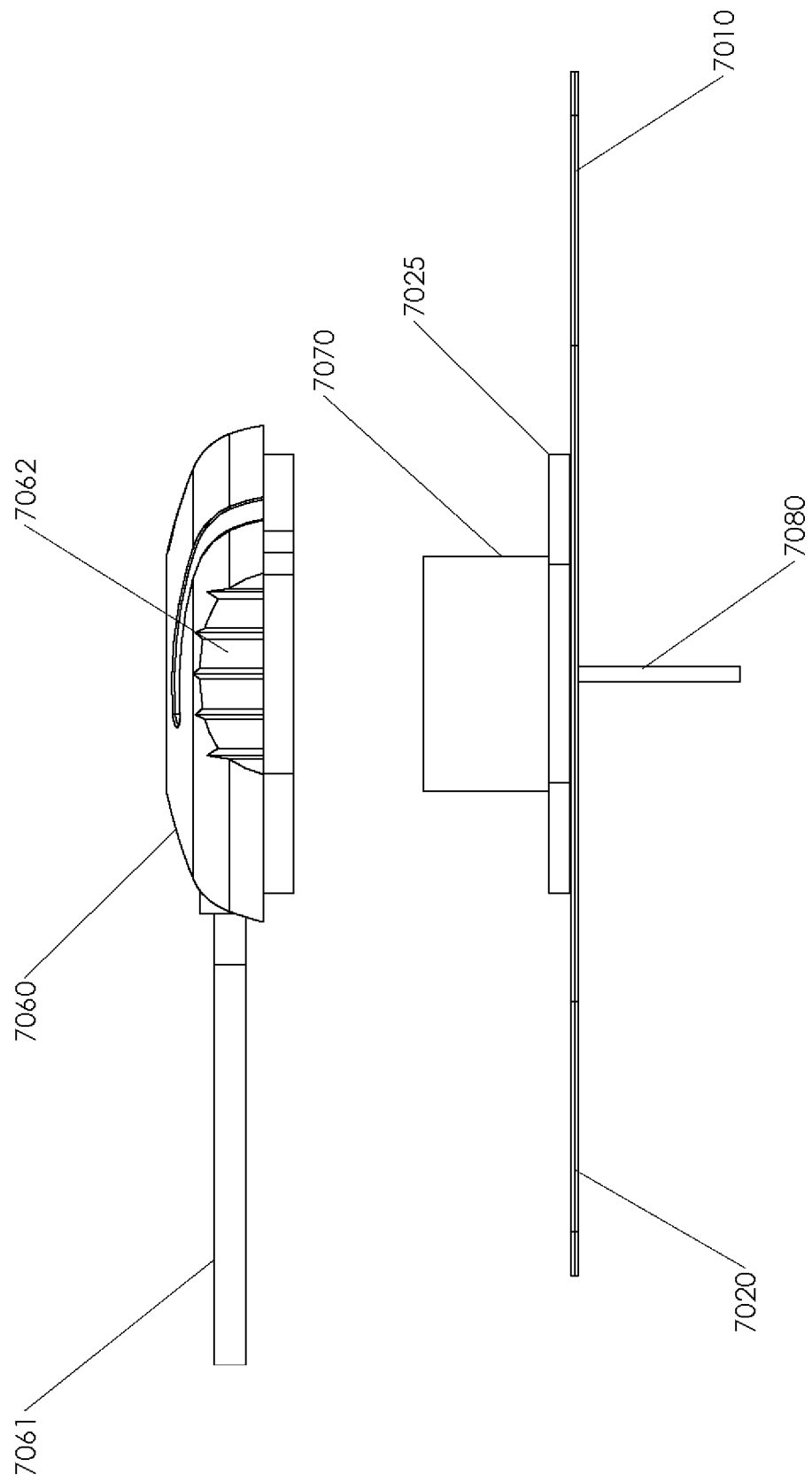
FIG. 70B is a side view of the treatment system, of FIG. 70A with the infusion set connector and tubing being removed.
Figure 70C:
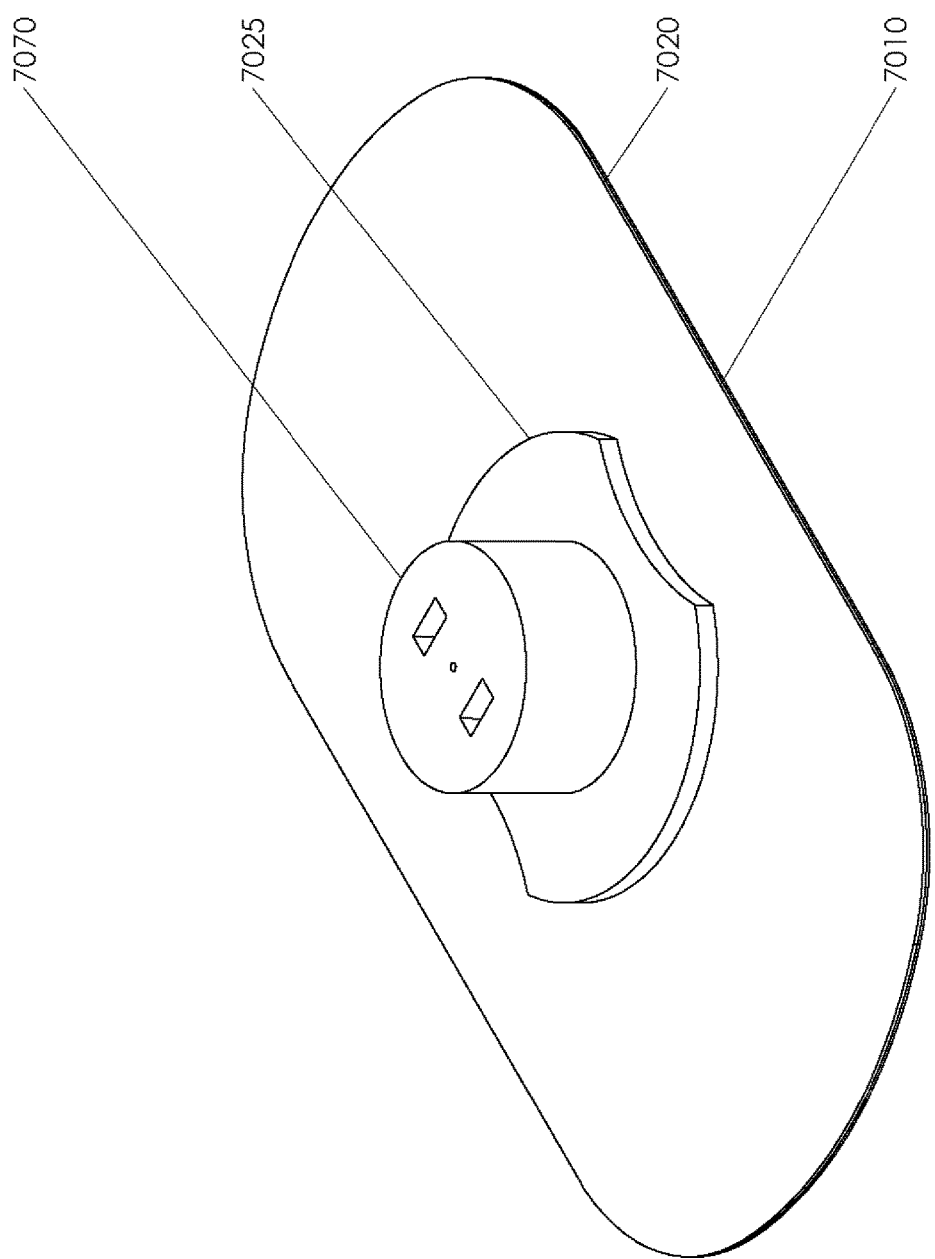
FIG. 70C is a superior perspective view of the system in FIGS. 70A and 70B with the infusion set connector and tubing removed.
Figure 70D:
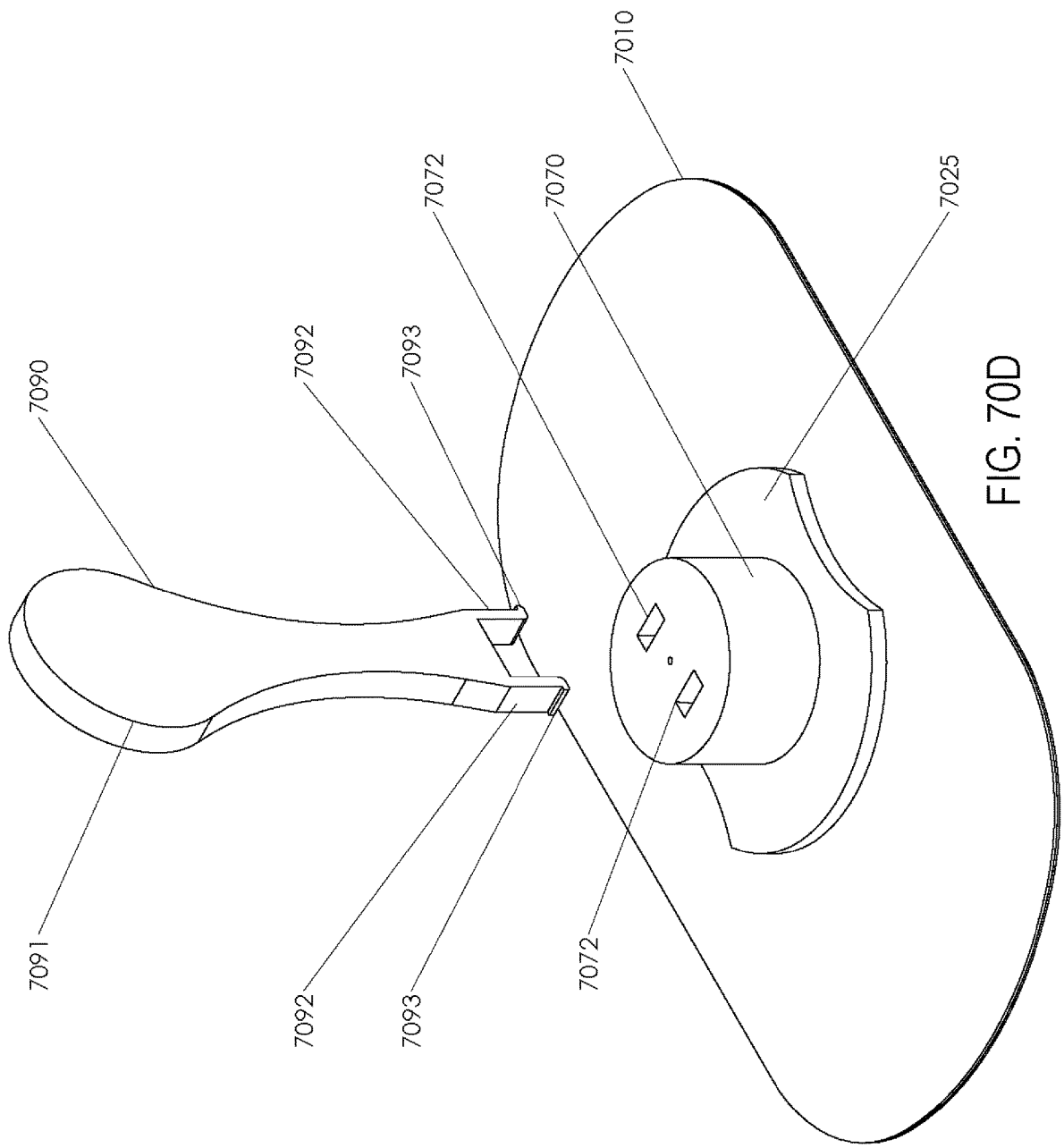
FIG. 70D is a superior perspective view of the system in FIG. 70C with a removal tool.
Figure 70E:
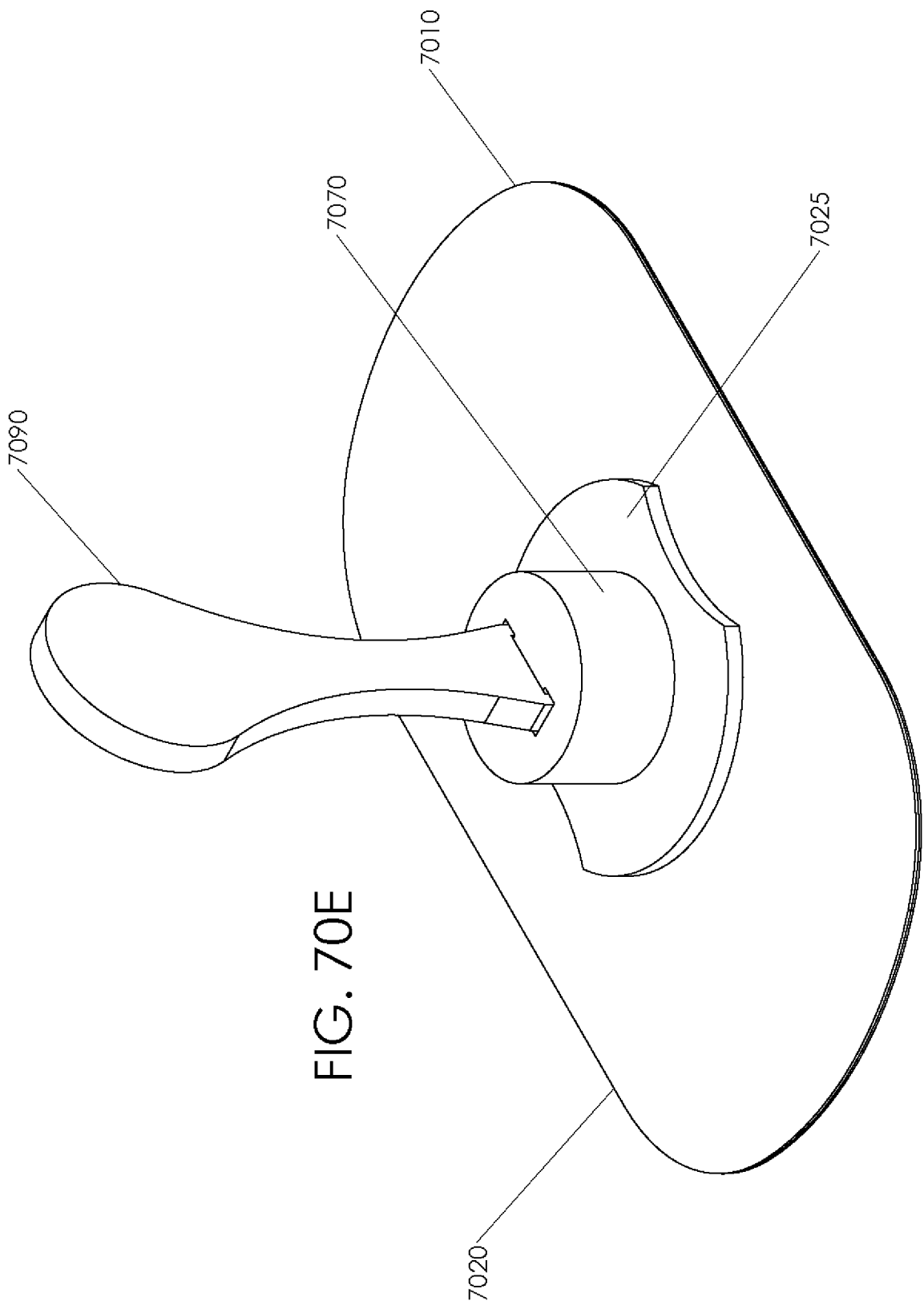
FIG. 70E is a superior perspective view of the system of FIG. 70D with the removal tool fully docked into the infusion hub.
Figure 70G:
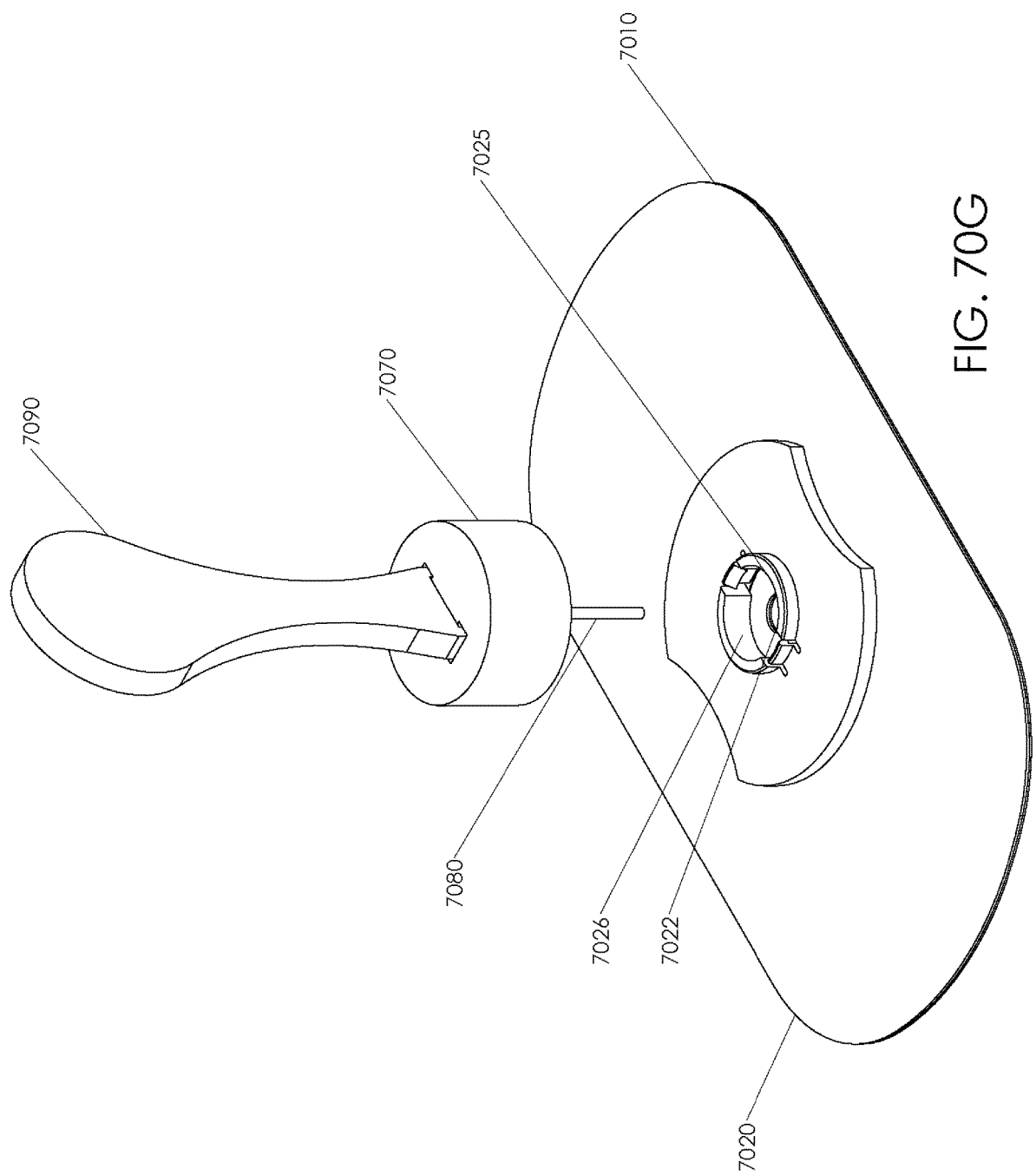
FIG. 70G is a superior perspective view of the dressing and dressing connector with the infusion hub removed.
Figure 70H:
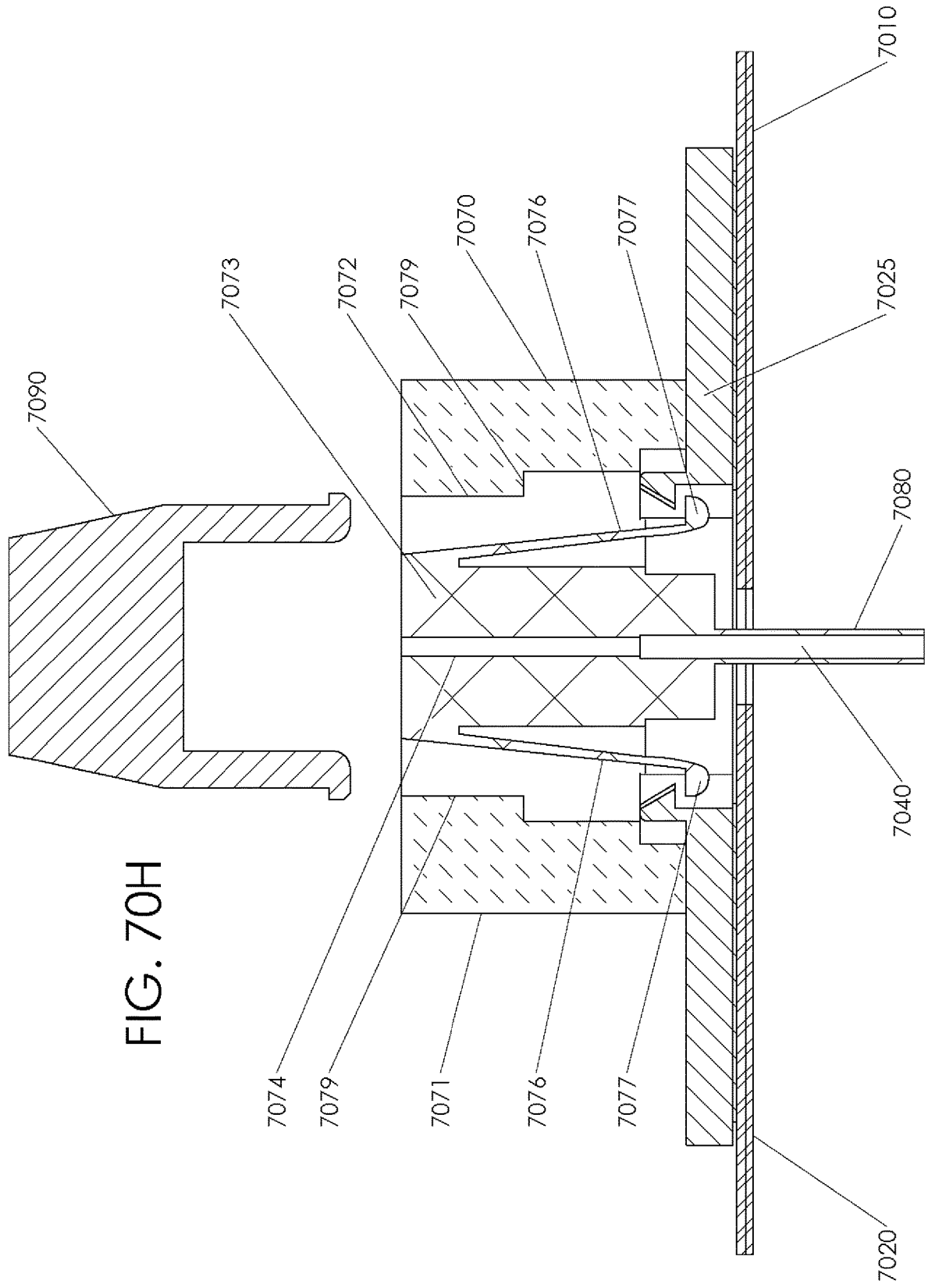
FIG. 70H is a side cross section of the system as shown in FIG. 70D.
Figure 70I:
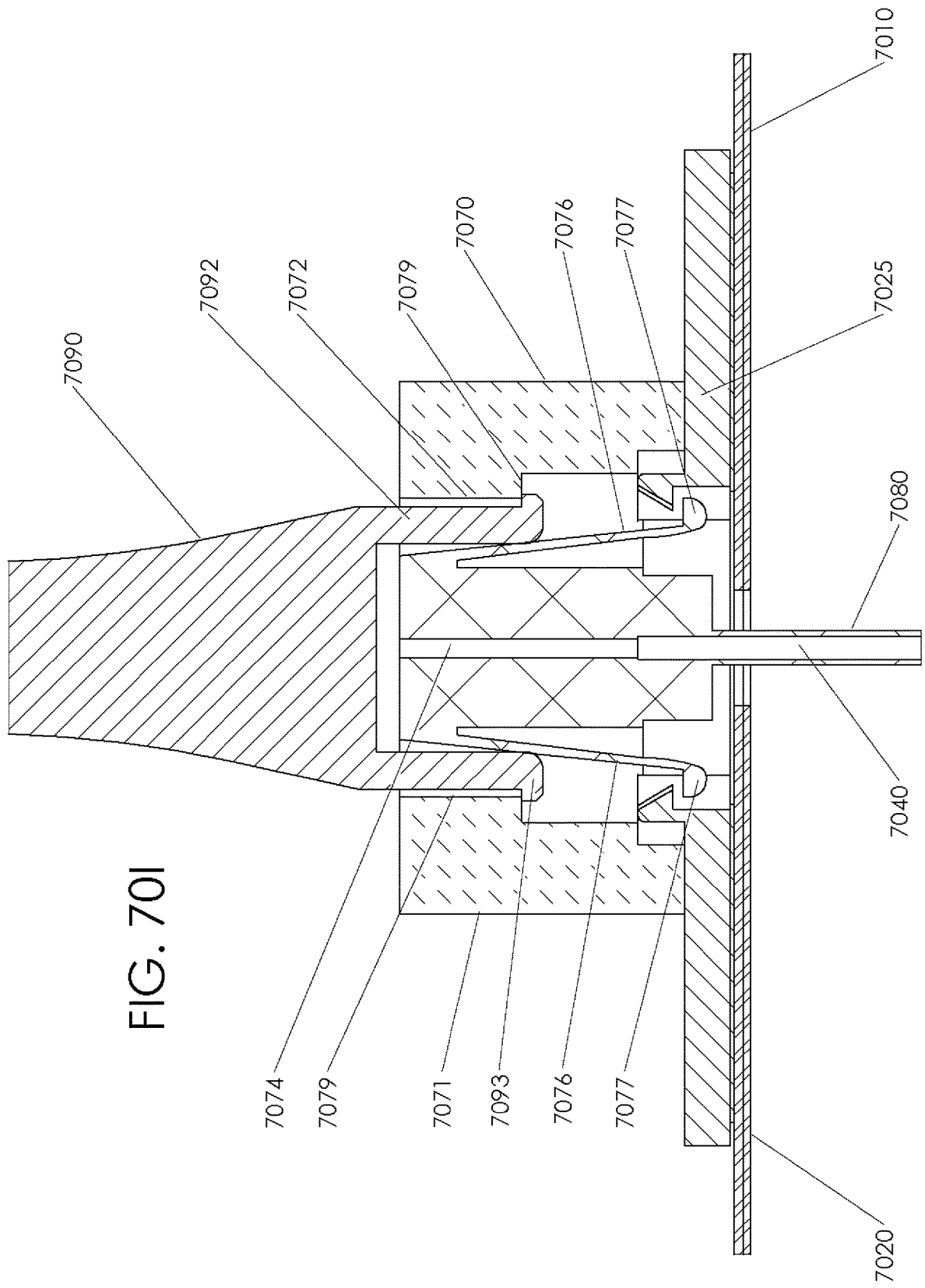
FIG. 70I is a side cross section of the system as shown in FIG. 70E.

In FIG. 70B, during use of the infusion set 7050, the infusion set housing 7060 may be placed on or removed from the infusion hub 7070 for example actuating the release elements 7062.

Figure 70J:
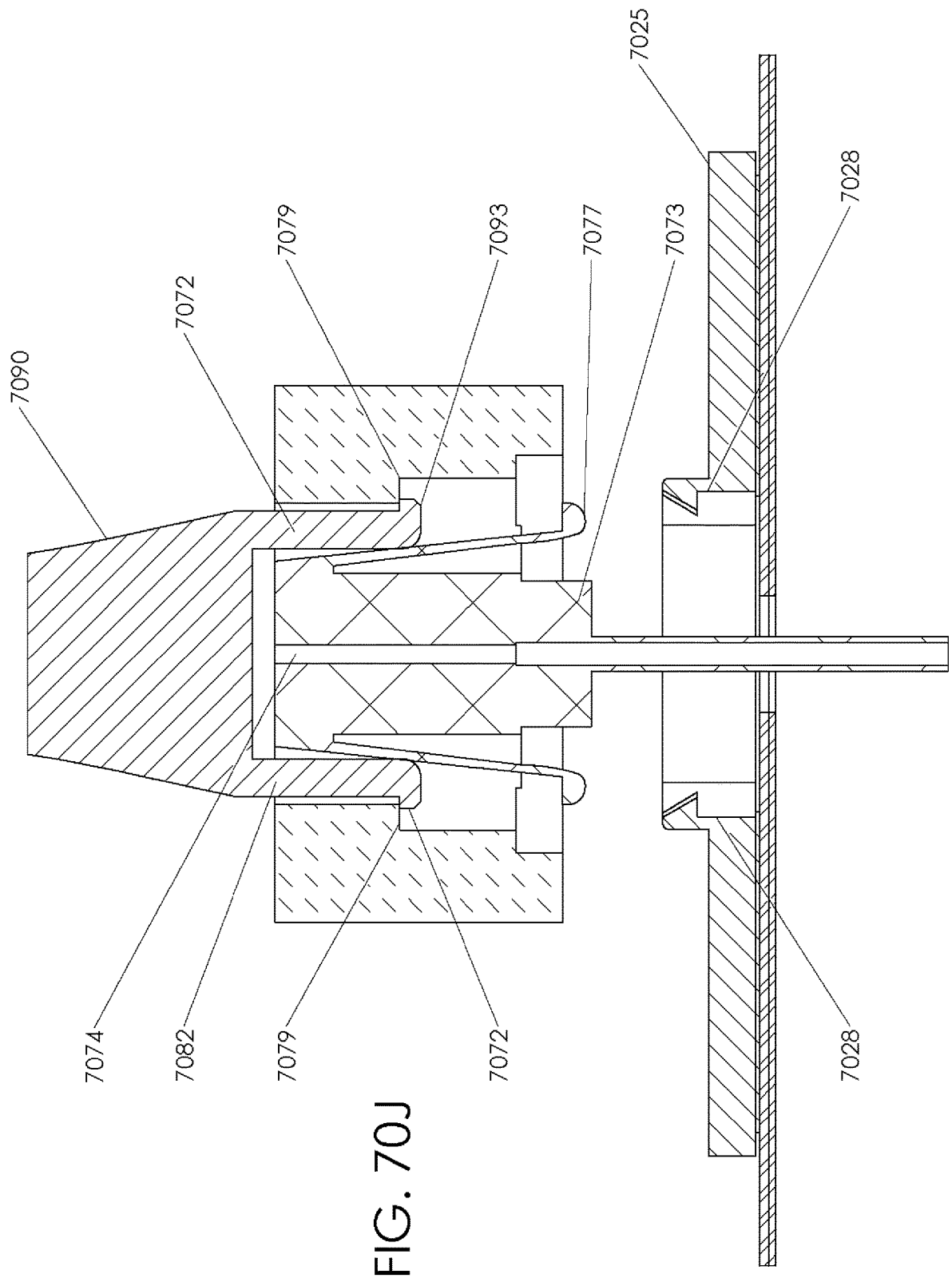
FIG. 70J is a side cross section of the system as shown in FIG. 70F.
Figure 70K:
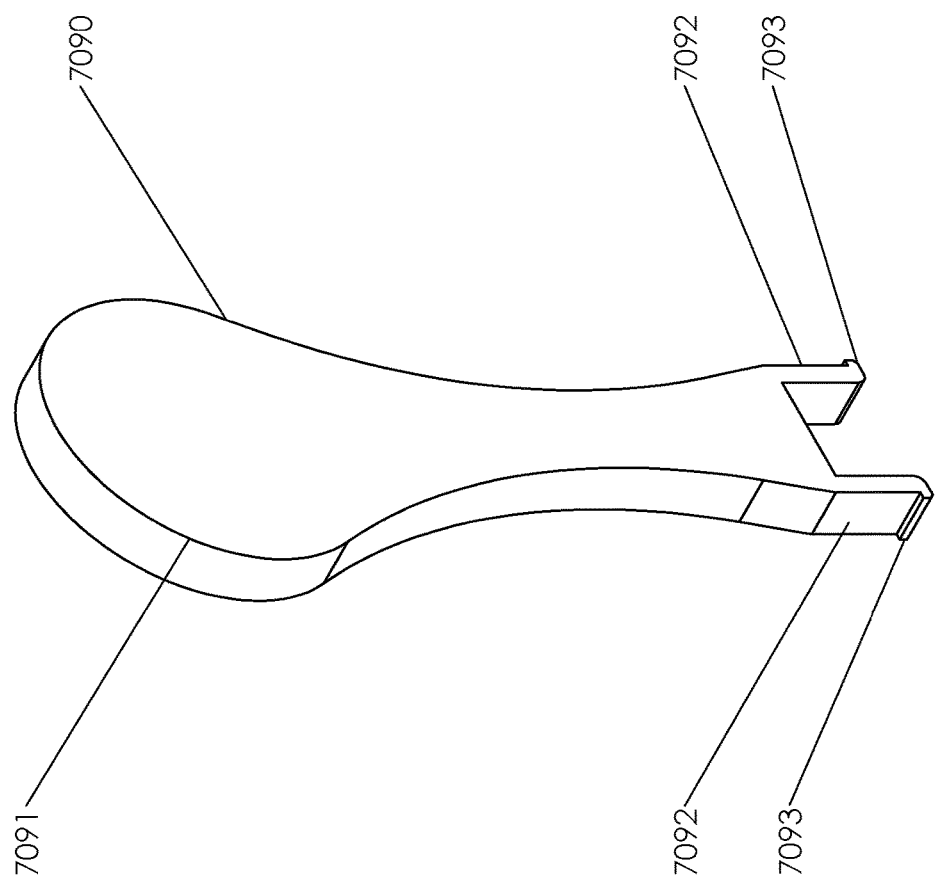
FIG. 70K is a superior perspective view of a tool for removing a portion of an infusion set.

When the infusion set 7050 is to be permanently or entirely removed, the hub 7070 is removed by using the release structure or removal tool shown in FIG. 70J. The removal tool 7090 includes a handle portion 7091 with distal spring-loaded prongs 7092 having attachment tabs 7093.

The prongs 7092 and attachment tabs 7093 are inserted into the receptacles 7072 in the hub 7070 deflecting the spring arms 7076 inward, disengaging connector tabs 7077 from engagement tabs 7028. The attachment tabs 7093 of the removal tool 7090 engage the cut out edge section 7079 of the infusion hub 7070 attaching the tool 7090 to the infusion hub 7070. The infusion hub 7070 may then be removed from the dressing 7010 using the tool.

The dressing substrate 7020 may then remain attached to the subject for an additional period of time without the catheter indwelling in skin.

The substrates of the dressings 6610, 6710, 6810, 6910, and 7010 may be flexible and resilient or may be relatively inflexible. According to one variation the dressing may be strained prior to application. The dressing may be provided in a pre-strained configuration as described detail herein. herein. The dressings 6610, 6710, 6810, 6910, and 7010 may include a removable applicator and strain support configured to maintain the strain in the strained elastic layer of the dressing substrate, as depicted in the exemplary embodiment in FIG. 39B. Other applicator and The systems 6600, 6700, 6800, 6900, and 7000 may also include a removable applicator as described herein. The strain support may be used as an applicator. Exemplary embodiments of applicators, strain supports, tension supports and dressing supports that may be used or incorporated with these dressings include those described for dressings or infusion systems 3006, 3921, 4500, 4800, 4900 and 5200 described elsewhere herein.

Figure 55A:
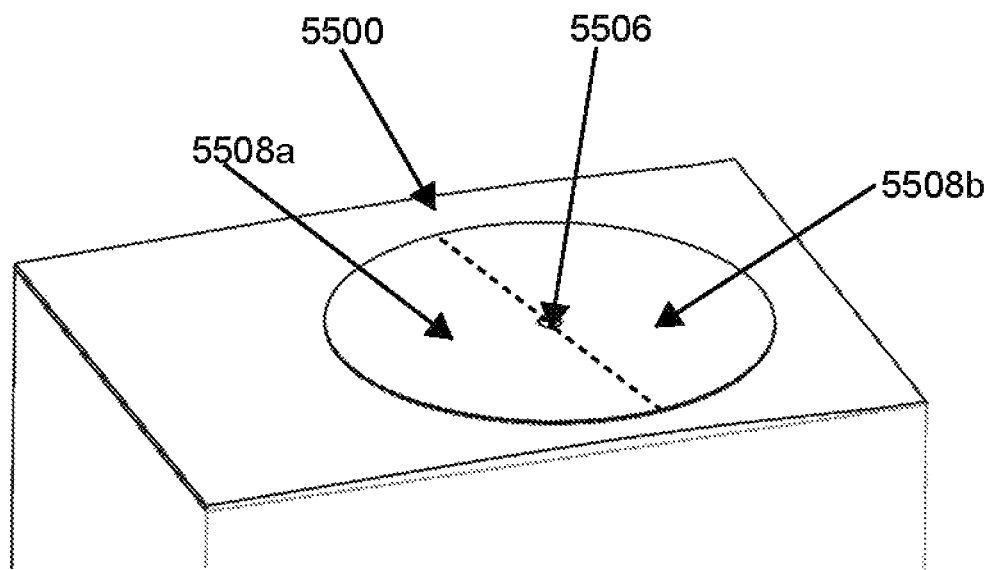
FIGS. 55A and 55B are schematic perspective views of a radially tensioned skin treatment device used for manual injection.
Figure 55B:
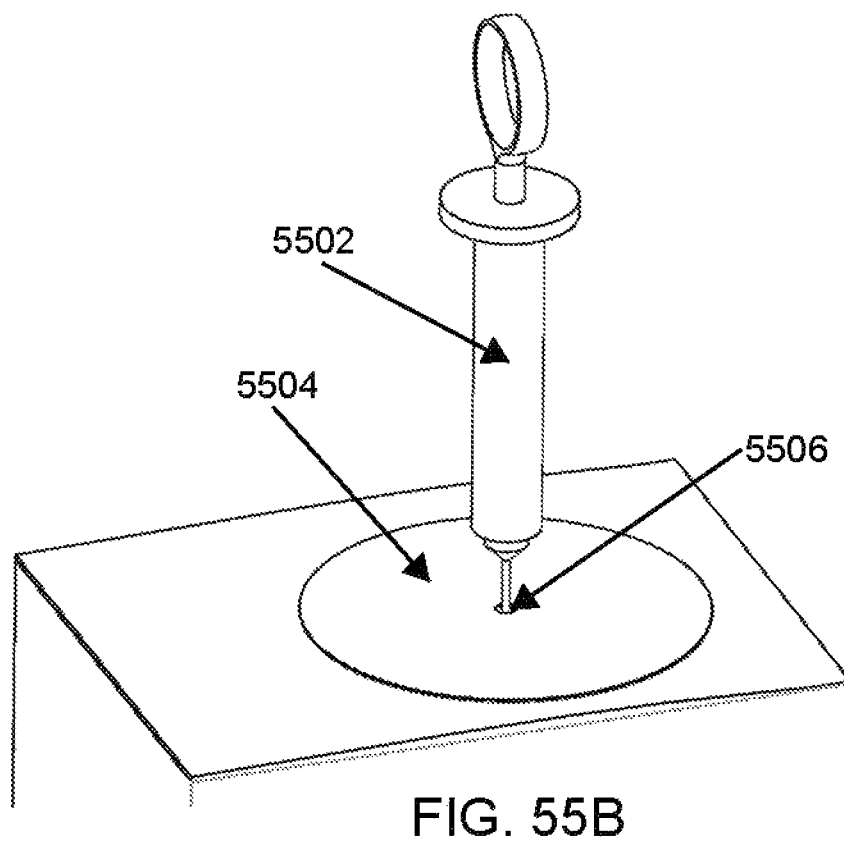

In addition to a radially strained infusion system 4800, a radially pre-strained skin tensioning device 5500 may be provided for use with manual injection with a syringe 5502, as shown in FIGS. 55A and 55B. The skin tensioning device 5500 comprises an elastic layer 5504 with an access opening 5506. The skin tensioning device 5500 may be adhered to the target location and then the radial strain supports 5508a, 5508b may be removed to permit the elastic layer 5504 to radially compress the underlying skin toward the access opening 5506. The access opening may comprise a diameter or a shape with a transverse dimension in the range of 1-20 mm, 2-10 mm, or 3-5 mm, for example.

Figure 56A:
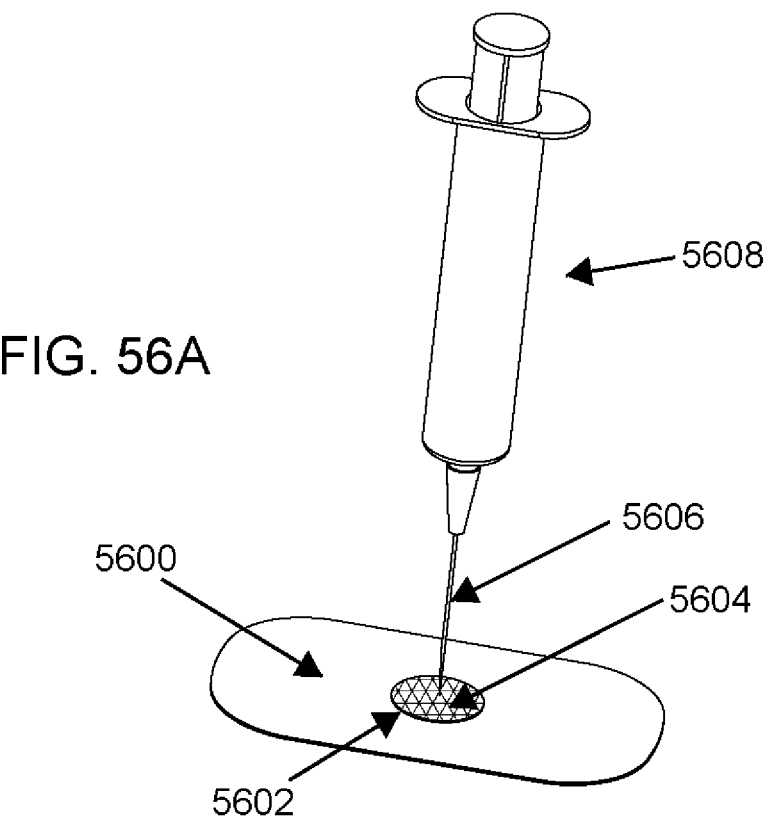
FIG. 56A is a superior perspective of a skin tensioning device with a woven needle injection aperture being used with a syringe.
Figure 56B:
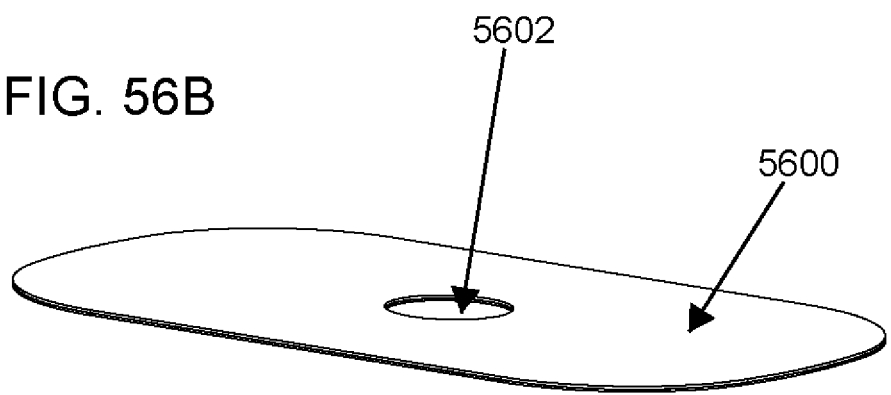
FIG. 56B is an inferior perspective view of the skin tensioning device in FIG. 56A.
Figure 57A:
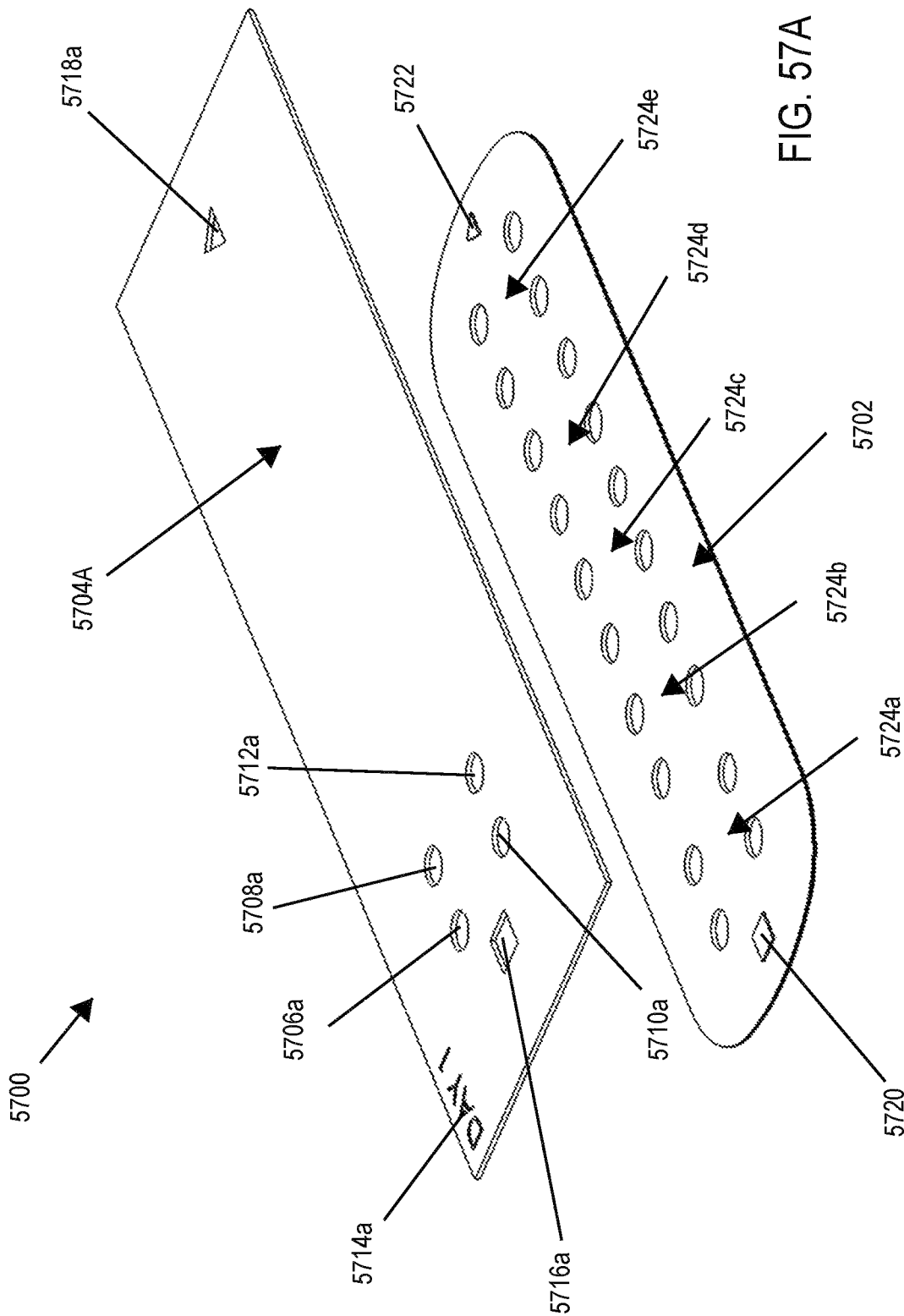
FIG. 57A is a perspective view of an exemplary tensioned skin treatment system comprising removable injection templates.
Figure 57B:
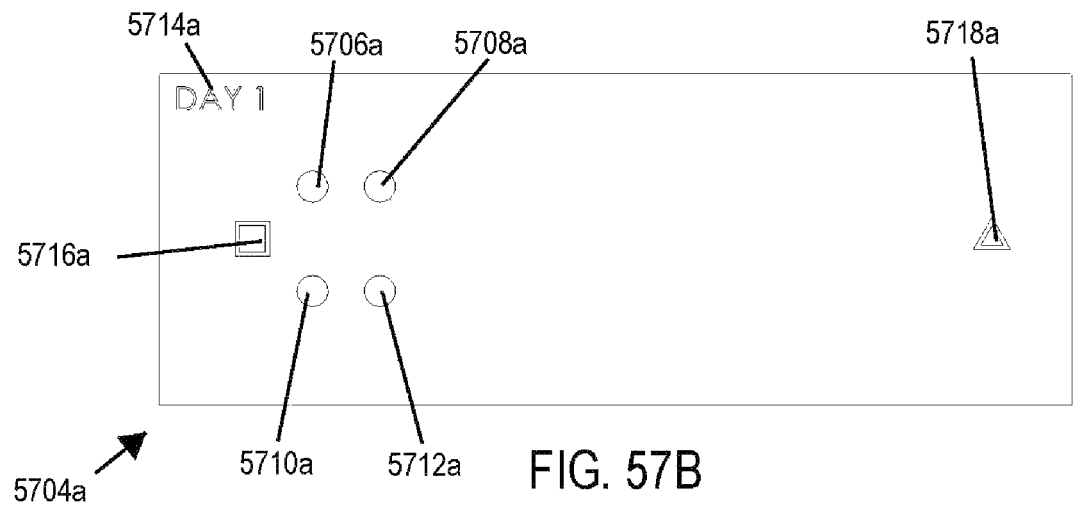
FIGS. 57B to 57D depict different injection templates that are usable with the system in FIG. 57A.
Figure 57C:
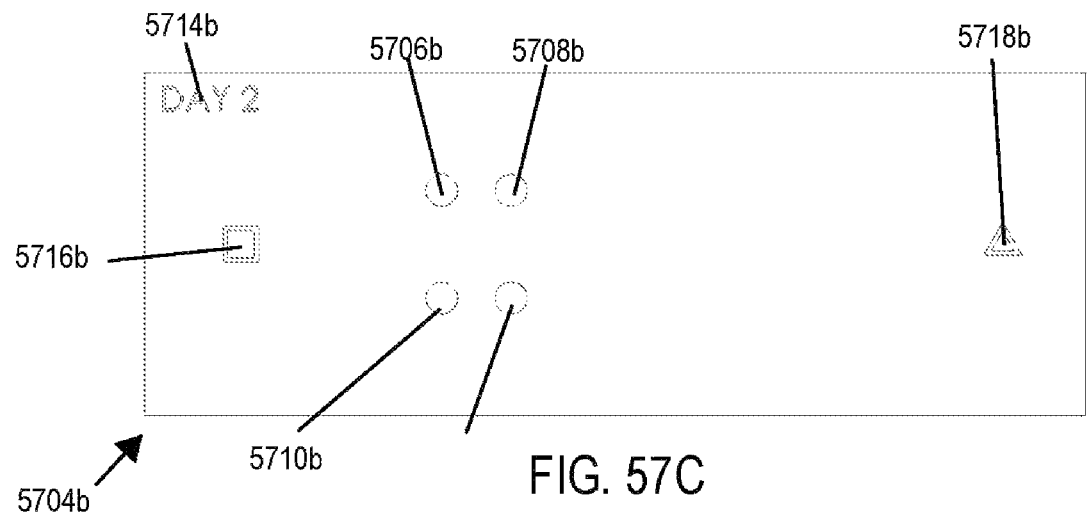
Figure 57D:
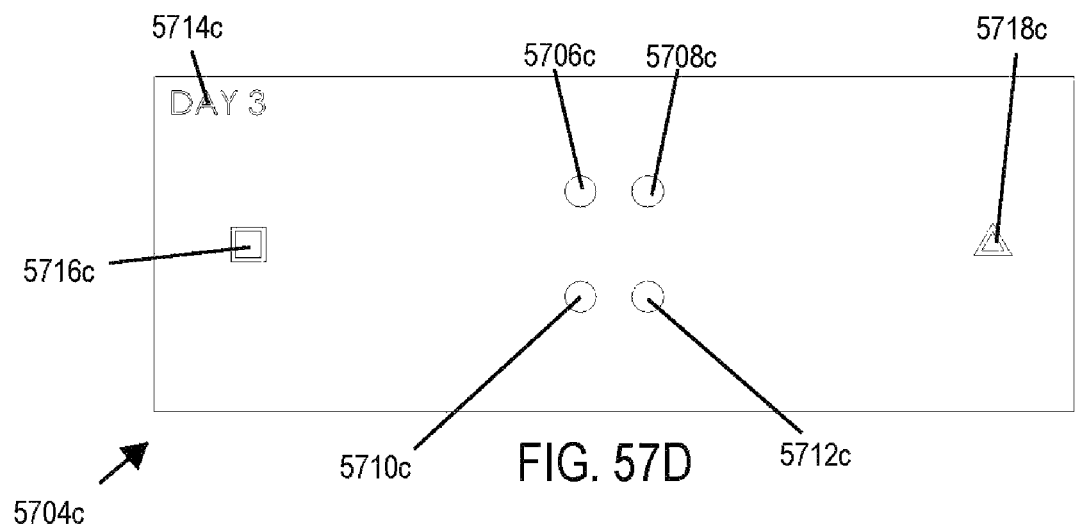

Referring to FIGS. 56A and 56B, in some other variations of a skin tensioning device 5600, whether radially strained or single-axis strained, the access opening 5602 of the device may comprise a fabric patch 5604. The patch 5604 may be configured with a woven fabric that permits the needle 5606 of the syringe 5608 to still pass through the access opening 5602 while providing some physical coverage of the injection site. The increased breathability may extend to use time of the device 5600. The fabric patch 5604 may provide increased water vapor transfer across the skin tensioning device 5600 and may also be used to absorb an excess insulin that may leak from the injection site. The fabric patch 5604 may be coated, infused or woven with an anti-infective agent, such as an antibiotic or silver strands. The fabric 5608 may comprise a nylon, non-woven cotton, polyester or polypropylene, an elastic polymer blend, or silver alginate, for example.

Figure 54A:
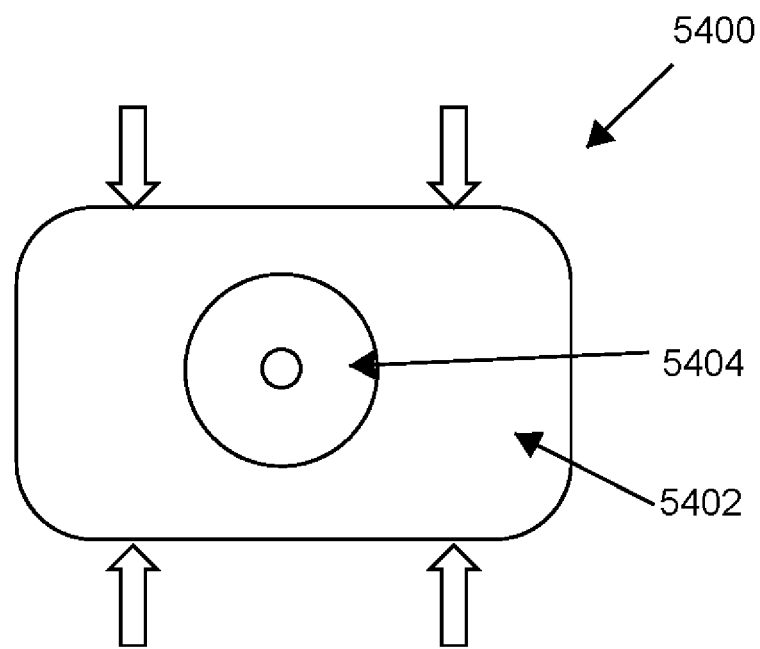
FIGS. 54A and 54B are superior plan and side elevational views of an exemplary infusion hub and catheter with a pre-attached skin tensioning device.
Figure 54B:
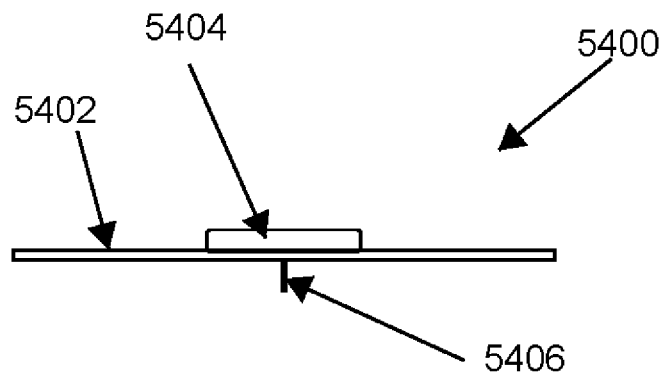

In still another alternative embodiment, a skin treatment system 5400 comprising a tension off-loading dressing 5402 but instead of an access opening or fabric patch, an injection port 5404 is provided on the dressing 5402, as shown in FIGS. 54A and 54B. The dressing 5402 and port 5404 may be provided with any of the applicators as described herein, noting that the region of the dressing 5402 attached to the port 5404 will not under the same strain as the portion of the dressing 5402 peripheral to the port 5404. The injection port 5404 includes a catheter 5406 such that syringes attached to the port 5402 or syringe needles inserted into the port are able to deliver therapeutic agents through the catheter 5406 and into the skin or tissue. Use of the port may reduce pain or discomfort associated with therapy, compared to direct needle injection.

Referring to FIGS. 41A to 43C, in another embodiment, an infusion set 4100 and a multi-layer tensioned dressing 4102 may be used for subcutaneous infusion or intravascular infusion. The infusion set 4100 comprises an infusion tubing 4104 that is connectable to an infusion source or pump, such as an insulin pump or other therapy pump, and is in fluid communication with an internal cavity of an infusion housing 4104 which is in turn in fluid communication with a subcutaneous needle or catheter 4106 which is inserted into the tissue or vasculature. The bottom surface of the infusion housing 4104 is adhered or attached to the top layer 4108a of the multi-layer tensioned dressing 4102. Each of layers 4108a to 4108c comprises a perimeter 4110a to 4110c that is sized to be smaller in size and is positioned within and offset from the perimeter 4110b to 4110d of the layer 4108b to 4108d immediately below it, except for an optional flap 4112a to 4112c. The elasticity of the top and intermediate layers 4108a, 4108b, 4108c may be configured to be lower than the modulus of elasticity of the base elastic layer 4108d.

The base layer 4108*d* may also have a higher durometer (e.g. 60 Shore A vs. 50 Shore A vs. 30 Shore A) or comprise a thicker material (e.g. 10 mil vs. 7 mil vs. 5 mil vs. 0.5 mil) compared to the other layers 4108*a*-*c*. In other variations, the non-base layers may comprise holes or perforations to reduce the total cross-sectional area of the non-base layer, which can reduce the amount of strain contributed from the non-base layers. With this configuration, the compressive force per unit width results primarily from the contribution of the base elastic layer 4108*d*, about 50%, 60%, 75%, 90% or any range between any two of these contribution percentages. Based on this, the amount of adhesion strength between the layers may be relatively lower than the bond strength between the skin and the base layer 4108*d*. The adhesive of layers 4108*a* to 4108*c*, may also be pattern coated onto the layers 4108*a* to 4108*c* to facilitate peeling in a direction orthogonal to the strain. For example, multiple narrow strips of adhesive may be provided in the direction of the peel. The width of the adhesive orthogonal to the direction of the strain in the elastic member may be 0.1", 0.165", 0.2", 0.3" or 0.5" or any range between any two of such widths. In another examples, an adhesive pattern may be provided where less adhesive is peel direction as compared to the strain direction, e.g. 20% less, 40% less, 60% less, 80% less, or a range between any two of these percentages, or other type of anisotropic adhesive pattern. The interlayer adhesives used to join all of the layers 4108*a*-*d* together may comprise a lower thickness compared to the skin adhesive (e.g. 0.5 mil, vs. 0.25 mil, vs. 0.1 mil). In other variations, an adhesive with a high-tensile strength but low shear strength may be used, to facilitate removal of an upper layer of the multi-layer tensioned dressing by pulling the layer or adhesive layer laterally rather than upward. This nested configuration results in a stepped dressing profile, as depicted in FIGS. 44A and 44B, which may redistribute edge stresses of a skin tensioning device across a greater surface area, rather than concentrate them at the edge of a single layer skin tensioning device. In some variations, the separation between the perimeters 4110*a* to 4110*d* of adjacent layers 4108*a* to 4108*d* may be uniform along the entire perimeter, e.g. a uniform perimeter difference in the range of 1 to 5 mm, 2 to 5 mm, or 2 to 4 mm, or 2 to 3 mm, for example. In some further examples, the uniform perimeter difference between two adjacent layers 4108*a* to 4108*d* is the same for every two adjacent layers 4108*a* to 4108*d*. In other examples, the uniform perimeter difference may be different between at least one pair of two adjacent layers. For example, the perimeters 4110*a* and 4110*b* may be the same as 4110*b* and 4110*c*, but the uniform perimeter difference between layers 4110*c* and 4110*d* may be smaller or larger then uniform perimeter difference of the other pairs of layers 4108*a* to 4108*c*. Layer 4108*d* in FIG. 41A does not have a flap, but in other embodiments may also be provided with a flap. The flaps 4112*a* to 4112*c* may or may not comprise adhesive on its inferior surface, which may facilitate separation and grasping of the flap 4112*a* to 4112*c* from the other layers for removal. Each of the layers 4108*a* to 4108*d* also comprises a center opening (not shown) through which the needle or catheter 4106 of the infusion set 4100 may be inserted. This nested layer configuration of the multi-layer dressing 4102 may not have a flap The flexible attachment sheet 4108 is sized and configured with a perimeter 4112 that is smaller than a perimeter 4114 of the multi-layer tensioned dressing 4102.

Figure 41A:
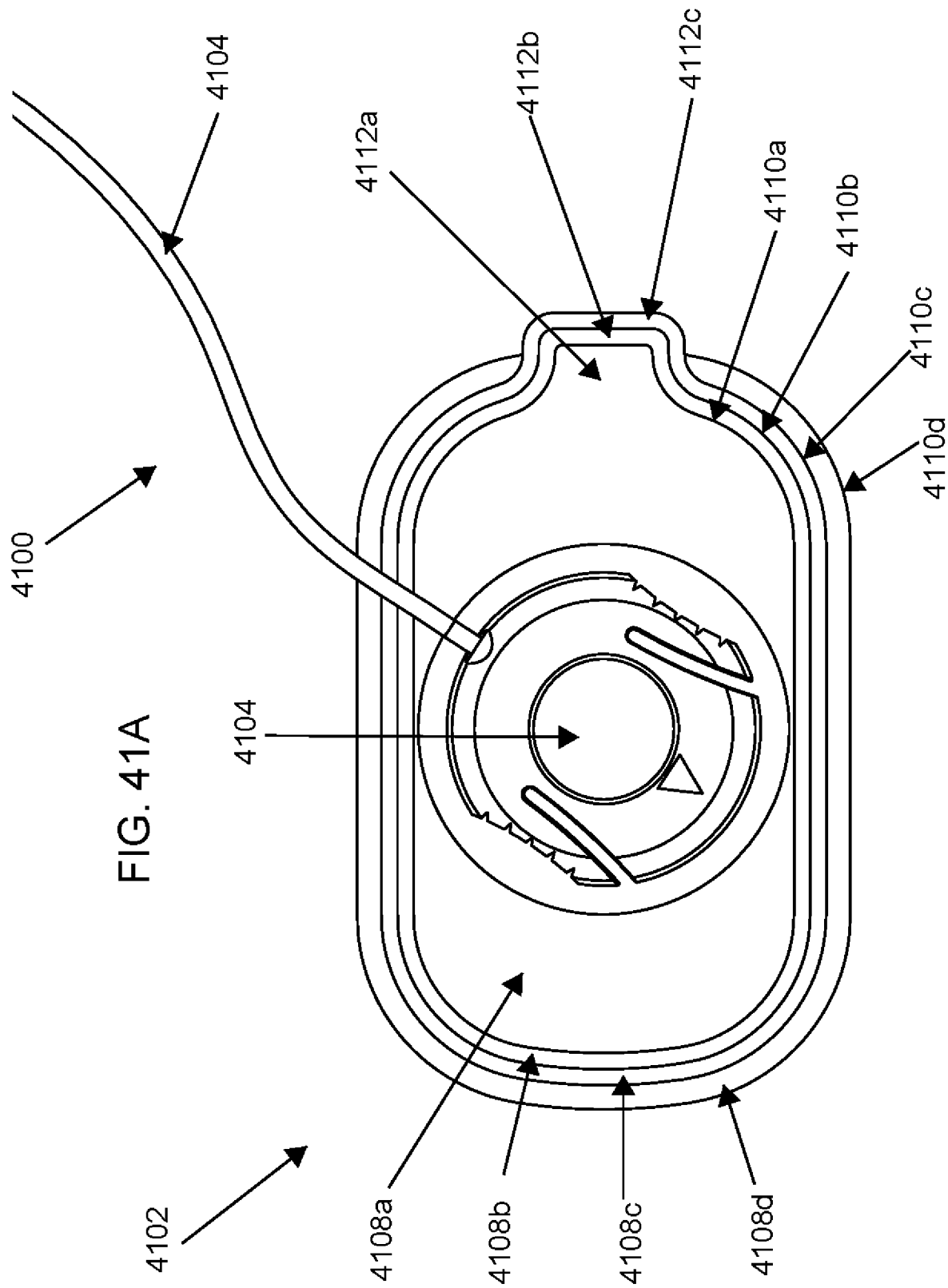
FIG. 41A is a superior plan view of another embodiment of a combined infusion set with a multiple separable tensioning layers.

Although the exemplary embodiment depicted in FIGS. 41A and 41B comprises a four-layer skin tensioning device 4102, in other examples, the skin tensioning device may comprise two, three, five or more layers. The infusion set 4100 and the skin tensioning device 4102 may be pre-assembled at the point of manufacture, assembled at the point-of-use, or assembled serially at the treatment site, with the skin tensioning device 4102 place first, followed by the infusion set 4100 through and onto the skin tensioning device 4102. The applicator for the skin tensioning device 4102 may be the book-type applicator as described herein. In another variation, the infusion device 4100 may be pre-attached to one flexible layer of adhesive material larger than the infusion set housing 4104 and comprises a similar material and adhesive as the layers of the multi-layer skin tensioning device. During use, the skin tensioning device is strained and applied to the skin, but the infusion device 4100 and its pre-attached flexible layer of material are not strained when applied to the multi-layer skin tensioning device.

As depicted in FIGS. 42A to 43C, when the infusion set 4100 needs to be replaced, e.g. due to occlusion or to reduce the risk of infection, the flap 4112*a* of the top layer 4108*a* may be grasped and then lifted up to separate the adhesive of the top layer 4108*a* from the intermediate layer 4108*b*, or to otherwise peel away the top layer 4108*a* from the intermediate layer 4108*b*, thereby also lifting up the infusion 4100 up with the top layer 4108*a*, and pulling out the catheter 4106 from the skin, while leaving the other layers 4108*b*-*d* of the multi-layer skin tensioning device on the skin, thereby minimizing the frequency that the adhered skin tensioning device is separate from the skin. This may reduce irritation of the underlying skin from repeated removal of an adhered device. Once the infusion set 4100 is removed along with the top layer 4108*a*, a new infusion set 4100 may be applied to directly to the intermediate layer 4108*b*, by aligning the delivery location of the catheter 4106 of the new infusion set 4100 with the opening 4114*b* of the intermediate layer 4108*b*. This cycle of removal and reapplication may be performed several times equal to the number of layers in the skin tensioning device, with subsequent cycles of new infusion sets removed and applied to the next layer, with the base layer 4108*d* also being used and later removed with the final infusion set 4100.

Like other embodiments described herein, the skin adhesive on the bottom layer of the skin tensioning device may be the same or different adhesive used to attach the strain support to the dressing, and/or the adhesive used to attach the multiple layers of the skin tensioning device together. In some examples, the skin adhesive may be selected with a greater T-peel force than the adhesive used to attach the support. In other examples, the adhesive used to attach the support may have a higher T-peel force. A higher T-peel force may be selected where the predetermined strain in the dressing is needed to resist strain loss during storage of a pre-strained device. A protective or adhesive release sheet may be applied to the skin adhesive to protect the skin adhesive against unintentional adhesion during storage or application. Coatings on the release sheet, and layers of the dressing may also be provided to facilitate peeling or removal of the release sheet, the layers, and the strain support during use. The strain support for this embodiment may include the perforation and pull tab separation mechanism (not shown) as described for dressing 3926 in FIGS. 39A, to releasably maintain the strain with at least layer 4108*d*, but may also be configured to directly releasably maintain strain in the other layers 4108*a*-*c* as well.

Figure 45A:
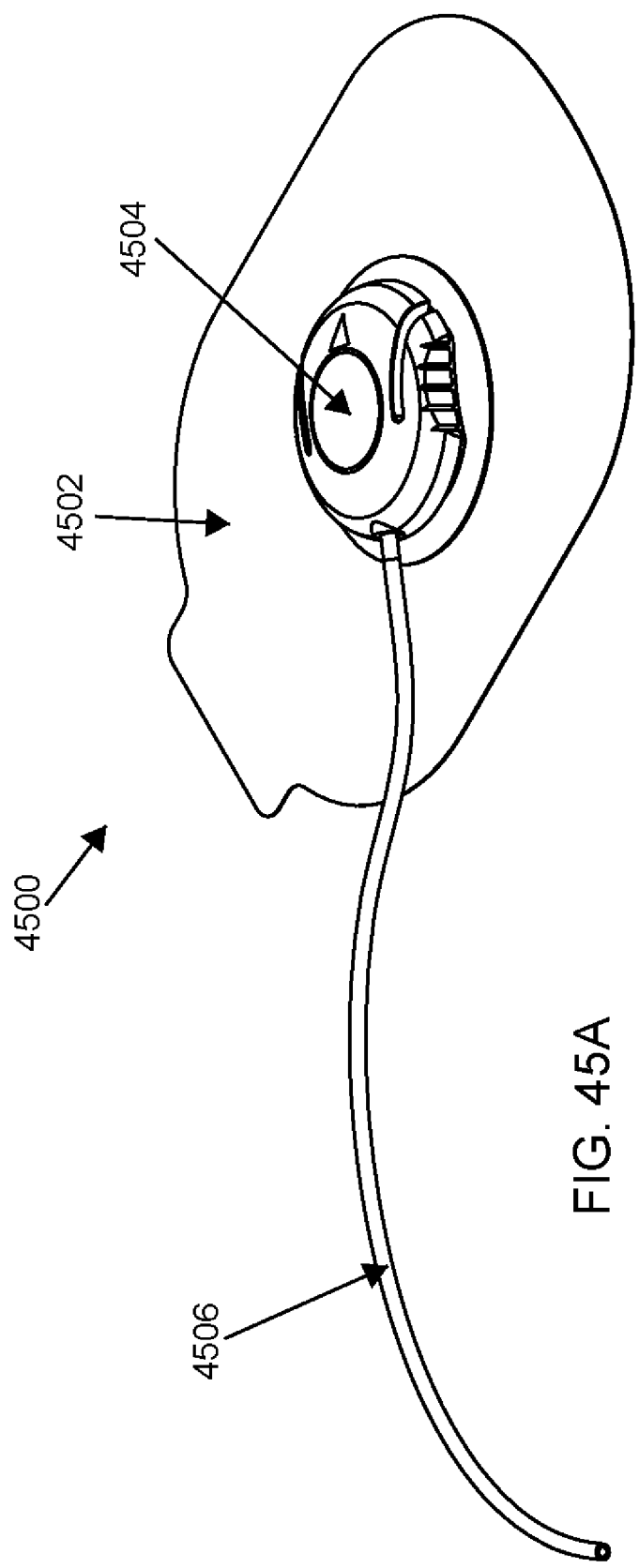
FIG. 45A is a superior plan view of another embodiment of a combined infusion set with a multiple separable tensioning layers.
Figure 45B:
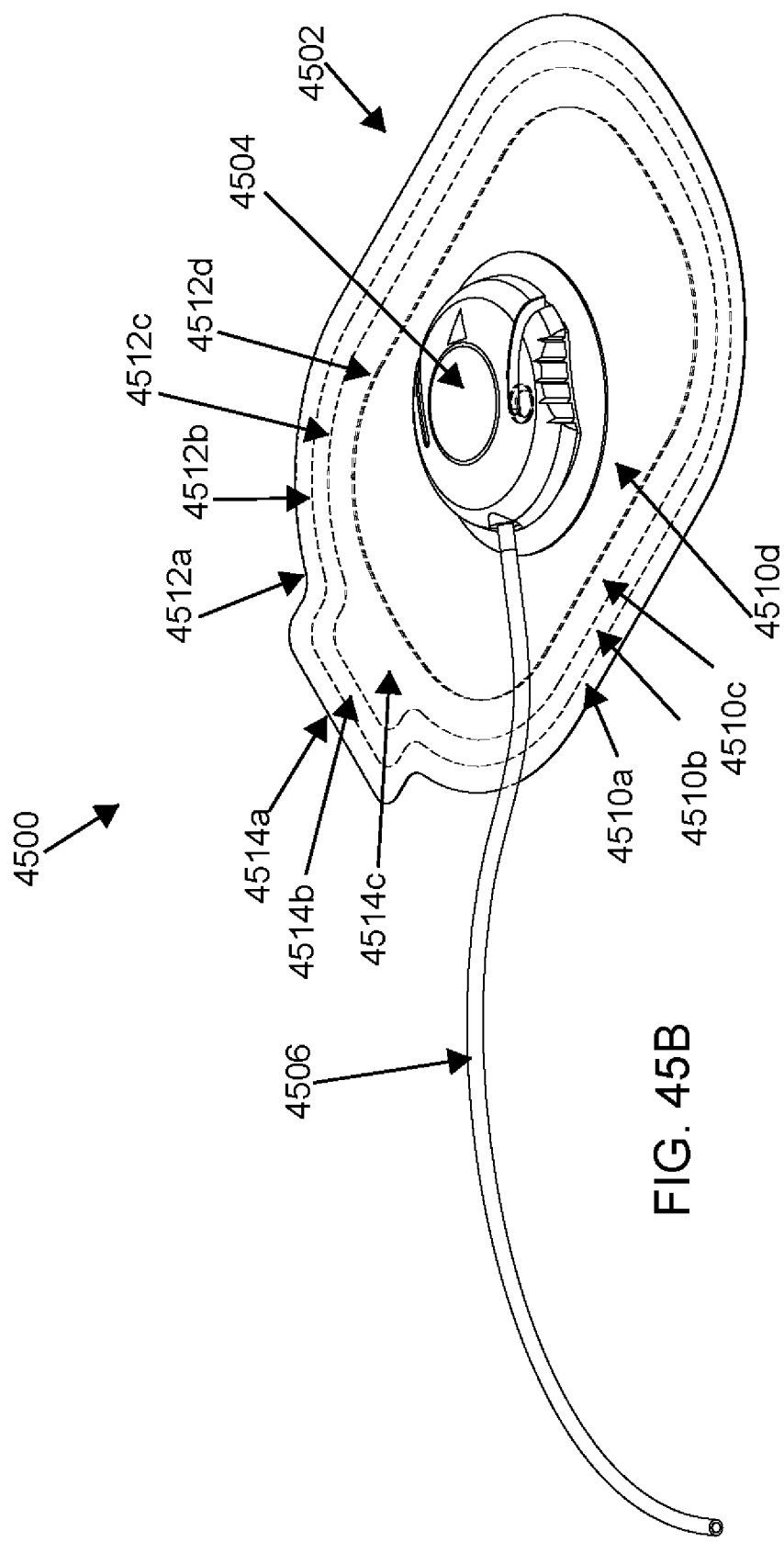
FIG. 45B is a superior perspective schematic view of the embodiment in FIG. 45A.
Figure 47B:
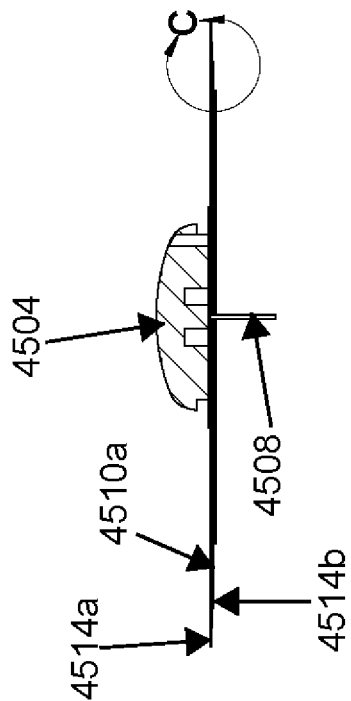
FIGS. 47A and 47B are top and side elevational views of the method depicted in FIGS. 46A to 46C.
Figure 47C:
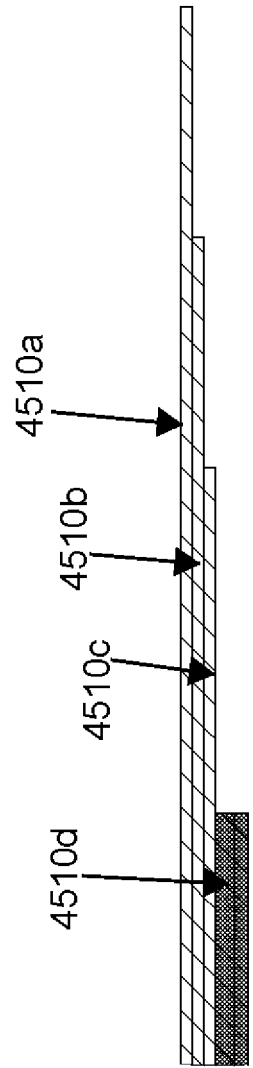
FIG. 47c is a detailed view of the edges of the multiple tensioning layers in FIG. 47B.
Figure 47A:
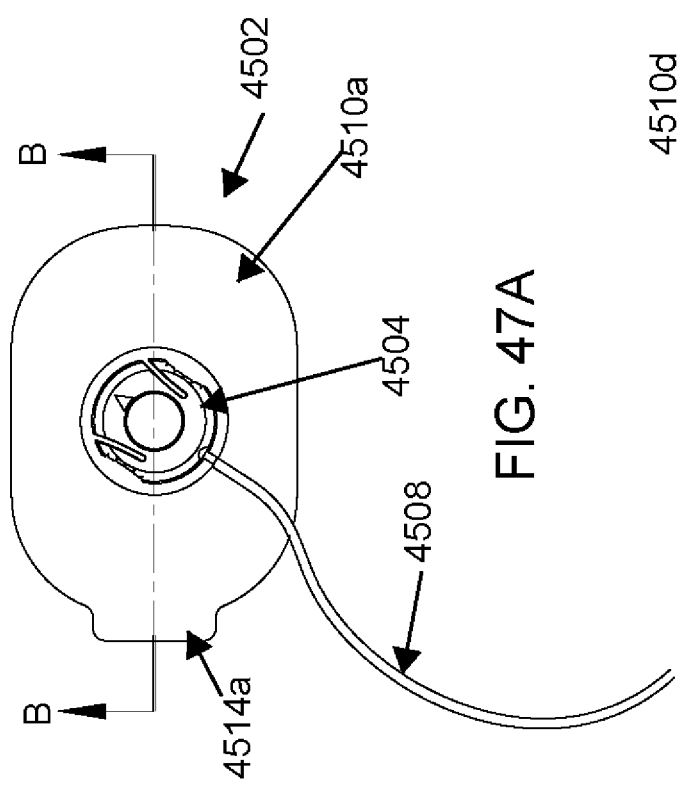

FIGS. 45A and 45B depict another example of an infusion set 4500 with a multi-layer dressing 4502 pre-attached to an infusion hub 4504, tubing 4506 and catheter 4508, but in this variation, the lower layers 4510*b*-*d* are smaller than the adjacent upper layers 4510a-c. This configuration is also a stepped dressing profile, which may redistribute edge stresses of a skin tensioning device across a greater surface area, rather than concentrate them at the edge of a single layer skin tensioning device. The base layer 4510d, however, has a smaller adhered surface area, and the upper layers 4510a-c are only adhered to the skin about their periphery. Like the embodiment depicted in FIGS. 41A to 44B, the separation between the perimeters 4512a to 4512d of adjacent layers 4512a to 4512d may be uniform along the entire perimeter, e.g. a uniform perimeter difference in the range of 1 to 5 mm, 2 to 5 mm, or 2 to 4 mm, or 2 to 3 mm, for example. The uniform perimeter difference between two adjacent layers 4510a 4510b may be the same for each two adjacent layers 4510a to 4510d, or may be different. In other examples, the uniform perimeter difference may be different between at least one pair of two adjacent layers. The layers 4510a-d may also comprise optional flaps 4514a-c, to facilitate grasping and removal of the layers 4510a-c. The other features of the device may otherwise be similar to the four-layer skin tensioning device 4102 in FIGS. 41A and 41B, e.g. the heat staking and adhesive configurations.

As depicted in FIGS. 46A to 47C, when the infusion set 4500 needs to be replaced, e.g. due to occlusion or to reduce the risk of infection, the flap 4514a of the top layer 4510a may be grasped and then lifted up to separate the adhesive of the top layer 4510a from the intermediate layer 4510b, or to otherwise peel away the top layer 4510a from the intermediate layer 4510b, thereby also lifting up the infusion hub 4504 up with the top layer 4108a, and pulling out the catheter 4108 out of the skin, while leaving the other layers 4510b-d of the multi-layer skin tensioning device 4502 on the skin. This minimizes the frequency that the adhered skin tensioning device 4502 is pulled off of the skin. This may reduce irritation of the underlying skin from repeated removal of an adhered device 4502. Once the infusion hub 4504 is removed along with the top layer 4510a, a new infusion set 4500 may be applied to directly to the intermediate layer 4510b, by aligning the delivery location of the catheter 4508 of the new infusion set 4500 with the opening 4516 of the intermediate layer 4510b. This cycle of removal and reapplication may be performed several times equal to the number of layers in the skin tensioning device, with subsequent cycles of new infusion sets removed and applied to the next layer, with the base layer 4510d also being used and later removed with the final infusion set 4100. The strain support for this embodiment may include the perforation and pull tab separation mechanism (not shown) as described for dressing 3926 in FIGS. 39A, to releasably maintain the strain with at least layer 4510d, but may also be configured to directly releasably maintain strain in the other layers 4510a-c as well.

In another embodiment, a skin tensioning system for treating a therapy injection or infusion site may comprise a pair of tension dressings 5200 and 5202, as depicted in FIG. 52. Each of the dressings 5200 and 502 may be provided a dressing tension applicator (not shown) as described herein, e.g. book applicator. The dressings 5200, 5202 may have separate applicators, but in some embodiments, may be provided on the same applicator with a predetermined spacing or gap 5204 between the dressings 5200, 5202 as configured in the applicator. During use, or as supplied in the applicator, the gap 5204 may be in the range of about 1-20 mm, 2-10 mm, 3-8 mm, 4-6 mm, for example. Each of the dressings 5200, 5202 are tensioned along a tensioning axis 5206, 5208, if the dressings were not pretensioned at the point-of-manufacture. The applicator may also comprise visual alignment indicia so that any prespecified spacing or gap 5204 between the dressings 5200, 5202 may be aligned or oriented as needed to a particular injection or infusion site. Each of the dressings 5200, 5202 are placed adjacent to the desired injection or infusion site 5210, on opposite sides of the target site 5210. Each dressing 5200, 5202 may comprise a treatment edge 5212, 5214 that are aligned in a parallel fashion to define the gap 5204 between the dressings 5200, 5202. The gap 5204 on the skin or on the applicator may be characterized by a longitudinal gap axis 5216, which may also be parallel to the tension axes 5206, 5208 of the corresponding dressings 5200, 5202. After each dressing 5200, 5202 is positioned about the target site 5210, the applicator or strain support for each is released, allowing the dressings 5200, 5202 to at least partially relax and compress the skin surrounding the target site 5210. This resulting skin compression is generated at the target site 5210 without any dressing completely surrounding or covering the target site 5210, although support of skin tension orthogonal to the tensioning axes 5206, 5208 and gap axis 5216 is reduced because the two dressings 5206, 5208 are completely separate along that direction.

In still another embodiment, a skin tensioning dressing 5300 for treating a therapy injection or infusion site may comprise a pair of tension lobes or sections 5302 and 5304, as depicted in FIG. 53. Each of the sections 5302 and 5304 are integrally formed with an interconnect or bridge 5306 and a separated by a section gap 5308. The gap 5308 may be in the range of about 1-20 mm, 2-10 mm, 3-8 mm, 4-6 mm, for example. The dressing 5300 may be provided with an applicator as described elsewhere herein. Each of the dressing section 5302, 5304 are tensioned along a tensioning axes 5310, 5312. The applicator may also comprise visual alignment indicia so that the gap 5308 may be aligned or oriented as needed to a particular injection or infusion site. Each of the dressing sections 5302, 5304 are positioned with the target site is in the gap 5308. After the dressing 5300 is located and adhered to the desired target site, the applicator or strain support is released, allowing the dressing sections 5302, 5304 to at least partially relax and compress the skin surrounding the target site.

Any of the skin tension off-loading devices corresponding to FIGS. 30A to 56B may be evaluated with proposed study designs to evaluate the effects of skin tension offloading on insulin pharmacokinetics, dosing, therapeutic efficacy, and/or the development of lipohypertrophy are described below, including potential health economic benefits. Diabetes patients currently treated with insulin will be randomized to a treatment group or control group, with treatment comprising use of the skin tension offloading devices selected from those corresponding to FIGS. 30A to 56B may be used for 4 weeks to 5 years or more, 4 weeks to 2 years, 8 weeks to 1 year as described herein. The dressings or skin tension offloading devices, or a layer and/or infusion set may be changed every three days, or every 2 to 14 days, 3 to 10 days, 10 to 14 days, 5 to 7 days, 3 to 5 days, 2 to 3 days for the selected study period.

It is hypothesized that applying a skin tension offloading device in a substantially continuous fashion may reduce the risk, progression or severity of a lipodystrophy, including lipohypertrophy in insulin-dependent patients. By reducing or limited the development of lipohypertrophy, dose progression or therapeutic effect variability relating to lipohypertrophy may be slowed or reduce. It is also hypothesized that some of the effects on dose progression and therapeutic effect variability may be independent of the development or progression of lipohypertrophy, and may be a direct result of the skin tension off-loading device on tissue mechanics and pharmacokinetics. The use of a skin tension offloading device configured with predetermined levels of strain will permit controlled and consistent delivery of strain level and to measure effects of different consistent levels of strain, compared to other skin tensioning devices that are manually adjusted in an ad hoc fashion, as with many sutureless wound closure devices. Initial studies may include patients with preexisting lipohypertrophy and/or high daily insulin dosing requirements, to more easily identify clinical effects. Using the long-term data from the studies, an outcome flowchart will be developed and costs per event will be estimated so that a cost-effectiveness and/or health economic analysis may be performed. In conjunction with patient quality of life measures, a quality-adjusted life-year cost may also be calculated.

In one proposed study evaluating the effects of one or more of the tension offloading devices will be evaluated in insulin-dependent patients with preexisting lipohypertrophy mass, to assess whether the tension offloading devices can alter the pharmacokinetics or delivery kinetics of insulin to patients who inject or infusion insulin or an insulin analogue to a site with pre-existing lipohypertrophy. Diabetes patients will be screened for lipohypertrophy masses in the range of 6-10 cm and then randomized to have a tension offloading device applied during the study. Each patient will be randomized to a test day where they will each undergo two glucose absorption tests after an overnight fast, where the tests are separated by a minimum of 7 days and an overnight fast before the tests. An indwelling catheter will be placed for each patient to provide blood samples for blood glucose and insulin levels during the test period. Baseline levels are measured and then each patient will receive a subcutaneous injection of 10 units of insulin through the access opening of the skin tension offloading device in the treatment group, or directly to the skin location in the control group. Blood samples will be obtained every five minutes for the first thirty minutes, then every ten minutes for the next 60 minutes, then every 30 minutes for the next 2.5 hours. The maximum concentration of plasma insulin at each time period will be determined as well as the time to maximum insulin concentration, and the area under the insulin concentration curve will be analyzed to assess any direct effect of the skin offloading device on insulin absorption.

In another proposed study, patients will be randomized to receive skin offloading treatment kits in conjunction with insulin or insulin analogue injection or infusion, for use over a treatment period of 4 weeks, 6 weeks, 8 weeks, 3 months, 4 months, 6 months 9 months, 12 months, 18 months or 24 months, for example. The tension off-loading treatments will be used as directed with replacement of the device, or change in a layer of a multi-layer device, every 2 days, 3 days, 4 days or 5 days, or as needed. Blood glucose will be measured at least 4 times per day, and compliance with blood glucose measurements and use of tension offloading devices will be assessed. The analysis will be an intent-to treat analysis and the mean amplitude of glucose excursion will be calculated over the treatment period and the postprandial area under the curve will be calculated for each mealtime over the treatment period. Alternatively or in addition, hemoglobin A1C will be measured at baseline and at each follow-up to assess the effects of the skin tension offloading device. A health economic study and/or a patient quality-of-life study may also be included in the analysis.

Patient inclusion criteria may include one or more of the following:
Patients with or without prior history of lipohyperdystrophy
Patients with a lipohypertrophy mass in the range 5-10 cm
Patients with high daily insulin dose requirements of a least 0.9 UI per Kg
Patients with minimum insulin use of 50 IU/day
Treatment with insulin or insulin analogue for at least one year prior to enrollment
Prior experience with rapid-acting insulin analog for at least 6 months
Type I or Type II diabetic patients
Treatment is self-administered or given by a caregiver
Current treatment includes at least two to four injections per day, or insulin pump use
Body Mass Index in the range of 20 to 35 kg/m 2.
Stable body weight for 3 months prior to enrollment (<5% change in body weight)
Hemoglobin A1C≤8.5%
C-peptide <0.6 nmol/L at screening
Patient exclusion criteria may include one or more of the following:
Pre-existing lipodystrophy or lipohypertrophy
Children under the age of 5 years
Patient not currently treated with insulin or analogue
Women with gestational diabetes
History of hypoglycemic unawareness
History of diabetic ketoacidosis within 6 months of screening
History of cardiovascular disease
History of arrhythmia The primary and secondary endpoint(s) will assess the development or presence of lipohypertrophy and/or changes in blood glucose or blood glucose variability factors at each visit. The initial assessment and each follow-up visit will include evaluation of:
Serial ultrasound scans using a linear 20 MHz probe using B-mode imaging:
Classification:
Simple subcutaneous hypertrophy
Diffuse hyperechoic subcutaneous dystrophy
Nodular hyperechoic dystrophy
Focal and diffuse hyperechoic subcutaneous dystrophy
Nodular hypoechoic subcutaneous dystrophy
Subcutaneous atrophy
Complex multilayer dystrophy
Fibrosis level
Iso-hyperechogenic
Isoechogenic
Iso-hypoechogenic
Direct and tangential light inspection and color photography of the treatment site, against a dark background
Classification of the treatment site as to shape and size using palpation and skin calipers:
Small nodule—visible on inspection, easy to palpate with an elastic consistency
Large nodule—clearly visible on inspection, easy to palpate, with a hard to elastic consistency
Flat plate—slightly raised and somewhat visible, difficult to palpate except with skin pinching, with an elastic consistency
Flat nodule—not visible but palpable on deep palpation or skin pinching, with an elastic consistency
Size, including <4 cm and >4 cm
Clinical Grading, from zero to 3:
0—no changes 1—visible hypertrophy but normal consistency on palpation
2—substantial thickening and denser consistency
3—evidence of lipoatrophy Validated diabetes questionnaires (start and end of study only)
Problem Areas in Diabetes Questionnaire
Diabetes Treatment Satisfaction Questionnaire At the end of the study, the percentage change in prandial insulin and total daily insulin dosing, time-in-range (70-140 mg/dl) and out-of-range (<70 mg/dl and >180 mg/dl) for studies with patients using continuous glucose monitoring devices, hemoglobin A1C, the number of hypoglycemic events, the number of diabetic ketoacidosis events will be calculated and compared between the treatment and control groups. For studies involving patients with CGM or insulin pumps, pain assessments during cannula/infusion set insertion removal, cannula/infusion set malfunction (occlusion, needle deformation), will be assessed and compared.

In some further variations, the various tissue tension off-loading devices and systems described herein may be used for both a continuous subcutaneous insulin infusion set (SCII) and for a sensor of a CGM system, i.e. a closed loop therapy/sensing system, also known as an "artificial pancreas" or a double subcutaneous approach. It is hypothesized that the tension off-loading devices may promote a longer wear time, reduce physiologic or sensor-based latency, sensor drift for the infusion set and/or CGM sensor system, which may result in improved glucose control. This may be the result of reducing mechanical irritation or inflammation at the infusion and/or sensor site, which may lead to fibrosis. CGM devices measure glucose concentrations in the interstitium. Interstitial glucose fluctuations relate to blood glucose presumably via diffusion. CGM calibration quality and inaccuracy from loss of sensitivity and random noise, are all affected by the time lag due to blood glucose to interstitial glucose transport.

In another proposed study, the effects of applying a tensioned tissue treatment device to an insulin injection or infusion site with lipohypertrophy will be analyzed. Eligible participants will include adults aged 18 to 70 years with type 1 diabetes taking insulin by multiple daily injections (at least three injections daily) for at least two years and who have at least two distinct palpable lipohypertrophy lesions on the abdomen for use for the injections. Each LH lesion must be a minimum of 3 cm in one dimension. LH lesions less than 2 years old will be selected. Subjects may or may not be using a continuous glucose monitor but will be asked to wear a CGM as part of the study protocol. HbA1c must be in the range of 7.5% to 10.5% at the screening visit. A punch biopsy of an LH lesion may be obtained at the start and at the last study visit.

The initial examination and patient screening procedure may include a physical examination for the LH lesions, with recordation of the LH dimensions. CBC/chemistry blood panels, urinalysis, HbA1c will be obtained. A CGM will be applied for 10 to 14 days to monitor the patients.

Patients meeting eligibility criteria return for the next visit, where the CGM data is downloaded to capture glycemic profiles establish baseline blood glucose and insulin use. A punch or needle biopsy of one of the lipohypertrophy region is performed and closure is performed, if needed, with sutures. For patients with three or more LH lesions satisfying eligibility criteria, the two LH lesions will be selected based on randomized selection, and the biopsied LH lesion is randomly selected from the two selected LH lesions. For punch biopsies, the biopsy size may be in the range of 1 mm to 10 mm, 1 mm to 8 mm, or 5 mm to 8 mm in diameter, and verified during the biopsy procedure to include at least some subcutaneous tissue. For needle biopsies, the needle size may be 18 gauge to 25 gauge needle. A tensioned tissue treatment device is then applied to the LH lesion that was biopsied. Each patient is taught the two locations of the LH lesions and taught not to perform any injections into the either of the LH lesions for the duration of the study. The patient is also instructed on how to change over their insulin regimen to a rapid-acting insulin analogue. Because of the limited availability of drug assays, such as those available for insulin lispro, e.g. HUMALOG (Lilly; Indianapolis, IN), and rapid-acting insulin lispro, e.g. LYUMJEV (Lilly; Indianapolis, IN), the rapid-acting insulin selected for the regimen may be selected to be different from that used during insulin PK-PD testing, e.g. insulin aspart, e.g. NOVOLOG® (Novo Nordisk; Plainsboro, NJ).

The tensioned tissue treatment devices are applied to selected LH lesion for a time period in the range of 4 to 12 weeks, or 6 to 8 weeks, or 4 to 6 weeks before returning for study follow-up. At the next follow-up visit, insulin sensitivity will be measured by a hyperinsulinemic euglycemic clamp (HEC) testing. The blood glucose of each subject will be adjusted to 100 mg/dL (±5 mg/dL) prior to the start of the test procedure, using either glucose or insulin, without simultaneous infusion. Any insulin infusion is tapered off and stopped for at least 10 minutes prior to clamp testing. Each subject will undergo six 6-hour HEC tests, two for each of the injection sites, with the sequence individually randomized. At the start of each test, 0.15 units/kg of insulin will be initially injected, into normal adipose tissue, the untreated LH lesion, and the LH lesion that was treated with the tensioned tissue treatment device, as specified by the randomized sequence. The euglycemic clamp equipment is then used to record blood glucose levels every minute during the clamp procedure, and to automatically adjust a glucose infusion rate to maintain the blood glucose within the target range. Insulin levels are measured during the test, e.g. at 15, 30, 45 60, 80, 100, 120, 150, 180, 210, 240 and 300 minutes after the insulin injection into the test site. From the HEC testing, the area-under-the insulin concentration curve, the $C_{max}$ insulin level and the area-under-the blood glucose infusion rate curve, and the intrasubject coefficient of variation for each of these measures may be calculated for each test injection into normal adipose tissue, the untreated LH lesion and the treated LH lesion. It is hypothesized that the untreated LH lesion will have the lowest $AUC_{INS}$, $C_{max}$ and $AUC_{GIR}$, and the highest corresponding coefficient of variation for each test compared to normal adipose tissue and the treated LH lesion site, with the treated LH lesion site showing an improvement over the untreated LH lesion site. The change or progression in tissue stiffness, as measured by a CUTOMETER® (Courage+Khazaka electronic GmbH; Kohn, DE) and/or the effect size of the pharmacokinetic/pharmacodynamics improvements is hypothesized to be at least 10%, 15%, 20% or 25% for the treated LH lesion compared to the untreated LH lesion. Following completion of the HEC testing, each subject will resume their usual diabetes therapy for two weeks, while continuing to use the CGM and to apply the tensioned tissue treatment device to the same LH lesion that was selected for treatment.

Upon the next two week return visit, the LH lesions are re-measured, and last period of CGM data will be downloaded and pre-testing labs are obtained. Each subject will also re-initiate the use of a shorter acting insulin as before with the HEC testing, in order to wash-out any longer-acting insulin used by the subject with their usual diabetes therapy.

The a washout period will be at least 12 hours to three days prior to the mixed-meal tolerance testing (MMTT), depending on the type of insulin used in their usual diabetes regimen. During the MMTT, a rapidly absorbed of 75 g of carbohydrate (56% meal caloric content), 20 g of fat (33%) and 15.2 g protein (11%) is consumed. The data acquisition for the MMTTs would otherwise be the same as for the HEC testing. It is hypothesized that the untreated LH lesion will again have the lowest $AUC_{INS}$, $C_{max}$ and $AUC_{GIR}$, and the highest corresponding coefficient of variation for each test compared to normal adipose tissue and the treated LH lesion site, with the treated LH lesion site showing an improvement over the untreated LH lesion site. Following completion of the MMTTs, each subject will resume their usual diabetes therapy and cease the use of the tensioned tissue treatment. End-of-study labs and physical examination will be performed. In some variations of the study, the MMTT is performed once for each test site, but in other variations of the study, may be performed twice for each site and the results averaged.

In another study, the effects of applying tensioned tissue treatment on normal adipose tissue will be assessed. Eligible participants will include adults aged 18 to 70 years with type 1 diabetes taking insulin by multiple daily injections (at least three injections daily) for at least two years. Subjects may or may not be using a continuous glucose monitor but will be asked to wear a CGM as part of the study protocol. HbA1c must be in the range of 7.5% to 10.5% at the screening visit. The initial examination includes a physical examination, lab tests for CBC/chemistry blood panels, urinalysis, and HbA1c. A CGM will be applied for 10 to 14 days to monitor the patients.

At the next visit, the CGM data is downloaded to establish baseline blood glucose and insulin use. A tensioned tissue treatment device is then applied to one of two selected injection sites that is free of lipohypertrophy. The patient is also instructed on how to change over their insulin regimen to a rapid-acting insulin analogue Because of the limited availability of drug assays, such as those available for insulin lispro, e.g. HUMALOG (Lilly; Indianapolis, IN), and rapid-acting insulin lispro, e.g. LYUMJEV (Lilly; Indianapolis, IN), the rapid-acting insulin selected for the regimen may be selected to be different from that used during insulin PK-PD testing, e.g. insulin aspart, e.g. NOVOLOG® (Novo Nordisk; Plainsboro, NJ).

The tensioned tissue treatment devices are applied to selected injection sites for a time period in the range of 4 to 12 weeks, or 6 to 8 weeks, or 4 to 6 weeks before returning for study follow-up. At the next follow-up visit, insulin sensitivity will be measured by a hyperinsulinemic euglycemic clamp (HEC) testing. The blood glucose of each subject will be adjusted to 100 mg/dL (±5 mg/dL) prior to the start of the test procedure, using either glucose or insulin, without simultaneous infusion. Any insulin infusion is tapered off and stopped for at least 10 minutes prior to clamp testing. Each subject will undergo four 6-hour HEC tests, two for each injection site, with the sequence individually randomized. At the start of each test, 0.15 units/kg of insulin will be initially injected, twice into untreated normal adipose tissue, twice into the treated injection site, for a total of four tests. The euglycemic clamp equipment is then used to record blood glucose levels every minute during the clamp procedure, and to automatically adjust a glucose infusion rate to maintain the blood glucose within the target range. Insulin levels are measured during the test, e.g. at 15, 30, 45 60, 80, 100, 120, 150, 180, 210, 240 and 300 minutes after the insulin injection into the test site. From the HEC testing, the area-under-the insulin concentration curve, the $C_{max}$ insulin level and the area-under-the blood glucose infusion rate curve, and the intrasubject coefficient of variation for each of these measures may be calculated for each test injection into untreated normal adipose tissue, and the treated injection site. It is hypothesized that the untreated injection site will have the lowest $AUC_{INS}$, $C_{max}$ and $AUC_{GIR}$, and the highest corresponding coefficient of variation for each test compared to the treated injection site. Following completion of the HEC testing, each subject will resume their usual diabetes therapy for two weeks, while continuing to use the CGM and to apply the tensioned tissue treatment device to the same injection site that was selected for treatment with the tensioned tissue treatment system.

Upon the next two week return visit, injection sites will be re-evaluated, and last period of CGM data will be downloaded and pre-testing labs are obtained. Each subject will also reinitiate the use of a shorter acting insulin as before with the HEC testing, in order to wash-out any longer-acting insulin used by the subject with their usual diabetes therapy. The washout period will be at least 12 hours to three days prior to the mixed-meal tolerance testing (MMTT), depending on the type of insulin used in their usual diabetes regimen. During the MMTT, a rapidly absorbed of 75 g of carbohydrate (56% meal caloric content), 20 g of fat (33%) and 15.2 g protein (11%) is consumed. The data acquisition for the MMTTs would otherwise be the same as for the HEC testing. It is hypothesized that the untreated injection site will again have the lowest $AUC_{INS}$, $C_{max}$ and $AUC_{GIR}$, and the highest corresponding coefficient of variation for each test compared to the treated LH lesion site. Following completion of the MMTTs, each subject will resume their usual diabetes therapy and cease the use of the tensioned tissue treatment. End-of-study labs and physical examination will be performed. In some variations of the study, the MMTT is performed once for each test site, but in other variations of the study, may be performed twice for each site and the results averaged.

In variant of the proposed studies above, patients will wear and collecting 14 days of continuous glucose monitoring data for multiple periods. Using the data, time-in-range (TIR), the glucose management index (GMI) and various hyperglycemic measurements will be assessed using three different injection sites: normal adipose tissue, a lipohypertrophy site that is treated with a tensioned tissue treatment device, and a lipohypertrophy site control that is not treated with a tensioned tissue treatment device. Insulin usage during the study period will also be tracked. The three sites would be measured, using blinded CGM at the following time points: 0 to 2 weeks for a baseline, 6 to 8 weeks for the first comparison point and 10 to 12 weeks for the second comparison point. The order of data gathering is randomized, between an analysis of treated and untreated LH lesions, and an analysis between the treated LH lesion and normal adipose tissue. The glucose management index for the measurement period will be calculated by:

GMI(%)=3.31+0.02392×mean glucose in mg/dl

The TIR will be calculated as percentage of the CGM data spent in very low and low hypoglycemic states of <54 mg/dl and <70 mg/dl, in range between 70-180 mg/dl, and in high and very high hyperglycemic states of >180 md/dl and >250 mg/dl. The glycemic variability will be calculated using coefficient of variation (CV) and standard deviation for the measurement periods. Daily glucose profile graphs with the median glucose value, the middle 50% value and the 10% and 90% distributions lines are generated. The LH lesions will be measured at baseline and tracked during the study period for size, density and stiffness, as measured by various stiffness metrics generated by a CUTOMETER®. It is hypothesized that treatment of an LH lesion with a tensioned tissue treatment device may increase TIR, reduce measures of GV, reduce the percentage time spent in hypoglycemia states (alone or combined), hyperglycemic states (alone or combined), or total hypoglycemia/hyperglycemia (combined).

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

The invention claimed is:

1. An integrated infusion set, comprising:
    a pre-strained dressing, the pre-strained dressing comprising:
        a tensioned dressing layer;
        a skin adhesive on a lower surface of the tensioned dressing layer;
        one or more adhesive protective liners removably covering the skin adhesive; and
        a tension support structure configured to maintain the tensioned dressing layer in a stressed configuration, the tension support structure comprising one or more pull tabs; and
    an infusion assembly attached to an upper surface of the tensioned dressing layer,
    wherein the infusion assembly comprises:
        an infusion hub and an infusion housing attachable to the infusion hub, the infusion housing comprising tubing in fluid communication with a cavity of the infusion housing;
        an infusion conduit configured for insertion into a treatment location and
        a releasable attachment structure attaching the infusion hub to an upper surface of the tensioned dressing layer;
        wherein the cavity is configured to receive the infusion hub and to provide fluid communication between the tubing and the infusion conduit.

2. The infusion set of claim 1, wherein the infusion conduit is an infusion needle or an infusion catheter.

3. The infusion set of claim 1, further comprising an infusion set applicator releasably attachable to the infusion hub and further comprising a needle configured to removably extend through the infusion hub and out of a distal end of the infusion conduit.

4. The infusion set of claim 1, wherein the releasable attachment structure comprises a removable section to which the infusion hub is attached.

5. The infusion set of claim 4, wherein the releasable attachment structure comprises two or more non-removable sections coupled to the removable section.

6. The infusion set of claim 5, wherein the two or more non-removable sections coupled to the removable section are coupled via a tear or frangible structure.

7. The infusion set of claim 6, wherein the tear structure comprises a plurality of perforations.

8. The infusion set of claim 6, wherein the frangible structure comprises a frangible strut.

9. The infusion set of claim 6, wherein the non-removable sections comprise a plurality of arcuate bodies attached to the tensioned dressing layer.

10. The infusion set of claim 5, wherein the non-removable sections each comprise a slot configured to movably receive a tab located on the removable section.

11. The infusion set of claim 10, wherein the removable section is integrally formed with the infusion hub.

12. The infusion set of claim 10, wherein each slot is an arcuate slot.

13. The infusion of claim 4, wherein the removable section comprises a pull tab or handle.

14. The infusion set of claim 1, wherein the infusion hub further comprises a hub body and a hub base, and wherein the hub body is releasably attachable to the hub base, and the hub base is attached to the tensioned dressing layer.

15. The infusion set of claim 14, wherein the hub body comprises a releasable latch.

16. The infusion set of claim 15, further comprising a removal tool, the removal tool configured to actuate the releasable latch of the hub body and to facilitate separation of the hub body from the hub base.

17. The infusion set of claim 16, wherein the removal tool comprises prongs with tabs, wherein the prongs are configured to actuate the releasable latch of the hub body, and the tabs of the prongs are configured to lock to the hub body.

18. The infusion set of claim 17, wherein the hub body comprises access channels to the releasable latch which are configured to receive the prongs with tabs.

19. The infusion set of claim 1, wherein the infusion housing comprises a release latch configured to unlock the infusion housing from the infusion hub.

20. The infusion set of claim 14, wherein the hub base comprises a softer material than the hub body.

* * * * *